US012779047B2

(12) United States Patent
Giese et al.

(10) Patent No.: US 12,779,047 B2
(45) Date of Patent: Nov. 3, 2026

(54) LINKERS FOR IMPROVING THE STABILITY OF BIOCONJUGATES AND THE SELECTIVITY OF PAYLOAD RELEASE

(71) Applicant: EQIP, LLC, Plain City, OH (US)

(72) Inventors: Matthew Giese, Columbus, OH (US); Paul Davis, Dublin, OH (US)

(73) Assignee: EqIP, LLC, Plain City, OH (US)

(*) Notice: Subject to any disclaimer, the term of this patent is extended or adjusted under 35 U.S.C. 154(b) by 1012 days.

(21) Appl. No.: 17/952,108

(22) Filed: Sep. 23, 2022

(65) Prior Publication Data

US 2023/0158169 A1 May 25, 2023

Related U.S. Application Data

(62) Division of application No. 17/554,668, filed on Dec. 17, 2021, now Pat. No. 11,510,994.

(60) Provisional application No. 63/143,470, filed on Jan. 29, 2021.

(51) Int. Cl.
*A61K 47/68* (2017.01)
*A61K 47/54* (2017.01)
*A61K 47/60* (2017.01)

(52) U.S. Cl.
CPC ........ *A61K 47/6889* (2017.08); *A61K 47/542* (2017.08); *A61K 47/545* (2017.08); *A61K 47/60* (2017.08)

(58) Field of Classification Search
CPC .............. A61K 47/6889; A61K 47/542; A61K 47/545; A61K 47/60
See application file for complete search history.

(56) References Cited

U.S. PATENT DOCUMENTS

| | | | |
|---|---|---|---|
| 4,946,778 | A | 8/1990 | Ladner et al. |
| 5,359,030 | A | 10/1994 | Ekwuribe |
| 5,932,462 | A | 8/1999 | Harris et al. |
| 6,294,697 | B1 | 9/2001 | Wilbur et al. |
| 6,432,662 | B1 | 8/2002 | Davis et al. |
| 6,492,560 | B2 | 12/2002 | Wilbur et al. |
| 6,667,392 | B2 | 12/2003 | Xia et al. |
| 6,713,452 | B2 | 3/2004 | Ekwuribe et al. |
| 6,818,749 | B1 | 11/2004 | Kashmiri et al. |
| 7,553,816 | B2 | 6/2009 | Senter et al. |
| 7,888,536 | B2 | 2/2011 | Davis et al. |
| 7,994,272 | B2 | 8/2011 | Kozlowski et al. |
| 8,119,132 | B2 | 2/2012 | Hong et al. |
| 8,637,711 | B2 | 1/2014 | Davis et al. |
| 10,722,592 | B2 | 7/2020 | Lewis et al. |
| 10,786,497 | B2 | 9/2020 | Davis |
| 11,007,275 | B2 | 5/2021 | Bouchard et al. |
| 11,103,593 | B2 | 8/2021 | Lyon et al. |
| 11,135,307 | B2 | 10/2021 | Yurkovetskiy et al. |
| 11,229,708 | B2 | 1/2022 | Burke et al. |
| 11,505,525 | B2 | 11/2022 | Davis et al. |
| 11,510,994 | B2 | 11/2022 | Giese et al. |
| 11,541,128 | B2 | 1/2023 | Levengood |
| 11,583,541 | B2 | 2/2023 | Wang et al. |
| 11,617,798 | B2 | 4/2023 | Sandall et al. |
| 11,629,122 | B2 | 4/2023 | Tsuchikama et al. |
| 11,638,760 | B2 | 5/2023 | Thomas et al. |
| 11,725,024 | B2 | 8/2023 | Xu et al. |
| 11,730,822 | B2 | 8/2023 | Mao et al. |
| 11,793,880 | B2 | 10/2023 | Burke et al. |
| 11,844,839 | B2 | 12/2023 | Mao et al. |
| 11,857,565 | B2 | 1/2024 | Doronina et al. |
| 2003/0203856 | A1 | 10/2003 | Rosazza et al. |
| 2005/0164235 | A1 | 7/2005 | Manoharan et al. |
| 2006/0020134 | A1 | 1/2006 | Davis et al. |
| 2007/0031371 | A1 | 2/2007 | McManus et al. |
| 2008/0020043 | A1 | 1/2008 | Gingras et al. |
| 2010/0164065 | A1 | 7/2010 | Lee |
| 2010/0210505 | A1 | 8/2010 | Bossard et al. |
| 2011/0014151 | A1 | 1/2011 | Nilsson et al. |
| 2011/0124844 | A1 | 5/2011 | Davis et al. |
| 2012/0164068 | A1 | 6/2012 | Hudson et al. |
| 2013/0052130 | A1 | 2/2013 | Davis et al. |

(Continued)

FOREIGN PATENT DOCUMENTS

| | | | |
|---|---|---|---|
| WO | WO-0053661 | A1 | 9/2000 |
| WO | WO-02098446 | A1 | 12/2002 |

(Continued)

OTHER PUBLICATIONS

Arseneault, et al., "Efficient and Rapid Divergent Synthesis of Ethylene Oxide-Containing Dendrimers through Catalyst-Free Click Chemistry," Macromolecules 2012, 45(9):3687-94.
Author Unknown, Quanta Biodesign Limited, "What Is a dPEG®," 2011, 1 page.
Bailon, et al., "Rational design of a potent, long-lasting form of interferon: a 40 kDa branched polyethylene glycol-conjugated interferon alpha-2a for the treatment of hepatitis C," Bioconjug Chem. Mar.-Apr. 2001;12(2):195-202.
Bandyopadhyay, et al., "An ion conductor that recognizes osmotically-stressed phospholipid bilayers," J Am Chem Soc. Sep. 25, 2002; 124(38):11254-5.
Beadle, et al., "Syntheses and properties of arenediazonium and anilinium cation lariat ether complexes: an "ostrich molecule" complex and evidence for intramolecular sidearm-macroring interaction," Tetrahedron. 1984; 40:3935-44.
Betancourt, et al., "PEGylation strategies for active targeting of PLA/PLGA nanoparticles," J Biomed Mater Res A. Oct. 2009; 91(1):263-76.

(Continued)

*Primary Examiner* — Michael P Cohen
(74) *Attorney, Agent, or Firm* — Cooley LLP

(57) ABSTRACT

Disclosed herein are linker architectures for conjugates that do not rely on the SAR of the cleavable trigger or the large steric bulk of a closely positioned antibody to alter payload release. These linkers are expected to reduce off-target payload release facilitated by extracellular cathepsins, and may also be applicable to conjugates of antibody fragments that lack the steric protection from a full antibody. In addition, the linkers disclosed herein are expected to provide more selective intracellular payload release. Thus, these linkers can function synergistically with the targeting vector to confer differential payload release rates in vivo that improve the selectivity of intracellular payload release and reduce off target toxicity.

19 Claims, 100 Drawing Sheets

(56) References Cited

U.S. PATENT DOCUMENTS

| | | | |
|---|---|---|---|
| 2013/0202548 | A1 | 8/2013 | Rowan et al. |
| 2016/0310612 | A1 | 10/2016 | Lyon et al. |
| 2017/0313656 | A1* | 11/2017 | Davis .................... C07C 279/24 |
| 2019/0298844 | A1 | 10/2019 | Liu et al. |
| 2020/0093934 | A1 | 3/2020 | Bouchard et al. |
| 2020/0230133 | A1 | 7/2020 | Davis |
| 2020/0317612 | A1 | 10/2020 | Davis et al. |
| 2020/0345863 | A1 | 11/2020 | Viricel |
| 2020/0361870 | A1 | 11/2020 | Stafford et al. |
| 2021/0009757 | A1 | 1/2021 | Hamura et al. |
| 2021/0179720 | A1 | 6/2021 | Geall et al. |
| 2021/0308207 | A1 | 10/2021 | Robillard et al. |
| 2021/0353766 | A1 | 11/2021 | Van Berkel et al. |
| 2022/0040320 | A1 | 2/2022 | Jeffrey et al. |
| 2022/0072146 | A1 | 3/2022 | Lyon et al. |
| 2022/0118105 | A1 | 4/2022 | Zhu et al. |
| 2022/0233707 | A1 | 7/2022 | Lowinger et al. |
| 2022/0265848 | A1 | 8/2022 | Giese et al. |
| 2022/0339290 | A1 | 10/2022 | Hamura et al. |
| 2022/0339291 | A1 | 10/2022 | Park et al. |
| 2022/0362397 | A1 | 11/2022 | Matsuno et al. |
| 2023/0021500 | A1 | 1/2023 | Toader et al. |
| 2023/0038373 | A1 | 2/2023 | Satomaa et al. |
| 2023/0043447 | A1 | 2/2023 | Yurkovetskiy et al. |
| 2023/0131121 | A1 | 4/2023 | Davis et al. |
| 2023/0172910 | A1 | 6/2023 | Duvall et al. |
| 2023/0173093 | A1 | 6/2023 | Neumann et al. |
| 2023/0295330 | A1 | 9/2023 | Sandall et al. |
| 2023/0295346 | A1 | 9/2023 | Krystek, Jr. et al. |
| 2023/0346969 | A1 | 11/2023 | Wang et al. |
| 2023/0399356 | A1 | 12/2023 | Xu et al. |
| 2024/0000800 | A1 | 1/2024 | Wang et al. |
| 2024/0033372 | A1 | 2/2024 | Levengood |
| 2024/0148721 | A1 | 5/2024 | Davis |

FOREIGN PATENT DOCUMENTS

| | | | |
|---|---|---|---|
| WO | WO-02098451 | A1 | 12/2002 |
| WO | WO-02098452 | A1 | 12/2002 |
| WO | WO-03022210 | A2 | 3/2003 |
| WO | WO-2004046167 | A2 | 6/2004 |
| WO | WO-2004073620 | A2 | 9/2004 |
| WO | WO-2007080114 | A2 | 7/2007 |
| WO | WO-2007140282 | A1 | 12/2007 |
| WO | WO-2008034120 | A2 | 3/2008 |
| WO | WO-2010048582 | A1 | 4/2010 |
| WO | WO-2013033476 | A1 | 3/2013 |
| WO | WO-2013072717 | A1 | 5/2013 |
| WO | WO-2015023979 | A1 | 2/2015 |
| WO | WO-2015057699 | A2 | 4/2015 |
| WO | WO-2022165335 | A1 | 8/2022 |

OTHER PUBLICATIONS

Boisselier, et al., "Encapsulation and stabilization of gold nanoparticles with "click" polyethyleneglycol dendrimers," J Am Chem Soc. Mar. 3, 2010; 132(8):2729-42.

Burns, et al., "A convenient synthetic route to differentially functionalized long chain polyethylene glycols," Synth Commun. 1999; 29:2337-47.

Capule, et al., "Oligovalent amyloid-binding agents reduce SEVI-mediated enhancement of HIV-1 infection," J Am Chem Soc. Jan. 18, 2012; 134(2):905-8. Epub Jan. 3, 2012.

Chatti, et al., "Synthesis of New Diols Derived from Dianhydrohexitols Ethers under Microwave-Assisted Phase Transfer Catalysis," Tetrahedron 2000, 56(32):5877-83.

Chen, et al., "Synthesis and Properties of ABA Amphiphiles," J Org Chem. Sep. 3, 1999; 64(18):6870-6873.

Delgado, et al., "Enhanced tumour specificity of an anti-carcinoembrionic antigen Fab' fragment by poly(ethylene glycol) (PEG) modification," Br J Cancer. Jan. 1996; 73(2):175-82.

Ding, et al., "Site specific discrete PEGylation of (124)I-labeled mCC49 Fab' fragments improves tumor MicroPET/CT imaging in mice," Bioconjug Chem. Nov. 20, 2013; 24(11):1945-54. Epub Oct. 31, 2013.

Fee, C.J., "Size comparison between proteins PEGylated with branched and linear poly(ethylene glycol) molecules," Biotechnol Bioeng. Nov. 1, 2007; 98(4):725-31.

Fee, et al., "Prediction of the viscosity radius and the size exclusion chromatography behavior of PEGylated proteins," Bioconjug Chem. Nov.-Dec. 2004; 15(6):1304-13.

Fishburn, C.S., "The pharmacology of PEGylation: balancing PD with PK to generate novel therapeutics," J Pharm Sci. Oct. 2008; 97(10):4167-83.

Greenwald, et al., "Controlled release of proteins from their poly-(ethylene glycol) conjugates: drug delivery systems employing 1,6-elimination," Bioconjug Chem. Mar.-Apr. 2003; 14(2):395-403.

Gutierrez-Nava, et al., "Synthesis of copolymers alternating oligophenylenevinylene subunits and fullerene moieties," Tetrahedron Letters, vol. 44, Issue 24, Jun. 9, 2003, pp. 4487-4490.

Hermanson, Greg T., Chapter 18—Discrete PEG Compounds, Bioconjugate Techniques 2008 (2nd Edition), Elsevier Academic Press, 36 pages.

Hermanson, Greg T., Chapter 6—Heterobifunctional Crosslinkers, Chapter 18—PEGylation and Synthetic Polymer Modification, and Chapter 20—Antibody Modification and Conjugation, Bioconjugate Techniques 2013 (Third Edition). Elsevier Inc., 147 pages.

Hurwitz, et al., "Inhibition of tumor growth by poly(ethylene glycol) derivatives of anti-ErbB2 antibodies," Cancer Immunol Immunother. Jul. 2000; 49(4-5):226-34.

International Preliminary Report on Patentability dated Feb. 16, 2016 for International Application No. PCT/US2014/051338, 6 pages.

International Preliminary Report on Patentability dated Mar. 4, 2014 for International Application No. PCT/US2012/053250, 7 pages.

International Preliminary Report on Patentability dated Sep. 27, 2006 for International Application No. PCT/US2004/004274, 6 pages.

International Search Report and Written Opinion mailed on Dec. 4, 2014, for International Application No. PCT/US2014/051338, 7 pages.

International Search Report and Written Opinion mailed on Dec. 7, 2012, for International Application No. PCT/US2012/053250, 8 pages.

International Search Report and Written Opinion mailed on Jun. 2, 2006, for International Application No. PCT/US2004/004274, 9 pages.

Jevsevar, et al., "PEGylation of therapeutic proteins," Biotechnol J. Jan. 2010; 5(1):113-28.

Kang, et al., "Emerging PEGylated drugs," Expert Opin Emerg Drugs. Jun. 2009; 14(2):363-80.

Katre, N.V., "The conjugation of proteins with polyethylene glycol and other polymers: Altering properties of proteins to enhance their therapeutic potential," Advanced Drug Delivery Reviews 1993; 10(1):91-114.

Keegstra, et al., "A highly selective synthesis of monodisperse oligo(ethylene glycols)," The Journal of Organic Chemistry 1992; 57(24):6678-80.

Kim, et al., "Low molecular weight (1 kDa) polyethylene glycol conjugation markedly enhances the hypoglycemic effects of intranasally administered exendin-4 in type 2 diabetic db/db mice," Biol Pharm Bull. 2012; 35(7):1076-83.

Kusterle, et al., "Size of pegylated protein conjugates studied by various methods," Acta Chim Slov. 2008; 55(3):594-601.

Lee, et al., "Prolonged circulating lives of single-chain Fv proteins conjugated with polyethylene glycol: a comparison of conjugation chemistries and compounds," Bioconjug Chem. Nov.-Dec. 1999; 10(6):973-81.

Li, et al., "Improved biodistribution and radioimmunoimaging with poly(ethylene glycol)-DOTA-conjugated anti-CEA diabody," Bioconjug Chem. Jan.-Feb. 2006; 17(1):68-76.

Li, et al., "Monodispersed DOTA-PEG-conjugated anti-TAG-72 diabody has low kidney uptake and high tumor-to-blood ratios resulting in improved 64Cu PET," J Nucl Med. Jul. 2010; 51(7):1139-46. Epub Jun. 16, 2010.

(56) References Cited

OTHER PUBLICATIONS

Lu, et al., "Effect of PEGylation on the solution conformation of antibody fragments," J Pharm Sci. Jun. 2008; 97(6):2062-79.
Molineux, G., "The design and development of pegfilgrastim (PEG-rmetHuG-CSF, Neulasta)," Curr Pharm Des. 2004; 10(11):1235-44.
Pai, et al., "The conformation of the poly(ethylene glycol) chain in mono-PEGylated lysozyme and mono-PEGylated human growth hormone," Bioconjug Chem. Nov. 16, 2011; 22(11):2317-23. Epub Oct. 6, 2011.
Pine, Stanley H., "Organic Chemistry" in: "Organic Chemistry", Jan. 1, 1987, McGraw Hill, pp. 341-342.
Quiles, S., et al., "Synthesis and preliminary biological evaluation of high-drug-load paclitaxel-antibody conjugates for tumor-targeted chemotherapy," J Med Chem. Jan. 28, 2010; 53(2):586-94.
Rosendahl, et al., "A long-acting, highly potent interferon alpha-2 conjugate created using site-specific PEGylation," Bioconjug Chem. Jan.-Feb. 2005; 16(1):200-7.
Simpson, et al., "Short-chain PEG mixed monolayer protected gold clusters increase clearance and red blood cell counts," ACS Nano. May 24, 2011; 5(5):3577-84. Epub Apr. 19, 2011.
Supplementary European Search Report dated Feb. 19, 2015 for EP 12828094.8, 16 pages.
Supplementary European Search Report dated Nov. 22, 2006 for EP 04711102.6, 2 pages.
Tollas, S., et al., "Nano-sized clusters of a teicoplanin ?-aglycon-fullerene conjugate. Synthesis, antibacterial activity and aggregation studies," Eur J Med Chem. Aug. 2012; 54:943-8. Epub Jul. 4, 2012.
Uchio, et al., "Site-specific insulin conjugates with enhanced stability and extended action profile," Adv Drug Deliv Rev. Feb. 1, 1999; 35(2-3):289-306.
Veronese, et al., "PEGylation, successful approach to drug delivery," Drug Discov Today. Nov. 1, 2005; 10(21):1451-8.
Veronese, et al., "Protein PEGylation, basic science and biological applications," from PEGylated Protein Drugs: Basic Science and Clinical Applications, 2009, Birkhauser, 21 pages.
Zalipsky, S., et al., "Chemistry of Polyethylene Glycol Conjugates with Biologically Active Molecules," Advanced Drug Delivery Reviews 1995; 16:157-82.
Bakalova, Rumiana, et al. "Chemical nature and structure of organic coating of quantum dots is crucial for their application in imaging diagnostics," International Journal of Nanomedicine, 2011, 6, 1719-1732.
Banerjee, S.S. et al. (2012, e-published May 7, 2012). "Poly(ethylene glycol)-Prodrug Conjugates: Concept, Design, and Applications," J Drug Deliv 2012:103973, 17 pages.
Bargh, J.D., et al., "Cleavable linkers in antibody-drug conjugates," Chemical Society Reviews, 2019, 48, 4361-4374 (DOI: 10.1039/c8cs00676h).
Benezra et al., "Multimodal silica nanoparticles are effective cancer-targeted probes in a model of human melanoma," The Journal of Clinical Investigation 121(7):2768-2780 (2011).
Burke, P. J., et al., "Optimization of a PEGylated Glucuronide-Monomethylauristatin E Linker for Antibody-Drug Conjugates," Molecular Cancer Therapeutics 2017, 16(1), 116-123.
Chames, P. et al., "Bispecific antibodies for cancer therapy," InMAbs, Nov. 2009, vol. 1, No. 6, pp. 539-547.
Declaration under rule 132 filed for U.S. Appl. No. 13/600,188, filed Jun. 8, 2016, 15 pages.
Declaration under rule 132 filed for U.S. Appl. No. 13/600,188, filed Mar. 17, 2016, 19 pages.
Declaration under rule 132 filed for U.S. Appl. No. 15/630,986, filed Apr. 2, 2018, 18 pages.
Declaration under rule 132 filed for U.S. Appl. No. 15/630,986, filed Feb. 22, 2019, 60 pages.
Declaration under rule 132 filed for U.S. Appl. No. 15/630,986, filed Sep. 20, 2018, 24 pages.
Defrees, Shawn, et al.; "GlycoPEGylation of recombinant therapeutic proteins produced in *Escherichia coli*," Glycobiology vol. 16 No. 9 pp. 833-843, 2006.
Ditto, Steven. R., et al.; On the photocycloaddition of dimethyl acetylenedicarboxylate to benzo(b)thiophene, Tetrahedron Letters, vol. 22, Issue 6, 1981, pp. 521-524.
Famulok, M., et al., "Functional Aptamers and Aptazymes in Biotechnology, Diagnostics, and Therapy," Chem. Rev., 107(9),3715-3743 (2007).
Gibson, H.W. et al.; "Difunctional derivatives of bis(mphenylene)-32-crown-10," Canadian Journal of Chemistry, vol. 75, No. 10, Oct. 1997, pp. 1375-1384.
Giese, M., et al. Bioconjugate Chem. 2021, 32, 10, S-1 to S-124 (Supporting Information).
Giese, M., et al., "Linker Architectures as Steric Auxiliaries for Altering Enzyme-Mediated Payload Release from Bioconjugates," Bioconjugate Chem. 2021, 32, 10, 2257-2267.
International Preliminary Report on Patentability for International Application No. PCT/US2022/014566 issued Jul. 31, 2023, 7 pages.
International Search Report and Written Opinion for International Application No. PCT/US2022/014566, mailed Apr. 12, 2022, 8 pages.
Levengood, M. R., et al., "Orthogonal Cysteine Protection Enables Homogeneous Multi-Drug Antibody-Drug Conjugates," Angew. Chem. In. Ed. 2017, 56, 733-737.
Lyon, R. P., et al., "Reducing hydrophobicity of homogeneous antibody-drug conjugates improves pharmacokinetics and therapeutic index," Nature Biotechnology 2015, 33, 4 pages.
Millard, Melissa, et al.; "Integrin Targeted Therapeutics," Theranostics, 2011, 1, pp. 154-188.
Müller, M. K. et al., "Protein assembly along a supramolecular wire," Chem. Commun., (Camb), Jan. 7, 2011, vol. 47(1), pp. 310-312.
Mufamadi, M., et al.; "A Review on Composite Liposomal Technologies for Specialized Drug Delivery," Journal of Drug Delivery, 2011, pp. 1-19.
Muraoka, T. et al., "Mimicking multipass transmembrane proteins: synthesis, assembly and folding of alternating amphiphilic multiblock molecules in liposomal membranes," Chem Commun (Camb), Jan. 7, 2011, 47(1):194-196.
Pabst, M., et al., "Modulation of drug-linker design to enhance in vivo potency of homogeneous antibody-drug conjugates," J. Contr. Rel., 2017, 253, 160-164.
Rush, Jason S. and Carolyn R. Bertozzi, "New Aldehyde Tag Sequences Identified by Screening Formylglycine Generating Enzymes in Vitro and in Vivo," J. Am. Chem. Soc., 2008, 130 (37), pp. 12240-12241.
Simpson, Carrie A., et al.; "Short-Chain PEG Mixed-Monolayer Protected Gold Clusters Increase Clearance and Red Block Cell Counts," ACSNano, 2011, 5(5), pp. 3577-3584.
Steevens N. S. Alconcel, Arnold S. Baas and Heather D. Maynard; "FDA-approved poly(ethylene glycol)-protein conjugate drugs," Polym. Chem., 2, 2011, 2, 1442-1448.
Su, D., et al., "Modulating Antibody-Drug Conjugate Payload Metabolism by Conjugation Site and Linker Modification," Bioconj. Chem., 2018, 29, 1155-1167.
Viricel, Warren, et al. "Monodisperse polysarcosine-based highly-loaded antibody-drug conjugates," Chem. Sci., 2019, 10, pp. 4048-4053.
Wong, L.S. et al. (2009) "Selective Covalent Protein Immobilization: Strategies and Applications" Chem. Rev., 109(9)4025-4053.
Zawada, J.F., et al.; "Microscale to Manufacturing Scale-up of Cell-Free Cytokine Production—A New Approach for Shortening Protein Production Development Timelines," Biotechnology and Bioengineering, 2011, 108(7), 1570-1578.
EP Application No. 22746801.4, Extended European Search Report mailed Dec. 17, 2025; Applicant Equip, LLC; 11 pages.

* cited by examiner (12)

(13)

(1)

(2)

(20)

(21)

(22)

(24)

(25)

(26)

(29)

(79, 109) x=8, x=24; R =H (80, 110) x=8, x=24; R = TFP (81, 111) x=8, x=24

Orthogonal n=3, x=8
O - (27,6)3x8

Orthogonal n=3, x=8
Q - (27,10)3x8

Orthogonal n=3, x=24
P - (27,6)3x24

Orthogonal n=3,
x=24 R - (27,10)3x24

D'+4 3x8

D' 3x8

D'+4 3x24

D' 3x24

LINKERS FOR IMPROVING THE STABILITY OF BIOCONJUGATES AND THE SELECTIVITY OF PAYLOAD RELEASE

CROSS-REFERENCE TO RELATED APPLICATIONS

This application is a divisional of U.S. application Ser. No. 17/554,668, filed Dec. 17, 2021, which claims the benefit of and priority to U.S. Provisional Application No. 63/143,470, filed Jan. 29, 2021, the disclosures of each of which are herein incorporated by reference in their entireties.

FIELD OF THE INVENTION

The present disclosure relates to antibody-drug conjugates (ADCs), fragment-drug conjugates (FDCs), and peptide-drug conjugates (PDCs), where the disclosed linker architectures may widen therapeutic windows.

BACKGROUND

A number of antibody-drug conjugates (ADCs) utilize linkers with cleavable triggers that are substrates for enzymes found in the endolysosomal compartments. Ideally, this increases the therapeutic window of an ADC by reducing the amount of cytotoxin released in extracellular tissues while still allowing for cytotoxin release after internalization by the targeted cells. Dipeptide triggers (e.g., Val-Cit, Val-Ala, and Phe-Lys) are some of the most common cleavable triggers in ADCs under development, and are cleaved by the lysosomal protease cathepsin B (CTB). However, it has been found that these dipeptide triggers are not selective for CTB. Consequently, other enzymes such as esterases (CES1c), neutrophil elastase, and other cysteine cathepsins (CTK, CTL, and CTS) can trigger enzyme-mediated release of the cytotoxin.

Furthermore, many of these enzymes have been found in extracellular/pericellular locations and elevated levels of circulating cathepsins in the serum of cancer patients have been evaluated for use as diagnostic biomarkers. While catalytic activity is optimal at the low pH in the lysosome, there are potent regulators of their activity in the extracellular milieu, and studies have found all the cathepsins are capable of processing substrates at neutral and oxidizing conditions. This is especially true of CTS, which maintains activity over a broad pH optimum, and thus is likely of more physiological importance in the extracellular environment.

One approach to eliminating CES1c-mediated release is to leverage steric hindrance from the antibody by utilizing short linkers or engineered conjugation sites in sterically shielded regions of the antibody. Since the cathepsins are unaffected by steric hindrance from the antibody, this approach provides specific CTB-mediated payload release relative to CES1c, but does not address payload release by the other cysteine cathepsins.

Consequently, alternative approaches to altering selectivity and rates of cathepsin-mediated payload release are needed.

SUMMARY

The present disclosure is based, in part, on the surprising and unexpected discovery that the selectivity and rates of cathepsin-mediated payload release can be influenced by the architecture of an orthogonally placed branched linker. In some embodiments, the rate of cathepsin-mediated payload release can be reduced by a synergistic effect provided by steric factors of the targeting vector (e.g., an antibody) and the novel linker architectures.

According to the present studies, the linker architectures for conjugates disclosed herein do not solely rely on the structure-activity relationship (SAR) of the cleavable trigger or the large steric bulk of a closely positioned targeting vector (e.g., antibody) to alter payload release. As a result, the trigger can be conjugated at large distances from the antibody and still exhibit altered payload release, including reductions of payload release by exopeptidases such as CTL and CTS. Thus, in some embodiments, these linkers improve therapeutic windows by reducing off-target payload release caused by extracellular cathepsins. In some embodiments, these linkers exhibit altered payload release even within conjugates that lack the steric protection from a full antibody (e.g., from an scFv, FAB, or other small targeting biologic). In some embodiments, the linkers of the present disclosure further increase the effectiveness of steric hindrance of the targeting vector.

In some embodiments, the present disclosure provides a compound of Formula (I) or a pharmaceutically acceptable salt, solvate, or isomer thereof:

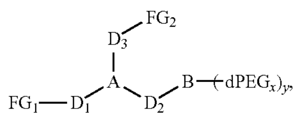

(I)

wherein:

- $FG_1$ is a reactive functional group capable of conjugation to a targeting vector;
- $FG_2$ is a reactive functional group capable of conjugation to a trigger and/or payload;
- A is an amino acid residue or a trivalent or tetravalent atom;
- B is a first branch point;
- PEG is a polyethylene glycol-based chain comprising linear, branched, monodisperse, and/or polydisperse PEG;
- x is an integer from 4 to 48;
- y is 2 or 3; and
- $D_1$, $D_2$, and $D_3$ are each independently a spacer moiety, wherein D' represents the sum of atoms in a linear chain between B and $FG_2$.

In some embodiments, the present disclosure provides a compound of Formula (II) or a pharmaceutically acceptable salt, solvate, or isomer thereof:

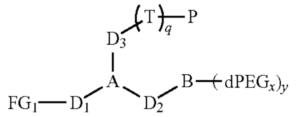

(II)

wherein:

- $FG_1$ is a reactive functional group capable of conjugation to a targeting vector;
- A is a trivalent or tetravalent atom;
- B is a first branch point;
- T is a releasable trigger;
- P is a payload;

PEG is a polyethylene glycol-based chain comprising linear, branched, monodisperse, and/or polydisperse PEG;

q is 0 or 1;

x is an integer from 4 to 48;

y is 2 or 3; and $D_1$, $D_2$, and $D_3$ are each independently a spacer moiety, wherein D' represents the sum of atoms in a linear chain between B and T.

In some embodiments, the present disclosure provides a compound of Formula (III) or a pharmaceutically acceptable salt, solvate, or isomer thereof:

(III)

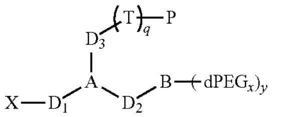

wherein:

A is a trivalent or tetravalent atom;

B is a first branch point;

T is a releasable trigger;

P is a payload;

X is a targeting vector;

PEG is a polyethylene glycol-based chain comprising linear, branched, monodisperse, and/or polydisperse PEG;

q is 0 or 1;

x is an integer from 4 to 48;

y is 2 or 3; and $D_1$, $D_2$, and $D_3$ are each independently a spacer moiety, wherein D' represents the sum of atoms in a linear chain between B and T.

DEFINITIONS

Figure 1A:
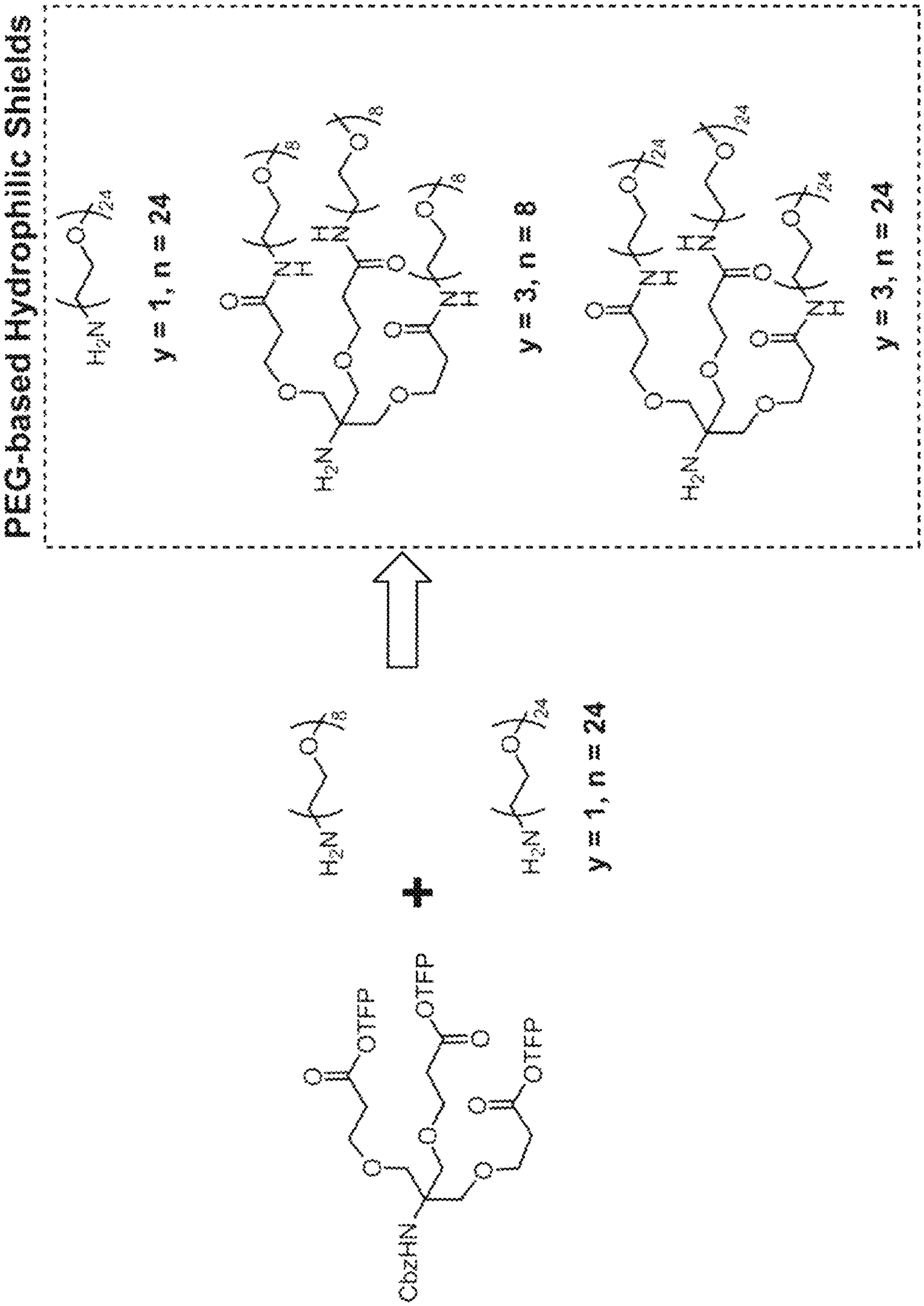
FIG. 1A shows a non-limiting modular approach to the synthesis of linker architectures of the present disclosure with varying y, n D' and D, where a is the number of methylene groups in the amino acid side chain (e.g., 1 or 2), b is the number of beta-alanine spacers (e.g., 0 or 1), and c is the number of atoms in the chain between the maleimide nitrogen and the carbonyl group (e.g., 2, 5, and 18). In the final conjugates D' includes both a and b, and D includes both a and c.
Figure 1A:
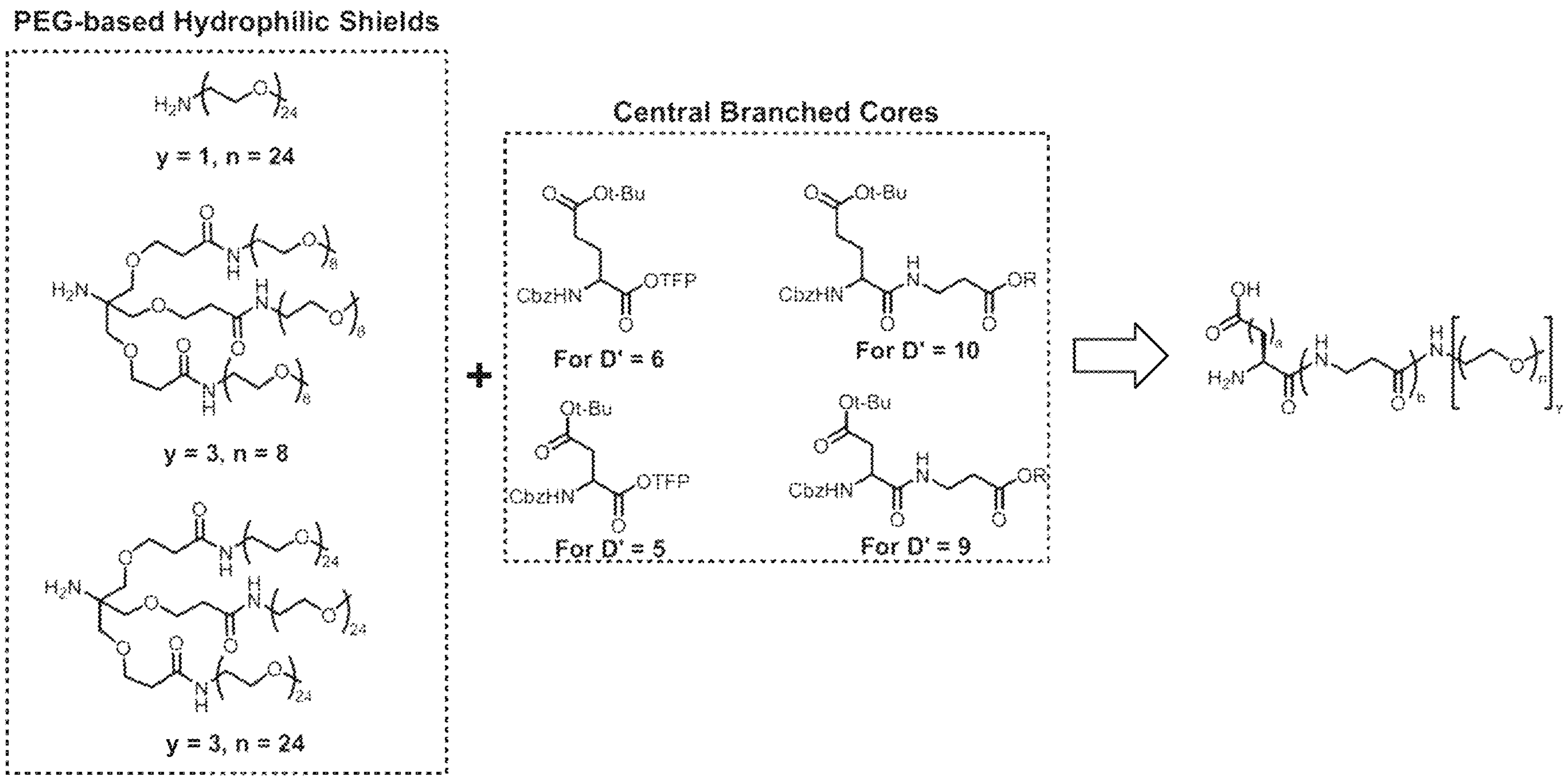
Figure 1A:
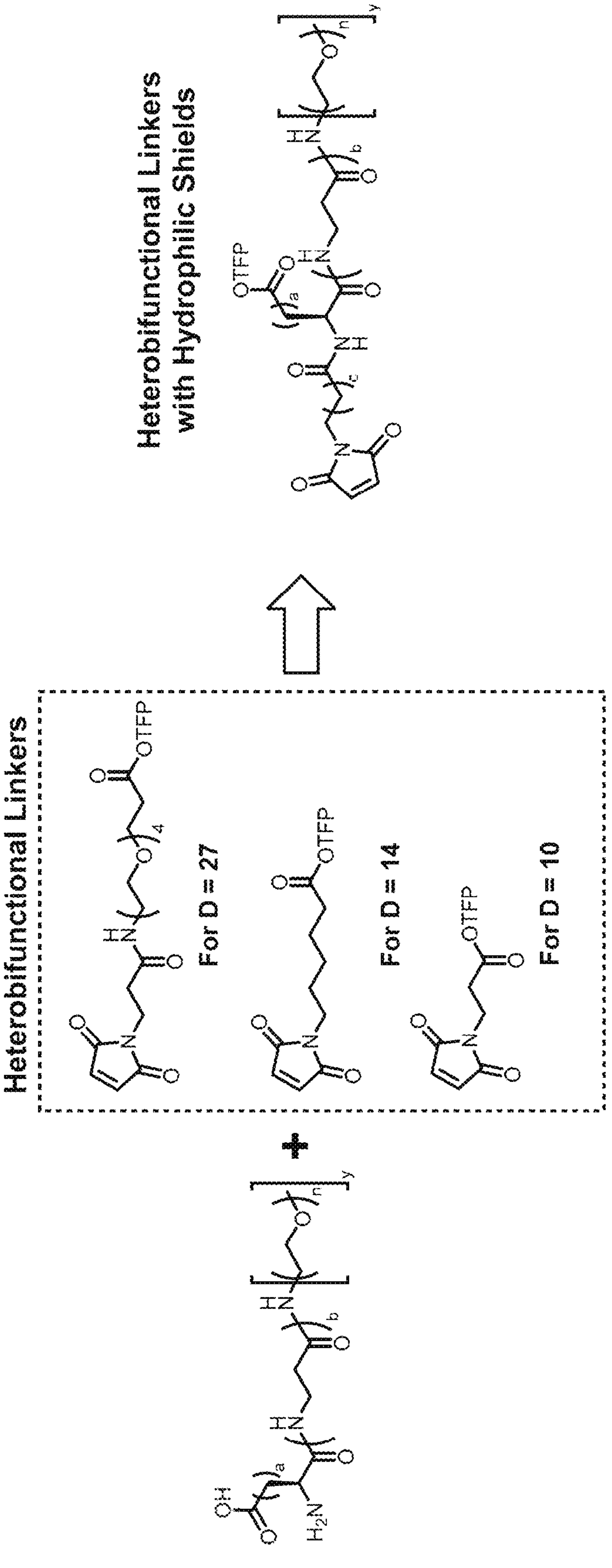
Figure 1A:
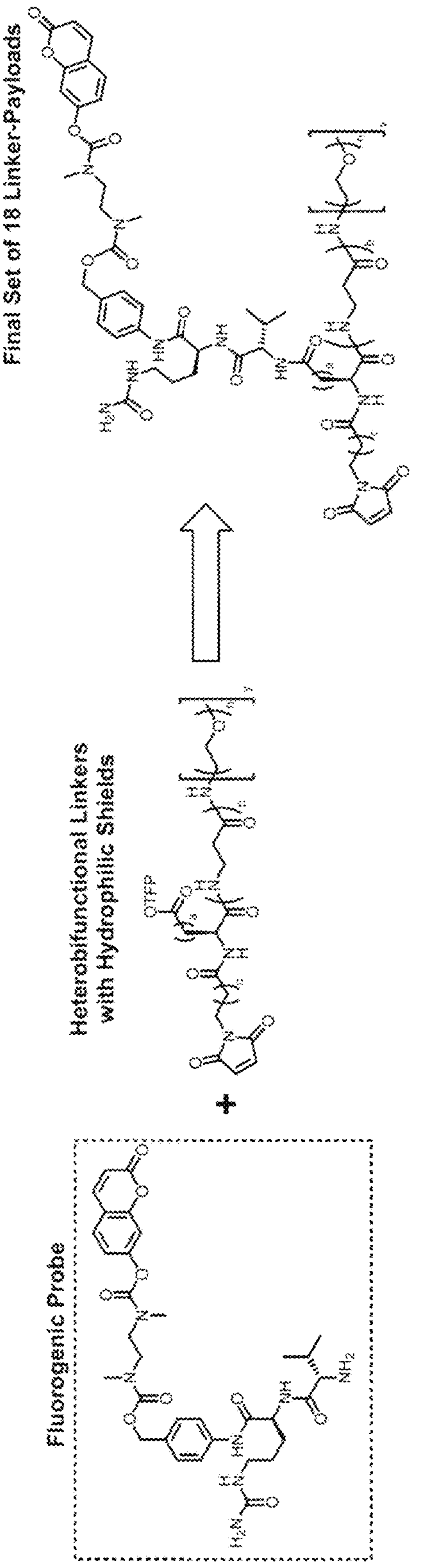

While the following terms are believed to be well understood by one of ordinary skill in the art, the following definitions are set forth to facilitate explanation of the presently disclosed subject matter.

As used in this specification and the appended claims, the singular forms “a,” “an” and “the” include plural references unless the content clearly dictates otherwise.

As used in this specification and the appended claims, the term “and/or” is used in this disclosure to either “and” or “or” unless indicated otherwise.

The term “alkylene” or “alkylene chain”, as used herein, refers to a fully saturated, straight or branched divalent hydrocarbon chain radical, and having from one to twelve carbon atoms. Non-limiting examples of $C_1$-$C_{12}$ alkylene include methylene, ethylene, propylene, n-butylene, and the like. The alkylene chain is attached to the rest of the molecule through a single bond and to a radical group (e.g., those described herein) through a single bond. The points of attachment of the alkylene chain to the rest of the molecule and to the radical group can be through one carbon or any two carbons within the chain. Unless stated otherwise specifically in the specification, an alkylene chain can be optionally substituted.

The term “alkenylene” or “alkenylene chain”, as used herein, refers to an unsaturated, straight or branched divalent hydrocarbon chain radical having one or more olefins and from two to twelve carbon atoms. Non-limiting examples of $C_2$-$C_{12}$ alkenylene include ethenylene, propenylene, n-butenylene, and the like. The alkenylene chain is attached to the rest of the molecule through a single bond and to a radical group (e.g., those described herein) through a single bond. The points of attachment of the alkenylene chain to the rest of the molecule and to the radical group can be through one carbon or any two carbons within the chain. Unless stated otherwise specifically in the specification, an alkenylene chain can be optionally substituted.

The term “alkynylene” or “alkynylene chain”, as used herein, refers to an unsaturated, straight or branched divalent hydrocarbon chain radical having one or more alkynes and from two to twelve carbon atoms. Non-limiting examples of $C_2$-$C_{12}$ alkynylene include ethynylene, propynylene, n-butynylene, and the like. The alkynylene chain is attached to the rest of the molecule through a single bond and to a radical group (e.g., those described herein) through a single bond. The points of attachment of the alkynylene chain to the rest of the molecule and to the radical group can be through any two carbons within the chain having a suitable valency. Unless stated otherwise specifically in the specification, an alkynylene chain can be optionally substituted.

“Amino acid residue” refers to the subunit or portion of an amino acid that is incorporated into a compound of the present disclosure. In some embodiments, the amino acid residue is formed by replacing at least one atom of an amino acid, e.g., a hydrogen of a —COOH and/or —NH group with a bond to a second moiety. As a result of bond-formation to the second moiety, the amino acid is modified such that the disclosed compound contains an "amino acid residue" or "residue of an amino acid" and not the amino acid itself. For example, in some embodiments, the A moiety of Formula (I), Formula (II), and Formula (III) is an amino acid residue that binds each of $D_1$, $D_2$, and $D_3$ as shown in the following non-limiting structure:

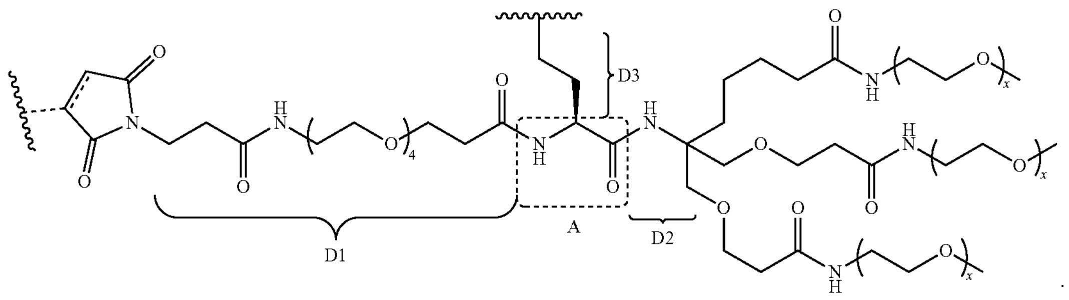

The term "pharmaceutically acceptable salts" include those obtained by reacting the active compound functioning as a base, with an inorganic or organic acid to form a salt, for example, salts of hydrochloric acid, sulfuric acid, phosphoric acid, methanesulfonic acid, camphorsulfonic acid, oxalic acid, maleic acid, succinic acid, citric acid, formic acid, hydrobromic acid, benzoic acid, tartaric acid, fumaric acid, salicylic acid, mandelic acid, carbonic acid, etc. Those skilled in the art will further recognize that acid addition salts may be prepared by reaction of the compounds with the appropriate inorganic or organic acid via any of a number of known methods.

The term "substituted" used herein means any of the groups described herein (e.g., alkyl, alkenyl, alkynyl, alkoxy, aryl, aralkyl, carbocyclyl, cycloalkyl, cycloalkenyl, cycloalkynyl, haloalkyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $—NR_gR_h$, $—NR_gC(=O)R_h$, $—NR_gC(=O)NR_gR_h$, $—NR_gC(=O)OR_h$, $—NR_gSO_2R_h$, $—OC(=O)NR_gR_h$, $—OR_g$, $—SR_g$, $—SOR_g$, $—SO_2R_g$, $—OSO_2R_g$, $—SO_2OR_g$, $=NSO_2R_g$, and $—SO_2NR_gR_h$. "Substituted" also means any of the above groups in which one or more hydrogen atoms are replaced with $—C(=O)R_g$, $—C(=O)OR_g$, $—C(=O)NR_gR_h$, $—CH_2SO_2R_g$, $—CH_2SO_2NR_gR_h$. In the foregoing, $R_g$ and $R_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocycloalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocycloalkyl, heteroaryl, N-heteroaryl and/or heteroarylalkyl group. In addition, each of the foregoing substituents can also be optionally substituted with one or more of the above substituents.

"Discrete PEG" or "dPEG", as used herein, refers to a polyethylene oxide composition of a single molecular entity (in contrast to a mixture that contains two or more molecular entities). In some embodiments, the dPEGs described herein are specific to a single or discrete ethylene oxide homolog. In some embodiments, a specific dPEG product, and not a polydisperse mixture, is used in the linkers and conjugates of the present disclosure.

The term "antibody" as used herein is used in the broadest sense and specifically covers intact monoclonal antibodies, polyclonal antibodies, monospecific antibodies, multispecific antibodies (e.g., bispecific antibodies), and antibody fragments that exhibit the desired biological activity provided that the antibody fragment have the requisite number of attachment sites for a drug-linker. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system. (see, e.g., Janeway et al., 2001, *Immuno. Biology*, 5th Ed., Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some aspects, the antibody is of human or murine origin. An antibody can be, for example, human, humanized or chimeric.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

The term "antibody fragment", as used herein, refers to a portion of an intact antibody, comprising the antigen-binding or variable region thereof (e.g., VH and/or VL). In order to be of use in the present invention, the antibody fragment must have the requisite number of sites for attachment to a drug-linker. The attachment sites can be naturally occurring or non-naturally occurring.

The term "antigen" as used herein, refers to an entity to which an antibody specifically binds.

DETAILED DESCRIPTION

The present disclosure provides an alternative approach to altering selectivity and rates of cathepsin-mediated payload release through the effect of a modified architecture of an orthogonally placed linker, or through the combined effects of a targeting vector (e.g. an antibody or fragment) and the orthogonal linker architectures.

In some embodiments, the present disclosure provides a compound of Formula (I) or a pharmaceutically acceptable salt, solvate, or isomer thereof:

(I)

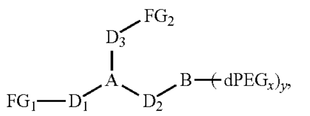

wherein:

- $FG_1$ is a reactive functional group capable of conjugation to a targeting vector;
- $FG_2$ is a reactive functional group capable of conjugation to a trigger and/or payload;
- A is an amino acid residue or a trivalent or tetravalent atom;
- B is a first branch point;
- PEG is a polyethylene glycol-based chain comprising linear, branched, monodisperse, and/or polydisperse PEG;
- x is an integer from 4 to 48;
- y is 2 or 3; and
- $D_1$, $D_2$, and $D_3$ are each independently a spacer moiety, wherein D' represents the sum of atoms in a linear chain between B and $FG_2$.

Functional Group Linking to Targeting Vectors

In some embodiments, $FG_1$ is a reactive functional group capable of reacting with a chemical moiety of a targeting vector (e.g., an antibody, antibody fragment, or peptide). In some embodiments, $FG_1$ is an electrophilic functional group capable of reacting with a nucleophilic moiety (e.g., a functional group) of a targeting vector. In some embodiments, $FG_1$ is a reactive functional group capable of conjugation to an amino acid side chain on a biologic (e.g., an antibody, antibody fragment, or peptide). In some embodiments, $FG_1$ is a reactive functional group disclosed in Hermanson, Greg T. (2013) *Bioconjugate Techniques* (Third Edition). Elsevier Inc., which is incorporated herein by reference in its entirety. In some embodiments, $FG_1$ is a reactive functional group selected from the group consisting of carboxylic acids, active esters (e.g., tetrafluorophenyl ester (TFP), N-hydroxysuccinimidyl ester (NHS), etc.), α,β-unsaturated amides, maleimides, and α-halo acetamides. In some embodiments, $FG_1$ is a reactive functional group selected from the group consisting of carboxylic acids, active esters, maleimide, and α-halo acetamides. In some embodiments, $FG_1$ comprises an imide

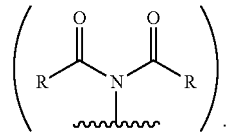

In some embodiments, the imide is a cyclic imide. In some embodiments, $FG_1$ is maleimide

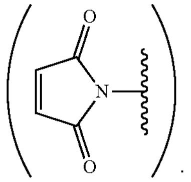

In some embodiments, $FG_1$ is a reactive functional group capable of conjugation to a non-natural amino acid side chain on a biologic. Accordingly, in some embodiments, $FG_1$ is an alkyne, azide, aminoxy, or other functional group known in the art, including those described in Hermanson, Greg T. (2013) *Bioconjugate Techniques* (Third Edition). Elsevier Inc., which is incorporated herein by reference in its entirety.

In some embodiments, $FG_1$ is a reactive group capable of reacting with another chemical moiety that can then be used for further conjugation or chemical reactions and is selected from oxygen, nitrogen, sulfur, carbon, or other functional groups known to those in the art. In some embodiments, the $FG_1$ employed for preparing the conjugates of the present disclosure is a bis-maleimide moiety. Without being bound by any particular theory, a bis-maleimide moiety can re-bridge the disulfide bond to improve stability of the biologic, provide a more uniform DAR, and/or reduce the probability of deconjugation of the linker-payload.

In some embodiments, $FG_1$ comprises a protecting group capable of masking a reactive chemical moiety. Examples of suitable protecting groups are described in Wuts, Peter G. M. and Greene, Theodora W. (2014) *Protecting Groups in Organic Chemistry* ($4^{th}$ edition). John Wiley & Sons, Inc., which is incorporated herein by reference in its entirety. In some embodiments, the protecting group of $FG_1$ is selected from the group consisting of Boc, Cbz, Fmoc, THP, and Bn.

Functional Group Linking to Trigger or Payload

As disclosed herein, $FG_2$ is a reactive functional group capable of conjugation to a trigger and/or payload. In some embodiments, $FG_2$ is a reactive functional group capable of conjugation to a trigger. In some embodiments, $FG_2$ is a reactive functional group capable of conjugation to a payload.

In some embodiments, $FG_2$ is a reactive functional group selected from the group consisting of carboxylic acids, esters (e.g., an active ester including, but not limited to a TFP or NHS ester), carboxylic anhydrides, acid chlorides, thiols, amines, and amides. In some embodiments, $FG_2$ is a reactive functional group selected from the group consisting of carboxylic acids, esters, carboxylic anhydrides, and acid chlorides. In some embodiments, $FG_2$ is a reactive functional group selected from the group consisting of carboxylic acids and esters. In some embodiments, $FG_2$ is an amine or amine masked with a protecting group. In some embodiments, the amine is a primary ($—NH_2—$) or secondary amine (—NHR—, wherein R is $—C_{1-5}$alkyl, $—CH_2C_{3-6}$cycloalkyl, $—C_{3-6}$cycloalkyl, and the like). In some embodiments, $FG_2$ is an acid halide, carboxylic acid, or ester. In some embodiments, $FG_2$ is a carboxylic acid or ester. In some embodiments, $FG_2$ is

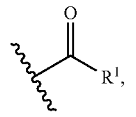

wherein $R^1$ is a halogen, —OH, —O-alkyl, —O-cycloalkyl, —O-heterocyclyl, —O-aryl, —O-heteroaryl, —OC(O)alkyl, or —OC(O)aryl. In some embodiments, $FG_2$ is

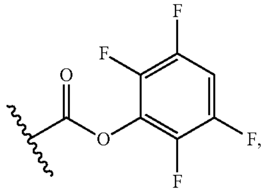

(TFP ester)

or

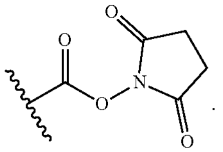

(NHS ester)

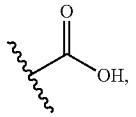 [SMILES: *C(=O)O]

In some embodiments, $FG_2$ is

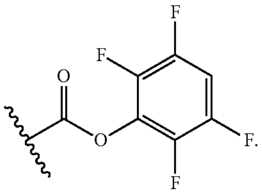 [SMILES: *C(=O)Oc1c(F)c(F)cc(F)c1F]

Branching Point B

In some embodiments, the linkers of the present disclosure comprise a Branching Point B. The Branching Point B can be any atom or moiety that connects the multiple arms of a polyethylene glycol-based chain of Formula (I) to the spacer $D_2$. In some embodiments, the Branching Point B is a carbon or nitrogen atom. In some embodiments, the Branching Point B is a carbon atom.

Central Hub

In some embodiments, the linkers of the present disclosure comprise hub A, to which the targeting vector linker $FG_1$, trigger/payload linker $FG_2$, and Branching Point B directly, or indirectly connect. In some embodiments, A is a carbon atom. In some embodiments, A is a nitrogen atom. In some embodiments A is an amino acid residue. In some embodiments, A is

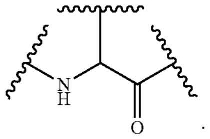 [SMILES: *NC(*)C(*)=O]

Spacer Moieties

In some embodiments of the present disclosure, $D_1$, $D_2$, and $D_3$ are each independently an alkylene, cycloalkenylene, alkenylene, or alkynylene, optionally comprising one or more heteroatoms selected from N or O, and optionally substituted with one or more oxo groups. In some embodiments of the present disclosure, $D_1$, $D_2$, and $D_3$ are each independently an alkylene, alkenylene, or alkynylene, optionally comprising one or more heteroatoms selected from N or O, and optionally substituted with one or more oxo groups. In some embodiments, $D_1$, $D_2$, and $D_3$ are each independently an alkylene, optionally comprising one or more heteroatoms selected from N or O, and optionally substituted with one or more oxo groups. In some embodiments, the alkylene is a C1-C10 alkylene. In some embodiments, the alkylene is a C1-C5 alkylene. In some embodiments, the alkylene is a C1-C3 alkylene. In some embodiments, the alkenylene is a C2-C10 alkenylene. In some embodiments, the alkynylene is a C2-C10 alkynylene. In some embodiments, $D_1$, $D_2$, and $D_3$ each independently comprises a $—(CH_2CH_2O)_z—$ subunit, wherein z is as defined herein, e.g., z is an integer from 1 to 5, including any subrange or value therebetween. In some embodiments, $D_1$, $D_2$, and $D_3$ each independently comprises one or more amide groups and/or one or more oxo groups. In some embodiments, $D_1$, $D_2$, and $D_3$ each independently comprises one or more amide groups.

As used herein, $D_1$ refers to a spacer moiety between $FG_1$ and A (not inclusive). In some embodiments, $D_1$ is a C1-C10 alkylene. In some embodiments, the C1-C10 alkylene is optionally substituted. In some embodiments, the C1-C10 alkylene comprises at least one amide and/or sulfonamide group. In some embodiments, the C1-C10 alkylene comprises at least one amide group. In some embodiments, the C1-C10 alkylene comprises at least one amide group and a $—(CH_2CH_2O)_z—$ subunit, wherein z is as defined herein, e.g., z is an integer from 1 to 5, including any subrange or value therebetween. In some embodiments, D1 is an optionally substituted C1-C3 alkylene. In some embodiments, e.g., when A is a carbon atom, $D_1$ is selected from the group consisting of: optionally substituted

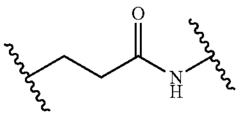

,

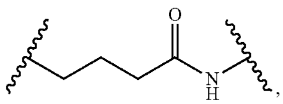

,

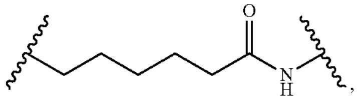

,

-continued

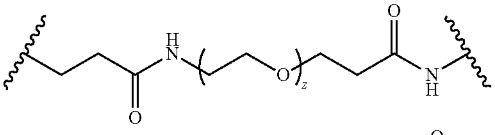

, and

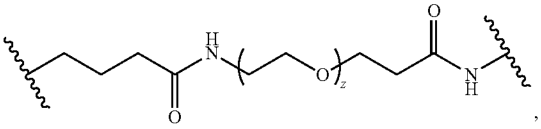

, wherein z is 1-4.

In some embodiments, z is 2 or 4. In some embodiments, e.g., when A is a carbon atom, $D_1$ is selected from the group consisting of:

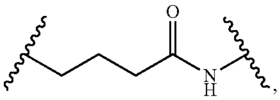

,

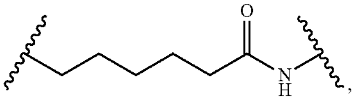

, and

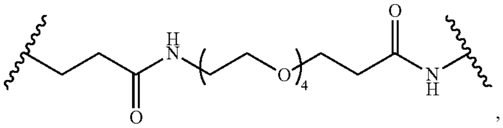

, each of which is optionally substituted. In some embodiments, e.g., when A is

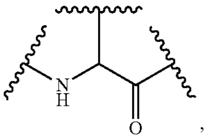 [SMILES: *NC(*)C(*)=O]

, $D_1$ is selected from the group consisting of: optionally substituted

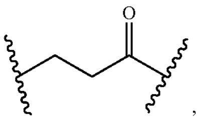

,

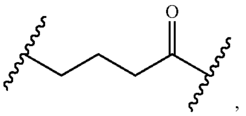

,

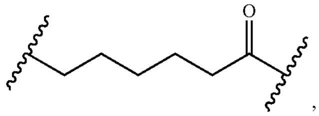

,

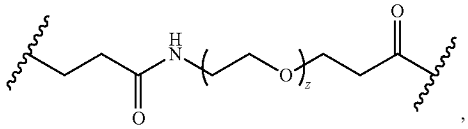

, and

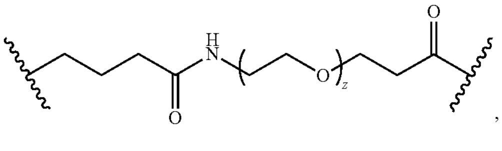

, wherein z is 1-4. In some embodiments, z is 2 or 4. In some embodiments, e.g., when A is

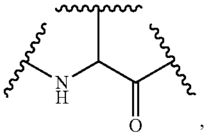 [SMILES: *NC(*)C(*)=O]

, $D_1$ is selected from the group consisting of:

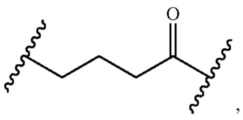

,

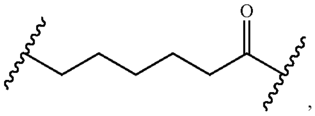

, and

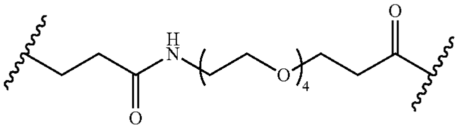

, each of which is optionally substituted.

As used herein, $D_2$ refers to a spacer moiety between A and Branch Point B (not inclusive). In some embodiments, $D_2$ is a C1-C10 alkylene. In some embodiments, the C1-C10 alkylene is optionally substituted. In some embodiments, the C1-C10 alkylene comprises at least one amide group. In some embodiments, the C1-C10 alkylene comprises at least one amide group and a $-(CH_2CH_2O)_z-$ subunit, wherein z is as defined herein, e.g., z is an integer from 1 to 5, including any subrange or value therebetween. In some embodiments, $D_2$ is an optionally substituted C1-C3 alkylene. In some embodiments, e.g., when A is a carbon atom, $D_2$ is

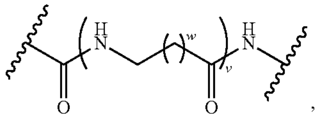

, wherein v is 0 or 1, such that when v is 1, w is 1 to 5. In some embodiments, e.g., when A is a carbon atom, $D_2$ is selected from the group consisting of optionally substituted

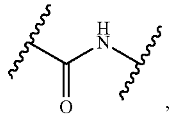

,

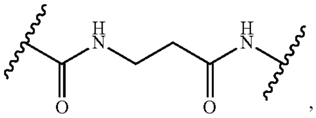

,

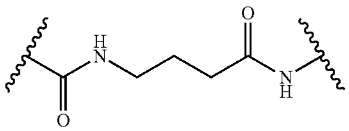

or

-continued

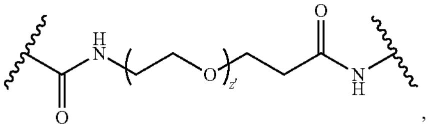

, wherein z' is an integer from 1 to 5, including any subrange or value therebetween. In some embodiments, z' is an integer from 1 to 4. In some embodiments, z' is an integer from 2 to 4. In some embodiments, e.g., when A is

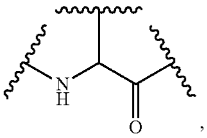 [SMILES: *NC(*)C(*)=O]

, $D_2$ is —NH— or

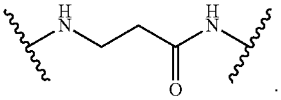 [SMILES: *NCCC(=O)N*]

.

As used herein, $D_3$ refers to a spacer moiety between A and $FG_2$ (not inclusive). In some embodiments, $D_3$ is the side chain of amino acid residue A, e.g., the side chain of a lysine, ornithine, 2,4-diaminobutyric acid (DAB), 2,3-diaminopropanoic acid (DAP), serine, threonine, tyrosine, cysteine, aspartic acid, or glutamic acid residue. In some embodiments, $D_3$ is an alkylene. In some embodiments, $D_3$ is a C1-C5 alkylene. In some embodiments, $D_3$ is a C1-C3 alkylene. In some embodiments, the alkylene is optionally substituted, e.g., with F, alkyl, alkoxy, oxo, or combination thereof. In some embodiments $D_3$ is methylene (—$CH_2$—) or ethylene (—$CH_2CH_2$—).

Distance Factors

As illustrated in the non-limiting examples below, D' as used herein in Formula (I) represents the sum of atoms in a linear chain between B and $FG_2$:

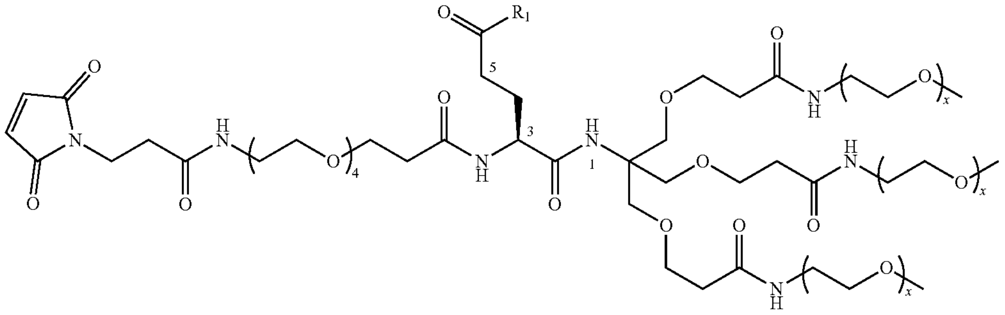

D' = 5

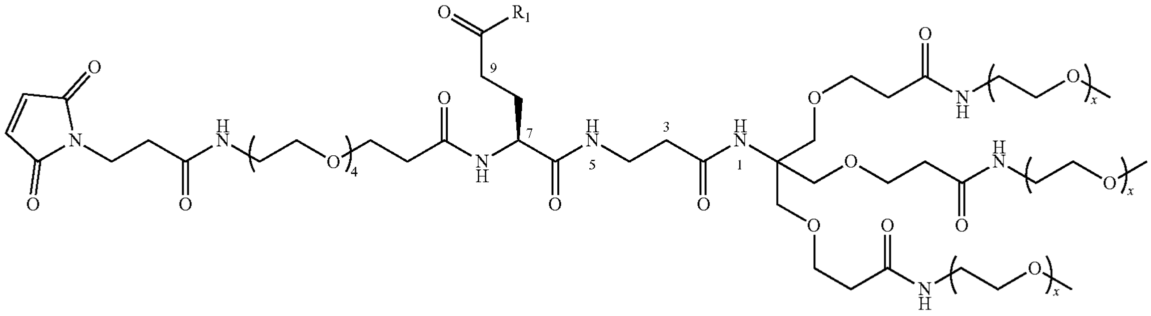

D' = 9

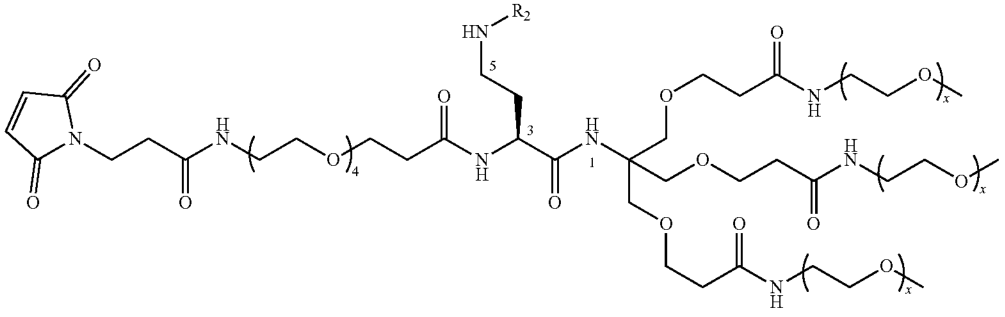

D' = 5

-continued

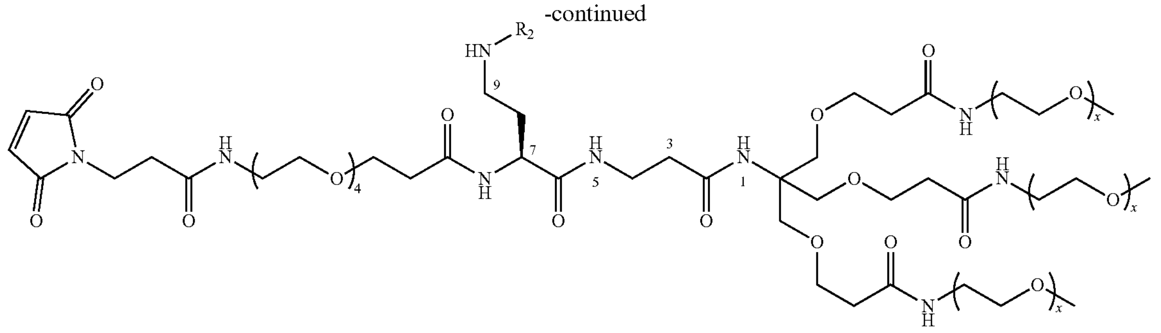

D' = 9

In some embodiments, D' is less than or equal to 22. In some embodiments, D' is less than or equal to 12. In some embodiments, D' is less than or equal to 11. In some embodiments, D' is less than or equal to 10. In some embodiments, D' is less than or equal to 9. In some embodiments, D' is 12. In some embodiments, D' is 11. In some embodiments, D' is 10. In some embodiments, D' is 9. In some embodiments, D' is 8. In some embodiments, D' is 7. In some embodiments, D' is 6. In some embodiments, D' is 4. In some embodiments, D' is 4. In some embodiments, D' is from 4 to 22, including any range or value therebetween. In some embodiments, D' is from 4 to 12. In some embodiments, D' is from 4 to 11. In some embodiments, D' is from 4 to 10. In some embodiments, D' is from 4 to 9. In some embodiments, D' is from 4 to 8. In some embodiments, D' is from 5 to 12. In some embodiments, D' is from 5 to 11. In some embodiments, D' is from 5 to 10. In some embodiments, D' is from 5 to 9. In some embodiments, D' is from 5 to 8. In some embodiments, D' is from 6 to 12. In some embodiments, D' is from 6 to 11. In some embodiments, D' is from 6 to 10. In some embodiments, D' is from 6 to 9. In some embodiments, D' is from 6 to 8. In some embodiments, D' is 6 or 10. In some embodiments, D' is 5 or 9. In some embodiments, D' is 8 or 9. In some embodiments, D' is 4 or 5. In some embodiments, D' represents the sum of contiguous atoms in $D_2$, $D_3$, and A. In some embodiments, D' represents the sum of atoms in $D_2$, $D_3$, and A.

D', as used herein in Formula (I), can also be defined as a distance in angstroms. For example, in some embodiments, D' is about 6 Å to about 30 Å, e.g., about 6 Å, 7 Å, 8 Å, 9 Å, 10 Å, 11 Å, 12 Å, 13 Å, 14 Å, 15 Å, 16 Å, 17 Å, 18 Å, 19 Å, 20 Å, 21 Å, 22 Å, 23 Å, 24 Å, 25 Å, 26 Å, 27 Å, 28 Å, 29 Å, or 30 Å, including all subranges and values therebetween. In some embodiments, D' is about 6 Å to about 20 Å. In some embodiments, D' is about 6 Å to about 10 Å. In some embodiments, D' is about 10 Å to about 15 Å. In some embodiments, D' is about 15 Å to about 20 Å. In some embodiments, D' is about 10 Å to about 30 Å. In some embodiments, when D' is measured in angstroms, the distance is through space as determined by crystallography (e.g., X-ray crystallography) or 3-D modeling software.

In some embodiments, the compound of Formula (I) is further characterized by a value D, which is defined as the number of atoms in a linear chain between the targeting vector $FG_1$ and $FG_2$. In some embodiments, D is greater than 10. In some embodiments, the distance D is from 10 to 30 atoms. In some embodiments, the distance D is 10 atoms, 14 atoms, or 27 atoms. In some embodiments, D is 10 atoms. In some embodiments, the percent of payload released from a linker compound of Formula (I) is reduced as the value D decreases. In some embodiments, there is a synergistic effect between D and D', such that percent payload release from a linker compound of Formula (I) is reduced when D' is less than or equal to 22 (e.g., 22, 21, 20, 19, 18, 17, 16, 15, 14, 13, 12, 11, 10, 9, 8, 7, 6, 5, 4) and D is greater than or equal to 10 atoms. In some embodiments, there is a synergistic effect between D and D', such that percent payload release from a linker compound of Formula (I) is reduced when D' is less than or equal to 22 (e.g., 22, 21, 20, 19, 18, 17, 16, 15, 14, 13, 12, 11, 10, 9, 8, 7, 6, 5, 4) and D is 10 atoms. In some embodiments, there is a synergistic effect between D and D', such that percent payload release from a linker compound of Formula (I) is reduced when D' is 4 to 12 atoms and the value of D is 10 atoms. In some embodiments, there is a synergistic effect between D and D', such that percent payload release from a linker compound of Formula (I) is reduced when D' is 5 and the value of D is 10 atoms. In some embodiments, there is a synergistic effect between D and D', such that percent payload release from a linker compound of Formula (I) is reduced when D' is 6 and the value of D is 10 atoms. In some embodiments, there is a synergistic effect between D and D', such that percent payload release from a linker compound of Formula (I) is reduced when D' is 9 and the value of D is 10 atoms. In some embodiments, there is a synergistic effect between D and D', such that percent payload release from a linker compound of Formula (I) is reduced when D' is 10 and the value of D is 10 atoms. The percent of payload released from a linker compound of Formula (I) can decrease as the value D decreases due to increased steric shielding from the antibody. Without being bound by any particular theory, linker compounds of Formula (I) with D'<22 magnify this effect. In some embodiments, as D is reduced from 27 to 10, both D' 6/5 and D' 10/9 magnify steric shielding and reduce payload release. In some embodiments, as D is reduced from 27 to 14, D' 6/5 magnifies steric shielding and reduces payload release.

Chain Length and Branch Number

As shown above, the compounds of Formula (I) include a $(dPEG_x)_y$ moiety, wherein x represents the number of repeating units and y the number of dPEG arms.

In some embodiments, x is an integer from 4 to 24, e.g., 4, 5, 6, 7, 8, 9, 10, 11, 12, 13, 14, 15, 16, 17, 18, 19, 20, 21, 22, 23, or 24. In some embodiments, x is 4. In some embodiments, x is 8. In some embodiments, x is 12. In some embodiments, x is 16. In some embodiments, x is 20. In some embodiments, x is 24. In some embodiments x is 8 or 24.

In some embodiments, y is 2. In some embodiments, y is 3.

In some embodiments, x is 4 and y is 2. In some embodiments, x is 8 and y is 2. In some embodiments, x is 12 and y is 2. In some embodiments, x is 16 and y is 2. In some embodiments, x is 24 and y is 2. In some embodiments, x is 4 and y is 3. In some embodiments, x is 8 and y is 3. In some embodiments, x is 12 and y is 3. In some embodiments, x is 16 and y is 3. In some embodiments, x is 24 and y is 3. In some embodiments x is an integer from 4 to 24 and y is 3. In some embodiments x is an integer from 8 to 24 and y is 3. In some embodiments, x is 8 or 24 and y is 3.

Linkers of Formula (I)

In some embodiments, the compound of Formula (I) is a compound of Formula (Ia) or a pharmaceutically acceptable salt, solvate, or isomer thereof:

(Ia)

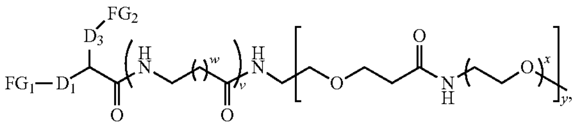

wherein:

$FG_1$, $FG_2$, $D_1$, $D_3$, D', x and y are as defined above in Formula (I);

v is 0 or 1; and when v is 1, w is 1 to 5;

In some embodiments, v is 0. In some embodiments, v is 1. In some embodiments, v is 1 and w is 1, 2, or 3. In some embodiments, v is 1 and w is 1 or 2. In some embodiments, v is 1, w is 1.

In some embodiments, the compound of Formula (I) is a compound of Formula (Ib) or a pharmaceutically acceptable salt, solvate, or isomer thereof:

(Ib)

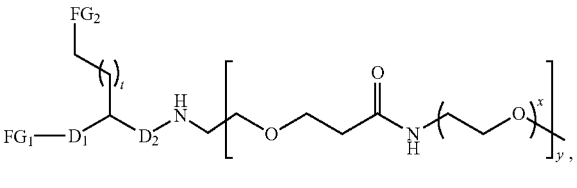

wherein:

$FG_1$, $FG_2$, $D_1$, $D_2$, D', x and y are as defined above in Formula (I); and t is an integer from 0 to 4.

In some embodiments, t is 0, 1, 2, or 3. In some embodiments, t is 0, 1, or 2. In some embodiments, t is 0 or 1. In some embodiments, t is 0. In some embodiments, t is 1.

In some embodiments, the compound of Formula (Ib) has the structure:

(Ib1)

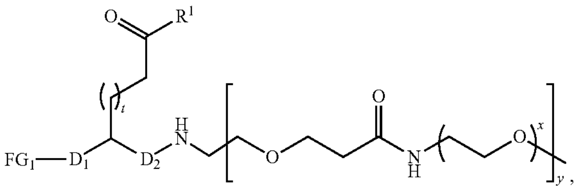

wherein $R^1$ is a leaving group and $FG_1$, $D_1$, $D_2$, D', t, x, and y are as defined herein. In some embodiments, $R^1$ is a halogen, —OH, —O-alkyl, —O-cycloalkyl, —O-heterocyclyl, —O-aryl, —O-heteroaryl, —OC(O)alkyl, or —OC(O)aryl.

In some embodiments, the compound of Formula (Ib) has the structure:

(Ib2)

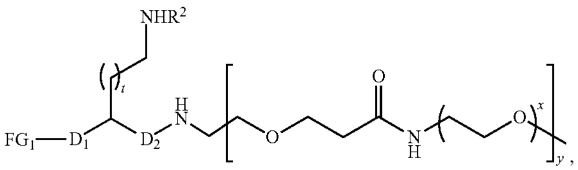

wherein $R^2$ is H, alkyl, aryl, cycloalkyl, alkylenecycloalkyl, alkylenearyl, or alkyleneheteroaryl and $FG_1$, $D_1$, $D_2$, D', t, x, and y are as defined herein. In some embodiments, $R^2$ is any nitrogen protecting group known in the art, including, but not limited to Boc, Cbz, Fmoc, THP, and Bn.

In some embodiments, the compound of Formula (I) is a compound of Formula (Ic) or a pharmaceutically acceptable salt, solvate, or isomer thereof:

(Ic)

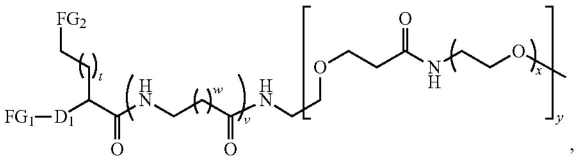

, wherein:

$FG_1$, $FG_2$, $D_1$, D', x and y are as defined above in Formula (I);

t is an integer from 0 to 4;

v is 0 or 1; and when v is 1, w is 1 to 5.

In some embodiments, t is 0, 1, 2, or 3. In some embodiments, t is 0, 1, or 2. In some embodiments, t is 0 or 1. In some embodiments, t is 0. In some embodiments, t is 1.

In some embodiments, v is 0. In some embodiments, v is 1. In some embodiments, v is 1 and w is 1, 2, or 3. In some embodiments, v is 1 and w is 1 or 2. In some embodiments, v is 1, w is 1.

In some embodiments, the compound of Formula (I) is a compound of Formula (Ic1), (Ic2), or a pharmaceutically acceptable salt, solvate, or isomer thereof:

(Ic1)

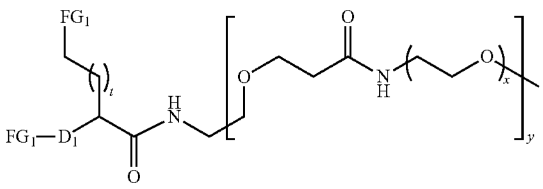

or (Ic2)

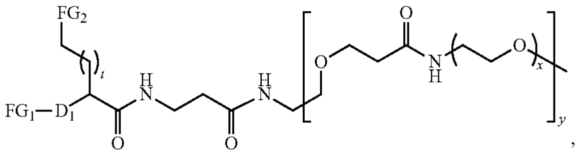

, wherein:

$FG_1$, $FG_2$, $D_1$, D', x and y are as defined above in Formula (I); and t is as defined above in Formula (Ic).

In some embodiments, the compound of Formula (I) is a compound of Formula (Id), or a pharmaceutically acceptable salt, solvate, or isomer thereof:

(Id)

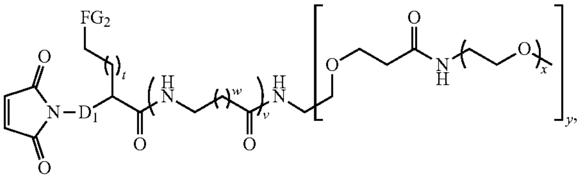

wherein:

$FG_2$, $D_1$, D', x and y are as defined above in Formula (I); and t is an integer from 0 to 4;

v is 0 or 1;

when v is 1, w is 1 to 5.

In some embodiments, t is 0, 1, 2, or 3. In some embodiments, t is 0, 1, or 2. In some embodiments, t is 0 or 1. In some embodiments, t is 0. In some embodiments, t is 1.

In some embodiments, v is 0. In some embodiments, v is 1. In some embodiments, v is 1 and w is 1, 2, or 3. In some embodiments, v is 1 and w is 1 or 2. In some embodiments, v is 1, w is 1.

In some embodiments, the compound of Formula (I) is a compound of Formula (Id1), or a pharmaceutically acceptable salt, solvate, or isomer thereof:

(Id1)

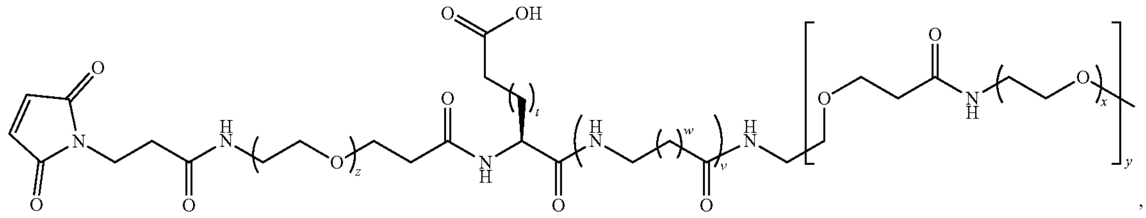

, wherein:

x, y, and D' are as defined above in Formula (I);

t, v, and w are as defined above in Formula (Id); and z is independently an integer from 1 to 10.

In some embodiments, z is an integer from 1 to 8. In some embodiments, z is an integer from 1 to 4. In some embodiments, z is an integer from 2 to 8. In some embodiments, z is an integer from 2 to 4. In some embodiments, z is 4. In some embodiments, z is 2. In some embodiments, z is 1.

In some embodiments, the compound of Formula (I) is a compound of Formula (Id2), or a pharmaceutically acceptable salt, solvate, or isomer thereof:

(Id2)

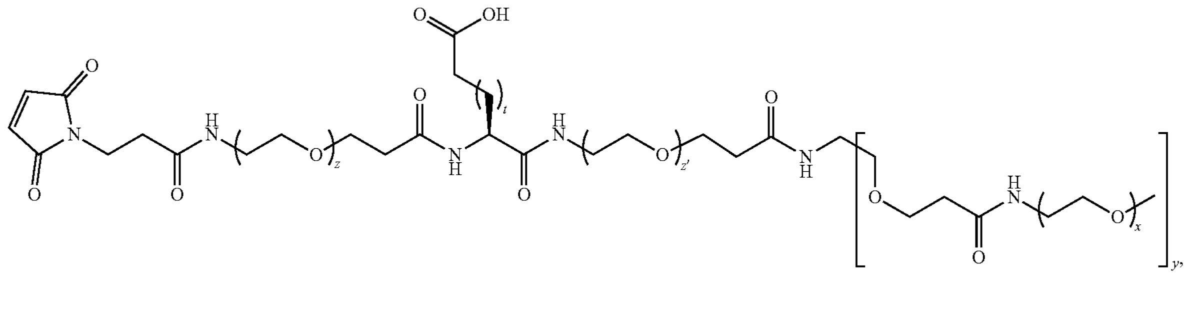

wherein:

x, y, and D' are as defined above in Formula (I);

t is as defined above in Formula (Id); and z and z' are each independently an integer from 1 to 10.

In some embodiments, z and z' are each independently an integer from 1 to 8. In some embodiments, z and z' are each independently an integer from 1 to 4. In some embodiments, z and z' are each independently an integer from 2 to 8. In some embodiments, z and z' are each independently an integer from 2 to 4. In some embodiments, z is 4. In some embodiments, z is 2. In some embodiments, z is 1. In some embodiments, z' is 4. In some embodiments, z' is 2. In some embodiments, z' is 1. In some embodiments, z is 2 or 4 and z' is 4.

In some embodiments, the compound of Formula (I) is a compound of Formula (Id3), or a pharmaceutically acceptable salt, solvate, or isomer thereof:

(Id3)

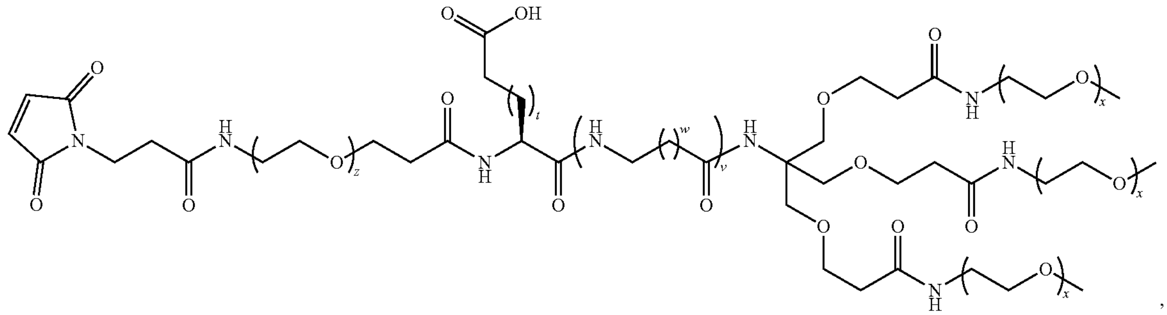

, wherein:

x and D' are as defined above in Formula (I);

t, v, and w are as defined above in Formula (Id); and z is as defined above in Formula (Id1).

In some embodiments, the compound of Formula (I) is selected from the group consisting of:

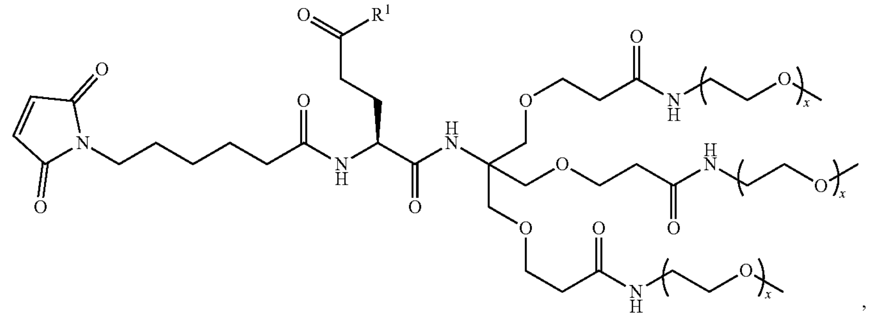

,

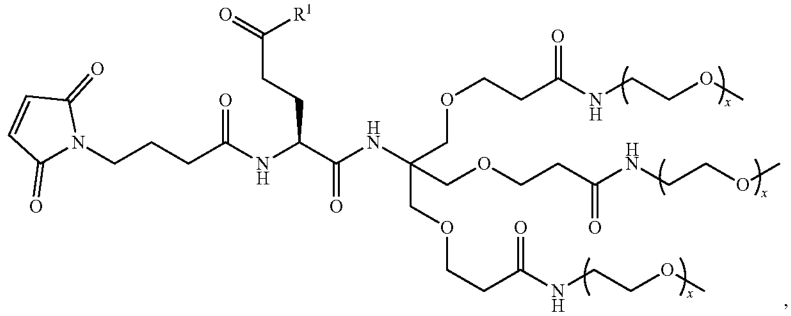

,

-continued
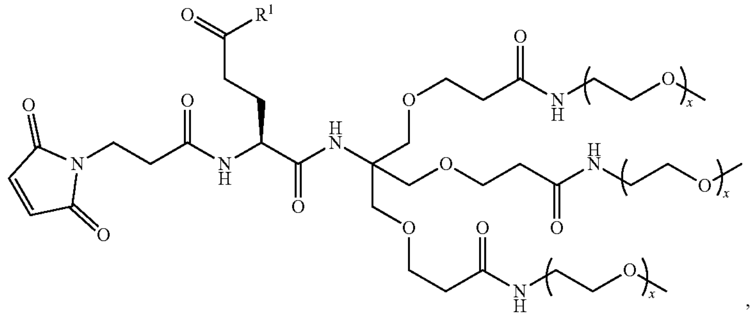
,
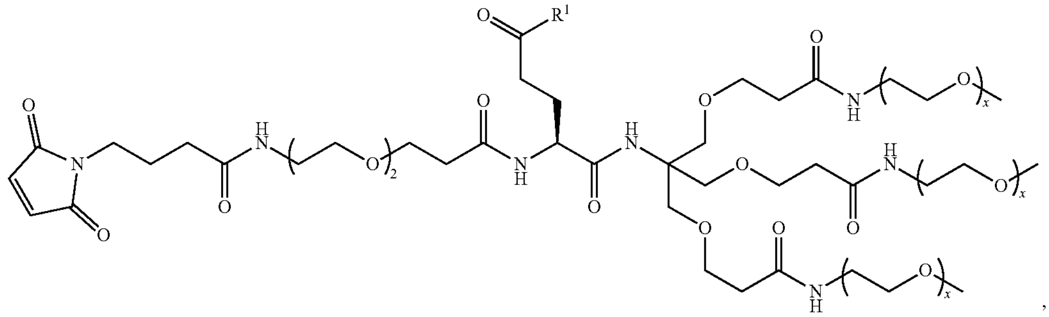
,
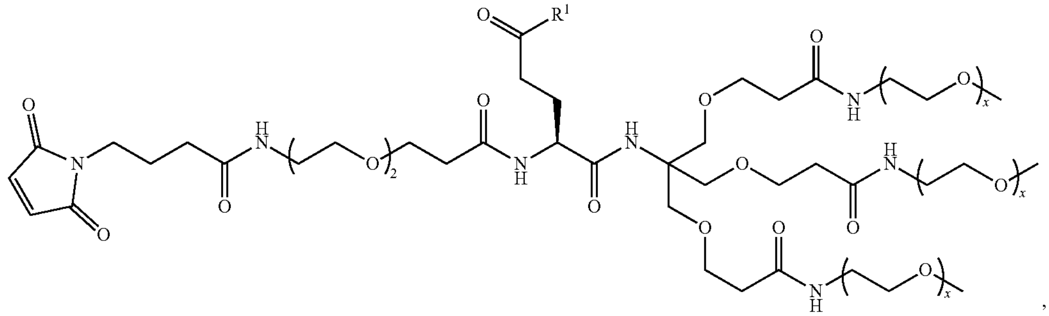
,
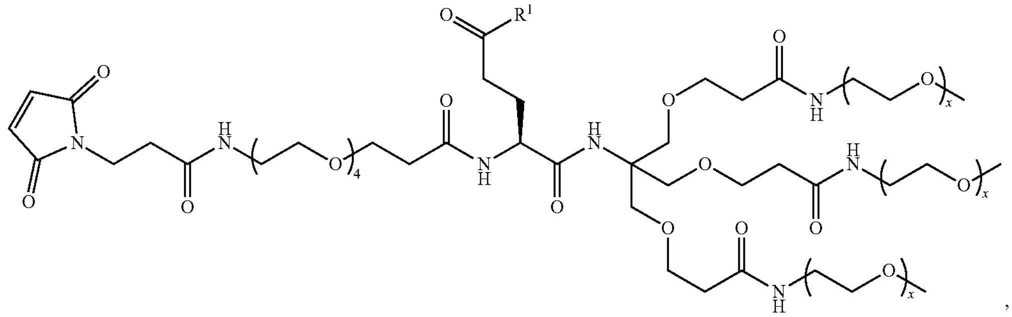
,
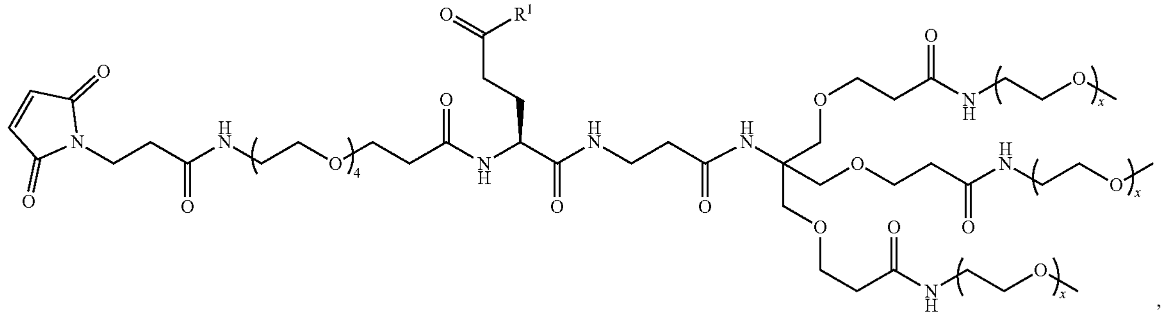
, -continued
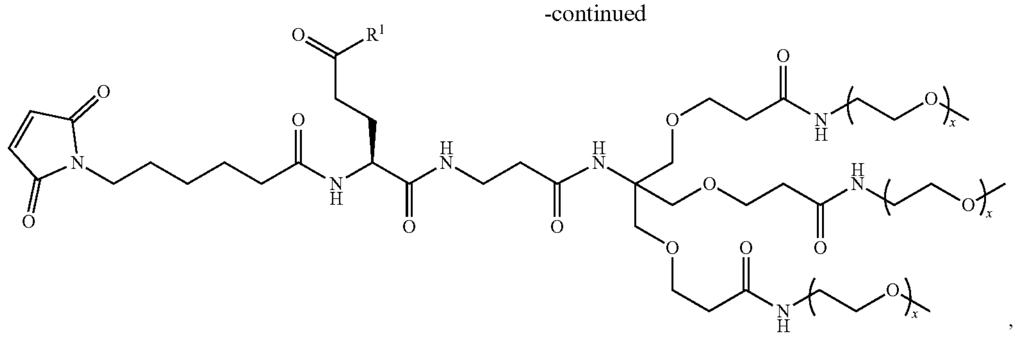
,
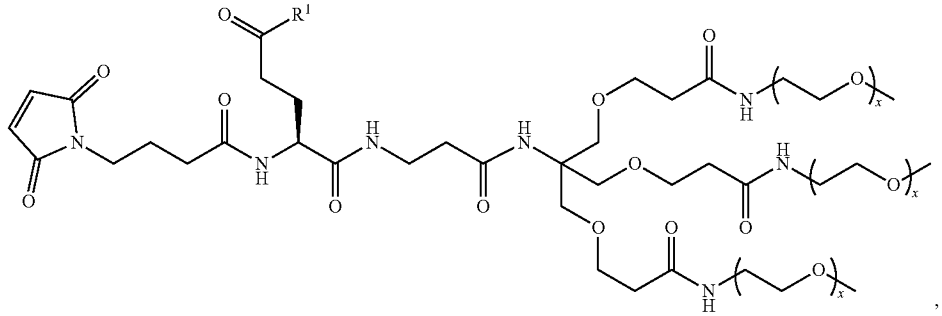
, and
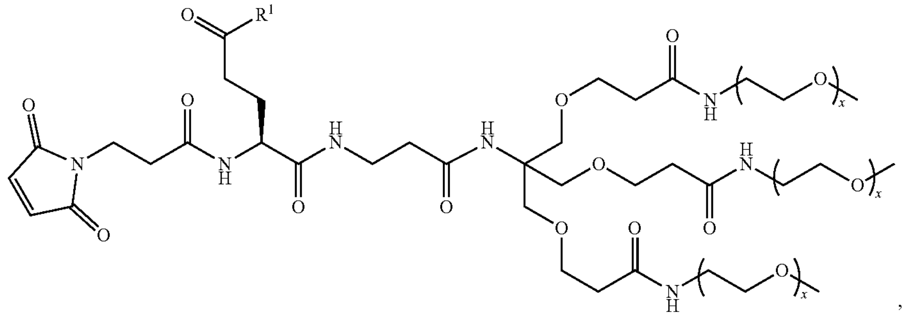
,
wherein $R^1$ is —OH,
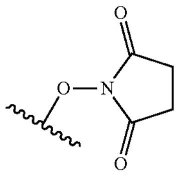
or
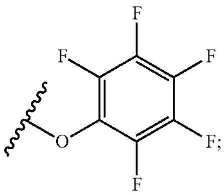
;
and x is 8 or 24.
In some embodiments, the compound of Formula (I) is selected from the group consisting of:
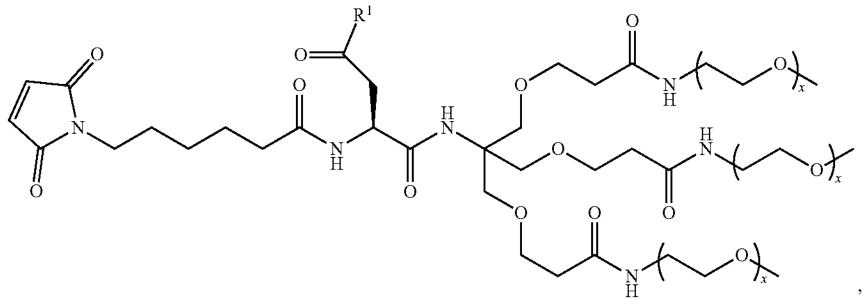
, -continued
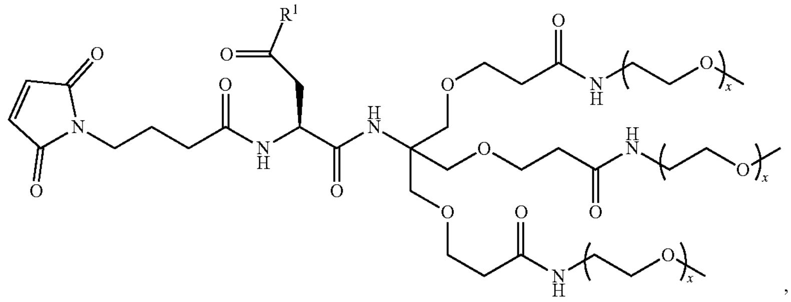
,
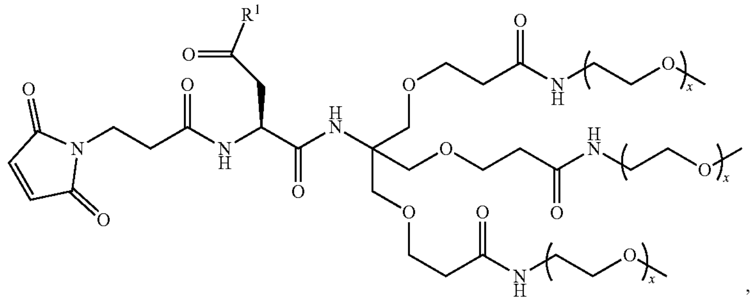
,
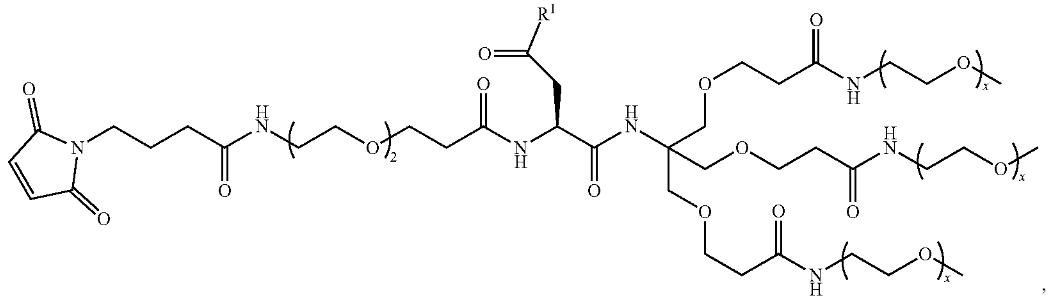
,
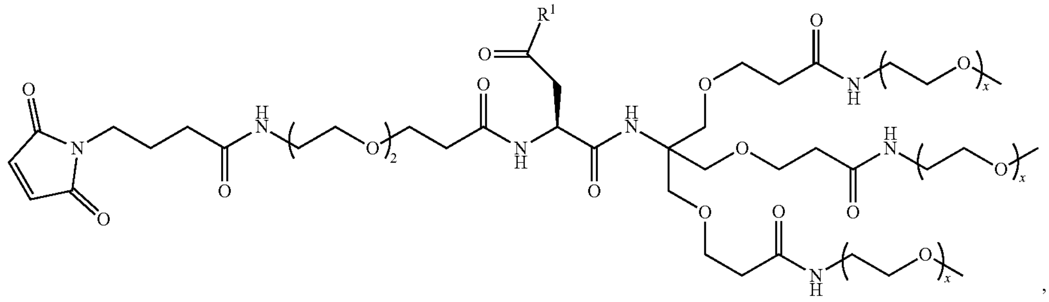
,
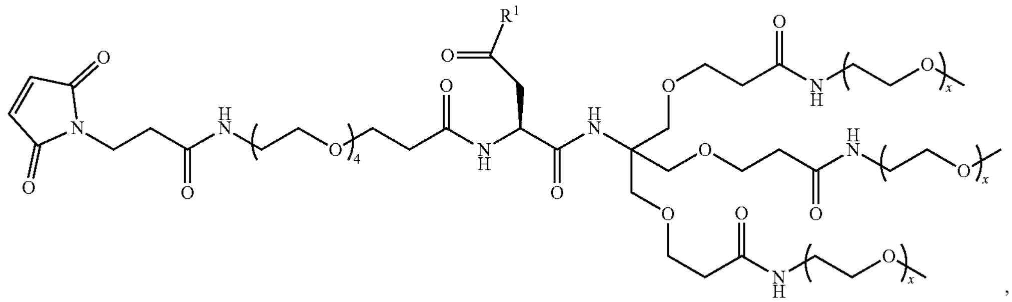
, -continued
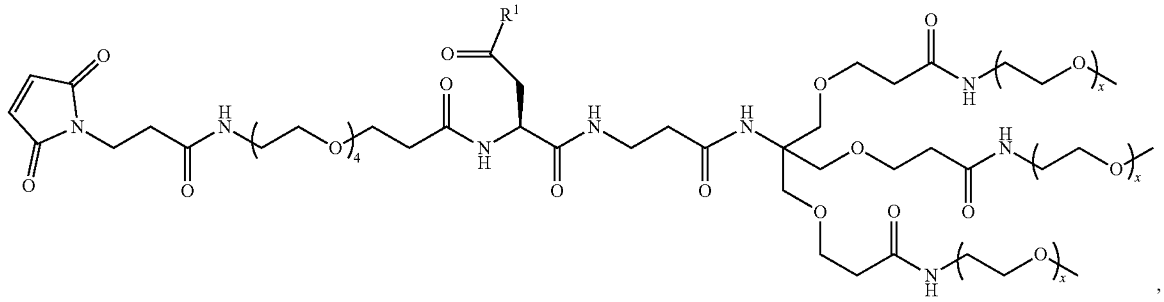
,
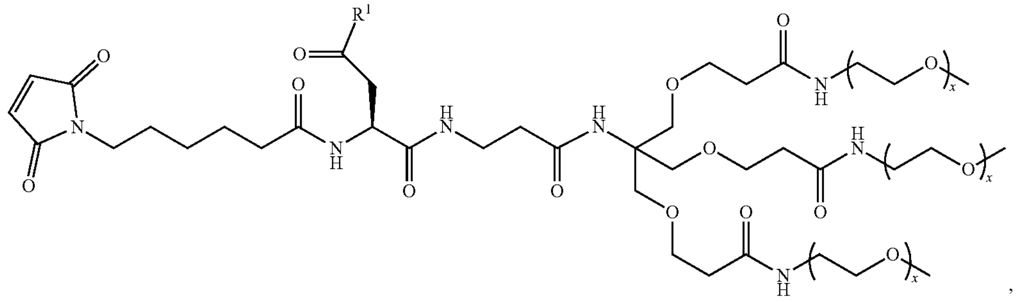
,
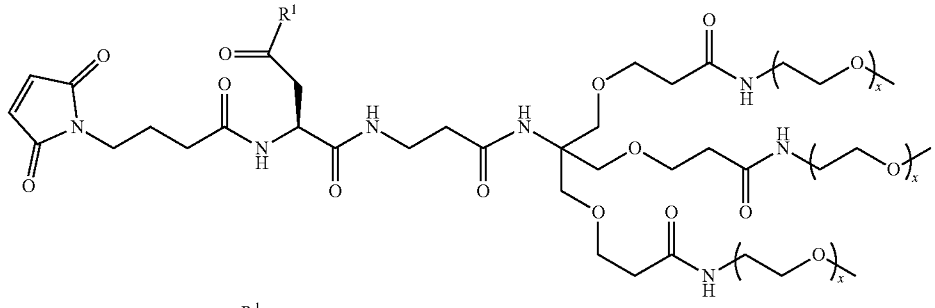
, and
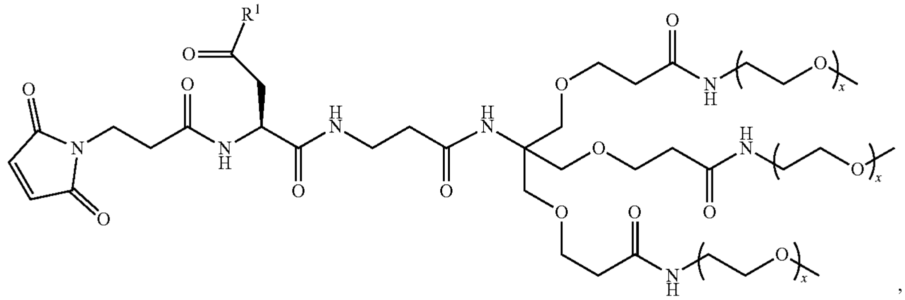
,
wherein $R^1$ is —OH,
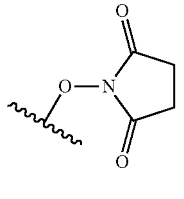
or
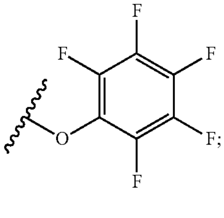
;
and x is 8 or 24.
In some embodiments, the compound of Formula (I) is selected from the group consisting of:

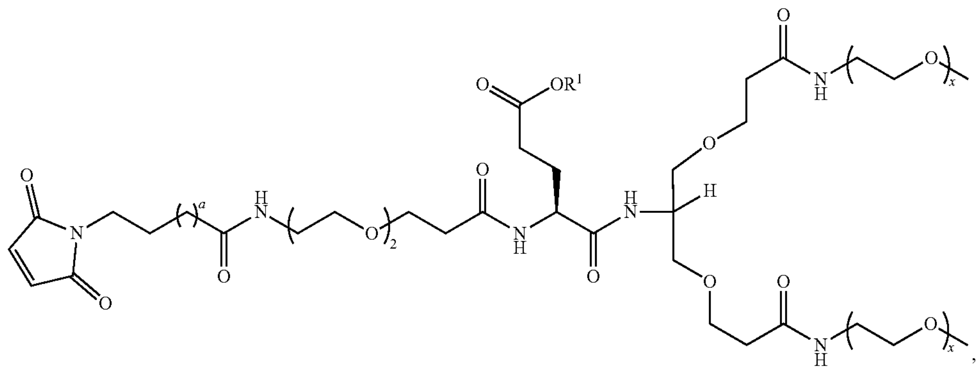
,
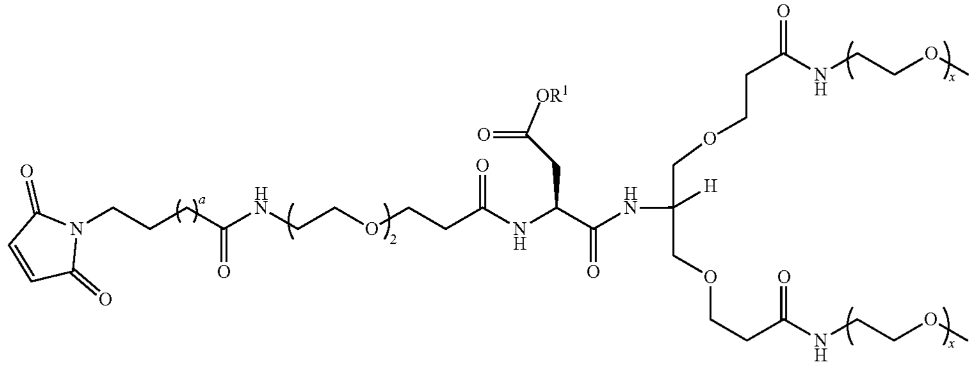
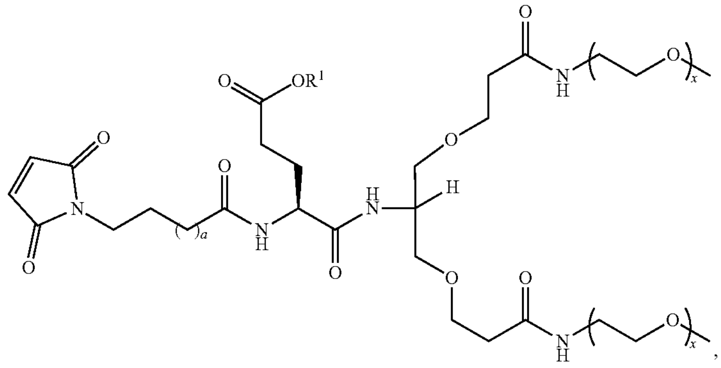
,
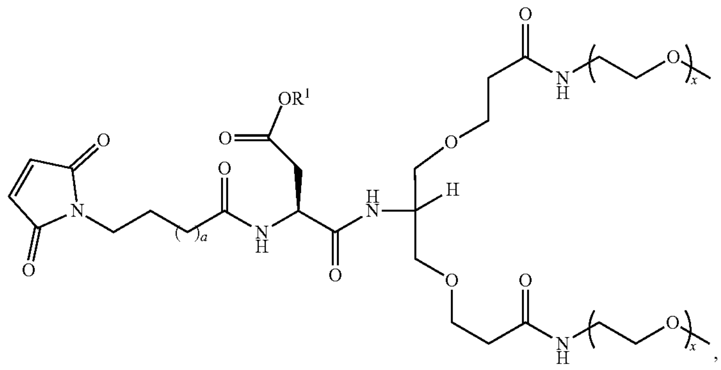
,

-continued

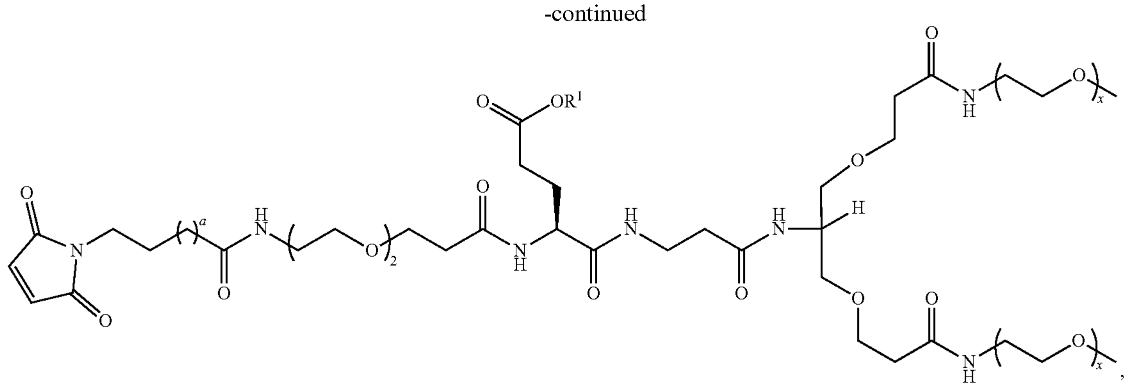

, and

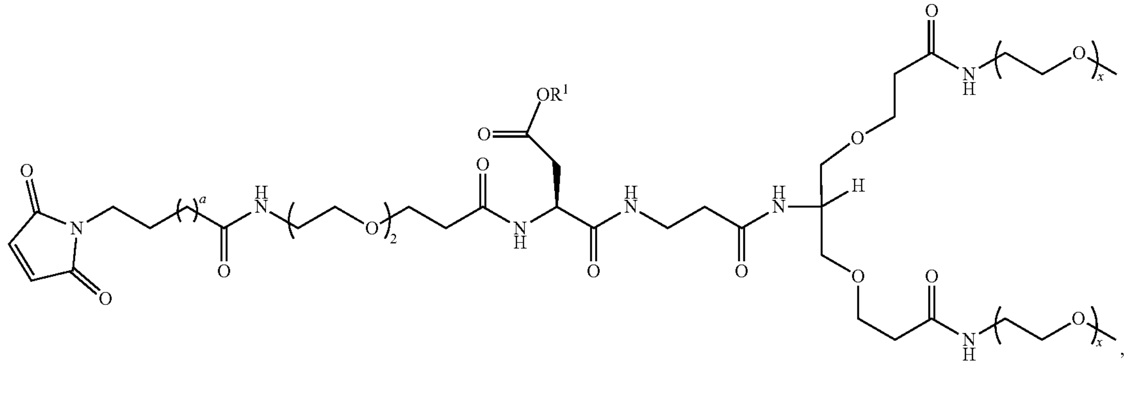

, wherein $R^1$ is H,

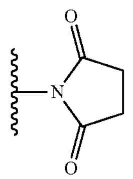

or

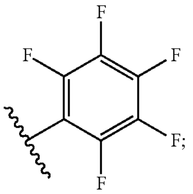

;

a is 0 or 1; and x is 8 or 24.

Conjugates of the Present Disclosure (Formula II)

In some embodiments, the present disclosure provides a compound of Formula (II) or a pharmaceutically acceptable salt, solvate, or isomer thereof:

(II)

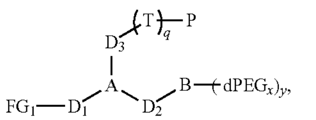

wherein:

$FG_1$, A, B, dPEG, $D_1$, $D_2$, $D_3$, x, and y are as defined herein;

q is 0 or 1;

T is a releasable trigger;

P is a payload; and

D' represents the sum of atoms in a linear chain between B and T.

Spacer Moieties

In some embodiments of Formula (II), $D_1$, $D_2$, and $D_3$ are each independently an alkylene, cycloalkenylene, alkenylene, or alkynylene, optionally comprising one or more heteroatoms selected from N or O, and optionally substituted with one or more oxo groups. In some embodiments of the present disclosure, $D_1$, $D_2$, and $D_3$ are each independently an alkylene, alkenylene, or alkynylene, optionally comprising one or more heteroatoms selected from N or O, and optionally substituted with one or more oxo groups. In some embodiments, $D_1$, $D_2$, and $D_3$ are each independently an alkylene, optionally comprising one or more heteroatoms selected from N or O, and optionally substituted with one or more oxo groups. In some embodiments, the alkylene is a C1-C10 alkylene. In some embodiments, the alkylene is a C1-C5 alkylene. In some embodiments, the alkylene is a C1-C3 alkylene. In some embodiments, the alkylene is a C1-C3 alkylene optionally substituted with an oxo. In some embodiments, the alkenylene is a C2-C10 alkenylene. In some embodiments, the alkynylene is a C2-C10 alkynylene. In some embodiments, $D_1$, $D_2$, and $D_3$ each independently comprises a $-(CH_2CH_2O)_z-$ subunit, wherein z is as defined herein, e.g., z is an integer from 1 to 5, including any subrange or value therebetween. In some embodiments, $D_1$, $D_2$, and $D_3$ each independently comprises one or more amide groups.

As used herein, $D_1$ refers to a spacer moiety between $FG_1$ and A (not inclusive). In some embodiments of Formula (II), $D_1$ is a C1-C10 alkylene. In some embodiments, the C1-C10 alkylene is optionally substituted. In some embodiments, the C1-C10 alkylene comprises at least one amide and/or sulfonamide group. In some embodiments, the C1-C10 alkylene comprises at least one amide group. In some embodiments, the C1-C10 alkylene comprises at least one amide group and a $-(CH_2CH_2O)_z-$ subunit, wherein z is as defined herein, e.g., z is an integer from 1 to 5, including any subrange or value therebetween. In some embodiments, D1 is an optionally substituted C1-C3 alkylene. In some embodiments, e.g., when A is a carbon atom, $D_1$ is selected from the group consisting of: optionally substituted

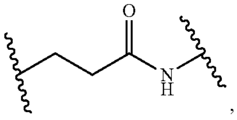
,
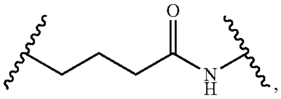
,
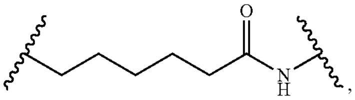
,
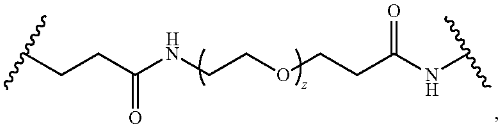
, and
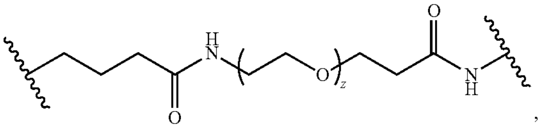
, wherein z is 1-4. In some embodiments, z is 2 or 4. In some embodiments, e.g., when A is a carbon atom, $D_1$ is selected from the group consisting of:

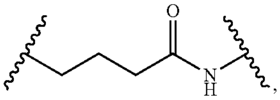
,
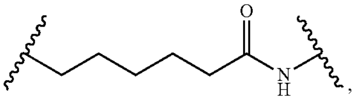
, and
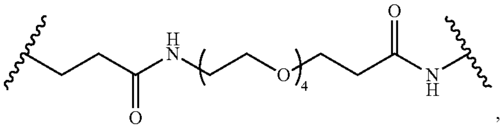
, each of which is optionally substituted. In some embodiments, e.g., when A is

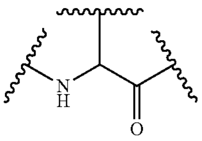
, $D_1$ is selected from the group consisting of: optionally substituted

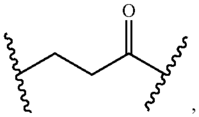
,
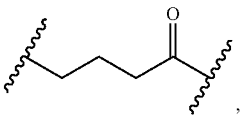
,
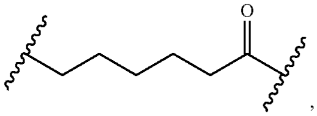
,

-continued

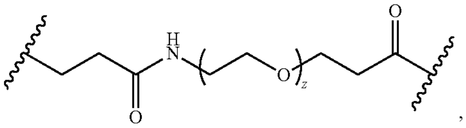
, and
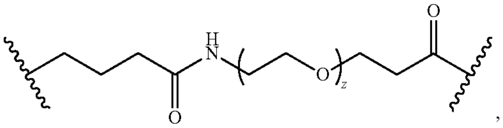
, wherein z is 1-4. In some embodiments, z is 2 or 4. In some embodiments, e.g., when A is

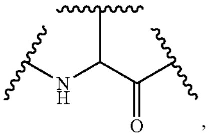 [SMILES: *NC(*)C(*)=O]
, $D_1$ is selected from the group consisting of:

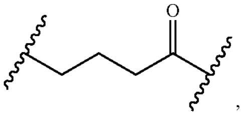
,
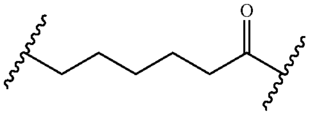
, and
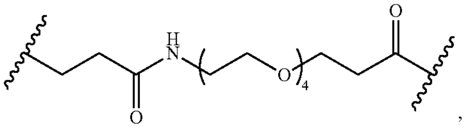
, each of which is optionally substituted.

As used herein, $D_2$ refers to a spacer moiety between A and Branch Point B (not inclusive). In some embodiments, $D_2$ is a C1-C10 alkylene. In some embodiments, the C1-C10 alkylene is optionally substituted. In some embodiments, the C1-C10 alkylene comprises at least one amide group. In some embodiments, the C1-C10 alkylene comprises at least one amide group and a $-(CH_2CH_2O)_z-$ subunit, wherein z is as defined herein, e.g., z is an integer from 1 to 5, including any subrange or value therebetween. In some embodiments, $D_2$ is an optionally substituted C1-C3 alkylene. In some embodiments, e.g., when A is a carbon atom, $D_2$ is

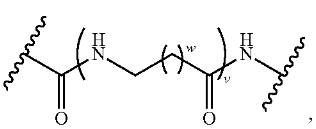
, wherein v is 0 or 1, such that when v is 1, w is 1 to 5. In some embodiments, e.g., when A is a carbon atom, $D_2$ is selected from the group consisting of optionally substituted

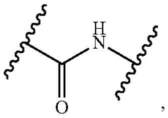,
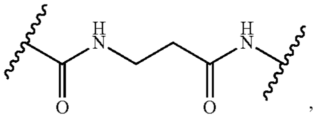,
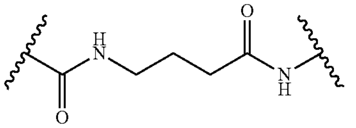
or
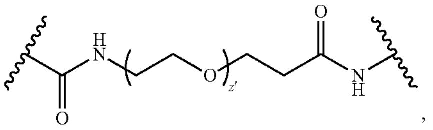, wherein z' is an integer from 1 to 5, including any subrange or value therebetween. In some embodiments, z' is an integer from 1 to 4. In some embodiments, z' is an integer from 2 to 4. In some embodiments, e.g., when A is

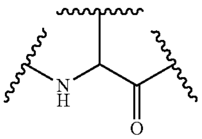, $D_2$ is —NH— or

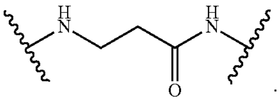 [SMILES: *NCCC(=O)N*].

As used herein, $D_3$ refers to a spacer moiety between A and Releasable Trigger T (not inclusive). In some embodiments of Formula (II), $D_3$ is the side chain of amino acid residue A, e.g., the side chain of a lysine, ornithine, 2,4-diaminobutyric acid (DAB), 2,3-diaminopropanoic acid (DAP), serine, threonine, tyrosine, cysteine, aspartic acid, or glutamic acid residue. In some embodiments, $D_3$ is an alkylene. In some embodiments, $D_3$ is a C1-C5 alkylene. In some embodiments, $D_3$ is a C1-C3 alkylene. In some embodiments, the alkylene is optionally substituted, e.g., with F, alkyl, alkoxy, oxo, or combination thereof. In some embodiments, $D_3$ is a C1-C3 alkylene optionally substituted with an oxo. In some embodiments, $D_3$ is a C2-C3 alkylene optionally substituted with an oxo. In some embodiments, $D_3$ is

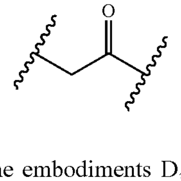
or
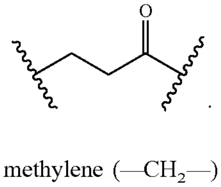.

In some embodiments $D_3$ is methylene ($—CH_2—$) or ethylene ($—CH_2CH_2—$). In some embodiments $D_3$ is ethylene ($—CH_2CH_2—$) or propylene ($—CH_2CH_2CH_2—$).

Cleavable Triggers

In some embodiments, T is a cleavable trigger that may be activated by some type of enzymatic or chemical stimuli. In some embodiments, the cleavable trigger is a polypeptide. In some embodiments, the polypeptide comprises 2, 3, 4, 5, or 6 amino acid residues. In some embodiments, the polypeptide comprises 2, 3, or 4 amino acid residues. In some embodiments, at least one amino acid residue in the polypeptide is a valine residue. In some embodiments, the polypeptide comprises Valine-Citrulline (Val-Cit), Valine-Alanine (Val-Ala), Valine-Valine (Val-Val), or other peptides found to be cleaved by cysteine proteases. In some embodiments, the cleavable trigger is a dipeptide that is acted upon (e.g., processed/digested) by certain enzymes such as cathepsins including B, K, L, or S. In some embodiments, the dipeptide is selected from the group consisting of Valine-Citrulline (Val-Cit), Valine-Alanine (Val-Ala), Valine-Valine (Val-Val), or other peptides found to be cleaved by cysteine proteases. In some embodiments, the cleavable trigger is a glucuronide, which can be acted upon by β-glucuronidase. In some embodiments, the cleavable trigger is selected from the group consisting of substituted or unsubstituted hydrazine or disulfides, which can be acted upon by chemical stimuli such as pH or biological thiols. Other cleavable triggers known to those in the art may be employed to modulate payload release. The cleavable trigger may include one or more optional self-immolative moieties between the trigger and the payload and may be selected from para-amino benzyl alcohol (PABA), dicarbamates, methylene alkoxy dicarbamate, or other self-immolative species known to those in the art. In some embodiments of the present disclosure, Val-Cit is used as an enzymatically cleavable trigger. In some embodiments, a disulfide is used as a chemically cleavable trigger. Non limiting examples of self-immolative linkers include, but are not limited to, PABA, thio ethyl carbamate, and bis carbamate. In some embodiments, the cleavable trigger is any trigger disclosed in Hermanson, Greg T. (2013) *Bioconjugate Techniques* (Third Edition). Elsevier Inc., which is incorporated herein by reference in its entirety.

In some embodiments, P is a payload and may include molecules intended for either therapeutic or diagnostic purposes. In certain embodiments, the payload is a therapeutic moiety designed to treat a specific condition and may be chosen from auristatins, maytansinoids, PBDs, tubulysins, amanatins, duocarmycins, or other payloads known to those in the art. In other embodiments, the payload may be a profluorophore, fluorophore, or chelator used for diagnostic and imaging purposes and may be chosen from the fluoresceins, rhodamines, cyanines, coumarins, DOTAs, NOTAs, or other functional molecules known to those in the art. In the present disclosure the payload is a profluorophore and is either an aminocoumarin or a hydroxycoumarin used in a non-limiting manner to demonstrate proof-of-concept.

Distance Factors

As illustrated in the non-limiting examples below, D' as used herein in Formula (II) represents the sum of atoms in a linear chain between B and cleavable trigger T.

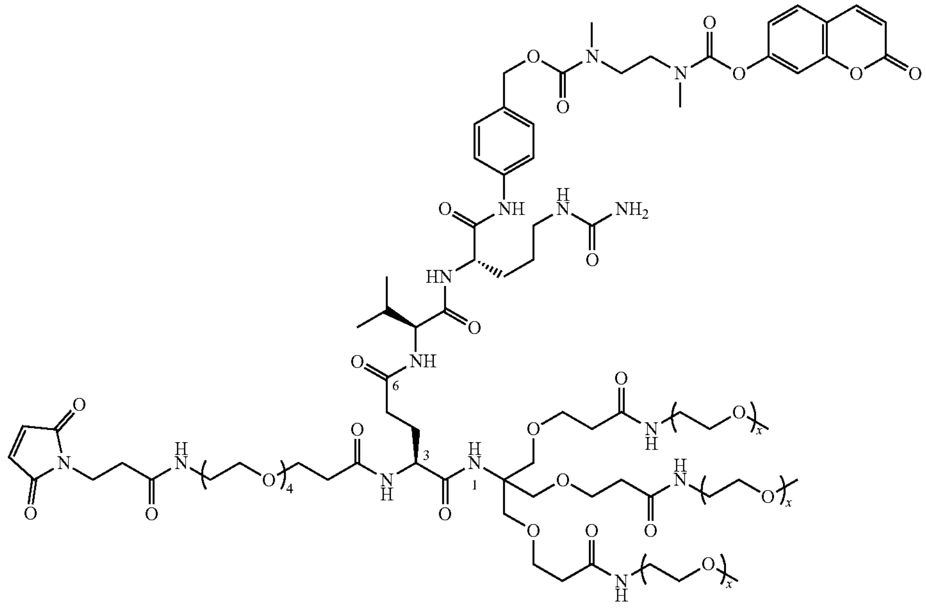

D' = 6

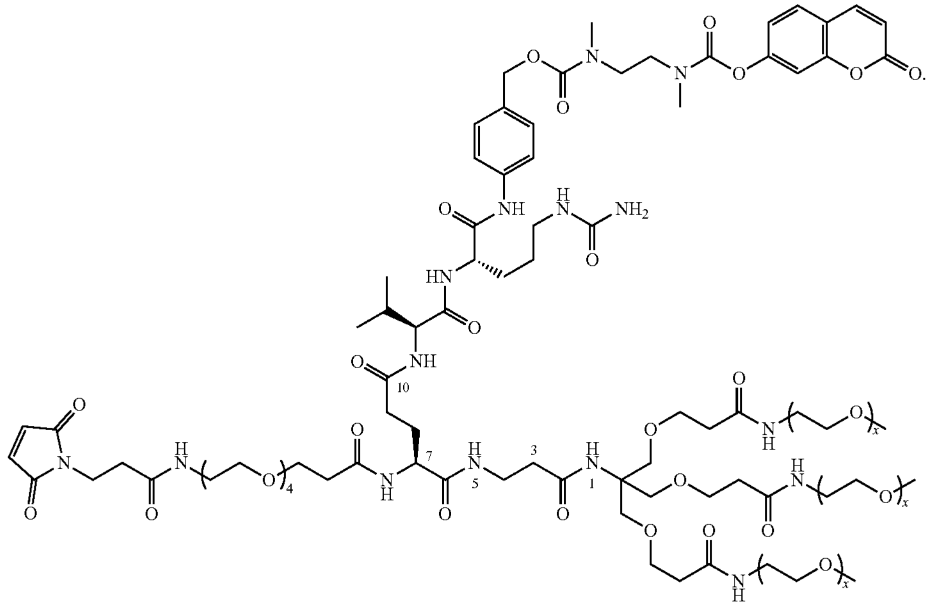

D' = 10

In some embodiments, D' is less than or equal to 22. In some embodiments, D' is less than or equal to 13. In some embodiments, D' is less than or equal to 12. In some embodiments, D' is less than or equal to 11. In some embodiments, D' is less than or equal to 10. In some embodiments, D' is less than or equal to 9. In some embodiments, D' is 13. In some embodiments, D' is 12. In some embodiments, D' is 11. In some embodiments, D' is 10. In some embodiments, D' is 9. In some embodiments, D' is 8. In some embodiments, D' is 7. In some embodiments, D' is 6. In some embodiments, D' is 5. In some embodiments, D' is 4. In some embodiments, D' is from 5 to 22, including any range or value therebetween. In some embodiments, D' is from 5 to 13. In some embodiments, D' is from 5 to 12. In some embodiments, D' is from 5 to 11. In some embodiments, D' is from 5 to 10. In some embodiments, D' is from 5 to 9. In some embodiments, D' is from 5 or 8. In some embodiments, D' is from 6 to 13. In some embodiments, D' is from 6 to 12. In some embodiments, D' is from 6 to 11. In some embodiments, D' is from 6 to 10. In some embodiments, D' is from 6 to 9. In some embodiments, D' is from 6 to 8. In some embodiments, D' is from 7 to 13. In some embodiments, D' is from 7 to 12. In some embodiments, D' is from 7 to 11. In some embodiments, D' is from 7 to 10. In some embodiments, D' is from 7 to 9. In some embodiments, D' is 7 or 8. In some embodiments, D' is 6 or 10. In some embodiments, D' is 5 or 9. In some embodiments, D' is 8 or 9. In some embodiments, D' is 4 or 5. In some embodiments, D' represents the sum of contiguous atoms in $D_2$, $D_3$, and A. In some embodiments, D' represents the sum of atoms in $D_2$, $D_3$, and A.

D', as used herein in Formula (II), can also be defined as a distance in angstroms. For example, in some embodiments, D' is about 6 Å to about 30 Å, e.g., about 6 Å, 7 Å, 8 Å, 9 Å, 10 Å, 11 Å, 12 Å, 13 Å, 14 Å, 15 Å, 16 Å, 17 Å, 18 Å, 19 Å, 20 Å, 21 Å, 22 Å, 23 Å, 24 Å, 25 Å, 26 Å, 27 Å, 28 Å, 29 Å, or 30 Å, including all ranges and values therebetween. In some embodiments, D' is about 6 Å to about 20 Å. In some embodiments, D' is about 6 Å to about 10 Å. In some embodiments, D' is about 10 Å to about 15 Å. In some embodiments, D' is about 15 Å to about 20 Å. In some embodiments, D' is about 10 Å to about 30 Å. In some embodiments, when D' is measured in angstroms, the distance is through space as determined by crystallography (e.g., X-ray crystallography) or 3-D modeling software.

In some embodiments, the compound of Formula (II) is further characterized by a value D, which is defined as the number of atoms in a linear chain between the targeting vector $FG_1$ and the cleavable trigger T. In some embodiments, the distance D is from 10 to 30 atoms. In some embodiments, the distance D is 10 atoms, 14 atoms, or 27 atoms. In some embodiments, D is 10 atoms. In in some embodiments, the percent of payload released from a compound of Formula (II) is reduced as the value D decreases. In some embodiments, there is a synergistic effect between D and D', such that percent payload release from a linker compound of Formula (II) is reduced when D' is less than or equal to 22 (e.g., 22, 21, 20, 19, 18, 17, 16, 15, 14, 13, 12, 11, 10, 9, 8, 7, 6) and D is greater than or equal to 10 atoms. In some embodiments, there is a synergistic effect between D and D', such that percent payload release from a linker compound of Formula (II) is reduced when D' is less than or equal to 22 (e.g., 22, 21, 20, 19, 18, 17, 16, 15, 14, 13, 12, 11, 10, 9, 8, 7, 6, 5, 4) and D is 10 atoms. In some embodiments, there is a synergistic effect between D and D', such that percent payload release from a linker compound of Formula (II) is reduced when D' is 4 to 12 atoms and the value of D is 10 atoms. In some embodiments, there is a synergistic effect between D and D', such that percent payload release from a linker compound of Formula (II) is reduced when D' is 5 and the value of D is 10 atoms. In some embodiments, there is a synergistic effect between D and D', such that percent payload release from a linker compound of Formula (II) is reduced when D' is 6 and the value of D is 10 atoms. In some embodiments, there is a synergistic effect between D and D', such that percent payload release from a linker compound of Formula (II) is reduced when D' is 9 and the value of D is 10 atoms. In some embodiments, there is a synergistic effect between D and D', such that percent payload release from a linker compound of Formula (II) is reduced when D' is 10 and the value of D is 10 atoms. The percent of payload released from a linker compound of Formula (II) can decrease as the value D decreases due to increased steric shielding from the antibody. Without being bound by any particular theory, linker compounds of Formula (II) with D'<22 magnify this effect. In some embodiments, as D is reduced from 27 to 10, both D' 6/5 and D' 10/9 magnify steric shielding and reduce payload release. In some embodiments, as D is reduced from 27 to 14, D' 6/5 magnifies steric shielding and reduces payload release.

In some embodiments, the compound of Formula (II) is a compound of Formula (IIa) or a pharmaceutically acceptable salt, solvate, or isomer thereof:

(IIa)

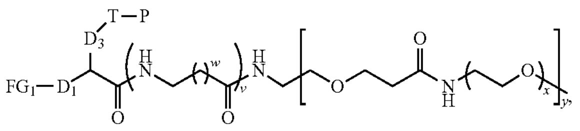

wherein:

$FG_1$, $D_1$, $D_3$, x and y are as defined herein;

T and P are as defined above in Formula (II);

v is 0 or 1; and when v is 1, w is 1 to 5;

In some embodiments, v is 0. In some embodiments, v is 1. In some embodiments, v is 1 and w is 1, 2, or 3. In some embodiments, v is 1 and w is 1 or 2. In some embodiments, v is 1, w is 1.

In some embodiments, the compound of Formula (II) is a compound of Formula (IIb) or a pharmaceutically acceptable salt, solvate, or isomer thereof:

(IIb)

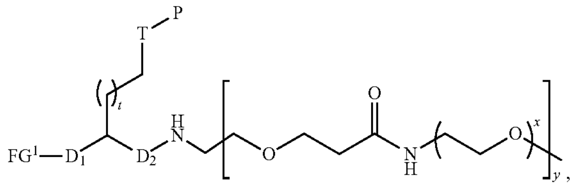

wherein:

$FG_1$, $D_1$, $D_2$, x and y are as defined herein; and

T and P are as defined above in Formula (II); and t is an integer from 0 to 4.

In some embodiments, t is 0, 1, 2, or 3. In some embodiments, t is 0, 1, or 2. In some embodiments, t is 0 or 1. In some embodiments, t is 0. In some embodiments, t is 1.

In some embodiments, the compound of Formula (II) is a compound of Formula (IIc) or a pharmaceutically acceptable salt, solvate, or isomer thereof:

(IIc)

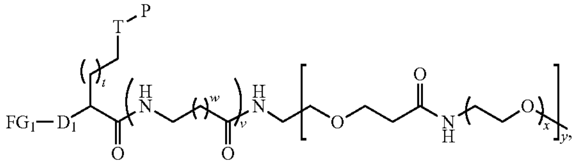

wherein:

$FG_1$, $D_1$, x and y are as defined herein;

T and P are as defined above in Formula (II);

t is an integer from 0 to 4;

v is 0 or 1; and when v is 1, w is 1 to 5.

In some embodiments, t is 0, 1, 2, or 3. In some embodiments, t is 0, 1, or 2. In some embodiments, t is 0 or 1. In some embodiments, t is 0. In some embodiments, t is 1.

In some embodiments, v is 0. In some embodiments, v is 1. In some embodiments, v is 1 and w is 1, 2, or 3. In some embodiments, v is 1 and w is 1 or 2. In some embodiments, v is 1, w is 1.

In some embodiments, the compound of Formula (II) is a compound of Formula (IIc1), (IIc2), or a pharmaceutically acceptable salt, solvate, or isomer thereof:

(IIc1)

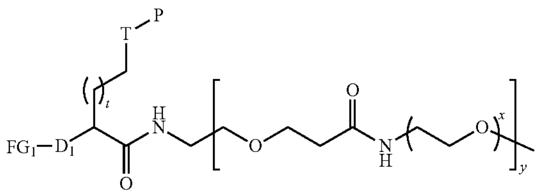

or (IIc2)

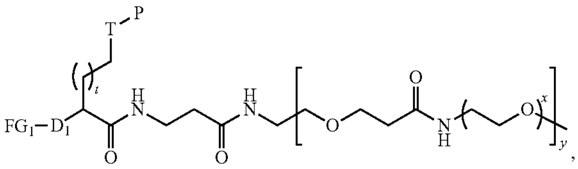

, wherein:

$FG_1$, $D_1$, x and y are as defined herein; and

T and P are as defined above in Formula (II); and t is as defined above in Formula (Ic).

In some embodiments, the compound of Formula (II) is a compound of Formula (IId), or a pharmaceutically acceptable salt, solvate, or isomer thereof:

(IId)

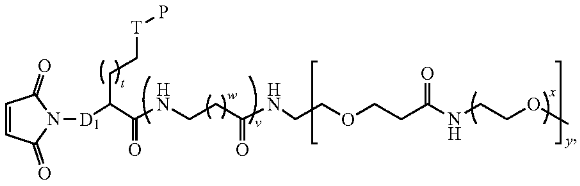

wherein:

$D_1$, x and y are as defined herein; and

T and P are as defined above in Formula (II);

t is an integer from 0 to 4;

v is 0 or 1; and when v is 1, w is 1 to 5.

In some embodiments, t is 0, 1, 2, or 3. In some embodiments, t is 0, 1, or 2. In some embodiments, t is 0 or 1. In some embodiments, t is 0. In some embodiments, t is 1.

In some embodiments, v is 0. In some embodiments, v is 1. In some embodiments, v is 1 and w is 1, 2, or 3. In some embodiments, v is 1 and w is 1 or 2. In some embodiments, v is 1, w is 1.

In some embodiments, the compound of Formula (II) is a compound of Formula (IId1), or a pharmaceutically acceptable salt, solvate, or isomer thereof:

(IId1)

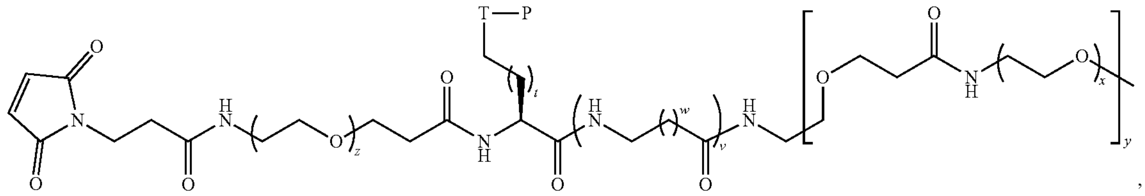

, wherein:

x and y are as defined herein;

T and P are as defined above in Formula (II);

t, v, and w are as defined above in Formula (IId); and z is independently an integer from 1 to 10.

In some embodiments, z is an integer from 1 to 8. In some embodiments, z is an integer from 1 to 4. In some embodiments, z is an integer from 2 to 8. In some embodiments, z is an integer from 2 to 4. In some embodiments, z is 4. In some embodiments, z is 2. In some embodiments, z is 1.

In some embodiments, the compound of Formula (II) is a compound of Formula (IId2), or a pharmaceutically acceptable salt, solvate, or isomer thereof:

(IId2)

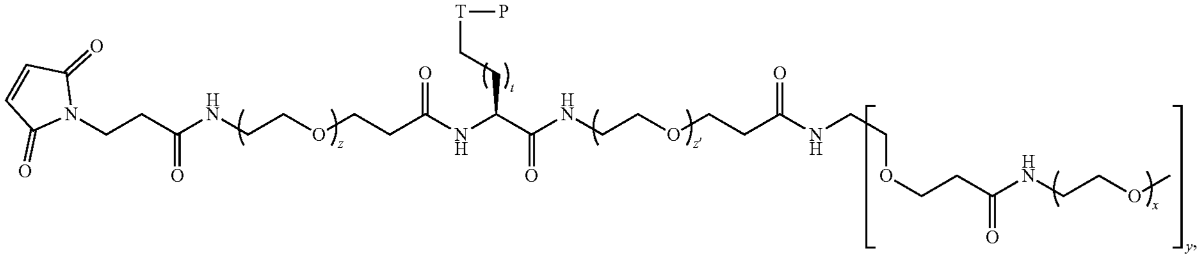

wherein:

x and y are as defined herein;

T and P are as defined above in Formula (II);

t is as defined above in Formula (IId); and z and z' are each independently an integer from 1 to 10.

In some embodiments, z and z' are each independently an integer from 1 to 8. In some embodiments, z and z' are each independently an integer from 1 to 4. In some embodiments, z and z' are each independently an integer from 2 to 8. In some embodiments, z and z' are each independently an integer from 2 to 4. In some embodiments, z is 4. In some embodiments, z is 2. In some embodiments, z is 1. In some embodiments, z' is 4. In some embodiments, z' is 2. In some embodiments, z' is 1. In some embodiments, z is 2 or 4 and z' is 4.

In some embodiments, the compound of Formula (II) is a compound of Formula (IId3), or a pharmaceutically acceptable salt, solvate, or isomer thereof:

(IId3)

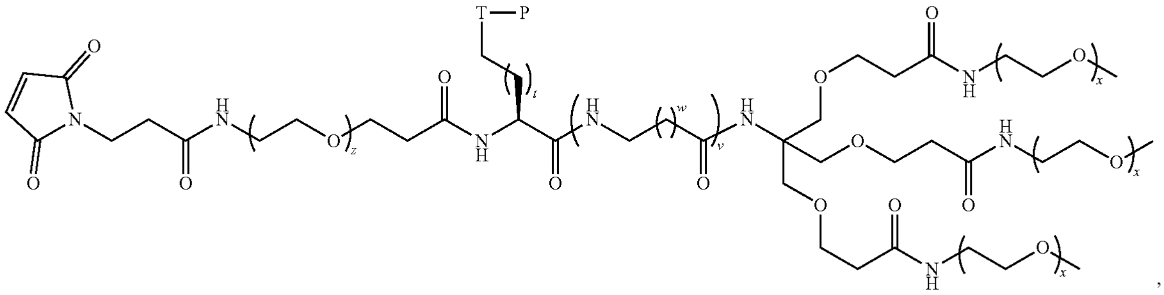

, wherein:

x is as defined herein;

T and P are as defined above in Formula (II);

t, v, and w are as defined above in Formula (IId); and z is as defined above in Formula (IId1).

Conjugates of the Present Disclosure (Formula III)

In some embodiments, the present disclosure provides a compound of Formula (III) or a pharmaceutically acceptable salt, solvate, or isomer thereof:

(III)

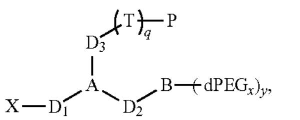

wherein:

A, B, dPEG, $D_1$, $D_2$, $D_3$, q, x, and y are as defined above in Formula (I) or Formula (II);

T, P, and D' are as defined above in Formula (II); and

X is a targeting vector.

In some embodiments of Formula (III), X is a targeting moiety that binds, complexes with, reacts, or associates with a specific epitope, antigen or targeted moiety on the vasculature, extracellular matrix, lymphatic system, cell surface, or any other surface. In some embodiments, X is an antibody. In some embodiments, the antibody is large antibody. In some embodiments, X is an antibody fragment or engineered domain. In some embodiments, X is a small polypeptide. In some embodiments, X is an organic moiety. In some embodiments, the present disclosure provides compounds that include a rabbit IgG conjugate (145 kDa). In some embodiments, the present disclosure provides compounds that include a "null" conjugate with no biologic, which represents the smallest size limit (0 kDa) of a targeting moiety and can be used to demonstrate proof-of-concept on targeting vectors of different sizes.

As used herein, $D_1$ refers to a spacer moiety between $FG_1$ and A (not inclusive). In some embodiments of Formula (III), $D_1$ is a C1-C10 alkylene. In some embodiments, the C1-C10 alkylene is optionally substituted. In some embodiments, the C1-C10 alkylene comprises at least one imide, amide and/or sulfonamide group. In some embodiments, the C1-C10 alkylene comprises at least one imide and/or amide group. In some embodiments, the imide is a cyclic imide. In some embodiments, the C1-C10 alkylene comprises at least one amide group. In some embodiments, the C1-C10 alkylene comprises at least one amide group and a $-(CH_2CH_2O)_z-$ subunit, wherein z is as defined herein, e.g., z is an integer from 1 to 5, including any subrange or value therebetween. In some embodiments, D1 is an optionally substituted C1-C3 alkylene. In some embodiments, e.g., when A is a carbon atom, $D_1$ is selected from the group consisting of: optionally substituted

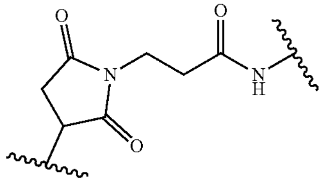

,

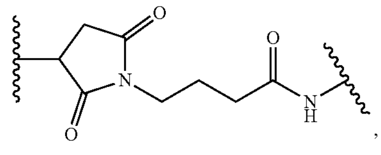

,

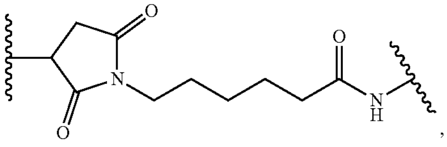

,

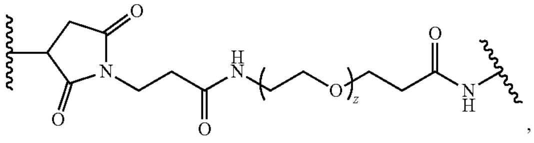

, and

-continued

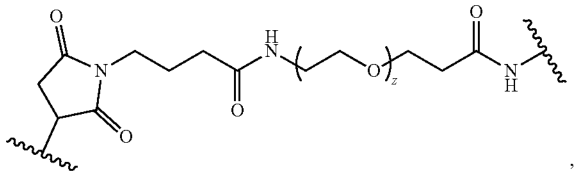

, wherein z is 1-4. In some embodiments, z is 2 or 4. In some embodiments, e.g., when A is a carbon atom, $D_1$ is selected from the group consisting of:

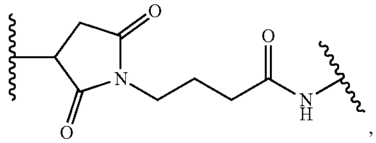

,

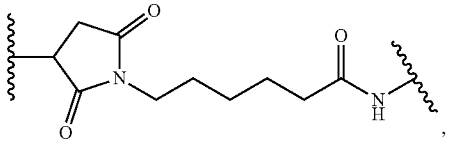

, and

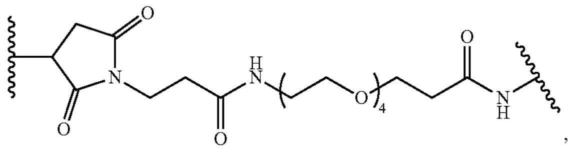

, each of which is optionally substituted. In some embodiments, e.g., when A is

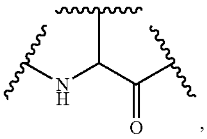 [SMILES: *NC(*)C(*)=O]

, $D_1$ is selected from the group consisting of: optionally substituted

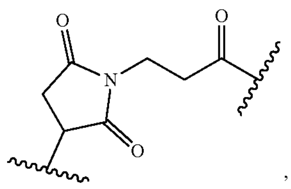

,

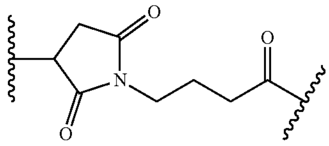

,

-continued

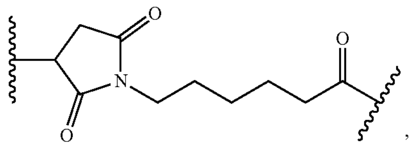

,

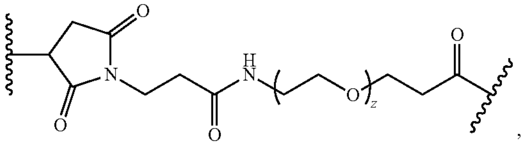

, and

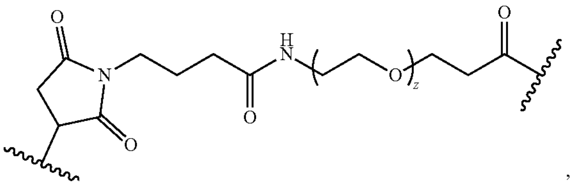

, wherein z is 1-4. In some embodiments, z is 2 or 4. In some embodiments, e.g., when A is

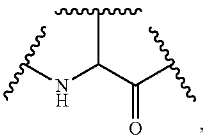 [SMILES: *NC(*)C(*)=O]

, $D_1$ is selected from the group consisting of:

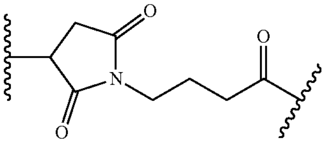

,

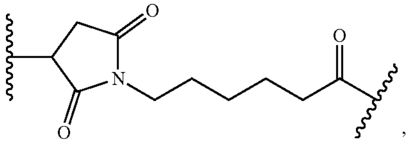

, and

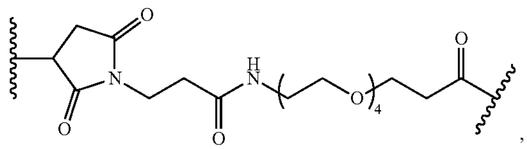

, each of which is optionally substituted.

Distance Factors

As illustrated in the non-limiting examples below, D' as used herein in Formula (III) represents the sum of atoms in a linear chain between B and cleavable trigger T.

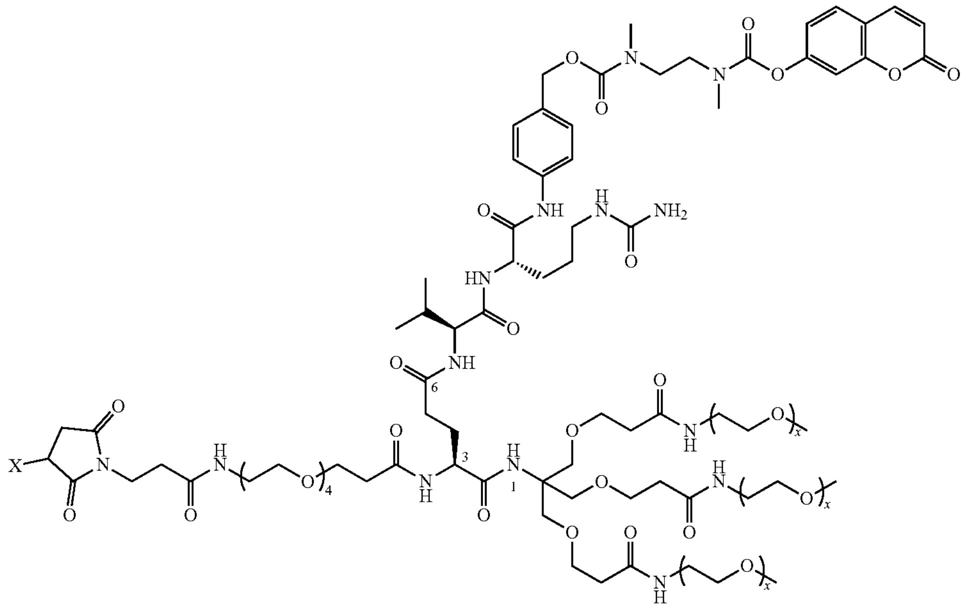

D' = 6

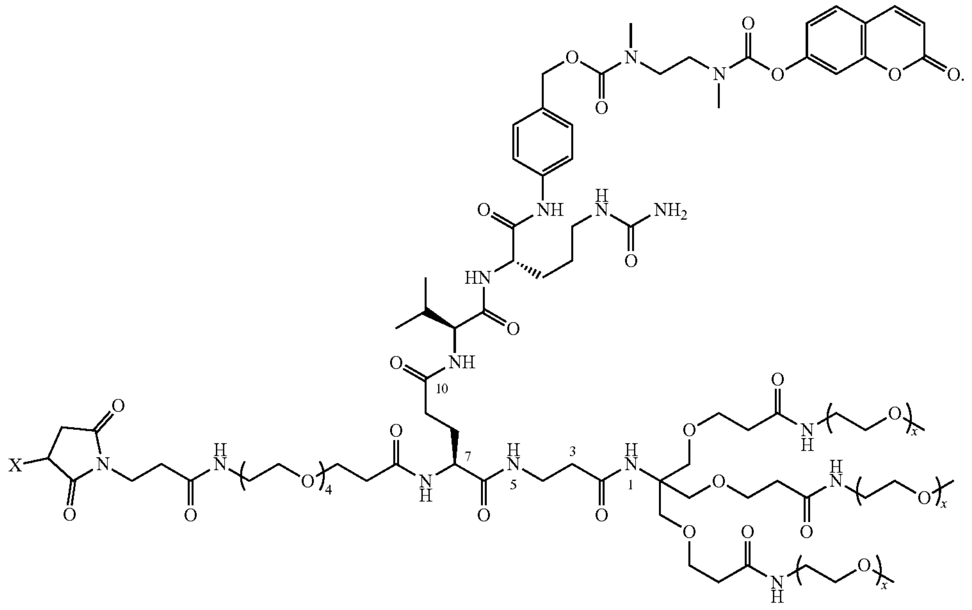

D' = 10

In some embodiments, D' is less than or equal to 22. In some embodiments, D' is less than or equal to 13. In some embodiments, D' is less than or equal to 12. In some embodiments, D' is less than or equal to 11. In some embodiments, D' is less than or equal to 10. In some embodiments, D' is less than or equal to 9. In some embodiments, D' is 13. In some embodiments, D' is 12. In some embodiments, D' is 11. In some embodiments, D' is 10. In some embodiments, D' is 9. In some embodiments, D' is 8. In some embodiments, D' is 7. In some embodiments, D' is 6. In some embodiments, D' is 5. In some embodiments, D' is 4. In some embodiments, D' is from 5 to 22, including any range or value therebetween. In some embodiments, D' is from 5 to 13. In some embodiments, D' is from 5 to 12. In some embodiments, D' is from 5 to 11. In some embodiments, D' is from 5 to 10. In some embodiments, D' is from 5 to 9. In some embodiments, D' is from 5 or 8. In some embodiments, D' is from 6 to 13. In some embodiments, D' is from 6 to 12. In some embodiments, D' is from 6 to 11. In some embodiments, D' is from 6 to 10. In some embodiments, D' is from 6 to 9. In some embodiments, D' is from 6 to 8. In some embodiments, D' is from 7 to 13. In some embodiments, D' is from 7 to 12. In some embodiments, D' is from 7 to 11. In some embodiments, D' is from 7 to 10. In some embodiments, D' is from 7 to 9. In some embodiments, D' is 7 or 8. In some embodiments, D' is 6 or 10. In some embodiments, D' is 5 or 9. In some embodiments, D' is 8 or 9. In some embodiments, D' is 4 or 5. In some embodiments, D' represents the sum of contiguous atoms in $D_2$, $D_3$, and A. In some embodiments, D' represents the sum of atoms in $D_2$, $D_3$, and A.

D', as used herein in Formula (III), can also be defined as a distance in angstroms. For example, in some embodiments, D' is about 6 Å to about 30 Å, e.g., about 6 Å, 7 Å, 8 Å, 9 Å, 10 Å, 11 Å, 12 Å, 13 Å, 14 Å, 15 Å, 16 Å, 17 Å, 18 Å, 19 Å, 20 Å, 21 Å, 22 Å, 23 Å, 24 Å, 25 Å, 26 Å, 27 Å, 28 Å, 29 Å, or 30 Å, including all ranges and values therebetween. In some embodiments, D' is about 6 Å to about 20 Å. In some embodiments, D' is about 6 Å to about 10 Å. In some embodiments, D' is about 10 Å to about 15 Å. In some embodiments, D' is about 15 Å to about 20 Å. In some embodiments, D' is about 10 Å to about 30 Å. In some embodiments, when D' is measured in angstroms, the distance is through space as determined by crystallography (e.g., X-ray crystallography) or 3-D modeling software.

In some embodiments, the compound of Formula (III) is further characterized by a value D, which is defined as the number of atoms in a linear chain between the targeting vector X and the trigger T. In some embodiments, the distance D is from 10 to 30 atoms. In some embodiments, the distance D is 10 atoms, 14 atoms, or 27 atoms. In some embodiments, D is 10 atoms. In some embodiments, the percent of payload release for a compound of Formula (III) is reduced as the value D decreases. In some embodiments, there is a synergistic effect between D and D', such that percent payload release from a linker compound of Formula (III) is reduced when D' is less than or equal to 22 (e.g., 22, 21, 20, 19, 18, 17, 16, 15, 14, 13, 12, 11, 10, 9, 8, 7, 6) and D is greater than or equal to 10 atoms. In some embodiments, there is a synergistic effect between D and D', such that percent payload release from a linker compound of Formula (III) is reduced when D' is less than or equal to 22 (e.g., 22, 21, 20, 19, 18, 17, 16, 15, 14, 13, 12, 11, 10, 9, 8, 7, 6, 5, 4) and D is 10 atoms. In some embodiments, there is a synergistic effect between D and D', such that percent payload release from a linker compound of Formula (III) is reduced when D' is 4 to 12 atoms and the value of D is 10 atoms. In some embodiments, there is a synergistic effect between D and D', such that percent payload release from a linker compound of Formula (III) is reduced when D' is 5 and the value of D is 10 atoms. In some embodiments, there is a synergistic effect between D and D', such that percent payload release from a linker compound of Formula (III) is reduced when D' is 6 and the value of D is 10 atoms. In some embodiments, there is a synergistic effect between D and D', such that percent payload release from a linker compound of Formula (III) is reduced when D' is 9 and the value of D is 10 atoms. In some embodiments, there is a synergistic effect between D and D', such that percent payload release from a linker compound of Formula (III) is reduced when D' is 10 and the value of D is 10 atoms. The percent of payload released from a linker compound of Formula (III) can decrease as the value D decreases due to increased steric shielding from the antibody. Without being bound by any particular theory, linker compounds of Formula (III) with D'<22 magnify this effect. In some embodiments, as D is reduced from 27 to 10, both D' 6/5 and D' 10/9 magnify steric shielding and reduce payload release. In some embodiments, as D is reduced from 27 to 14, D' 6/5 magnifies steric shielding and reduces payload release.

In some embodiments, the compound of Formula (III) is a compound of Formula (IIIb), or a pharmaceutically acceptable salt, solvate, or isomer thereof:

(IIIb)

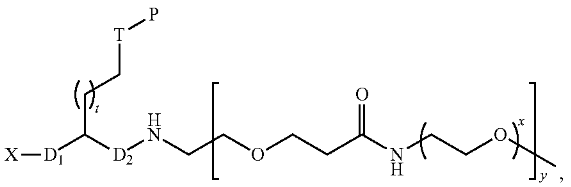

wherein:

$D_1$, $D_2$, x and y are as defined above in Formula (I) or Formula (II); and

T and P are as defined above in Formula (II);

X is as defined above in Formula (III); and t is an integer from 0 to 4.

In some embodiments, t is 0, 1, 2, or 3. In some embodiments, t is 0, 1, or 2. In some embodiments, t is 0 or 1. In some embodiments, t is 0. In some embodiments, t is 1.

In some embodiments, y=3 architectures impart variable in vivo release rates to cleavable triggers—a feature not available to approaches relying on the intrinsic enzyme-trigger SAR. In some embodiments, the linkers of the present disclosure improve the therapeutic window of an ADC. Thus, in some embodiments, the linkers of the present disclosure are expected to exhibit slower cathepsin-mediated release in extracellular tissues (where the targeting vector is usually intact and provides steric shielding due to the synergistic effect of the linker), while still exhibiting faster cathepsin-mediated release after internalization and catabolism of the targeting vector in the cell/lysosome.

Numbered Embodiments of the Disclosure.

A compound of Formula (I) or a pharmaceutically acceptable salt, solvate, or isomer thereof:

(I)

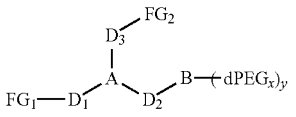

wherein:

- $FG_1$ is a reactive functional group capable of conjugation to a targeting vector;
- $FG_2$ is a reactive functional group capable of conjugation to a payload;
- A is a trivalent or tetravalent atom;
- B is a first branch point;
- PEG is a polyethylene glycol-based chain comprising linear, branched, monodisperse, and/or polydisperse PEG;
- x is an integer from 4 to 48;
- y is 2 or 3; and
- $D_1$, $D_2$, and $D_3$ are each independently a spacer moiety, wherein D' represents the sum of atoms in a linear chain between B and $FG_2$.

2. The compound of embodiment 1, wherein D' is less than 22.

3. The compound of embodiment 1 or 2, wherein D' is from 5 to 9.

4. The compound of any one of embodiments 1-3, wherein D' is 5.

4a. The compound of any one of embodiments, 1-3, wherein D' is 9.

5. The compound of any one of embodiments 1-4a, wherein $D_1$, $D_2$, and $D_3$ are each independently an alkylene, alkenylene, or alkynylene, optionally comprising one or more heteroatoms selected from N or O, and optionally substituted with one or more oxo groups.

6. The compound of any one of embodiments 1-5, wherein $D_1$, $D_2$, and $D_3$ each independently comprises a $-(CH_2CH_2O)_z-$ subunit, wherein z is an integer from 1 to 5.

7. The compound of any one of embodiments 1-6, wherein $D_1$, $D_2$, and $D_3$ each independently comprises one or more amide groups.

8. The compound of any one of embodiments 1-7, having the structure:

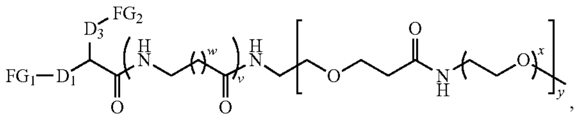, or a pharmaceutically acceptable salt, solvate, or isomer thereof, wherein:

$FG_1$ is a reactive functional group capable of conjugation to a targeting vector;

$FG_2$ is a reactive functional group capable of conjugation to a payload;

v is 0 or 1;

when v is 1, w is 1 to 5;

each x is independently an integer from 4 to 48;

y is 2 or 3; and $D_1$ and $D_3$ are each independently a spacer moiety.

9. The compound of any one of embodiments 1-7, having the structure:

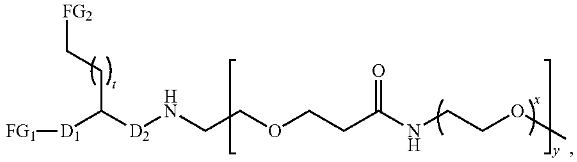, or a pharmaceutically acceptable salt, solvate, or isomer thereof, wherein:

$FG_1$ is a reactive functional group capable of conjugation to a targeting vector;

$FG_2$ is a reactive functional group capable of conjugation to a payload;

t is an integer from 0 to 4;

each x is independently an integer from 4 to 48;

y is 2 or 3; and $D_1$ and $D_2$ are each independently a spacer moiety.

10. The compound of any one of embodiments 1-7, having the structure:

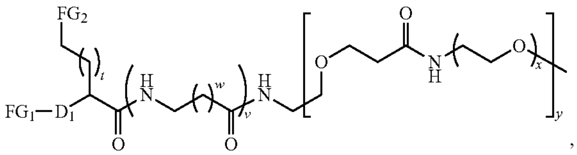, or a pharmaceutically acceptable salt, solvate, or isomer thereof, wherein:

$FG_1$ is a reactive functional group capable of conjugation to a targeting vector;

$FG_2$ is a reactive functional group capable of conjugation to a payload;

t is an integer from 0 to 4;

v is 0 or 1;

when v is 1, w is 1 to 5;

each x is independently an integer from 4 to 48;

y is 2 or 3; and $D_1$ is a spacer moiety.

11. The compound of embodiment 8 or 10, wherein v is 0.

12. The compound of embodiment 8 or 10, wherein v is 1 and w is 1.

13. The compound of embodiment 10, having the structure:

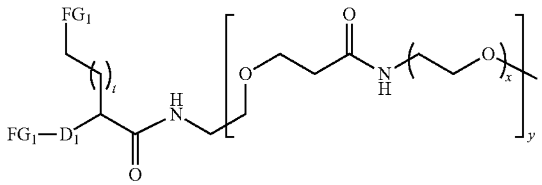

or

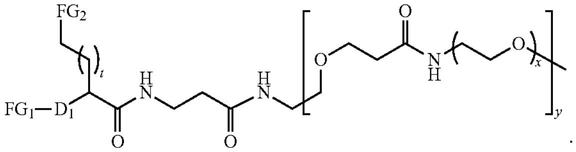.

14. The compound of any one of embodiments 9-13, wherein t is 0 or 1.

15. The compound of any one of embodiments 8-14, wherein y is 3.

16. The compound of any one of embodiments 8-14, wherein y is 2.

17. The compound of any one of embodiments 8-16, wherein x is 8.

18. The compound of any one of embodiments 8-16, wherein x is 24.

19. The compound of any one of embodiments 1-10, having the structure:

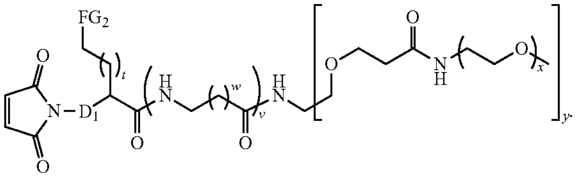.

20. The compound of any one of the preceding embodiments, wherein $FG_2$ comprises an amine or carbonyl group.

21. The compound of embodiment 19 or 20, having the structure:

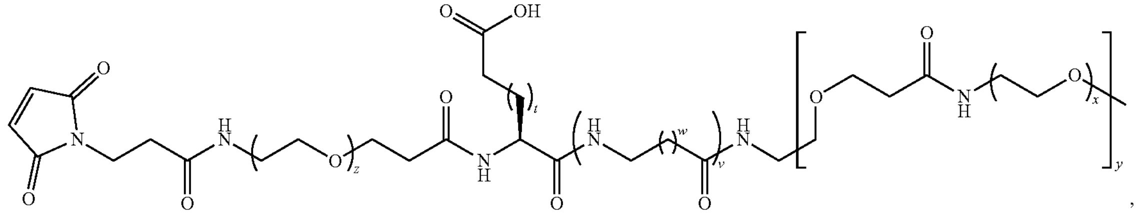
, or a pharmaceutically acceptable salt, solvate, or isomer thereof,
wherein:
t is an integer from 0 to 4;
v is 0 or 1;
when v is 1, w is 1 to 5;
each x is independently an integer from 4 to 48;
y is 2 or 3; and
z is an integer from 1 to 10.

22. The compound of any one of embodiments 19-21, having the structure:

or a pharmaceutically acceptable salt, solvate, or isomer thereof,
wherein:
t is an integer from 0 to 4;
v is 0 or 1;
when v is 1, w is an integer from 1 to 5;
each x is independently an integer from 4 to 48;
y is 2 or 3; and
z and z' are each independently an integer from 1 to 10.

26. The compound of any one of embodiments 21-26, wherein z is 4.

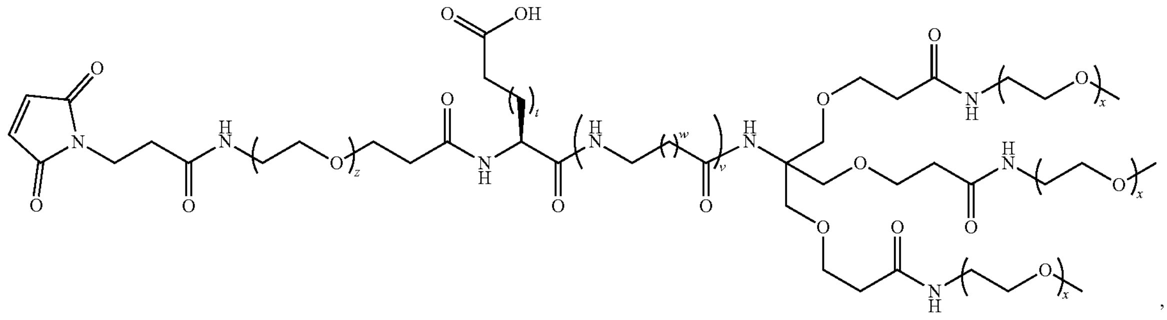
, or a pharmaceutically acceptable salt, solvate, or isomer thereof,
wherein:
t is an integer from 0 to 4;
v is 0 or 1;
when v is 1, w is an integer from 1 to 5;
each x is independently an integer from 4 to 48; and
z is an integer from 1 to 10.

23. The compound of any one of embodiments 19-22, wherein v is 0.

24. The compound of any one of embodiments 19-22, wherein v is 1 and w is 1.

25. The compound of any one of embodiments 1-7, having the structure:

27. The compound of any one of embodiments 21-26, wherein z is 2.

28. The compound of any one of embodiments 25-27, wherein z' is 4.

29. The compound of any one of embodiments 19-28, wherein t is 0 or 1.

30. The compound of any one of embodiments 19-29, wherein x is 8.

31. The compound of any one of embodiments 19-29, wherein x is 24.

32. The compound of any one of embodiments 25-30, wherein y is 3.

33. A conjugate of Formula (II) or a pharmaceutically acceptable salt, solvate, or isomer thereof:

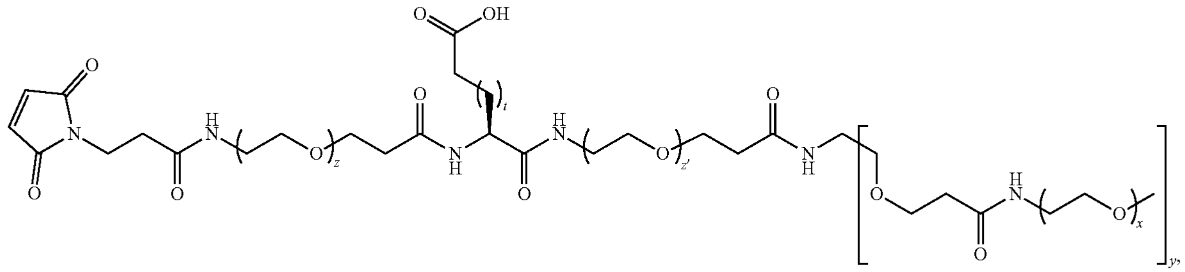

(II)

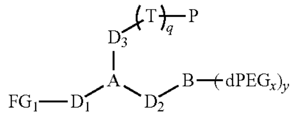

wherein:

$FG_1$ is a reactive functional group capable of conjugation to a targeting vector;

A is a trivalent or tetravalent atom;

B is a first branch point;

T is a releasable trigger;

P is a payload;

PEG is a polyethylene glycol-based chain comprising linear, branched, monodisperse, and/or polydisperse PEG;

q is 0 or 1;

x is an integer from 4 to 48;

y is 2 or 3; and $D_1$, $D_2$, and $D_3$ are each independently a spacer moiety, wherein D' represents the sum of atoms in a linear chain between B and T.

33a. The conjugate of embodiment 33, wherein $D_1$, $D_2$, and $D_3$ are each independently an alkylene, alkenylene, or alkynylene, optionally comprising one or more heteroatoms selected from N or O, and optionally substituted with one or more oxo groups.

33b. The conjugate of embodiment 33 or 33a, wherein $D_1$ is selected from the group consisting of:

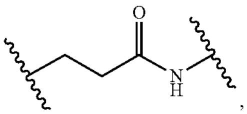
,
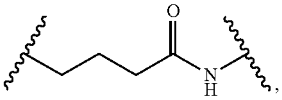
,
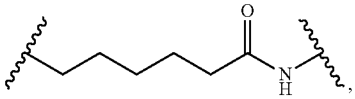
,
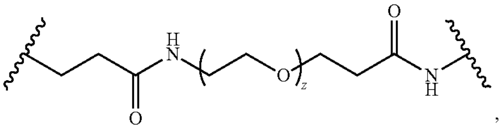
, and
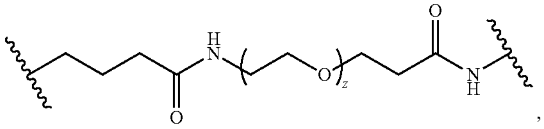
, wherein z is 2 or 4.

33c. The conjugate of any one of embodiments 33-33b, $D_2$ is selected from the group consisting of optionally substituted

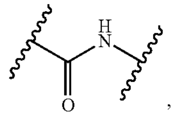
,
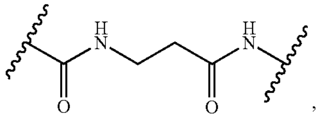
,
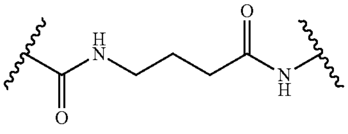
or

-continued

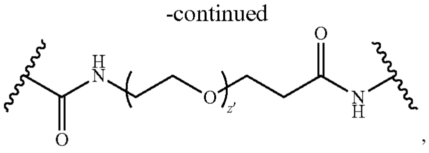
, wherein z' is an integer from 1 to 5.

33d. The conjugate of any one of embodiments 33-33c, wherein $D_3$ is a C1-C5 alkylene.

33e. The conjugate of any one of embodiments 33-33d, wherein x is 8 or 24.

33f. The conjugate of any one of embodiments 33-33e, wherein y is 3.

33g. The conjugate of any one of embodiments, 33-33f, wherein A is a nitrogen atom.

33h. The conjugate of any one of embodiments, 33-33g, wherein branching point B is a carbon or nitrogen atom.

33i. The conjugate of any one of embodiments 33-33h, wherein the releasable trigger T is a Val-Cit, Val-Ala, or Phe-Lys releasable trigger.

34. The conjugate of embodiment 33, having the structure:

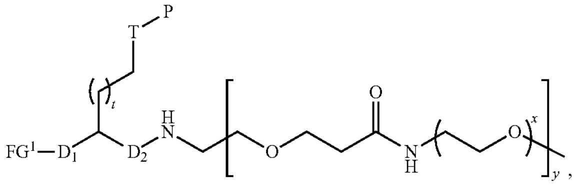
, or a pharmaceutically acceptable salt, solvate, or isomer thereof, wherein:

$FG_1$ is a reactive functional group capable of conjugation to a targeting vector;

T is a releasable trigger;

P is a payload;

t is an integer from 0 to 4;

each x is independently an integer from 4 to 48;

y is 2 or 3; and $D_1$ and $D_2$ are each independently a spacer moiety.

34a. The conjugate of embodiment 34, having a structure as shown in Table 1.

35. A conjugate of Formula (III) or a pharmaceutically acceptable salt, solvate, or isomer thereof:

(III)

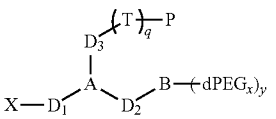

wherein:

A is a trivalent or tetravalent atom;

B is a first branch point;

T is a releasable trigger;

P is a payload;

X is a targeting vector;

PEG is a polyethylene glycol-based chain comprising linear, branched, monodisperse, and/or polydisperse PEG;

q is 0 or 1;

x is an integer from 4 to 48;

y is 2 or 3; and $D_1$, $D_2$, and $D_3$ are each independently a spacer moiety, wherein D' represents the sum of atoms in a linear chain between B and T.

35a. The conjugate of embodiment 35, wherein $D_1$, $D_2$, and $D_3$ are each independently an alkylene, alkenylene, or alkynylene, optionally comprising one or more heteroatoms selected from N or O, and optionally substituted with one or more oxo groups.

35b. The conjugate of embodiment 35 or 35a, wherein $D_1$ is selected from the group consisting of:

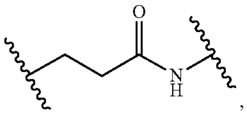
,
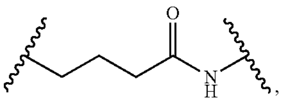
,
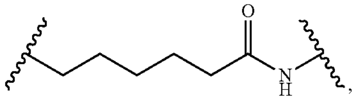
,
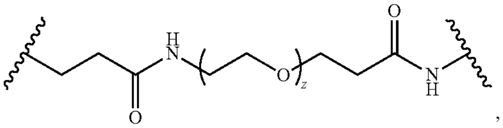
, and
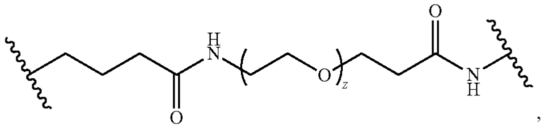
, wherein z is 2 or 4.

35c. The conjugate of any one of embodiments 35-35b, $D_2$ is selected from the group consisting of optionally substituted

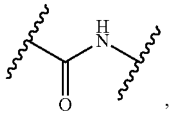
,
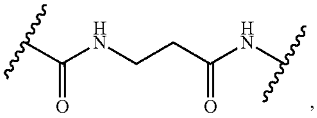
,
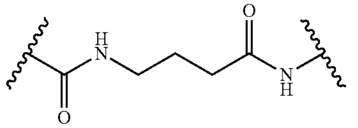
or
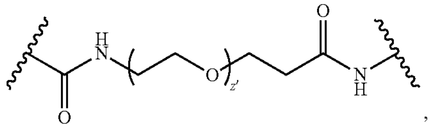
, wherein z' is an integer from 1 to 5.

35d. The conjugate of any one of embodiments 35-35c, wherein $D_3$ is a C1-C5 alkylene.

35e. The conjugate of any one of embodiments 35-35d, wherein x is 8 or 24.

35f. The conjugate of any one of embodiments 35-35e, wherein y is 3.

35g. The conjugate of any one of embodiments, 35-35f, wherein A is a nitrogen atom.

35h. The conjugate of any one of embodiments, 35-35g, wherein branching point B is a carbon or nitrogen atom.

35i. The conjugate of any one of embodiments 35-35h, wherein the releasable trigger T is a Val-Cit, Val-Ala, or Phe-Lys releasable trigger.

36. The conjugate of embodiment 35, having the structure:

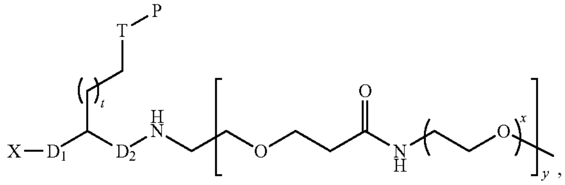
, or a pharmaceutically acceptable salt, solvate, or isomer thereof, wherein:

T is a releasable trigger;

P is a payload;

X is a targeting vector;

t is an integer from 0 to 4;

each x is independently an integer from 4 to 48;

y is 2 or 3; and $D_1$ and $D_2$ are each independently a spacer moiety.

EXAMPLES

The following examples are offered to illustrate, but not to limit the invention. It is understood that the examples and embodiments described herein are for illustrative purposes only and those skilled in the art will understand that there are numerous modifications, changes, and/or substitutions that may be made without departing from the scope and essence of the disclosure. In addition, many modifications may be made to adapt a particular situation or material in accordance with the teachings of the disclosure without departing from the essential scope thereof. Therefore, it is intended that the disclosure not be limited to the particular embodiments disclosed, but that the disclosure will include all embodiments falling within the scope of the appended claims. Also, all citations referred herein are expressly incorporated herein by reference. The exact synthetic routes to the desired targets may change improve isolation, purification, and/or yield. The exact number of ethylene oxide units in the shield and spacer may also change for best illustration of the results.

Flash Chromatography was performed on a Teledyne Isco Rf chromatography system with pre-packed RediSep Rf silica gel columns. Reactions were monitored and final products were characterized by thin-layer chromatography (TLC) using RediSep silica gel TLC plates. Plates were visualized with UV and/or iodine. Reactions were monitored and final products were characterized by HPLC analysis on an Agilent 1100 equipped with an ELSD detector using one of the methods below:

Mobile phases were either 50 mM triethylammonium acetate at pH 7.0 (A1), 10 mM ammonium formate at pH 3.5 (A2), or methanol (B).

Am3033: Ascentis Express C18, 90 Å, 2.7 μm, 150×4.6 mm, 45° C., 0.8 mL/min; 30% B for 0.3 min, gradient to 99% B over 27 min, hold at 99% B for 6 min.

Am6010: Ascentis Express C18, 90 Å, 2.7 μm, 150×4.6 mm, 45° C., 1.0 mL/min; 60% B for 1.4 min, gradient to 99% B over 7.6 min, hold at 99% B for 1 min.

Ac4025: Sepax BR-C18, 120 Å, 5 μm, 250×4.6 mm, 45° C., 1.0 mL/min; 60% B for 3.2 min, gradient to 99% B over 19.3 min, hold at 99% B for 2.5 min.

Ac5530: Sepax BR-C18, 120 Å, 5 μm, 250×4.6 mm, 45° C., 0.8 mL/min; 55% B for 3.9 min, gradient to 99% B over 22.1 min, hold at 99% B for 4 min.

Ac6022: Sepax BR-C18, 120 Å, 5 μm, 250×4.6 mm, 45° C., 1.0 mL/min; 60% B for 3.1 min, gradient to 99% B over 19.5 min, hold at 99% B for 2.4 min.

Ac7030: Sepax R-C18, 120 Å, 5 μm, 250×4.6 mm, 45° C., 1.0 mL/min; 70% B for 3.2 min, gradient to 99% B over 23.2 min, hold at 99% B for 3.5 min.

$^1H$ NMR spectra were recorded on a 600 MHz Bruker Avance III spectrometer. Chemical shifts (δ) are reported as ppm relative to the residual solvent peak. Mass spectra were obtained by low-resolution ESI, high resolution-ESI, MALDI, or FT-ICR. The method is noted for each compound and the data obtained are expressed in mass units (m/z).

Example 1

Reaction schemes for the synthesis of Compounds of Formula (I) and Formula (II) are provided in FIG. 1A, FIG. 3A, FIG. 3C, FIG. 3E, FIG. 4B, FIG. 4E, FIG. 5A, FIG. 5D, FIG. 6A, FIG. 6D and FIG. 6G. Reaction schemes for the synthesis of linear comparator compounds are provided in FIGS. 2A-2C.

Compound Design

Figure 2A:
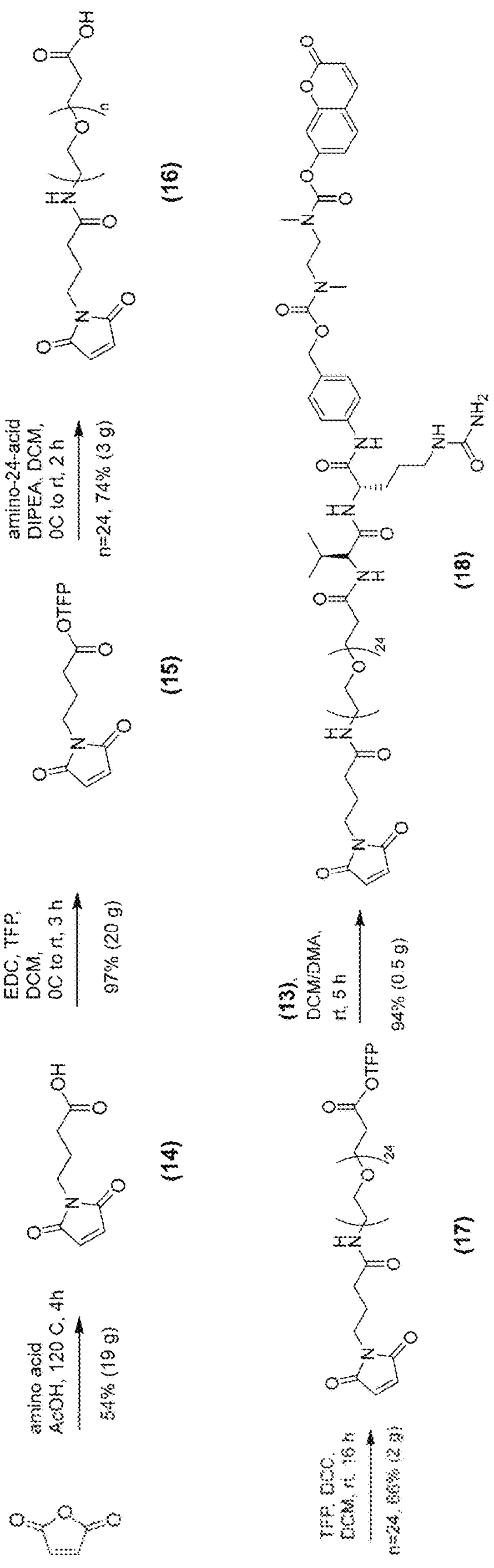
FIG. 2A shows the synthesis of linear control Compound 18 [A].
Figure 2B:
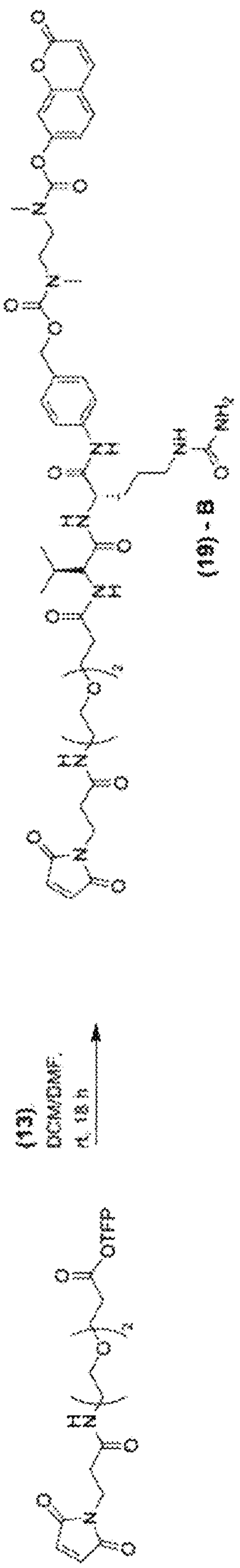
FIG. 2B shows the synthesis of linear control Compound 19 [B].
Figure 2C:
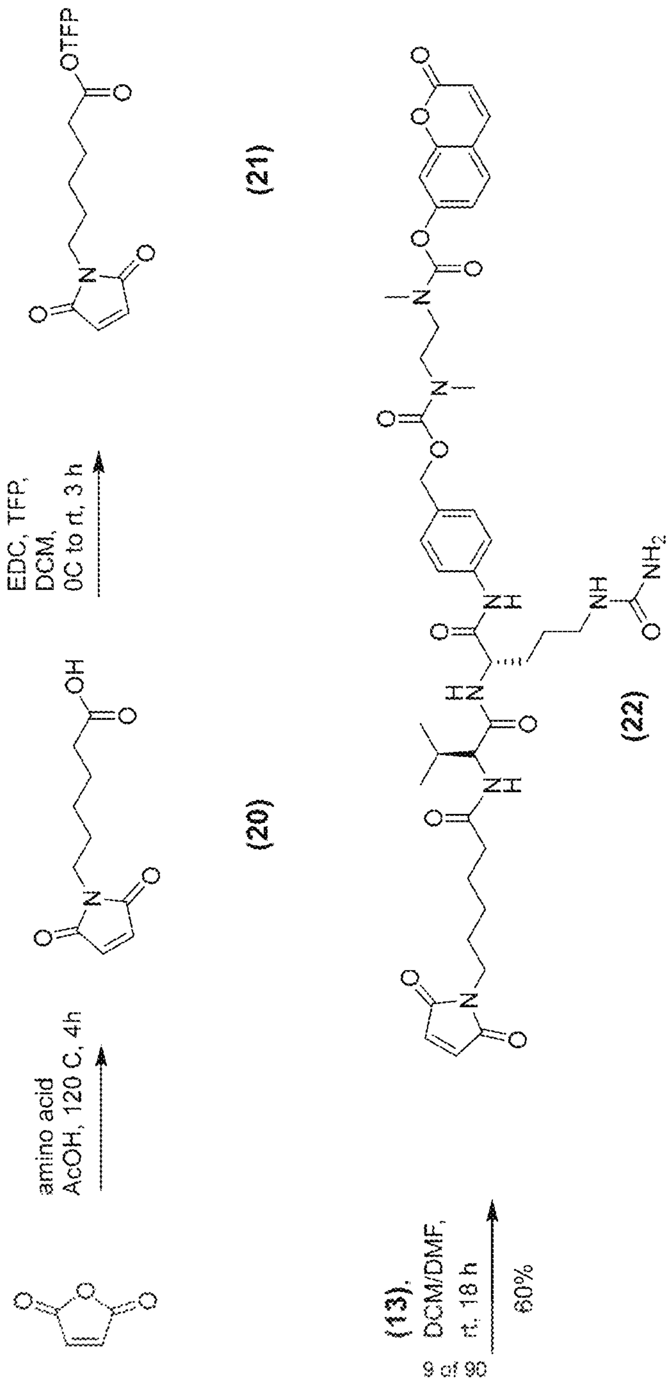
FIG. 2C shows the synthesis of linear control Compound 22 [C].

A modular approach was devised that established four basic structural variables (y, n, D', and D) that could be manipulated via the synthesis of three basic components with the general approach shown in FIG. 1A. Hydrophilic shielding structures could be prepared with different numbers of PEG arms (y), and different numbers of EO units (n) in each arm. Central branched cores based on amino acids provided attachment points for the trigger-payload, the hydrophilic shielding structure, and the biologic. The amino acid side chains of the central cores established the distance between the branch-point of the shielding structure and the cleavable trigger (D'), and this distance could be incremented by incorporating an additional spacer. In this case we coupled a four-atom spacer (β-alanine) to the carboxyl group. The side chain also contributed to the distance between the biologic and the cleavable trigger (D), and heterobifunctional linkers of different lengths attached to the central core would then combine with the amino acid side chain to establish the final overall distance between the biologic and the cleavable trigger (D). As explained above, the distances D and D' are defined in terms of atoms between the first nitrogen atom of the cleavable trigger and the biologic or the branch point of the hydrophilic shield, respectively.

Figure 1B:
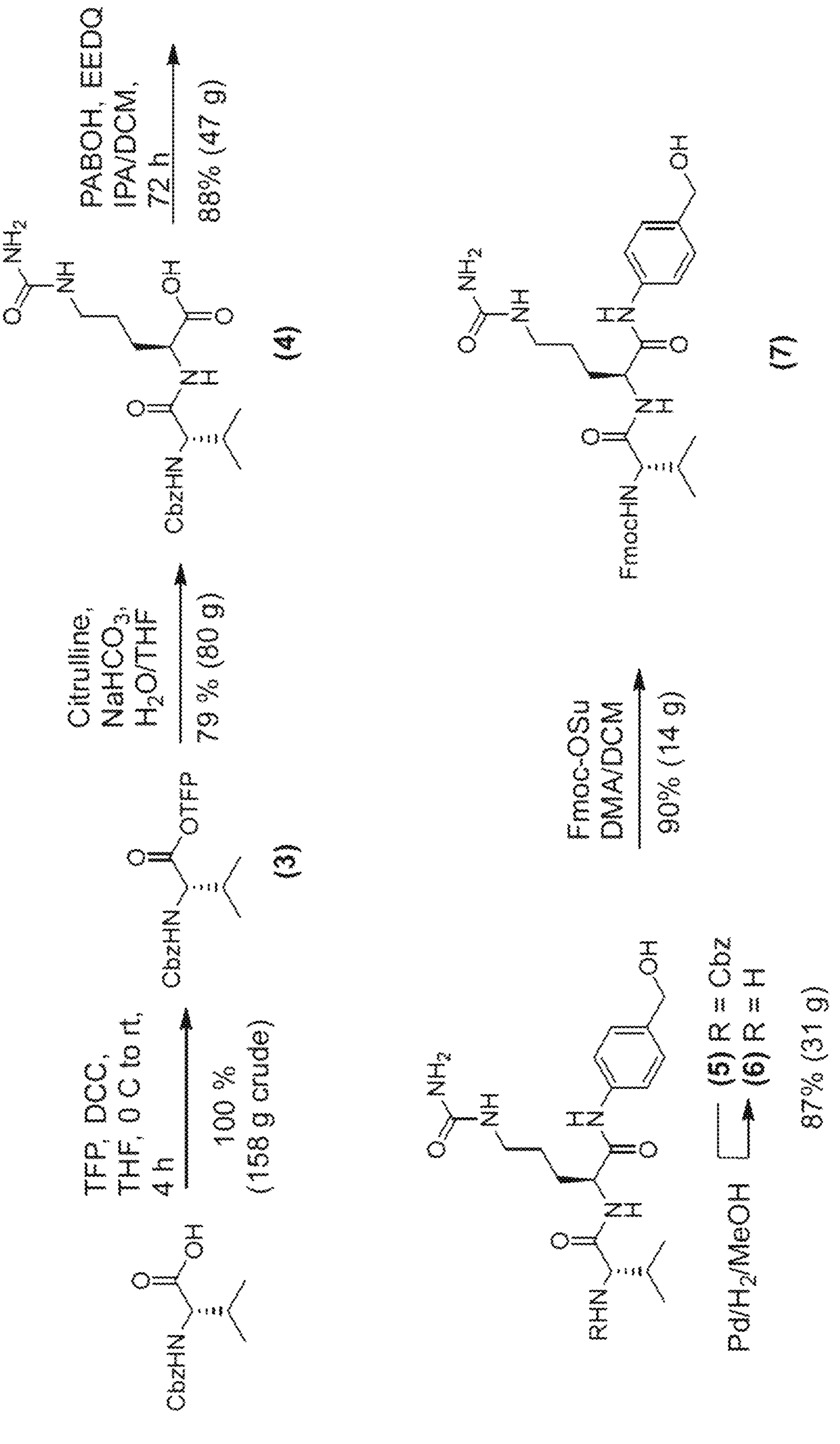
FIG. 1B shows the synthesis of Val-Cit cleavable linker 13.
Figure 1B:
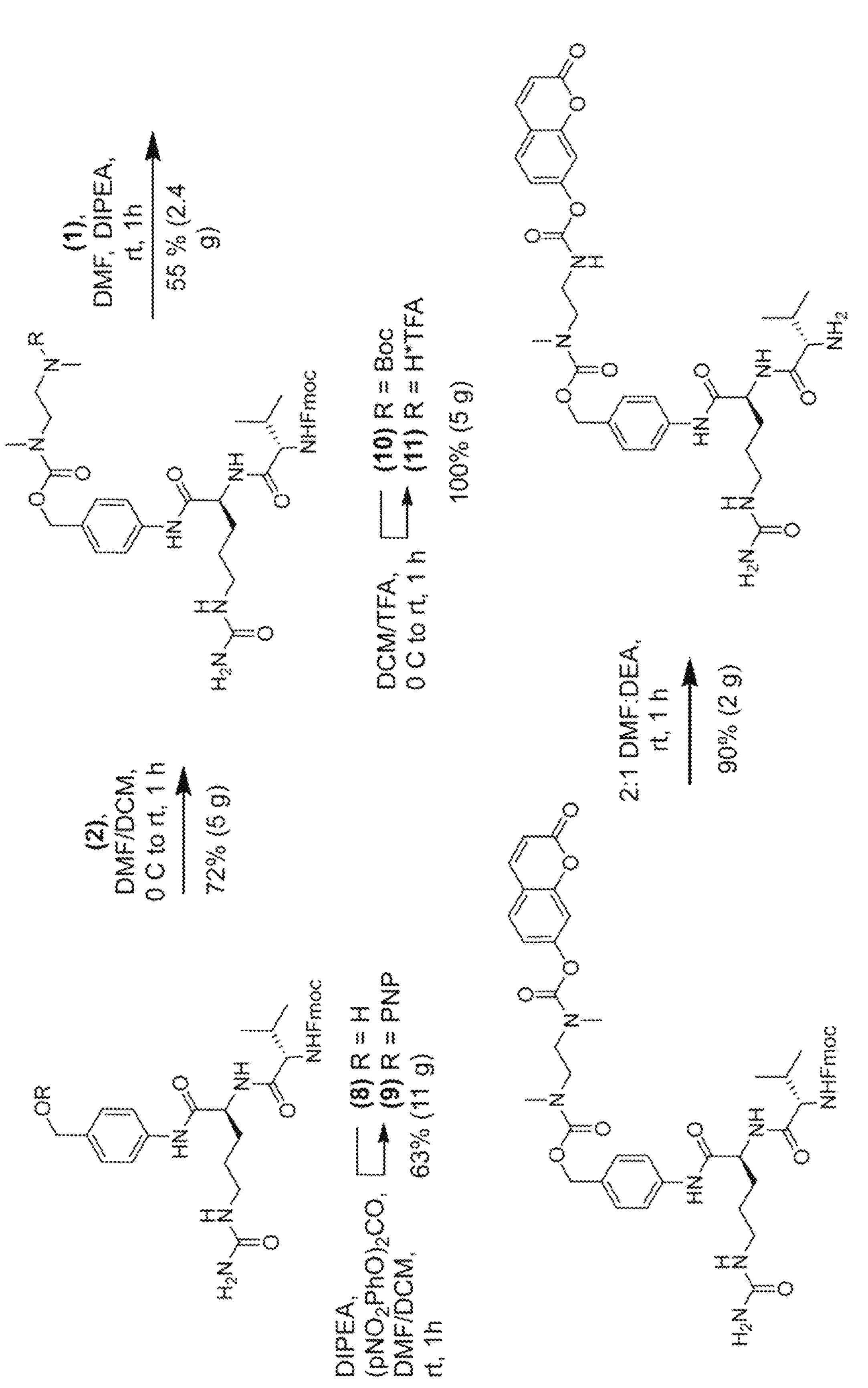
Figure 1B:
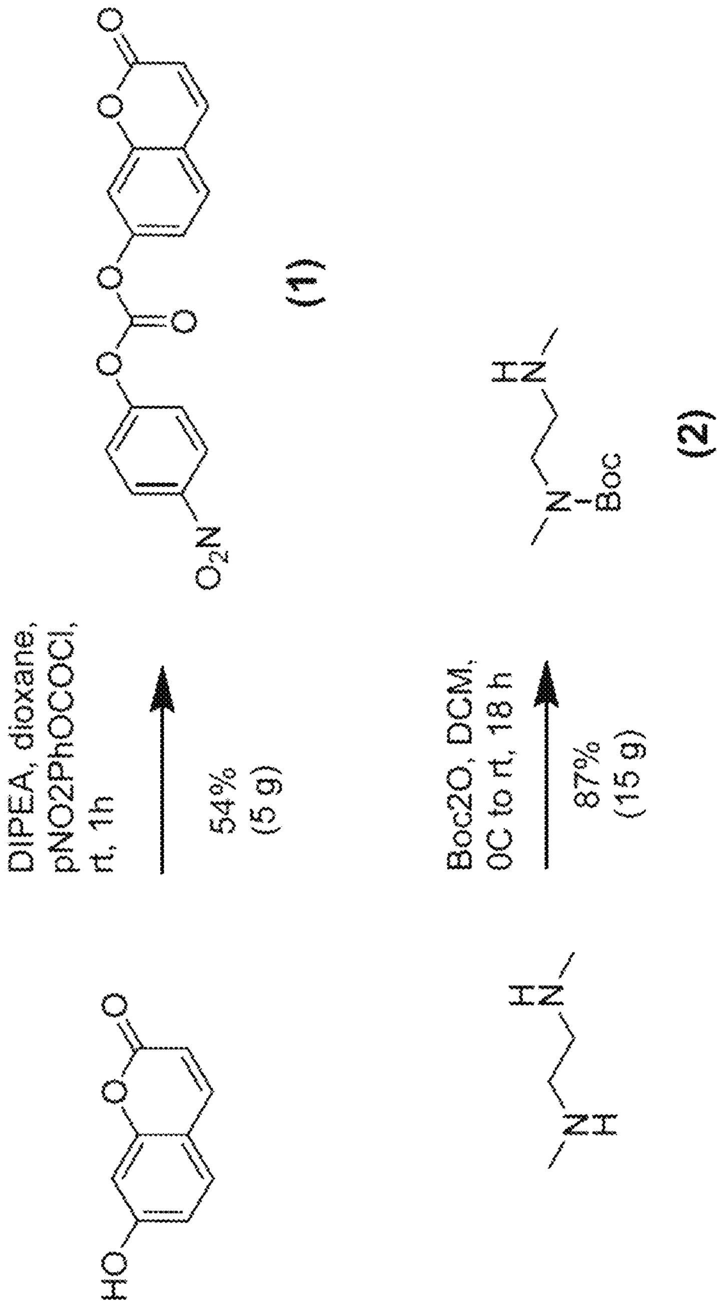

Synthesis of Compound 13 (FIG. 1B)

Synthesis of Compound 3

A 2 L flask was charged with Z-Val-OH (100 g, 398 mmol) and THF (100 ml). In a separate flask, 2,3,5,6-tetrafluorophenol (69.4 g. 418 mmol) was dissolved in THF (500 ml) and dcc (94.5 g, 458 mmol) was added in a single portion. After dissolution the mixture was placed in an addition funnel and added to the acid dropwise and the reaction was stirred overnight. The flask was chilled in an ice bath and the precipitate was filtered off. The solvent was removed on the rotary evaporator and the residue taken up in dichloromethane, allowed to stand for 2 hours at 4° C., and the solid was filtered off. The solvent was removed under reduced pressure to provide 196 g of 3 as a crude solid that was used in the subsequent step without further purification or characterization.

Synthesis of Compound 4

To a 1 L 3-neck flask was added H-Cit-OH (66 g, 376 mmol), $NaHCO_3$ (96 g, 1143 mmol), and DI water (300 mL). The mixture was stirred until dissolution was complete and then THF (200 mL) was added. This mixture was warmed to 35° C. In a separate flask crude Z-Val-TFP ester 3 (100 g, 250 mmol) was dissolved in THF (200 mL) and then added dropwise vial addition funnel. The reaction was stirred for 24 hours. The reaction was diluted with water (1 L) and washed with ethyl acetate (3×300 mL). The solution was acidified with 10% HCl until pH 3. The resultant precipitated product was collected on a Buchner funnel. The solid was once again dissolved in saturated aqueous $NaHCO_3$ (400 mL) and heated until dissolution. An additional 200 mL of water was added and the aqueous solution was extracted with ethyl acetate (4×100 mL). The aqueous layer was then placed in a flask fitted with an overhead stirrer and acidified to by the addition of 10% citric acid, and after white precipitate began to form additional water was added to aid with stirring. The addition of 10% citric acid was continued until the pH reached 3.1. The resulting slurry was collected on a Buchner funnel, the solid was rinsed with water (2×500 mL) while on the Buchner. The solid was slurried in toluene and the toluene was removed until no further water was azeotroped. Drying provided 80.4 g of a white solid. The solid was dissolved in 1.6 L of refluxing methanol, 4.8 L of MTBE was added, and the solution was cooled to room temp overnight. The solid was collected to provide 68 g (67%) of (4) as a white powdery solid. TLC (80:20 DCM:MeOH/HCOOH) was a single spot $R_f$=0.23. The product was characterized by LRMS (calculated: 408.2, observed: 409.3 $[M+H]^+$), HPLC, and $^1H$ NMR ($d_6$-DMSO).

Synthesis of Compound 5

A 5 L 3-neck flask was charged with Z-Val-Cit-OH (4) (42.6 g, 104 mmol) and 2-propanol (1.1 L) and DCM (3.1 L). The suspension was stirred and (4-aminophenyl)methanol (25.7 g, 209 mmol) was added in a single portion followed by ethyl 2-ethoxyquinoline-1(2H)-carboxylate (51.6 g, 209 mmol). The flask was held at 22° C. for 48 h. HPLC indicated complete consumption of starting material. The solvent was reduced to ~500 mL on the rotary evaporator and 1.5 L of ether was added while stirring. The solid was collected on a Buchner funnel and rinsed with MTBE. The solid was suspended in 1.5 L of MTBE with vigorous stirring for 15 minutes, collected on a Buchner funnel, and dried under high vacuum to give a pale yellow powdery solid. The solid was suspended in 250 mL MTBE and stirred vigorously overnight. The solid was collected on a Buchner funnel and dried under high vacuum to provide 47.3 g (88%) of Compound 5 as a pale yellow powdery solid. The product was characterized by HPLC and $^1H$ NMR ($d_6$-DMSO).

Synthesis of Compound 6

A 2 L 3-neck flask fitted with an overhead stirrer was charged with methanol-wet 10% palladium on activated charcoal (5.01 g) and methanol (628 mL). A hydrogen purge was started. Z-Val-Cit-PABOH 5 (48.38 g, 94 mmol) was dissolved in DMF (314 mL) and added to the flask and the mixture was stirred under a hydrogen purge for 5 hours. HPLC indicated consumption of the starting material. The reaction was filtered over methanol-wet celite, rinsed with methanol, and the solvent removed on the rotary evaporator. The oil was taken up in ~500 mL methanol and Darco was added. The flask was spun on the rotary evaporator in a warm water bath for ten minutes and then filtered over celite. Concentration gave a pale yellow oil that was triturated with ether (500 mL) to give an off-white gummy solid that was dried under high vacuum overnight. The solid was crushed under ether, the solvent decanted, and the solid was dried under high vacuum. The solid was then stirred vigorously in ether for 3 hours and collected on a Buchner funnel. This was repeated once more, the solid was rinsed with MTBE, and then dried under high vacuum to provide 31.18 g (87%) of Compound 6 as a white powdery solid. The product was characterized by LRMS (calculated: 379.22, observed: 380.3 $[M+H]^+$) and $^1$H NMR ($d_6$-DMSO).

Synthesis of Compound 7

A flask fitted with an overhead stirrer was charged with (9H-fluoren-9-yl)methyl (2,5-dioxopyrrolidin-1-yl) carbonate (9.78 g, 29.0 mmol) and dichloromethane (439 mL). The flask was chilled in an ice bath. H-Val-Cit-PABOH (6) (10 g, 26.4 mmol) was dissolved in N,N-dimethylacetamide (88 ml) and added dropwise to provide a very thick slurry. The ice bath was removed and the reaction was stirred for 2 hours. HPLC and TLC (80:20 DCM:MeOH/HCOOH) also indicated consumption of starting material. The reaction was stirred for an additional 2 hours and the solvent was removed on the rotary evaporator to give a thick slurry of product in DMA. Ethyl acetate (400 mL) was added to the slurry with vigorous stirring and the precipitate was collected on a Buchner funnel and rinsed with ethyl acetate. This was repeated two more times. The solid was then suspended in 400 mL ether, collected on a Buchner, and dried under high vacuum to give 14.05 g (89%) of Compound 7 as a pale orange solid. TLC (85:15 DCM:MeOH) was a single spot $R_f$=0.36. The product was characterized by HPLC and $^1$H NMR ($d_6$-DMSO).

Synthesis of Compound 8

A 500 mL 3-neck flask was charged with Fmoc-Val-Cit-PABOH (7) (14.05 g, 23.35 mmol) and DMF (195 mL). Bis(4-nitrophenyl) carbonate (14.21 g, 46.7 mmol) was dissolved in dichloromethane (195 mL) and added dropwise followed by the dropwise addition of N,N-diisopropylethylamine (8.16 mL, 46.7 mmol) dissolved in dichloromethane (10 mL). The reaction was stirred at room temperature for 18 hours. TLC (85:15 DCM:MeOH) and HPLC indicated consumption of starting material and formation of one major product. The solvent was removed on the rotary evaporator and ether was added to induce precipitation.

The solid was stirred vigorously for 15 minutes and collected on a Buchner. This was repeated once more with 200 mL ether and then with 100 mL MTBE. The solid was suspended in 100 mL ethyl acetate and collected on a Buchner. This was repeated once more. TLC indicated the filtrates contained impurities and the solid was fairly pure product. The solid was suspended in DCM and collected on a Buchner and then suspended in THF and collected on a Buchner. Drying under high vac provided (149.789-161.046=) 11.257 g of an off-white powdery solid. TLC (85:15 DCM:MeOH) was a single spot $R_f$=0.60. The purity was verified by HPLC and the product was carried into the subsequent step without further purification or characterization.

Synthesis of Compound 9

A 200 mL flask was charged with Fmoc-Val-Cit-PAB-PNP (8) (6.551 g, 8.54 mmol) and DMF (31 mL) and stirred vigorously until dissolution. The solution was then chilled to 0° C. In a separate flask, tert-butyl methyl(2-(methylamino) ethyl)carbamate (2) (1.769 g, 9.40 mmol) was dissolved in dichloromethane (8 mL) and added to the PNP carbonate dropwise. The reaction was warmed to room temperature and stirred for 1 hour. TLC (90:10 DCM:MeOH) and HPLC both indicated consumption of starting material and formation of a single major product. The reaction was filtered over a small Buchner to remove the solid residue and the flask was chilled in an ice bath and 360 mL ether was added dropwise to induce precipitation. The flask was stirred in the ice bath for 90 minutes and the solid was then collected on a Buchner and rinsed with ether. The solid was suspended in ether once more and collected on a Buchner. Drying under high vacuum provided 5.0 g (72%) of (9) as a pale tan powdery solid. TLC (90:10 DCM:MeOH) was a single spot $R_f$=0.44. The product was characterized by LRMS (calculated: 815.4, observed: 854.5 $[M+K]^+$), HPLC, and $^1$H NMR ($d_6$-DMSO).

Synthesis of Compound 10

To a cold flask of solid Compound 9 (5 g, 6.1 mmol) was added chilled 1/1 TFA/dichloromethane (82 mL) with stirring and the solid slowly dissolved. The flask was slowly allowed to reach room temp with stirring. After 30 min TLC (85:15 DCM:MeOH/$NH_4OH$) and HPLC indicated consumption of starting material and formation of a single major product. Most of the solvent was removed on the rotary evaporator, the flask was chilled in an ice bath, and 300 mL of ether was added. The precipitate was scraped from the sides of the flask, stirred an additional 15 minutes in the ice bath, and then collected on a Buchner. The solid was suspended once again in 300 mL of ether and stirred vigorously for 30 minutes. The solid was collected on a Buchner and dried under high vacuum to provide 5.1 g of Compound 10 as a white powdery solid. TLC (85:15 DCM:MeOH/$NH_4OH$) was a single spot $R_f$=0.21. The product was characterized by LRMS (calculated: 715.5, observed: 716.5 $[M+H]^+$), HPLC, $^1$H NMR ($d_6$-DMSO), and used in the subsequent step without further purification.

Synthesis of Compound 11

A flask was charged with Compound 10 (4 g, 4.82 mmol) and DMF (24 mL) and chilled in an ice bath. 4-nitrophenyl (2-oxo-2H-chromen-7-yl) carbonate (1) (2.051 g, 6.27 mmol) was added, the mixture was stirred until dissolution. N,N-diisopropylethylamine (1.01 mL, 5.78 mmol) was added slowly dropwise via syringe. After 60 minutes HPLC and TLC (85:15 DCM:MeOH/$NH_4OH$) indicated consumption of the starting materials and formation of a major product along with a minor less polar product. Ether (300 mL) was added and the flask was placed in an ice bath with vigorous stirring for 2 hours. The resulting solid was collected on a Buchner. The solid was dissolved in 500 mL of 90:10 DCM:MeOH/TFA, pre-absorbed onto 16 g of silica gel, and purified on a 220g column using DCM and 9:1 MeOH/TFA. The appropriate tubes (tubes 5-10 and tubes 14-39) were pooled and concentrated to give two fractions as oily residues, F1 and F2. To each fraction was added 300 mL of ether was added to induce precipitation and the flask was stirred in an ice bath for 1 hour and collected on a Buchner. The solid was again suspended in 100 mL of ether with vigorous stirring for 1 hour and then collected on a Buchner. Drying under high vacuum provided the fractions F1 (142 mg) and F2 (2.38 g, 55%) as pale yellow powdery solids. Analysis by LRMS and NMR indicated F1 was the PNP carbamate 12 and F2 was the desired product 11. TLC (90:10 DCM:MeOH) was a single spot $R_f$=0.29. The product was characterized by LRMS (calculated: 903.4, observed: 904.4 $[M+H]^+$, 926.4 $[M+Na]^+$), HPLC, and $^1$H NMR ($d_6$-DMSO).

Synthesis of Compound 13

Figure 1C:
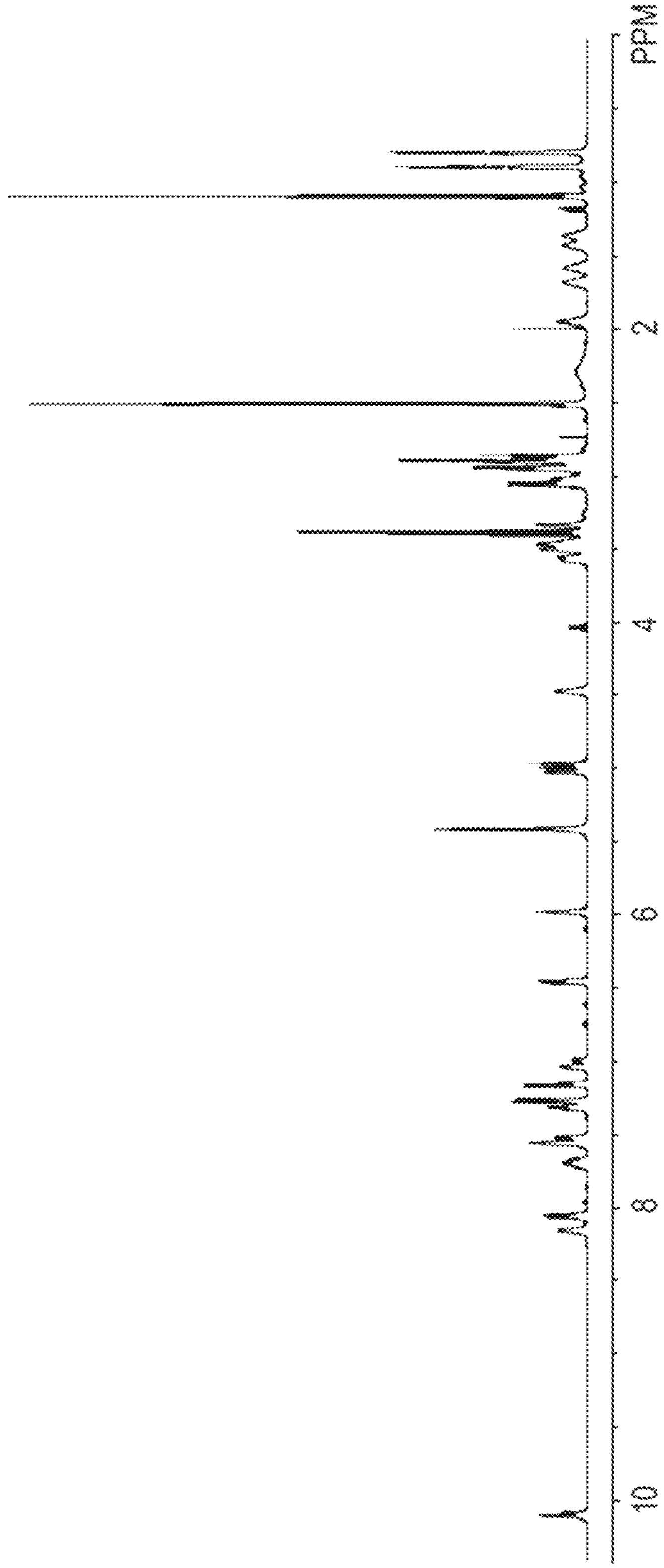
FIG. 1C provides the $^1$H NMR and HPLC spectrum obtained for Compound 13 of FIG. 1B.
Figure 1C:
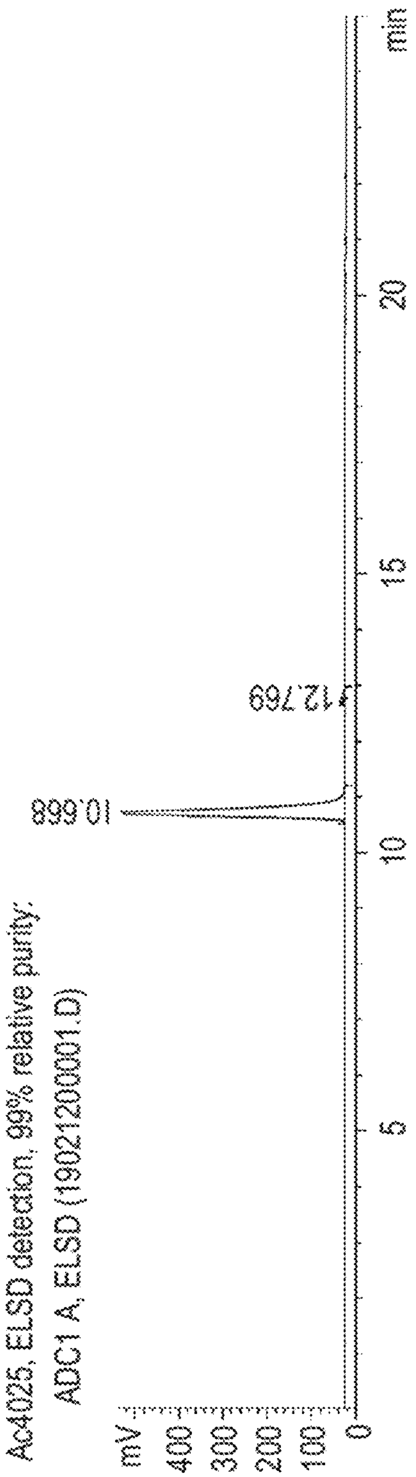

DMF (10.4 mL) and diethylamine (10.1 mL, 97 mmol) were placed in a round bottom flask. In a separate flask, Compound 11 (2.82 g, 3.12 mmol) was dissolved in DMF (10.4 mL) and added dropwise to the amine. The reaction was stirred at room temperature for 30 min. HPLC and TLC (85:15 DCM:MeOH/$NH_4OH$) indicated complete consumption of sm. The solvent was removed on the rotary evaporator, a few mL of ethyl acetate was added followed by ether (150 mL). The resultant slurry was placed in an ice bath and stirred vigorously for 30 minutes, allowed to settle, and the solvent was decanted. To the solid was added 20 mL of ethyl acetate followed by 75 mL of ether. The slurry was allowed to stir vigorously in an ice bath for 1 hour and the solvent decanted. The residue was dried under high vacuum and then suspended in 100 mL of ether with vigorous stirring overnight. The solid was collected on a Buchner funnel and rinsed with a small amount of ether. Drying under high vac provided 1.912 g of Compound 13 as a white powdery solid. TLC (85:15 DCM:MeOH/$NH_4OH$) was a single spot $R_f$=0.33. The product was characterized by LRMS (calculated: 681.3, observed: 682.4 $[M+H]^+$), HPLC, and $^1H$ NMR ($d_6$-DMSO) (FIG. 1C).

Figure 3A:
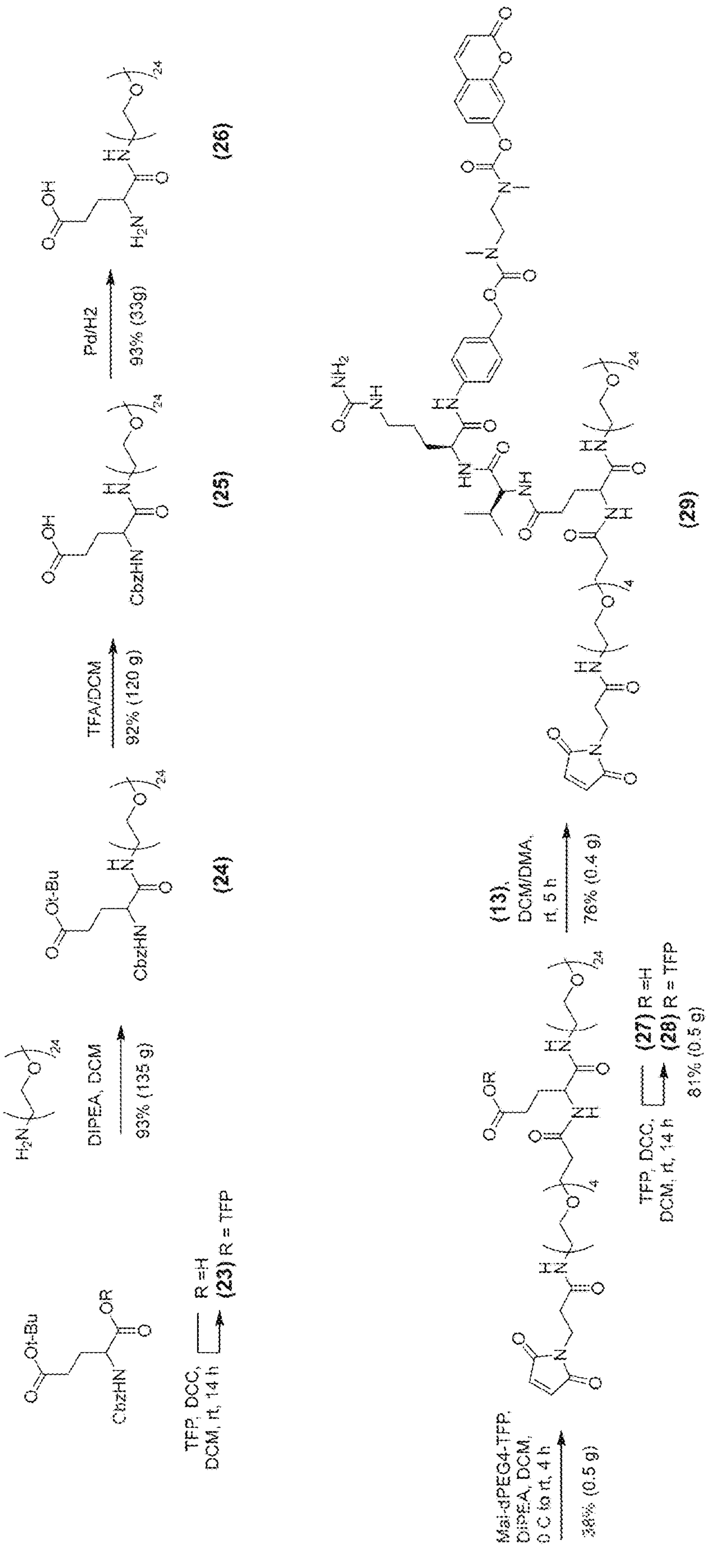
FIG. 3A shows the synthesis of conjugate 29, where x=24 and y=1 [D].

Synthesis of Compound 29 (FIG. 3A)

Synthesis of Compound 23

A 2 L flask was charged with Z-Glu(TBE)-OH (200 g, 593 mmol) and dichloromethane (1 L). In a separate flask EDC (131 g, 682 mmol) and 2,3,5,6-tetrafluorophenol (103 g, 622 mmol) were dissolved in dichloromethane (500 mL) and then added dropwise via addition funnel. The reaction was stirred at ambient temperature for 16 hours. TLC (60:40 hexanes:ethyl acetate) and HPLC indicated a single major product. The reaction was poured into a separatory funnel and washed with water (200 mL), 10% HCl (3×200 mL), brine (200 mL), dried over $MgSO_4$, filtered, and concentrate to provide 295 g (100%) of Compound 23 as a white powdery solid. TLC (60:40 hexanes:ethyl acetate) was a single spot $R_f$=0.7. The product was characterized by HPLC and $^1H$ NMR ($CDCl_3$), and used without further purification.

Synthesis of Compound 24

A 1 L flask was charged with Z-Glu(TBE)-OTFP (23) (50 g, 103 mmol) and dichloromethane (250 mL). In a separate flask, m-dPEG®$_{24}$-amine (118 g, 108 mmol) was dissolved in dichloromethane (250 mL) and N,N-diisopropylethylamine (36 mL, 206 mmol) was added via syringe. The mixture was poured into an addition funnel and added dropwise. The reaction was 48 hours at ambient temperature. TLC (90:10 DCM:MeOH) and HPLC showed a single major product. The reaction was diluted with 500 mL of dichloromethane and washed with 10% HCl (3×200 mL), washed with brine (200 mL), dried over $MgSO_4$, filtered over celite, and concentrated under reduced pressure to give 159 g (100%) of Compound 24 as an off-white powdery solid. TLC (90:10 DCM:MeOH, visualized with iodine) was a single major spot $R_f$=0.47 plus residual 2,3,5,6-tetrafluorophenol The purity was verified by HPLC and the product was used in the subsequent step without further purification or characterization.

Synthesis of Compound 25

A 100 mL flask was charged with Compound 24 (135 g, 96 mmol) and formic acid (185 mL, 4800 mmol) and stirred at 35° C. overnight. Both TLC (90:10 DCM:MeOH) and HPLC indicated complete consumption of starting material. The solvent was removed on the rotary evaporator and the oil was taken up in 1 L water and washed with ethyl acetate (3×200 mL) and MTBE (200 mL). The aq phase was acidified, salt was added, and the product was extracted with dichloromethane (3×500 mL). The organics were combined, washed with brine, dried over $MgSO_4$, filtered, concentrated, and dried under high vacuum to provide 119 g (92%) of (25) as an off-white waxy solid. TLC (90:10 DCM:MeOH, visualized with iodine) was a single spot $R_f$=0.30. The product was characterized by MALDI (calculated: 1350.750, observed: 1373.641 $[M+H+Na]^+$, 1389.626 $[M+H+K]^+$), HPLC, and $^1H$ NMR ($CDCl_3$).

Synthesis of Compound 26

A 1 L flask was charged with methanol-wet 10% palladium on activated charcoal (4.09 g) and methanol (592 mL). A hydrogen purge was started and Compound 25 (40 g, 29.6 mmol) was dissolved in a small amount of methanol and added to the flask and the reaction was stirred for 3 hours. HPLC indicated complete consumption of starting material. The palladium was filtered off over a methanol-wet bed of celite and the solvent was removed under reduced pressure. Trituration with MTBE and drying under high vacuum provided 33.4 g (93%) of Compound 26 as a white powdery solid. TLC (80:20 DCM:MeOH/$NH_4OH$, visualized with iodine) was a single streaky spot $R_f$=0.21. The product was characterized by MALDI (calculated: 1216.713, observed: 1217.644 $[M+H]^+$, 1239.613 $[M+H+Na]^+$, 1255.590 $[M+H+K]^+$), HPLC, and $^1H$ NMR ($CDCl_3$).

Synthesis of Compound 27

A 50 mL flask was charged with Mal-dPEG 4-TFP ester (0.5 g, 0.886 mmol) and dichloromethane (22 mL) and chilled in an ice bath. In a separate flask, Compound 26 (1.186 g, 0.974 mmol) was dissolved in dichloromethane (22 mL) and N,N-diisopropylethylamine (0.371 ml, 2.126 mmol) was added via syringe. The mixture was then added dropwise via addition funnel, the ice bath was removed, and the reaction was stirred for 3 hours. Both TLC (85:15 DCM:MeOH) and HPLC indicated a single major product. The reaction was diluted to 150 mL with dichloromethane, washed with 10% HCl (4×20 mL), washed with brine, dried over $MgSO_4$, filtered over celite, and concentrated under reduced pressure. The residue was pre-absorbed onto 3 g of silica gel and purified on a 40 g column with dichloromethane and methanol. Tubes 7-10 were pooled and concentrated, the oil was taken up in dichloromethane, dried with $MgSO_4$ filtered over celite, concentrated, and dried under high vacuum to provide 538 mg (38%) of Compound 27 as a white solid. TLC (85:15 DCM:MeOH, visualized with iodine) was a single spot $R_f$=0.55. The purity was verified by HPLC and the product was used in the subsequent step without further purification or characterization.

Synthesis of Compound 28

A 50 mL flask was charged with 2,3,5,6-tetrafluorophenol (0.111 g, 0.666 mmol) and dichloromethane (22 mL). DCC (0.103 g, 0.499 mmol) was added in a single portion and stirred for ten minutes. In a separate flask, Compound 27 (0.538 g, 0.333 mmol) was dissolved in dichloromethane (11 mL) and added dropwise. The reaction was stirred overnight. Both TLC (85:15 DCM:MeOH) and HPLC indicated a single major product. The reaction was chilled in an ice bath and the DCU was filtered off using a syringe filter. The solvent was removed and the oil was taken up in acetonitrile and chilled in a nice bath. The resultant DCU was filtered off via syringe filter. Removal of the solvent provided an off-white oil that was suspended in ether and the solvent decanted. Drying under high vacuum gave an off-white solid that was again suspended in ether and the solvent decanted. Drying under high vacuum provided 478 mg (81%) of Compound 28 as a white solid. TLC (90:10 DCM:MeOH, visualized with UV and iodine) was a single spot $R_f$=0.34. The purity was verified by HPLC and the product was used in the subsequent step without further purification or characterization.

Synthesis of Compound 29-(D)

Figure 3B:
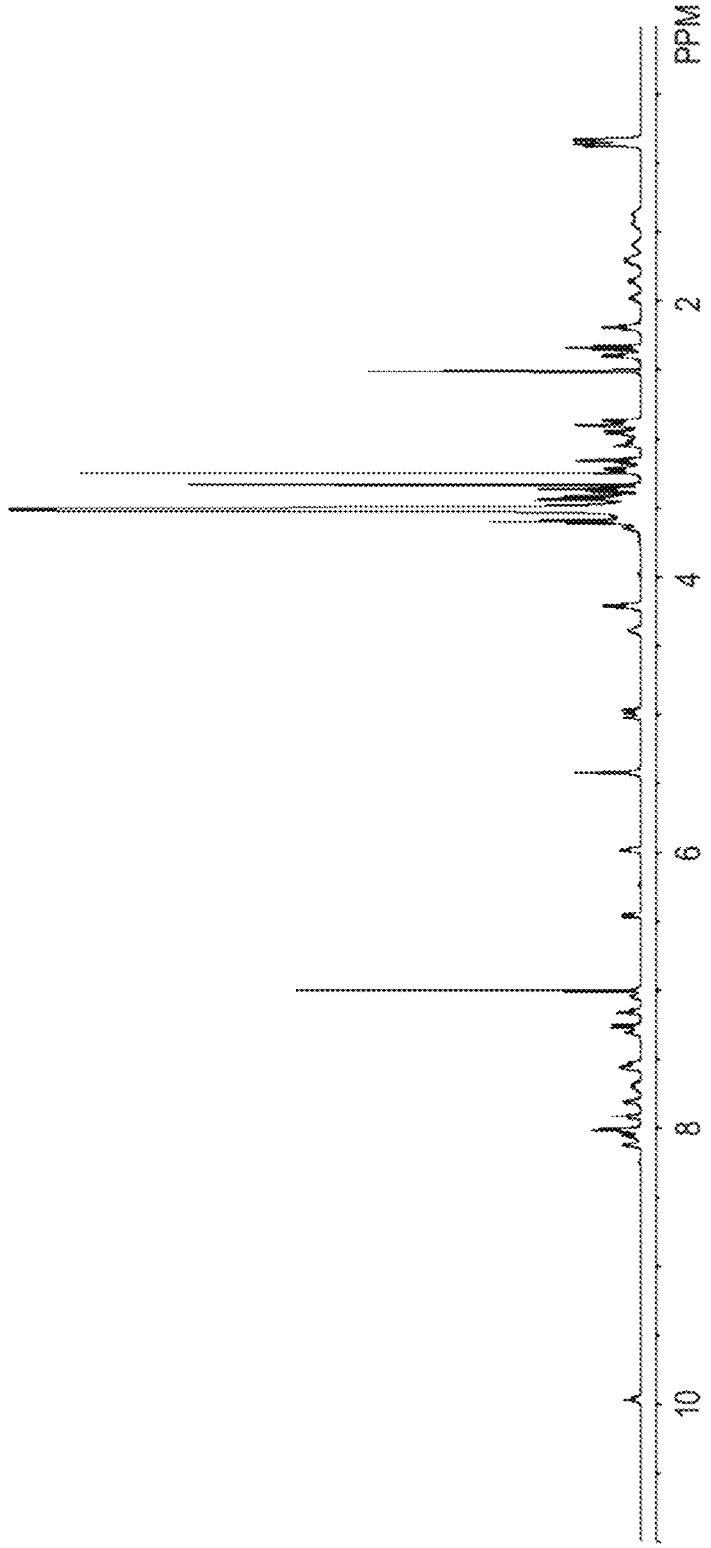
FIG. 3B provides the $^1$H NMR and HPLC spectrum obtained for Compound 29 of FIG. 3A
Figure 3B:
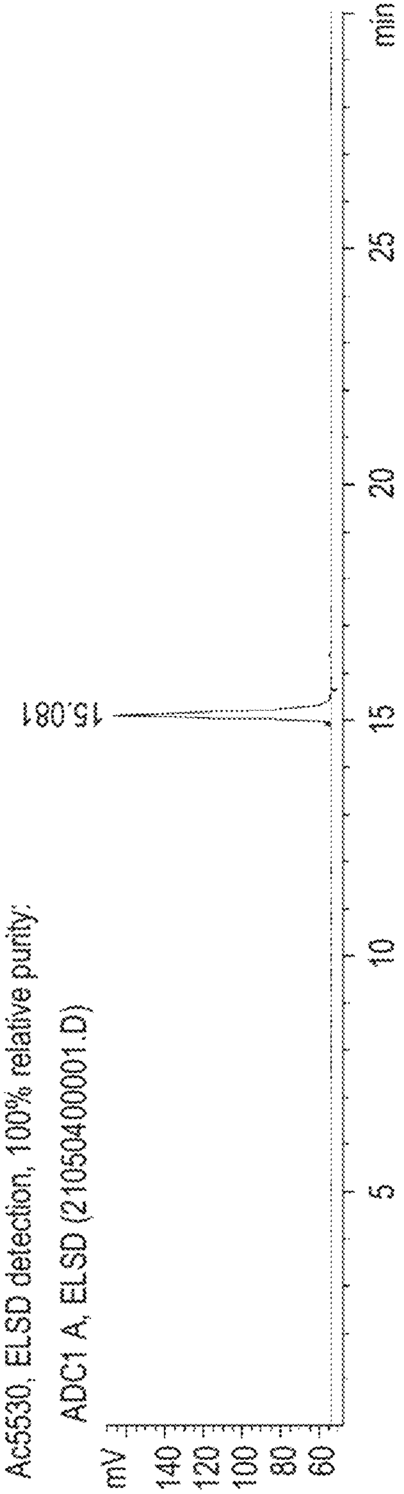

A 25 mL flask was charged with Compound 28 (0.36 g, 0.204 mmol) and dichloromethane (7 mL). In a separate flask (13) (0.160 g, 0.235 mmol) was dissolved in DMF (3 mL) and then added dropwise. The reaction was stirred at ambient temperature for 4 hours. Both TLC (85:15 DCM:MeOH) and HPLC indicated complete reaction. The solvent was removed under vacuum to give a viscous oil that was dried under high vacuum. The oil was dissolved in dichloromethane and pre-absorbed onto 2 g of silica gel and purified on a 12 g column with dichloromethane and methanol. Tubes 7-13 were pooled, concentrated, and dried under vacuum to provide 354 mg (76%) of Compound 29 as an off-white waxy solid. TLC (85:15 DCM:MeOH, visualized with UV and iodine) was a single spot $R_f$=0.57. The product was characterized by HRMS (calculated: 2278.1845, observed: 2279.1918 $[M+H]^+$), HPLC, and $^1H$ NMR ($d_6$-DMSO) (see FIG. 3B).

Figure 3C:
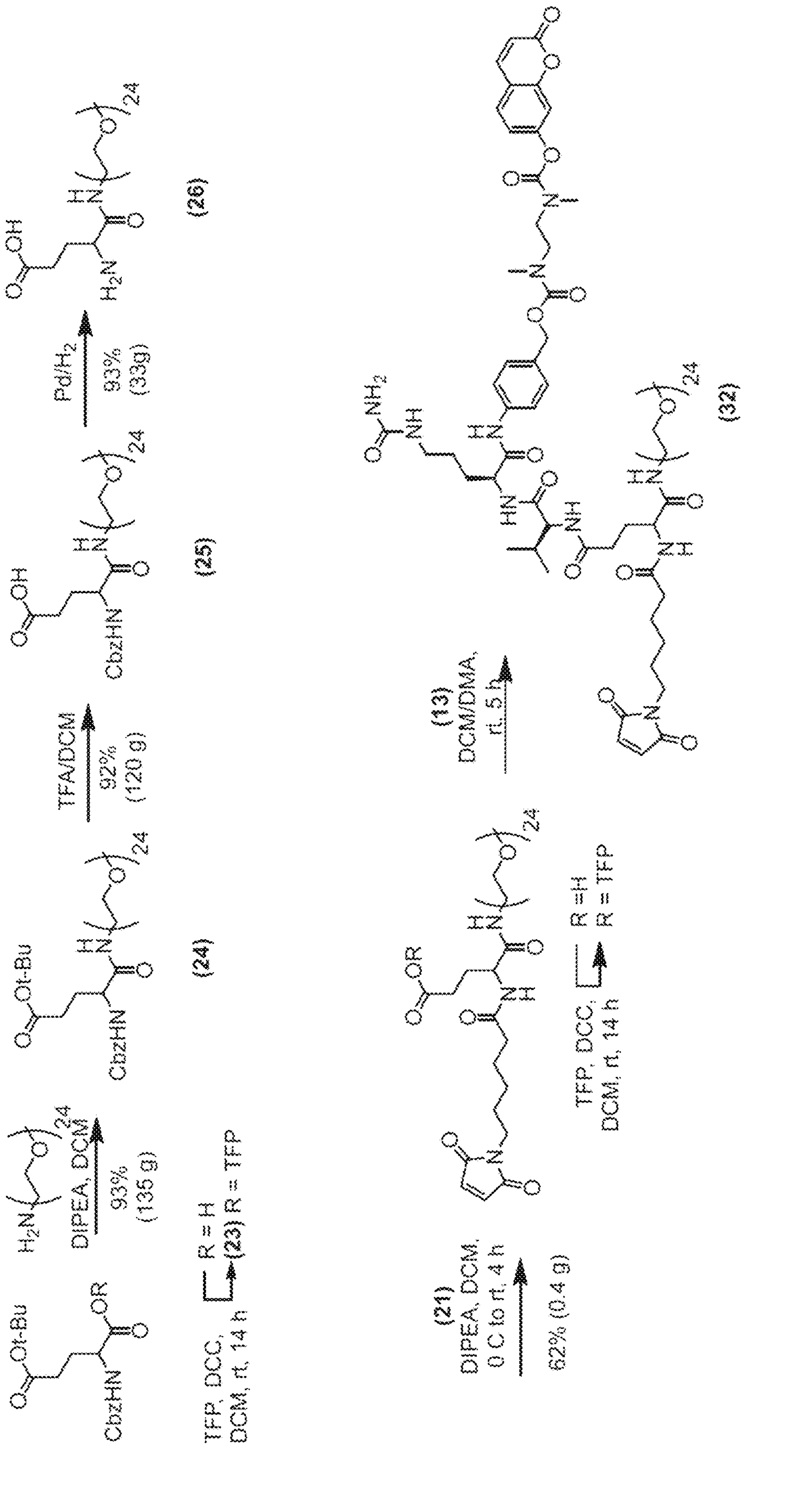
FIG. 3C shows the synthesis of conjugate 32, where x=24 and y=1 [E].

Synthesis of Compound 32 (FIG. 3C)

Synthesis of Compound 30

Compound 26 was prepared as described above for the synthesis of Compound 29.

A 50 mL flask was charged with Compound 21 (0.212 g, 0.591 mmol) and dichloromethane (12 mL) and chilled in an ice bath. In a separate flask, Compound 26 (0.6 g, 0.493 mmol) was dissolved in dichloromethane (12 mL) and N,N-diisopropylethylamine (0.207 ml, 1.183 mmol) was added. The mixture was placed in an addition funnel and added dropwise, the ice bath was removed, and the reaction was stirred for 3 hours. Both TLC (85:15 DCM:MeOH) and HPLC indicated formation of a single major product. The reaction was diluted with 75 mL dichloromethane, washed with 10% HCl (3×5 mL), and concentrated under reduced pressure. The residue was taken up in 75 mL water, washed with MTBE (3×10 mL), hexanes (10 mL), salt was added, the solution was acidified, and the product was extracted with dichloromethane (3×30 mL). The organics were dried over $MgSO_4$, filtered over celite, and concentrated under reduced pressure to provide 430 mg (62%) of Compound 30 as a white solid. TLC (85:15 DCM:MeOH, visualized with iodine) was a single spot $R_f$=0.51. The purity was verified by HPLC and the product was used in the subsequent step without further purification or characterization.

Synthesis of Compound 31

A 50 mL 3-neck flask was charged with 2,3,5,6-tetrafluorophenol (0.101 g, 0.610 mmol) and dichloromethane (20 mL). DCC (0.094 g, 0.457 mmol) was added in a single portion and after dissolution (30) (0.430 g, 0.305 mmol) was dissolved in dichloromethane (10 mL) and added dropwise via addition funnel. The reaction was stirred at overnight at ambient temperature. Both TLC (85:15 DCM:MeOH) and HPLC indicated complete consumption of starting material. The reaction was chilled in an ice bath and the DCU was filtered off over celite and rinsed with cold dichloromethane. The solvent was removed and the oil was taken up in acetonitrile and chilled in an ice bath. The DCU was filtered off via syringe filter. Removal of the solvent provided an orange oil that was suspended in ether and the solvent decanted. Drying under high vacuum gave a pale yellow solid. The solid was suspended in ether and the solvent decanted. Drying under high vacuum provided 399 mg (84%) of Compound 31 as a pale yellow powdery solid. TLC (85:15 DCM:MeOH, visualized with UV and iodine) was a single spot $R_f$=0.71. The purity was verified by HPLC and the product was used in the subsequent step without further purification or characterization.

Synthesis of Compound 32-(E)

Figure 3D:
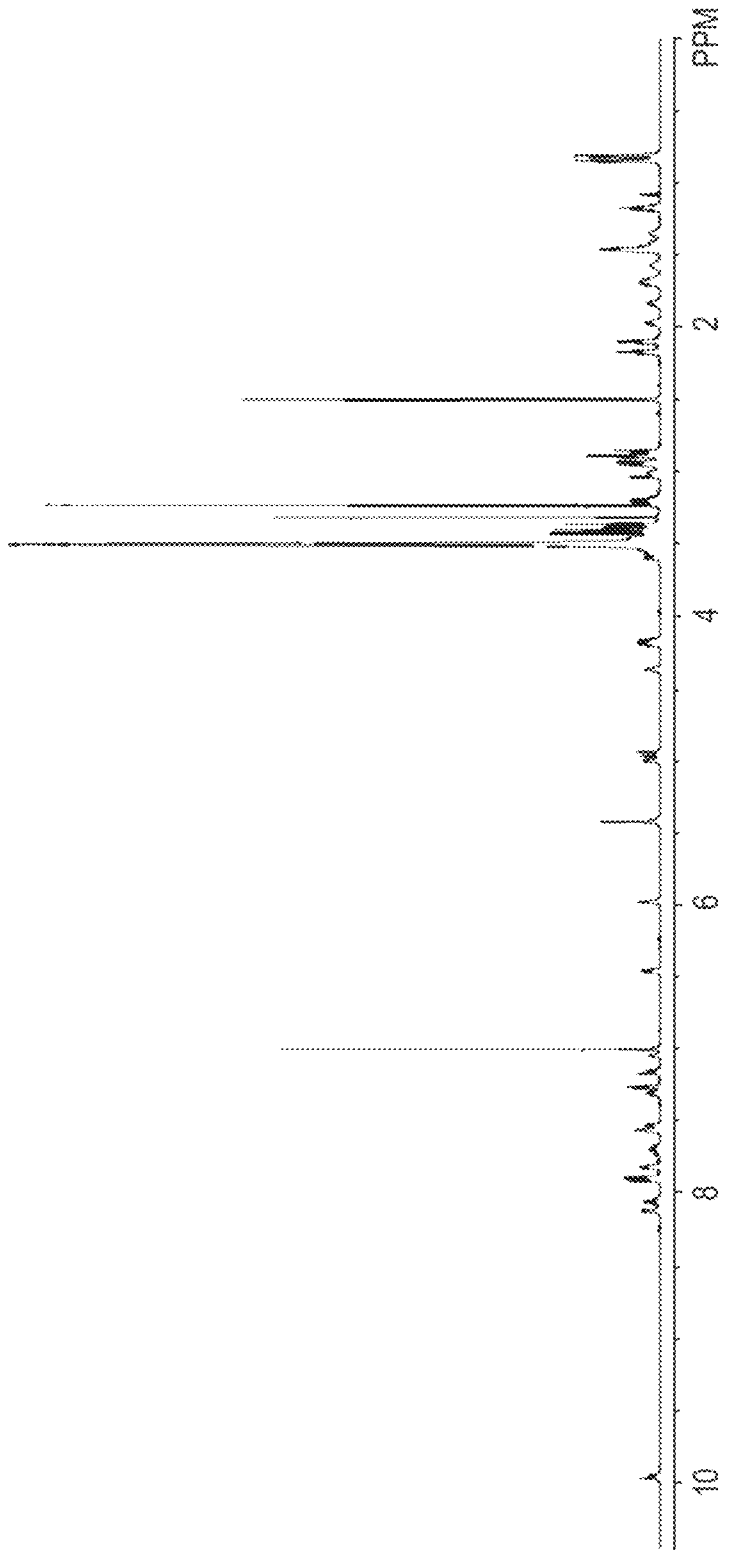
FIG. 3D provides the $^1$H NMR and HPLC spectrum obtained for conjugate 32 of FIG. 3C.
Figure 3D:
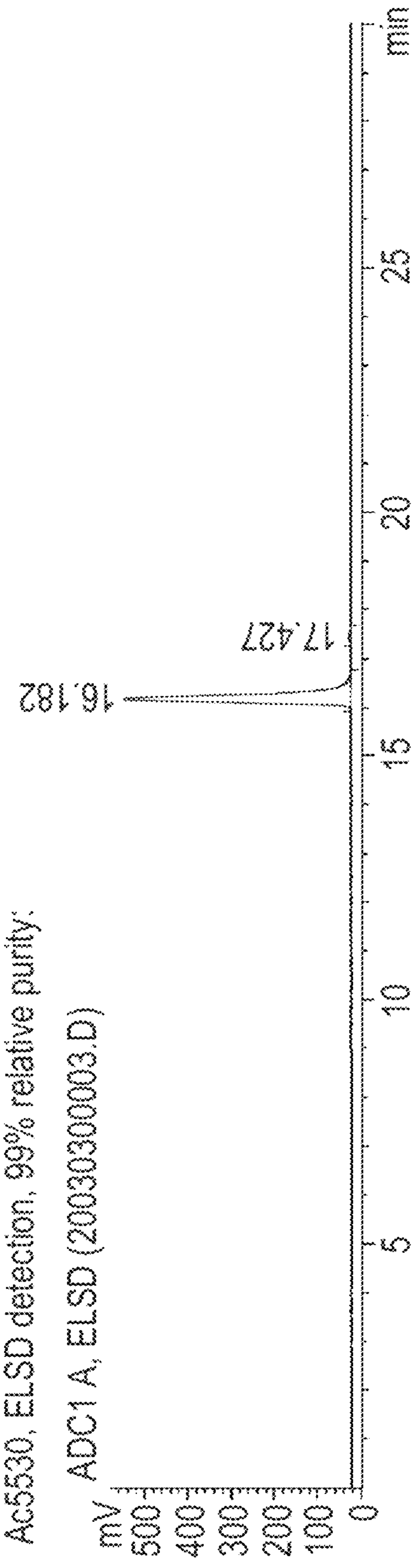

A 25 mL flask was charged with Compound (31) (0.38 g, 0.244 mmol) and dichloromethane (9 mL). In a separate flask Compound 13 (0.199 g, 0.293 mmol) was dissolved in DMF (4 mL) and added dropwise. The reaction was stirred at ambient temperature for three hours. Both TLC (85:15 DCM:MeOH) and HPLC indicated complete reaction. The solvent was removed under vacuum to give a viscous oil. Hexanes was added and then decanted from the oil, which was rinsed once more with hexanes. The oil was dried under high vacuum and then trituration with ether provided an oily solid. The residue was pre-absorbed onto 2 g of silica gel and purified on a 12 g column with dichloromethane and methanol. Tubes 6-12 were pooled and concentrated to give an oil that was triturated with ether and dried under high vacuum to provide 414 mg (82%) of Compound 32 as a white waxy solid. TLC (85:15 DCM:MeOH, visualized with UV and iodine) was a single spot $R_f$=0.55. The product was characterized by FT-ICR (calculated: 2073.0895, observed: 2073.0989 $[M+H]^+$, 2097.0928 $[M+H+Na]^+$, 2113.0577 $[M+H+K]^+$), HPLC, and $^1H$ NMR ($d_6$-DMSO) (FIG. 3D).

Figure 6A:
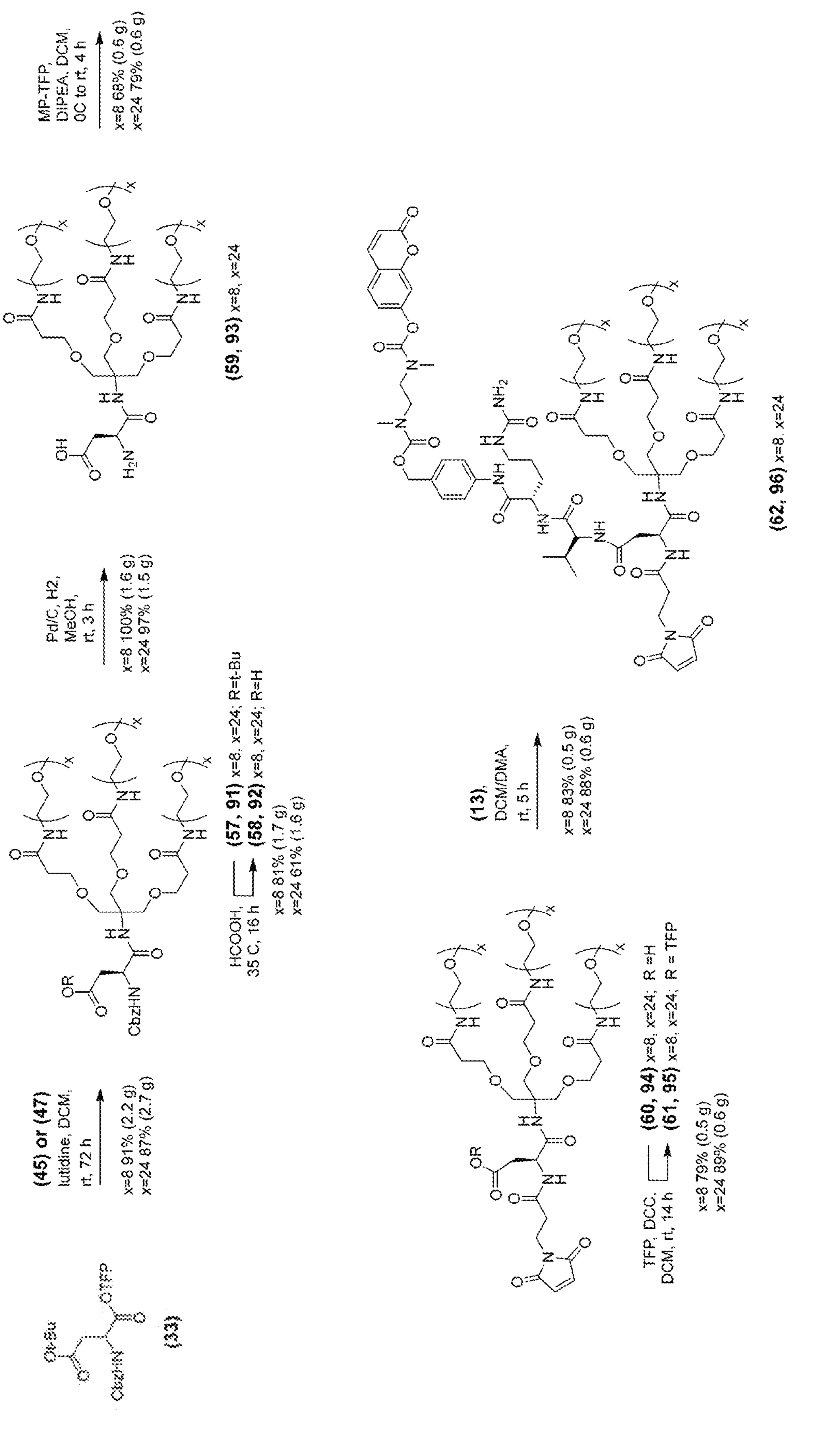
FIG. 6A shows the synthesis of conjugates 62 (L, x=8, y=3) and 96 (R, x=24, y=3) of Formula (II) disclosed herein.
Figure 6B:
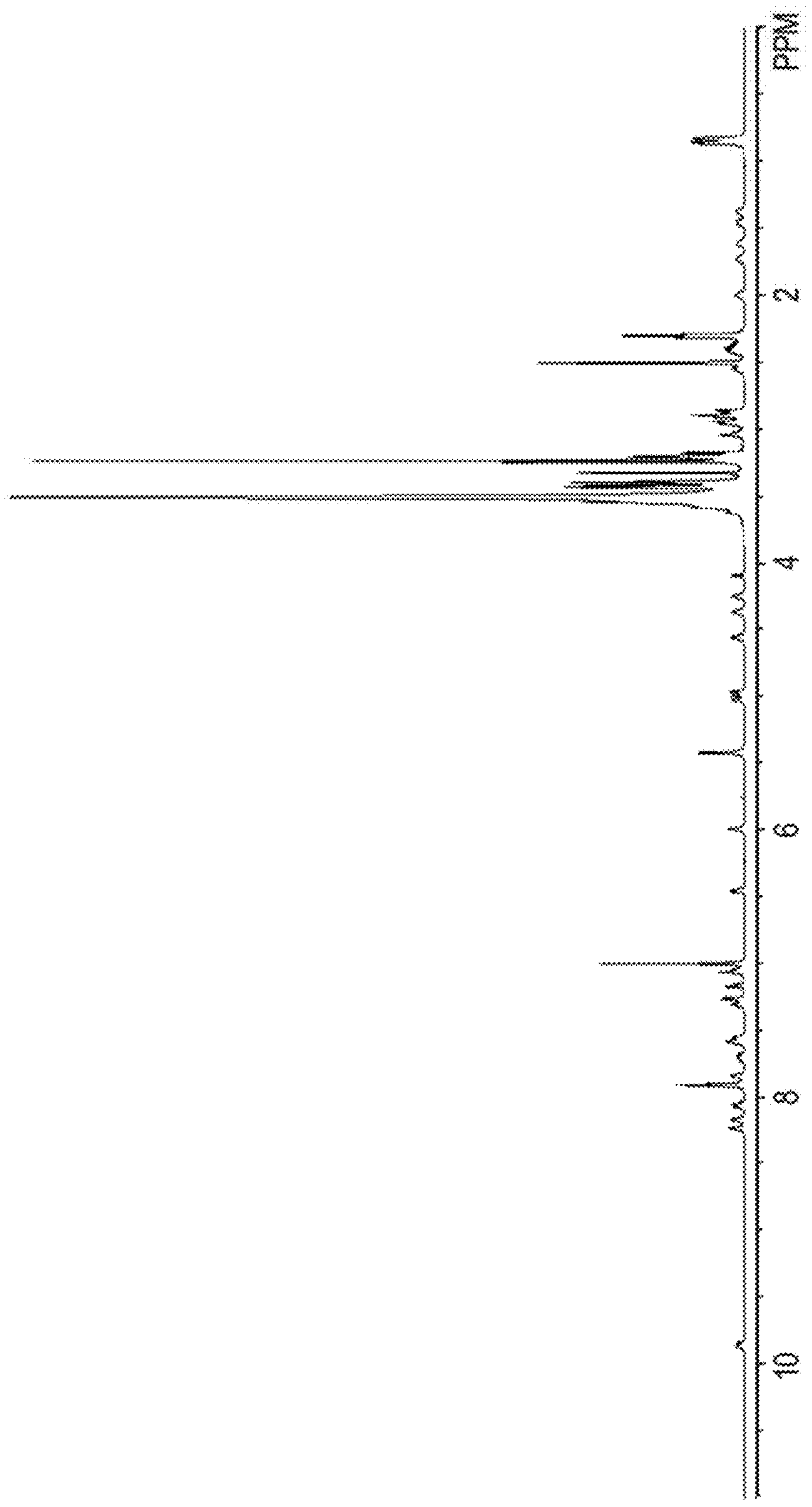
FIG. 6B provides the $^1$H NMR and HPLC spectrum obtained for conjugate 62 of FIG. 6A.
Figure 6B:
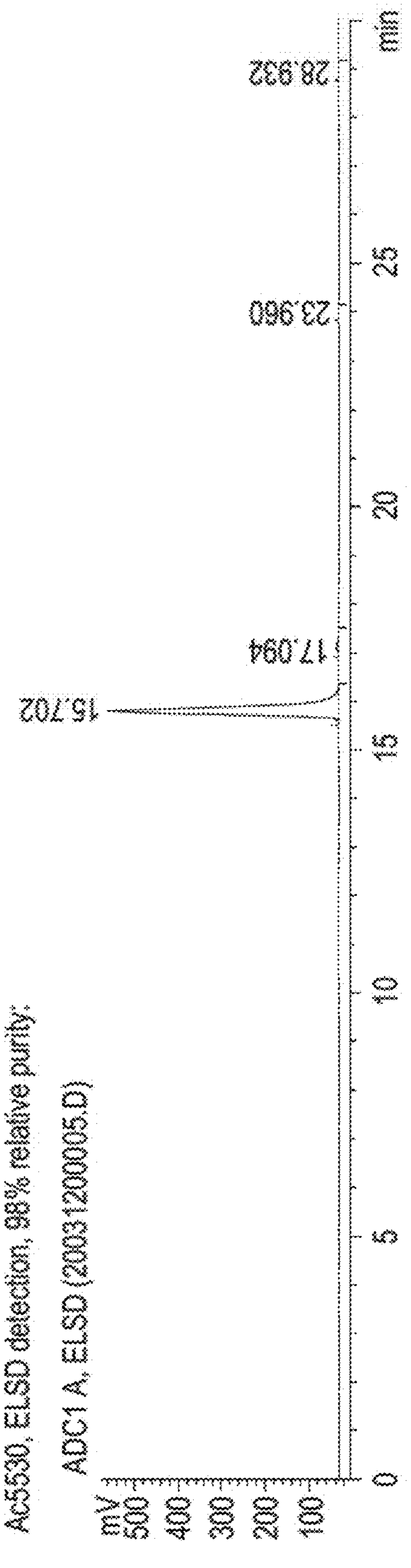
Figure 6C:
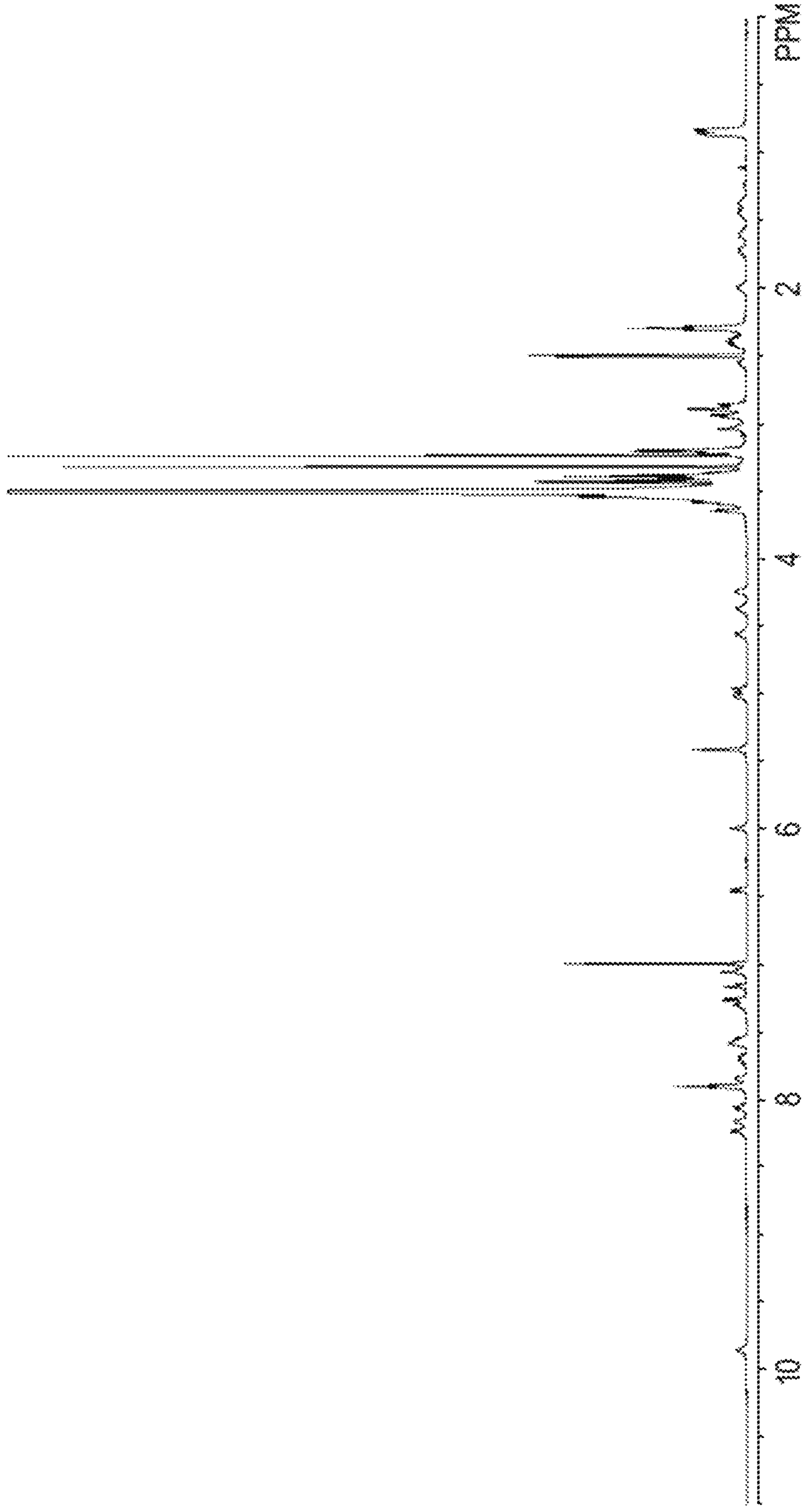
FIG. 6C provides the $^1$H NMR and HPLC spectrum obtained for conjugate 96 of FIG. 6A.
Figure 6C:
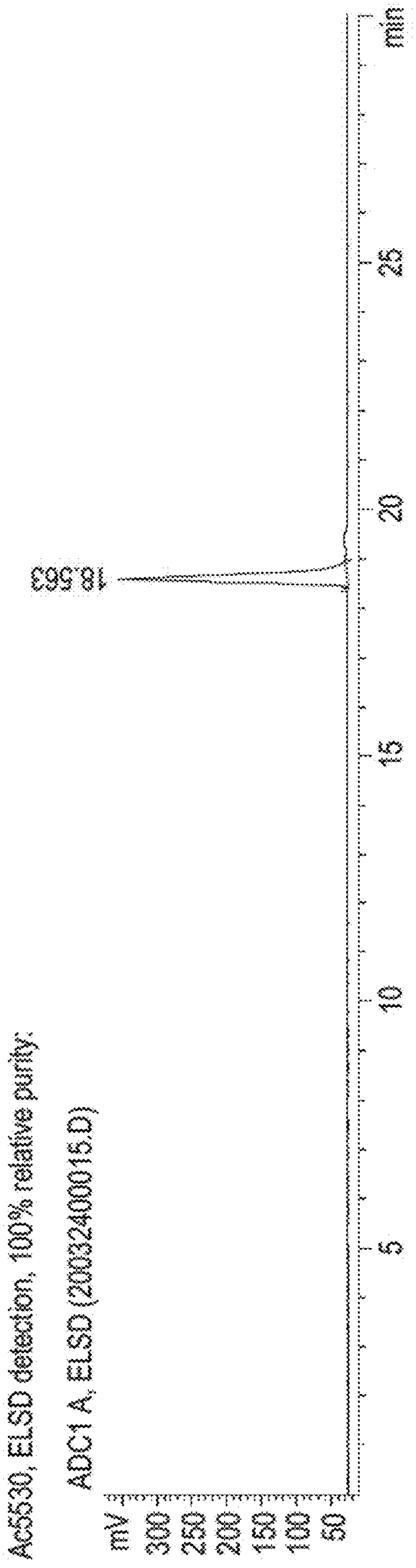
Figure 6D:
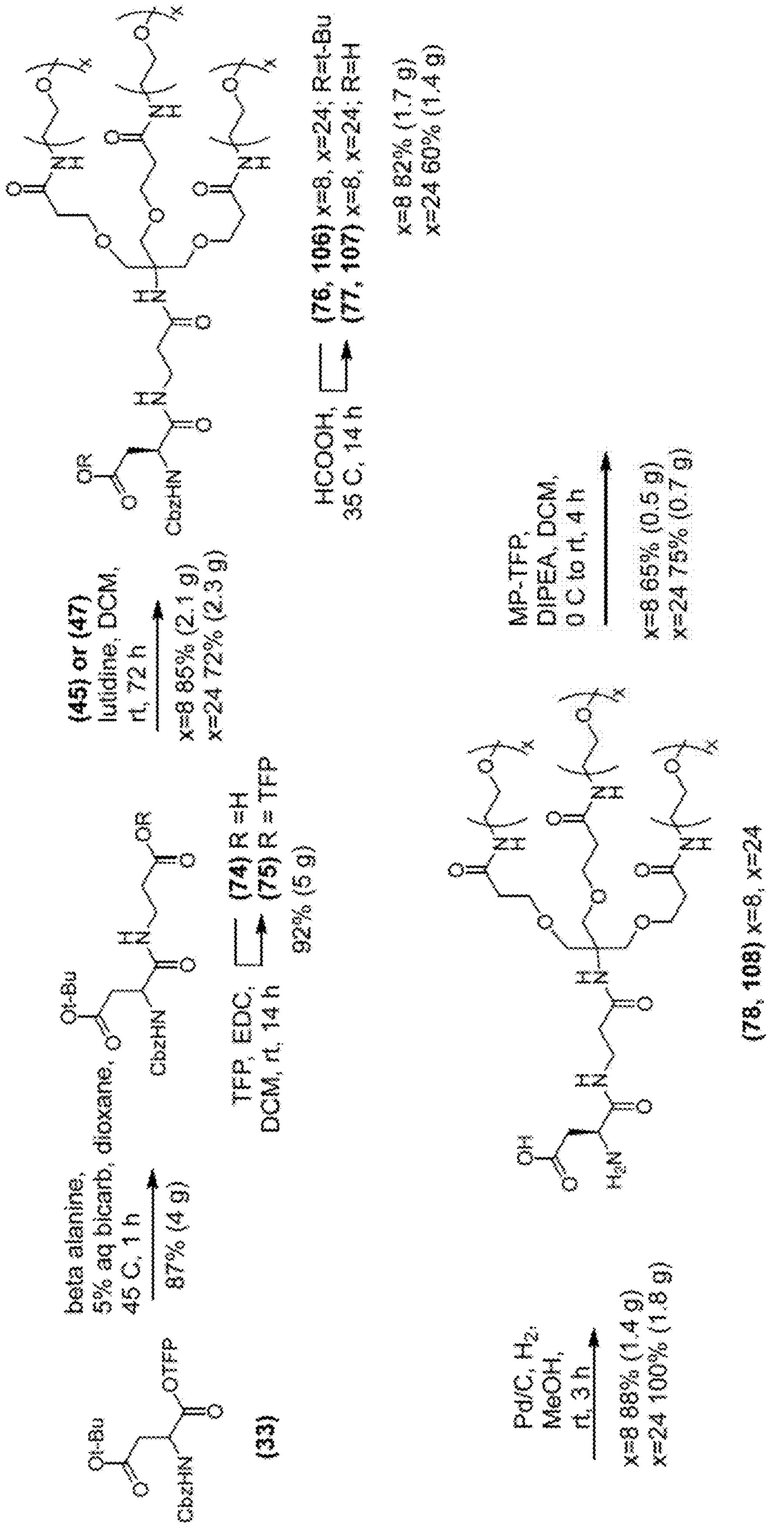
FIG. 6D shows the synthesis of conjugates 81 (I, x=8, y=3) and 111 (0, x=24, y=3) of Formula (II) disclosed herein.
Figure 6D:
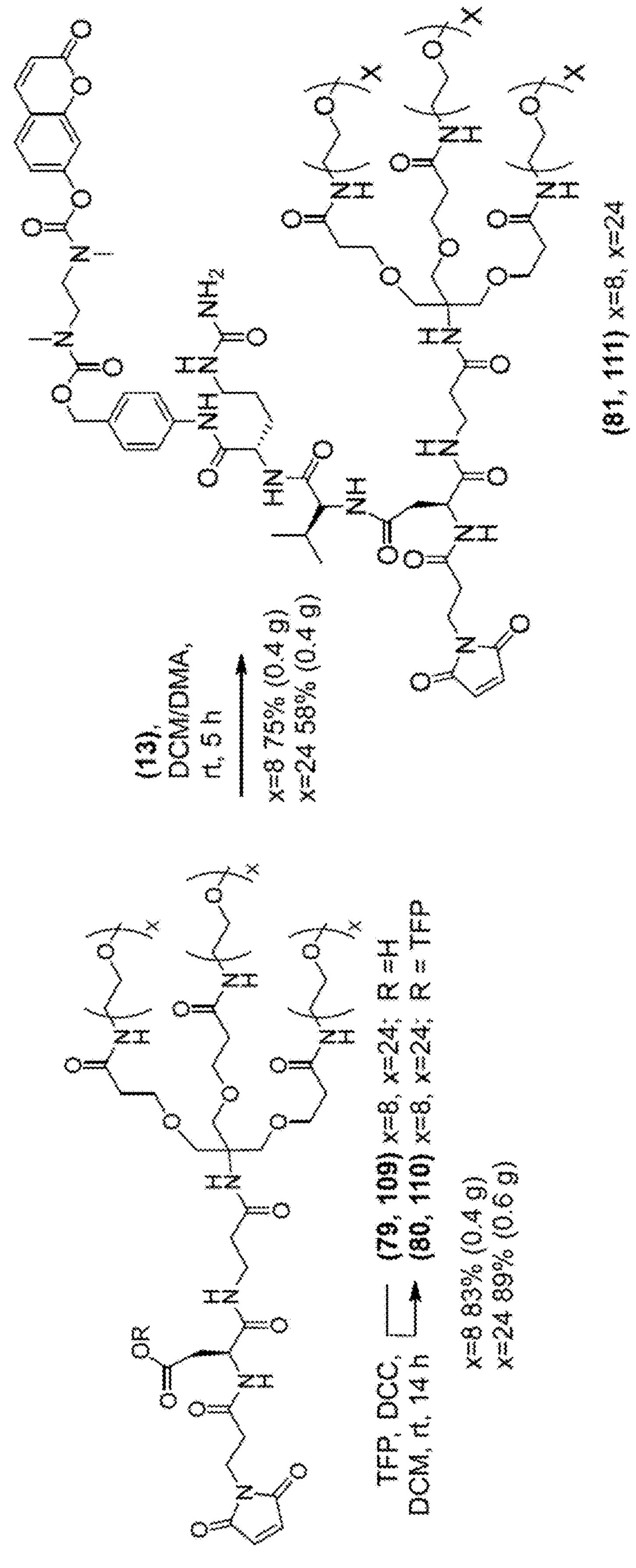
Figure 6E:
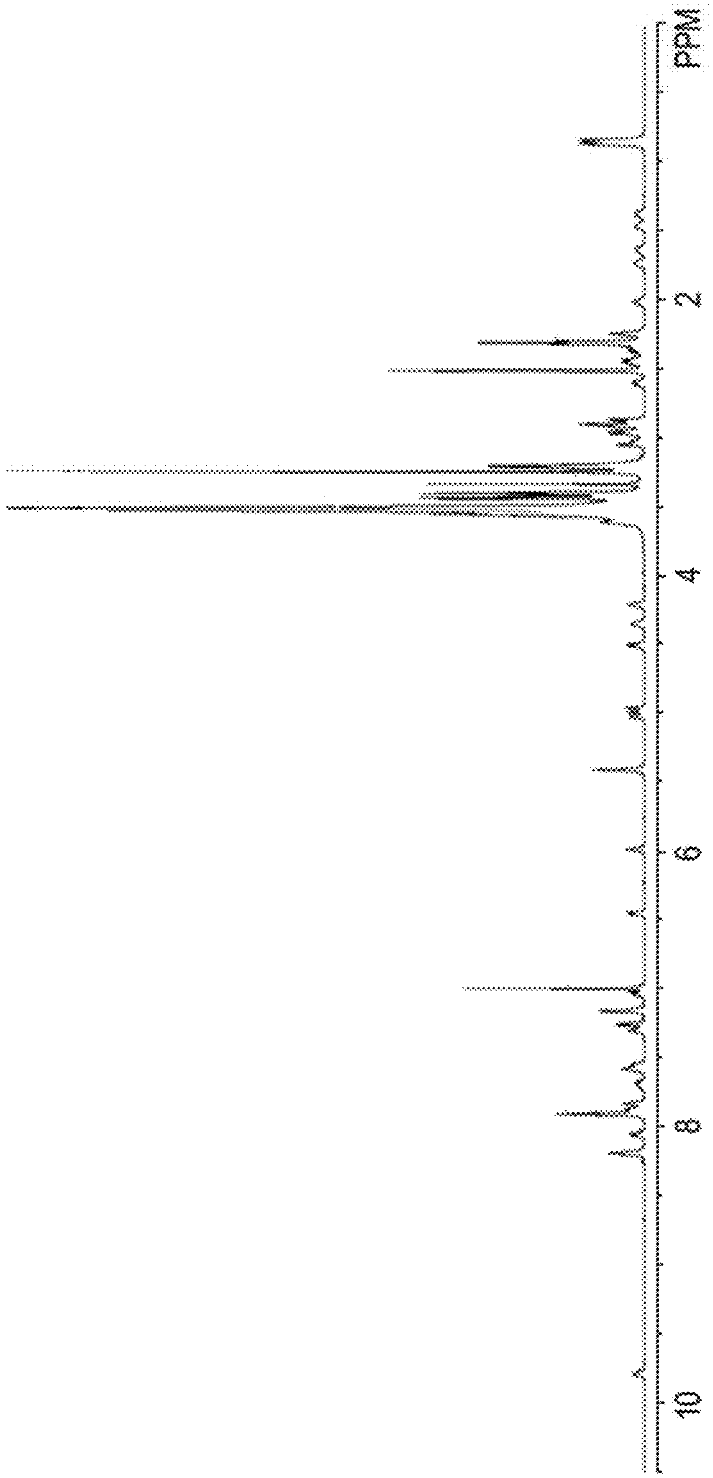
FIG. 6E provides the $^1$H NMR and HPLC spectrum obtained for conjugate 81 of FIG. 6D.
Figure 6E:
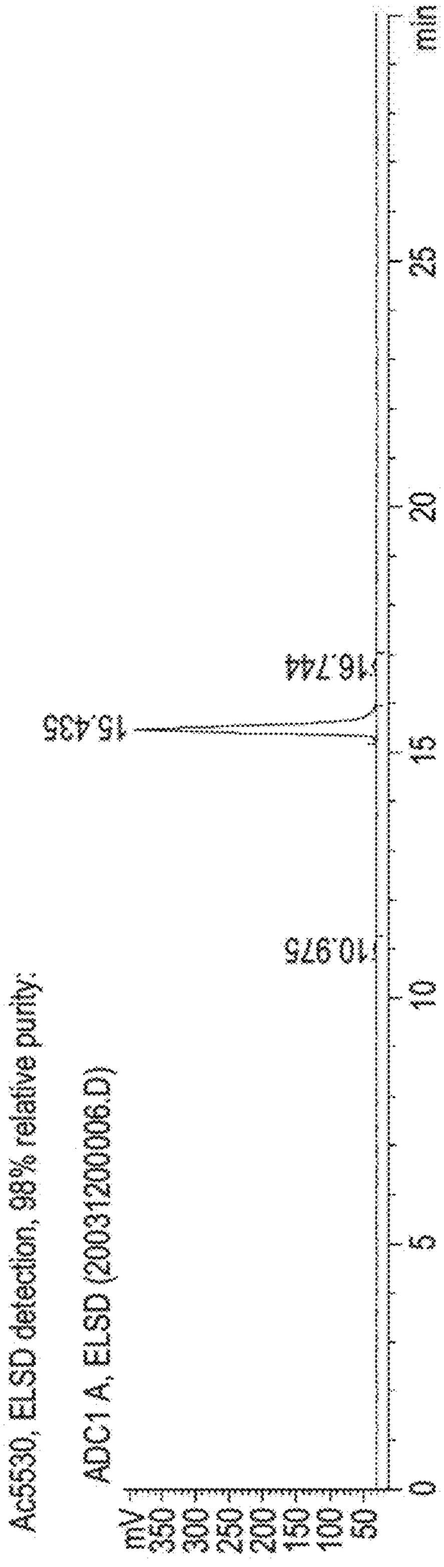
Figure 6F:
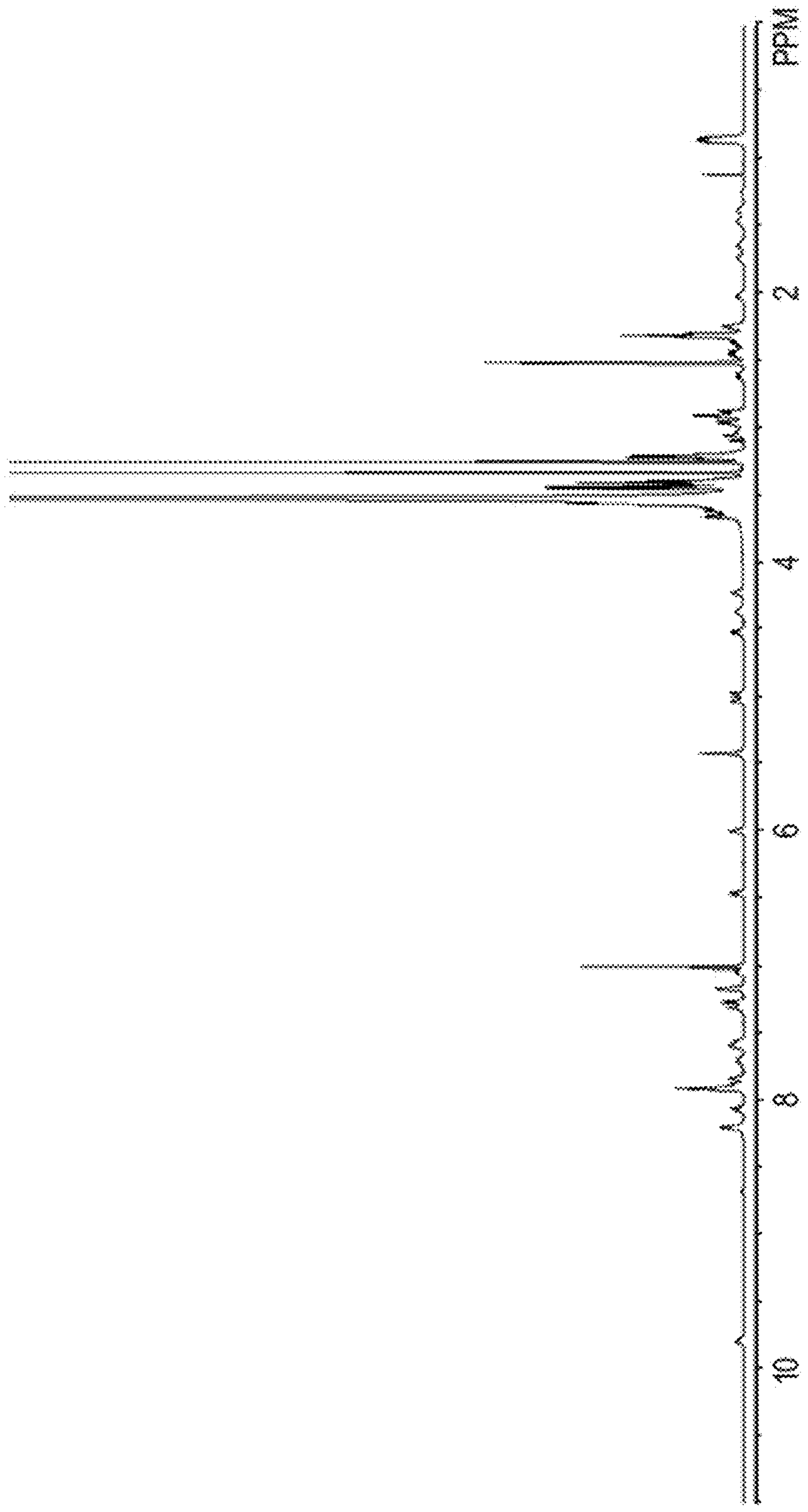
FIG. 6F provides the $^1$H NMR and HPLC spectrum obtained for conjugate 111 of FIG. 6D.
Figure 6F:
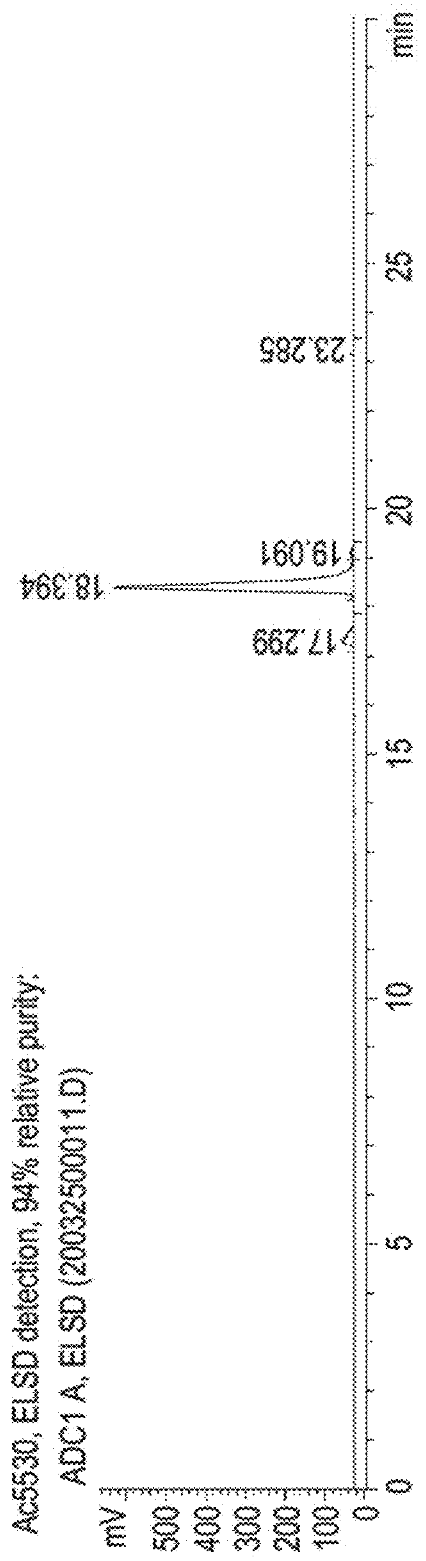
Figure 6G:
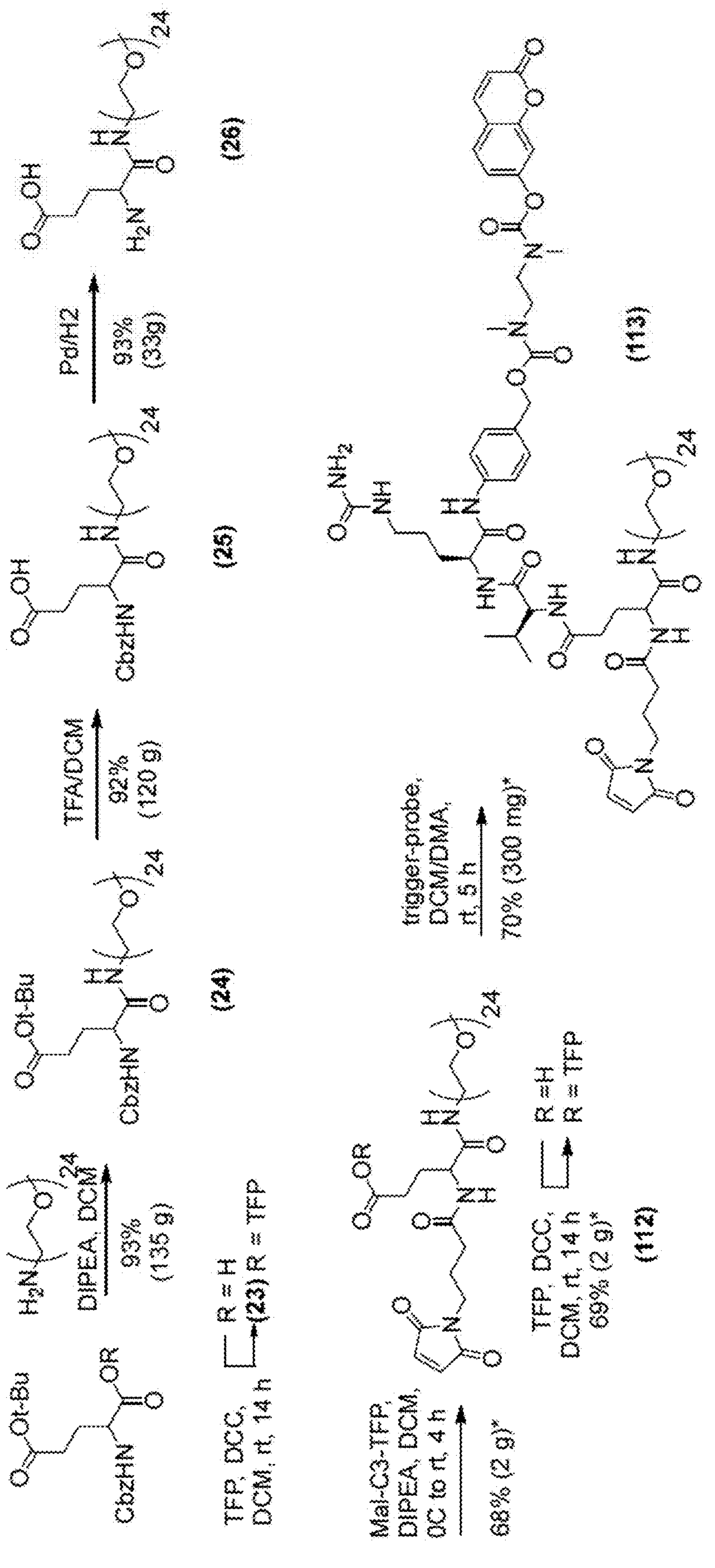
FIG. 6G shows the synthesis of conjugate 113, where x=24 and y=1.

Compound 113 in FIG. 6G was prepared from intermediate 26 by a synthetic route analogous to that described above for Compound 32.

Figure 3E:
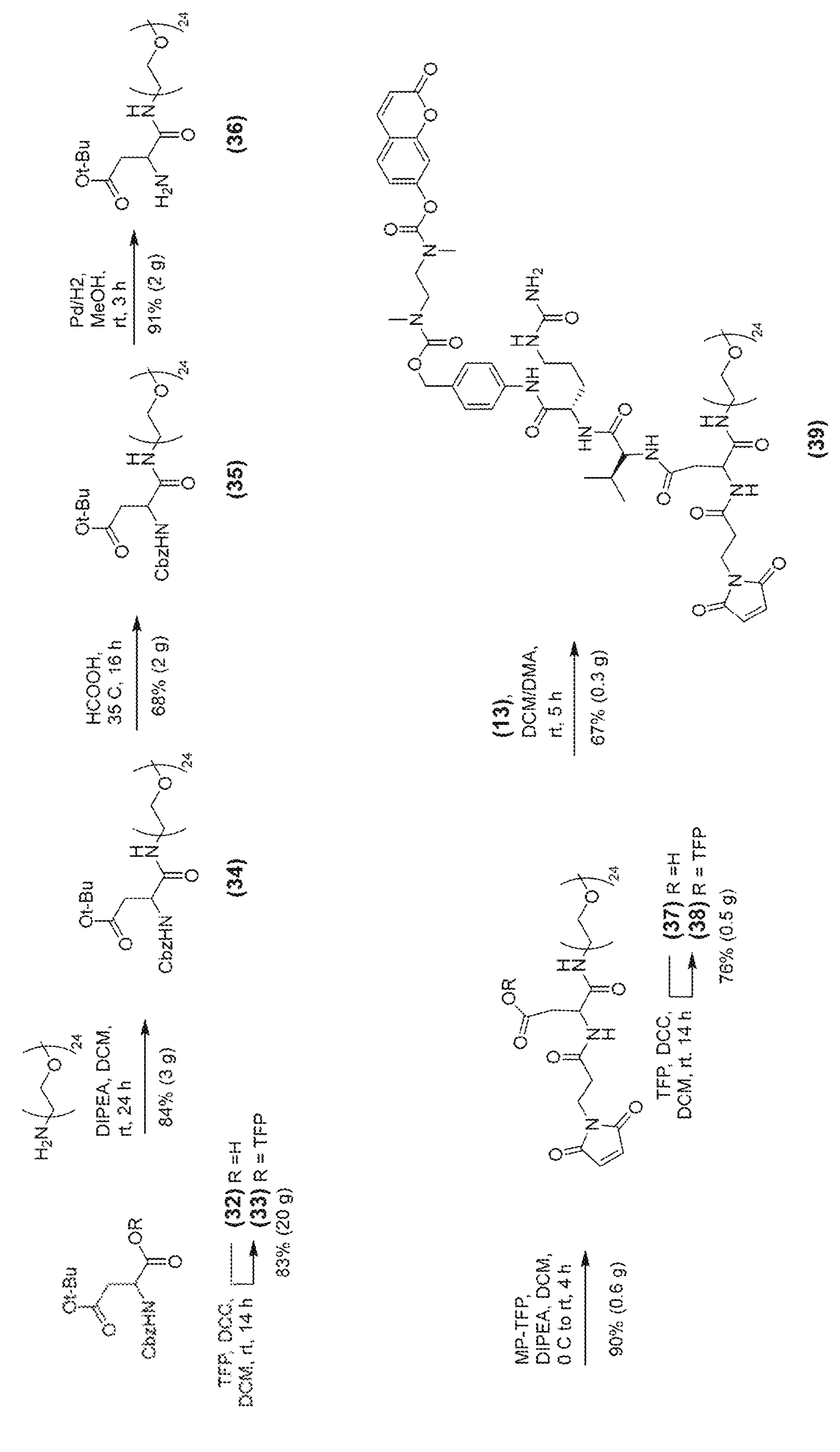
FIG. 3E shows the synthesis of conjugate 39, where x=24 and y=1 [F].

Synthesis of Compound 39 (FIG. 3E)

Synthesis of Compound 33

A 500 mL flask was charged with Z-Asp(TBE)-OH dicyclohexylamine (25 g, 49.5 mmol) and MTBE (250 mL) to give a suspension. To the resulting suspension was added 10% $H_3PO_4$ (150 mL) and the mixture was stirred to give a clear biphasic solution. The solution was poured into a separatory funnel and the organic phase was separated, washed with 10% $H_3PO_4$ (2×50 mL), dried over $MgSO_4$, filtered, and concentrated to provide 16.1 g of a clear pale yellow oil. In a separate 1 L flask, 2,3,5,6-tetrafluorophenol (9.94 g, 59.9 mmol) was dissolved in dichloromethane (250 mL) and EDC (12.43 g, 64.9 mmol) was added in a single portion. After dissolution the flask was chilled in an ice bath. The free acid (16.13 g, 49.9 mmol) was dissolved in dichloromethane (250 mL), placed in an addition funnel, and added dropwise. The ice bath was removed and the reaction stirred overnight at ambient temperature. Both TLC (90:10 DCM:MeOH and 60:40 hexanes:ethyl acetate) and HPLC indicated complete conversion of starting material. The reaction was poured into a separatory funnel and washed with water (3×100 mL), brine, dried over $MgSO_4$, filtered, and concentrated. The oil was pre-absorbed onto 45 g of silica gel and purified on a 330 g column with hexanes and ethyl acetate. Tubes 30-48 were pooled and concentrated to give a clear colorless oil that slowly solidified under high vacuum to provide 19.51 g (83%) of Compound 33 as a white solid. TLC (60:40 hexanes:ethyl acetate) was a single spot $R_f$=0.69. The product was characterized by LRMS (calculated: 471.1, observed: 494.2 $[M+H+Na]^+$), HPLC, and $^1H$ NMR ($CDCl_3$).

Synthesis of Compound 34

A 100 mL flask was charged with Compound 33 (1.689 g, 3.58 mmol) and dichloromethane (28 mL). In a separate flask, m-dPEG®$_{24}$-amine (3 g, 2.76 mmol) was dissolved in dichloromethane (28 mL), N,N-diisopropylethylamine (1.4 mL, 8.27 mmol) was added via syringe, and the mixture was added dropwise via addition funnel. The reaction was stirred at ambient temperature for 48 hours. Both TLC (90:10 DCM:MeOH) and HPLC indicated complete consumption of starting material. The reaction was diluted to 100 mL with dichloromethane, washed with 10% HCl (3×20 mL), and concentrated. The resultant oil was taken up in 60 mL of water, washed with MTBE (2×20 mL), ethyl acetate (20 mL), and hexanes (20 mL). Salt was added and the aqueous phase was extracted with dichloromethane (3×50 mL). The organics were washed with brine, dried over $MgSO_4$, filtered over celite, and concentrated under reduced pressure to give 3.238 g (84%) of an off-white powdery solid. TLC (90:10 DCM:MeOH, visualized with UV and iodine) was a single major spot with some minor impurities $R_f$=0.49. The product was characterized by HPLC and $^1$H NMR ($CDCl_3$) and used without further purification.

Synthesis of Compound 35

A 100 mL 3-neck flask was charged with Compound 34 (3.24 g, 2.325 mmol) and formic acid (44.6 ml, 1162 mmol) and stirred at 35° C. for 18 hours. Both TLC (90:10 DCM:MeOH) and HPLC indicated complete consumption of starting material. The solvent was removed on the rotary evaporator and the oil pre-absorbed onto 9 g of silica gel and purified on a 40 g column with dichloromethane and methanol. Tubes 10-20 were pooled and concentrated to provide 2.123 g (68%) of (35) as a white powdery solid. TLC (90:10 DCM:MeOH, visualized with iodine) was a single spot $R_f$=0.29. The product was characterized by FT-ICR (calculated: 1336.7351, observed: 1337.7397 $[M+H]^+$, 1359.7223 $[M+H+Na]^+$, 1373.6962 $[M+H+K]^+$), HPLC, and $^1$H NMR ($CDCl_3$).

Synthesis of Compound 36

A 100 mL flask was charged with 10% palladium on activated charcoal (0.220 g) and methanol (32 mL) and a hydrogen purge was started. Compound 35 (2.123 g, 1.587 mmol) was dissolved in a little methanol and added to the flask. The reaction was stirred under a hydrogen purge for 3 hours. Both TLC (85:15 DCM:MeOH) and HPLC indicated complete consumption of starting material. The reaction was filtered over a methanol-wet bed of celite and concentrated under reduced pressure to provide 1.739 g of a white powdery solid. The product was characterized by MALDI (calculated: 1202.6983, observed: 1203.663 $[M+H]^+$), HPLC, and $^1$H NMR ($CDCl_3$).

Synthesis of Compound 37

A 50 mL flask was charged with MP-TFP (0.190 g, 0.598 mmol) and dichloromethane (12 mL) and chilled in an ice bath. In a separate flask, Compound 36 (0.6 g, 0.499 mmol) was dissolved in dichloromethane (12 mL), N,N-diisopropylethylamine (0.209 ml, 1.197 mmol) was added, and the mixture was added dropwise via addition funnel. The ice bath was removed and the reaction was stirred at ambient temperature for 2 hours. Both TLC (85:15 DCM:MeOH) and HPLC indicated consumption of starting material. The reaction was diluted to 75 mL with dichloromethane, washed with 10% HCl (3×5 mL), and concentrated under reduced pressure. The residue was taken up in 75 mL water, washed with MTBE (3×10 mL), hexanes (10 mL), salt was added, the solution was acidified, and the product was extracted with DCM (3×30 mL). The organics were dried over $MgSO_4$, filtered over celite, and concentrated under reduced pressure to provide 606 mg (90%) of Compound 37 as a white solid. TLC (85:15 DCM:MeOH, visualized with iodine) was a single spot $R_f$=0.34. The purity was verified by HPLC and the product was used in the subsequent step without further purification or characterization.

Synthesis of Compound 38

A 50 mL 3-neck flask was charged with 2,3,5,6-tetrafluorophenol (0.149 g, 0.895 mmol) and dichloromethane (20 mL). DCC (0.138 g, 0.671 mmol) was added in a single portion. In a separate flask, (0.606 g, 0.447 mmol) was dissolved in dichloromethane (10 mL) and added dropwise. The reaction was stirred at ambient temperature for 18 hours. Both TLC (85:15 DCM:MeOH) and HPLC indicated complete consumption of starting material and formation of a single major product. The reaction was chilled in an ice bath and the DCU was filtered off over celite and rinsed with cold DCM. The solvent was removed and the oil was taken up in acetonitrile and chilled in an ice bath. The DCU was filtered off via syringe filter. Removal of the solvent provided an oil that was suspended in ether and the solvent decanted. Drying under high vacuum gave a pale yellow solid. The solid was suspended in ether and the solvent decanted. This was repeated once more. Drying under high vacuum provided 512 mg (76%) of as a pale yellow powdery solid. TLC (85:15 DCM:MeOH, visualized with UV and iodine) was a single spot $R_f$=0.71. The purity was verified by HPLC and the product was used in the subsequent step without further purification or characterization.

Synthesis of Compound 39-(F)

Figure 3F:
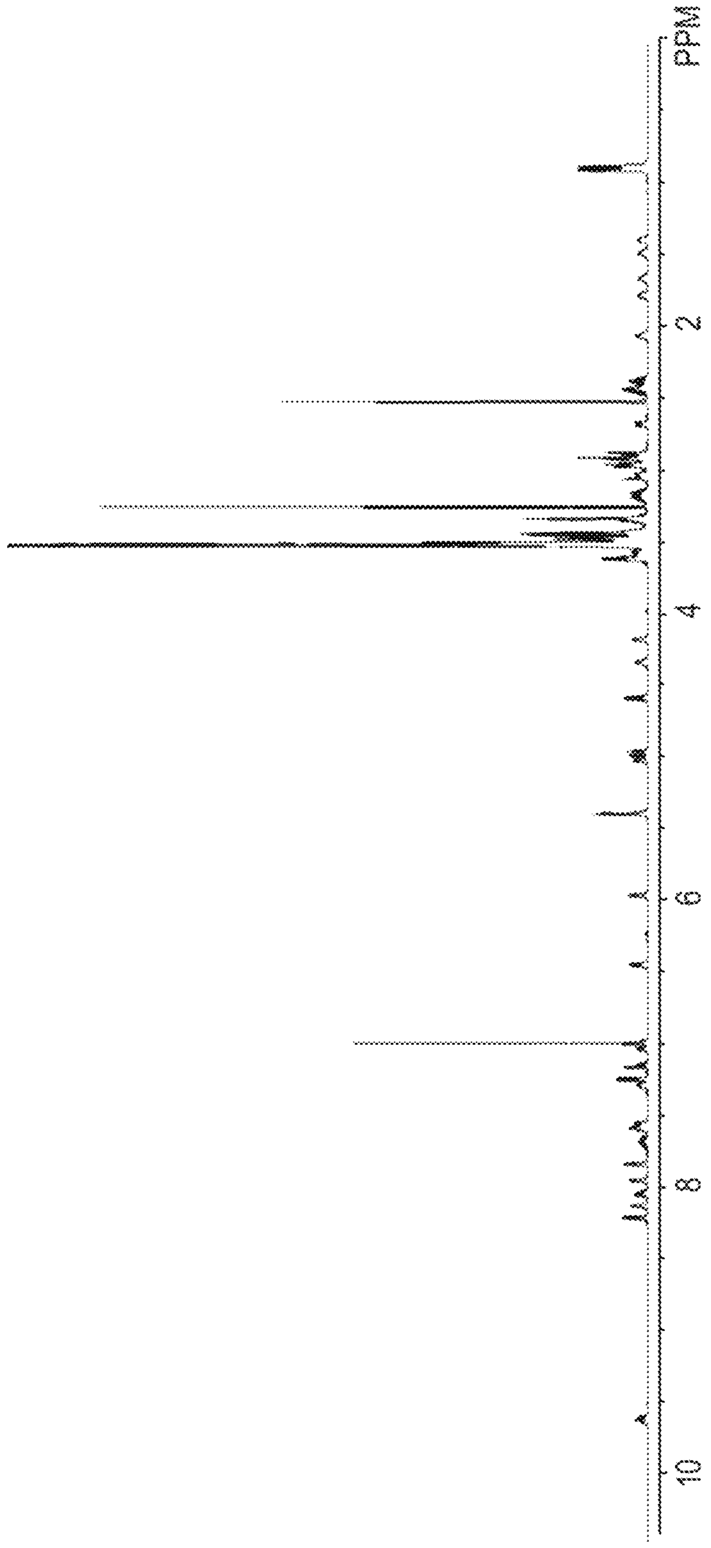
FIG. 3F provides the $^1$H NMR and HPLC spectrum obtained for conjugate 39 of FIG. 3E.
Figure 3F:
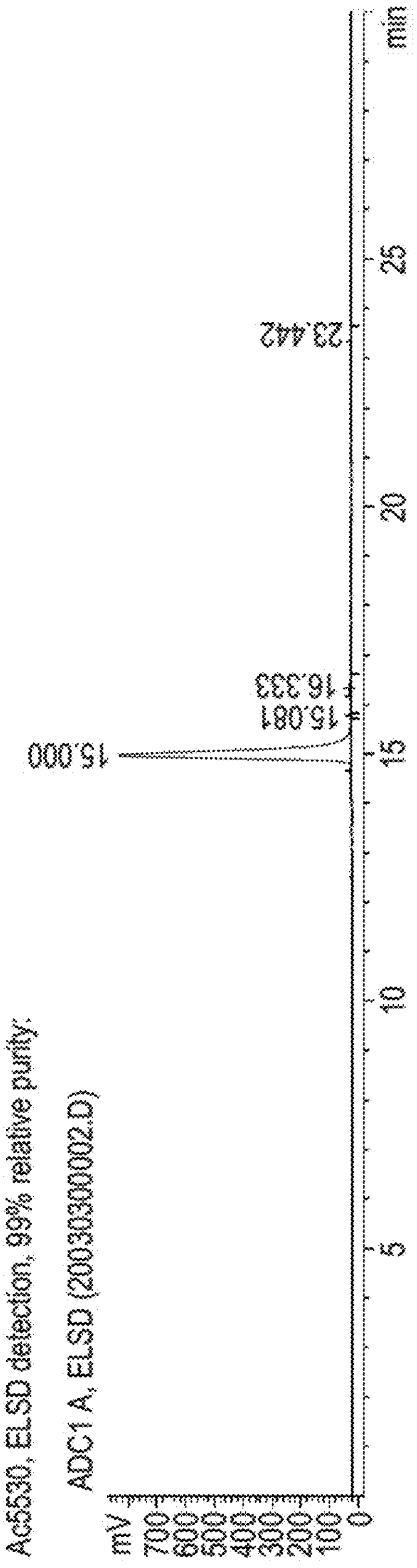

A 25 mL flask was charged with Compound 37 (0.38 g, 0.253 mmol) and dichloromethane (8 mL). In a separate flask, Compound 13 (0.207 g, 0.303 mmol) was dissolved in DMF (4 mL) and added dropwise. The reaction was stirred for three hours at ambient temperature. Both TLC (85:15 DCM:MeOH) and HPLC indicated complete reaction. The solvent was removed under vacuum to give a viscous oil and hexanes was added. The solvent was decanted from the oil, which was rinsed once more with hexanes. The oil was dried under high vacuum and then triturated with ether to give an oily solid. The solid was crushed under ether and the solvent decanted. The oil was dried under high vacuum to give an oily pale orange solid. The residue was pre-absorbed onto 2 g of silica gel and purified on a 12 g column with dichloromethane and methanol. Tubes 5-11 were pooled and concentrated to give an oily solid that was triturated with ether and dried under vacuum to provide 340 mg (67%) of Compound 39 as a white waxy solid. TLC (85:15 DCM:MeOH, visualized with UV and iodine) was a single spot $R_f$=0.39. The product was characterized by FT-ICR (calculated: 2017.0269, observed: 2019.0369 $[M+H]^+$), HPLC, and $^1$H NMR ($d_6$-DMSO) (FIG. 3F).

Figure 4A:
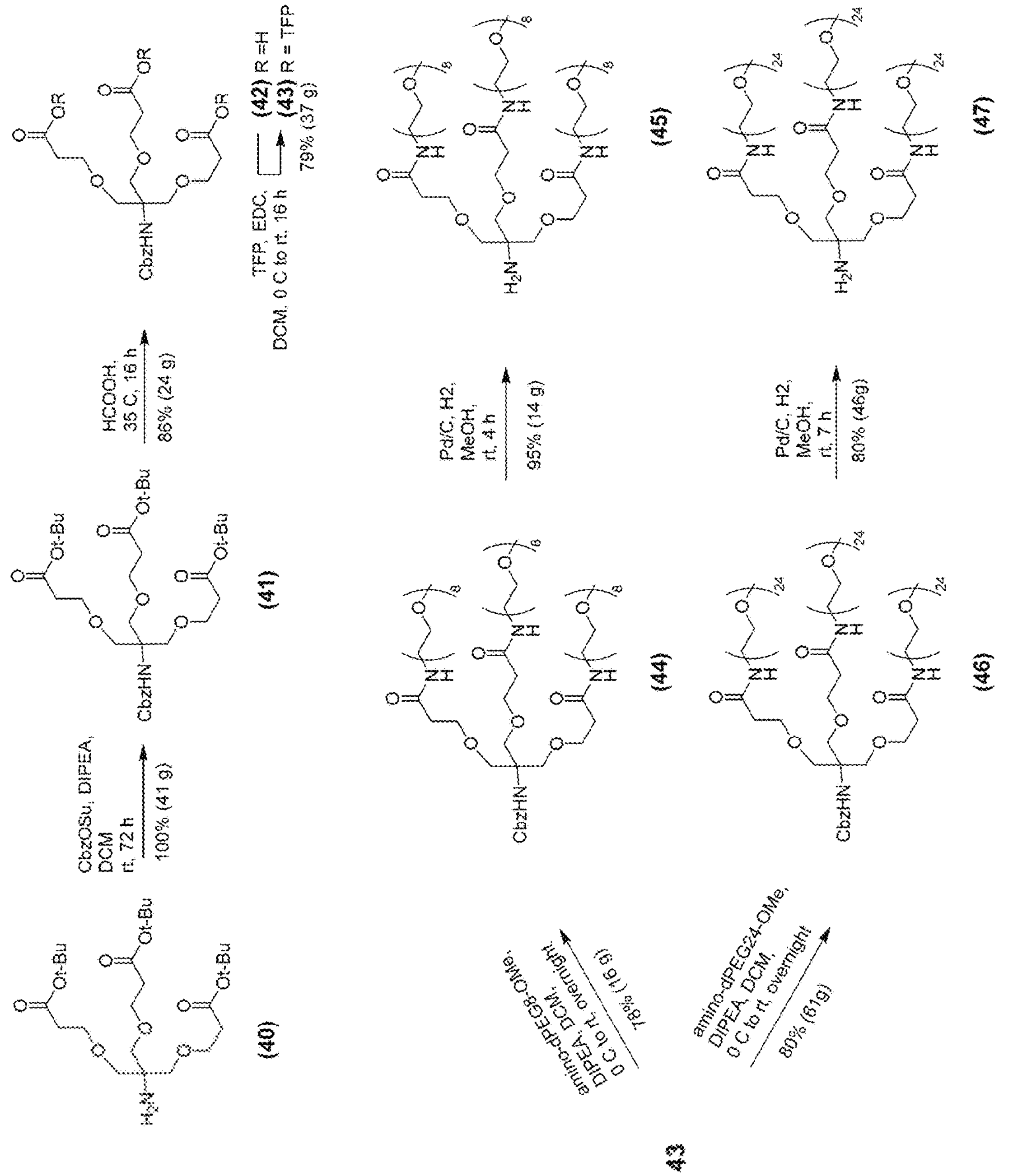
FIG. 4A shows the synthesis of a branched dPEG Compounds 45 (x=8, y=3) and 47 (x=24, y=3).

Synthesis of Compounds 45 and 47 (FIG. 4A)

Synthesis of Compound 41

A 500 mL flask was charged with Compound 40 (30 g, 59.3 mmol) and dichloromethane (200 mL). N,N-diisopropylethylamine (11.40 ml, 65.3 mmol) was added via syringe. Z—OSu (16.26 g, 65.3 mmol) was dissolved dichloromethane (100 mL) and added dropwise. The reaction was stirred at ambient temperature for 72 hours. Both TLC (90:10 DCM:EtOH) and HPLC indicated a single major product. The reaction was diluted with to 500 mL with dichloromethane and washed with 10% HCl (5×100 mL), washed with sat aqueous sodium bicarbonate (2×100 mL), washed with brine, dried over $Na_2SO_4$, filtered, and concentrated to give 40.175 g (100%) of Compound 41 as a clear pale yellow oil. TLC (90:10 DCM:MeOH, visualized with UV and iodine) was a single spot $R_f$=0.78. The product was characterized by LRMS (calculated: 639.4, observed: 662.5 $[M+H+Na]^+$), HPLC, and $^1$H NMR ($CDCl_3$).

Synthesis of Compound 42

A 500 mL flask was charged with Compound 41 (38 g, 59.4 mmol) and formic acid (342 mL, 8909 mmol) and stirred for 24 hours at 35° C. Both TLC (90:10 DCM:EtOH) and HPLC indicated complete consumption of starting material. The formic acid was removed on a rotary evaporator to give an orange viscous oil. The oil was taken up in MTBE, washed with 10% HCl (3×100 mL), dried over $MgSO_4$, filtered over celite, and concentrated under reduced pressure to give 29.4 g of a viscous pale orange oil. The oil was dissolved in 500 mL of 1M NaOH and stirred with activated charcoal. The charcoal was filtered out over celite, the aqueous phase washed with MTBE (3×50 mL), acidified with 1M HCl, saturated with salt and extracted with dichloromethane (5×300 mL). The extracts were dried over $MgSO_4$, filtered over celite, and concentrated under reduced pressure to provide 23.96 g (86%) of Compound 42 as a cloudy pale orange oil. The product was characterized by LRMS (calculated: 471.2, observed: 494.2 $[M+H+Na]^+$), HPLC, and $^1H$ NMR ($CDCl_3$).

Synthesis of Compound 43

A 1 L flask was charged with 2,3,5,6-tetrafluorophenol (27.9 g, 168 mmol) and dichloromethane (250 mL) and chilled in an ice bath. EDC (32.2 g, 168 mmol) was added in a single portion and the mixture was stirred for 15 minutes. Compound 42 (23.96 g, 50.8 mmol) was dissolved in dichloromethane (250 mL) and added dropwise via addition funnel. The ice bath was removed and the reaction was stirred overnight. HPLC indicated complete consumption of starting material and formation of a single major product. The reaction was diluted with dichloromethane, washed with water (2×200 mL), brine (100 mL), dried over $MgSO_4$, filtered over celite, and concentrated under reduced pressure. The oil was then taken up in 800 mL MTBE and washed with 10% HCl, (2×100 mL), brine, dried over $MgSO_4$, and filtered over celite. Concentration and drying under high vacuum provided 36.56 g of Compound 43 as a cloudy pale yellow oil. TLC (70:30 hexanes:MTBE, visualized with UV) was a single major spot $R_f$=0.34 and a minor spot corresponding to residual TFP. The product was characterized by LRMS (calculated: 915.2, observed: 938.3 $[M+H+Na]^+$), HPLC, and $^1H$ NMR ($CDCl_3$).

Synthesis of Compound 44

A 250 mL flask was charged with Compound 43 (12 g, 13.11 mmol) and dichloromethane (100 mL) and chilled in an ice bath. In a separate flask, m-dPEG®$_8$-amine (16.59 g, 43.2 mmol) was dissolved in dichloromethane (100 mL), 2,6-lutidine (5.04 mL, 43.2 mmol) was added via syringe, and the amine mixture was placed in an addition funnel and added dropwise. The ice bath was removed and the reaction was allowed to stir overnight. Both TLC (90:10 DCM:MeOH) and HPLC indicated complete consumption of the starting TFP ester. The reaction was diluted with dichloromethane and washed with 10% HCl (3×50 mL), brine, dried over $MgSO_4$, filtered over celite, and concentrated to give a pale orange viscous oil. The oil was taken up in 400 mL water, washed with MTBE (3×50 mL), hexanes (50 mL), the aqueous phase was saturated with salt and extracted with dichloromethane (3×200 mL). The extracts were dried, filtered, and concentrated onto 40 g of silica gel. The residue was purified on a 220 g column with dichloromethane and methanol. Tubes 10-42 were pooled, concentrated, and dried under high vacuum to provide 15.97 g of Compound 44 as a viscous pale yellow oil. TLC (90:10 DCM:MeOH, visualized with iodine) was a single major spot $R_f$=0.37. The product was characterized by MALDI (calculated: 1566.8981, observed: 1589.851 $[M+H+Na]^+$), HPLC, and $^1H$ NMR ($CDCl_3$).

Synthesis of Compound 45

A 250 mL flask was charged with methanol-wet 10% palladium on activated charcoal (1.6 g) and methanol (100 mL) and a hydrogen purge was started. Compound 44 (15.97 g, 10.19 mmol) was dissolved in a small amount of methanol and added to the flask. The reaction was stirred under a hydrogen purge for 2 hours. Both TLC (90:10 DCM:MeOH) and HPLC indicated complete consumption of sm. The reaction was filtered over a methanol-wet bed of celite and concentrated under high vacuum to provide 13.943 g of Compound 45 as a viscous yellow oil. The product was characterized by MALDI (calculated: 1432.8613, observed: 1433.896 $[M+H]^+$, 1455.876 $[M+H+Na]^+$), HPLC, and $^1H$ NMR ($CDCl_3$).

Synthesis of Compound 46

A 1 L flask was charged with Compound 43 (18.91 g, 20.65 mmol) and dichloromethane (170 mL) and chilled in a nice bath. In a separate flask, m-dPEG®$_{24}$-amine (70.8 g, 65.1 mmol) was dissolved in dichloromethane (170 mL), 2,6-lutidine (8.42 mL, 72.3 mmol) was added via syringe, and the amine mixture was added dropwise via addition funnel. The ice bath was removed and the reaction was allowed to stir overnight. Both TLC (90:10 DCM:EtOH) and HPLC indicated complete consumption of starting material. The reaction was diluted with dichloromethane and washed with 10% HCl (5×100 mL), brine, and concentrated to give a pale orange viscous oil. The oil was taken up in 750 mL water and washed with MTBE (2×100 mL), ethyl acetate (2×100 mL), and hexanes (100 mL). The aqueous phase was extracted with dichloromethane (3×200 mL). The combined extracts were washed with brine, dried over $MgSO_4$ and 5 g silica gel, filtered over celite and a 20 g bed of silica gel, and concentrated to give a pale orange solid. The solid was suspended in MTBE and stirred vigorously for 1 hour, collected on a Buchner, and dried under high vacuum to provide 60.5 of Compound 46 as a white powdery solid. TLC (85:15 DCM:MeOH, visualized with iodine) was a single major spot $R_f$=0.41. The product was characterized by MALDI (calculated: 3680.1564, observed: 3703.023 $[M+H+Na]^+$), HPLC, and $^1H$ NMR ($CDCl_3$).

Synthesis of Compound 47

A 1 L 3-neck flask was charged with methanol-wet 10% palladium on activated charcoal (3.50 g) and methanol (550 mL) and a hydrogen purge was began. Compound 46 (60.5 g, 16.43 mmol) was dissolved in a small amount of methanol and added to the flask and the reaction was stirred under a hydrogen purge for a total of 7 hours. Both TLC (85:15 DCM:MeOH) and HPLC indicated complete conversion. The reaction was filtered over a methanol-wet bed of celite and concentrated on a rotary evaporator to give a tan solid. The residue was taken up in 500 mL water and acidified with 10% HCl. The aqueous phase was washed with MTBE (2×50 mL), basified with 1M NaOH, saturated with salt, and extracted with dichloromethane (3×300 mL). The combined extracts were dried over $MgSO_4$, filtered over celite, and concentrated to 46 g (79%) of Compound 47 as a white powdery solid. The product was characterized by MALDI (calculated: 3546.1196, observed: 3547.669 $[M+H]^+$, 3569.662 $[M+H+Na]^+$, 3585.649 $[M+H+K]^+$), HPLC, and $^1H$ NMR ($CDCl_3$).

Figure 4B:
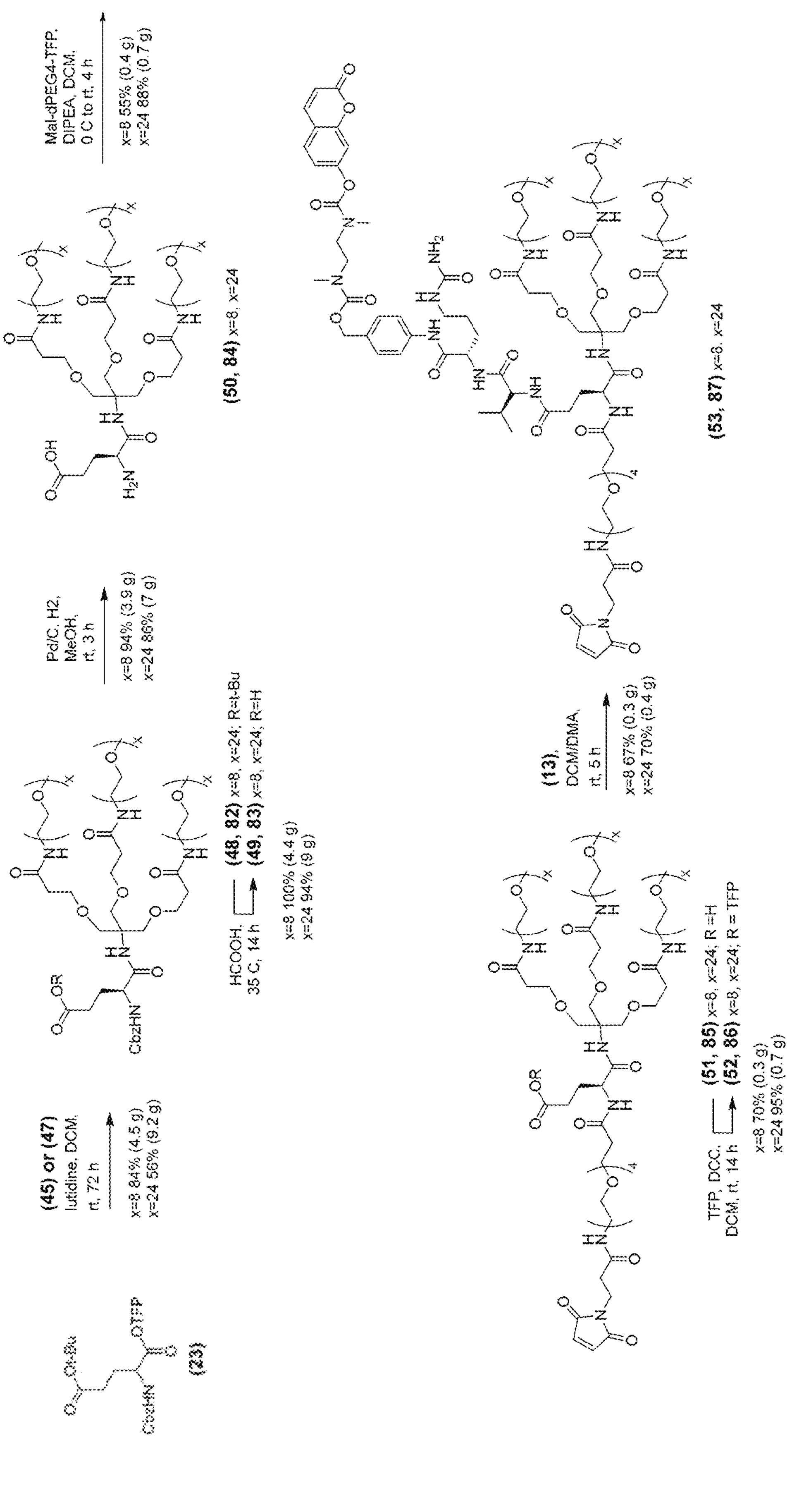
FIG. 4B shows the synthesis of conjugates 53 (J, x=8, y=3) and 87 (P, x=24, y=3) of Formula (II) disclosed herein.

Synthesis of Compound 53 (FIG. 4B)

Synthesis of Compound 48

A 250 mL flask was charged with Compound 23 (1.937 g, 3.99 mmol) and dichloromethane (15 mL). In a separate flask, Compound 45 (4.4 g, 3.07 mmol) was dissolved in dichloromethane (45 mL) and N,N-diisopropylethylamine (0.697 ml, 3.99 mmol) was added via syringe. The mixture was placed in an addition funnel and added dropwise. The reaction was stirred at ambient temperature for 72 hours. Both TLC (90:10 DCM:MeOH) and HPLC indicated complete consumption of starting material. The reaction was diluted to 200 mL with dichloromethane and washed with 10% HCl (3×10 mL). The dichloromethane was removed and the oil taken up in 100 mL water and washed with MTBE (3×25 mL) and hexanes (25 mL). The aqueous phase was saturated with salt and extracted with dichloromethane (3×100 mL). The organics were washed with brine, dried over $MgSO_4$, filtered over celite, and concentrated to give a pale yellow oil. The residue was pre-absorbed onto 12 g of silica gel and purified on an 80 g column with dichloromethane and methanol. Tubes 7-35 were pooled and concentrated to give 4.54 g (84%) of Compound 48 as a clear colorless viscous oil. TLC (90:10 DCM:MeOH, visualized with UV and iodine) was a single major spot $R_f$=0.41. The product was characterized by MALDI (calculated: 1752.0033, observed: 1775.071 $[M+H+Na]^+$), HPLC, and $^1H$ NMR ($CDCl_3$).

Synthesis of Compound 49

A 100 mL 3-neck flask was charged with Compound 48 (4.54 g, 2.59 mmol) and formic acid (49.7 mL, 1295 mmol) and heated to 35° C. for 24 hours. Both TLC (85:15 DCM:MeOH) and HPLC indicated complete consumption of starting material. The formic acid was removed on a rotary evaporator, the oil suspended in ether, allowed to settle, and the solvent decanted. This was repeated a second time. Drying under high vacuum provided 4.63 g (100%) of Compound 49 as a clear colorless oil. TLC (85:15 DCM:MeOH, visualized with iodine) was a single major spot $R_f$=0.55. The product was characterized by MALDI (calculated: 1695.9407, observed: 1718.955 $[M+H+Na]^+$), HPLC, and $^1H$ NMR ($CDCl_3$).

Synthesis of Compound 50

A 250 mL flask was charged with 10% palladium on activated charcoal (0.464 g) and methanol (90 mL) and a hydrogen purge was started. In a separate flask, Compound 49 (4.627 g, 2.73 mmol) was dissolved in methanol and added to the flask. The reaction was stirred for 4 hours under a hydrogen purge. Both TLC (85:15 DCM:MeOH) and HPLC indicated complete consumption of starting material. The reaction was filtered over a methanol-wet bed of celite and concentrated under reduced pressure to give 3.99 g (94%) of Compound 50 as a clear pale yellow viscous oil. The product was characterized by MALDI (calculated: 1561.9039, observed: 1562.9039 $[M+H]^+$), HPLC, and $^1H$ NMR ($CDCl_3$).

Synthesis of Compound 51

A 50 mL flask was charged with Mal-dPEG 4-TFP ester (0.260 g, 0.461 mmol) and dichloromethane (20 mL) and chilled in an ice bath. In a separate flask, Compound 50 (0.6 g, 0.384 mmol) was dissolved in dichloromethane (20 mL) and N,N-diisopropylethylamine (0.161 ml, 0.921 mmol) was added via syringe. The mixture was placed in an addition funnel and added dropwise. The ice bath was removed and the reaction was stirred for 16 hours. Both TLC (85:15 DCM:MeOH) and HPLC indicated consumption of starting material. The reaction was diluted to 200 mL with dichloromethane, washed with 10% HCl (5×10 mL), washed with brine, dried over $MgSO_4$, filtered over celite, and concentrated under reduced pressure to provide an oil. The oil was suspended in MTBE and stirred vigorously for 10 minutes. The solvent was decanted. This was repeated once more and the oil was pre-absorbed onto 2 g of silica gel and flashed on a 12 g column with dichloromethane and methanol. Tubes 5-10 were pooled and concentrated. Drying under high vacuum provided 416 mg (55%) of Compound 51 as a clear nearly colorless oil. TLC (85:15 DCM:MeOH, visualized with iodine) was a single major spot $R_f$=0.52 with a few minor impurity spots. The purity was verified by HPLC and the product was used in the subsequent step without further purification or characterization.

Synthesis of Compound 52

A 50 mL 3-neck flask was charged with 2,3,5,6-tetrafluorophenol (0.070 g, 0.424 mmol) and dichloromethane (10 mL). DCC (0.066 g, 0.318 mmol) was added in a single portion and the mixture was stirred for ten minutes. In a separate flask, Compound 51 (0.416 g, 0.212 mmol) was dissolved in dichloromethane (10 mL) and then added dropwise via addition funnel. The reaction was stirred at ambient temperature for 16 hours. Both TLC (85:15 DCM:MeOH) and HPLC indicated a single major product with some minor impurities. The reaction was chilled in an ice bath and the DCU was filtered off using a syringe filter. The solvent was removed and the oil was taken up in acetonitrile and chilled in an ice bath. The DCU was filtered off via syringe filter. Removal of the solvent provided an orange oil that was suspended in ether and the solvent decanted. The oil was dried under high vacuum and again suspended in ether and the solvent decanted. Drying under high vacuum provided 312 mg (70%) of Compound 52 as a pale orange oil. TLC (85:15 DCM:MeOH, visualized with UV and iodine) was a single major spot $R_f$=0.58 with a minor impurity spot. The purity was verified by HPLC and the product was used in the subsequent step without further purification or characterization.

Synthesis of Compound 53-(J)

Figure 4C:
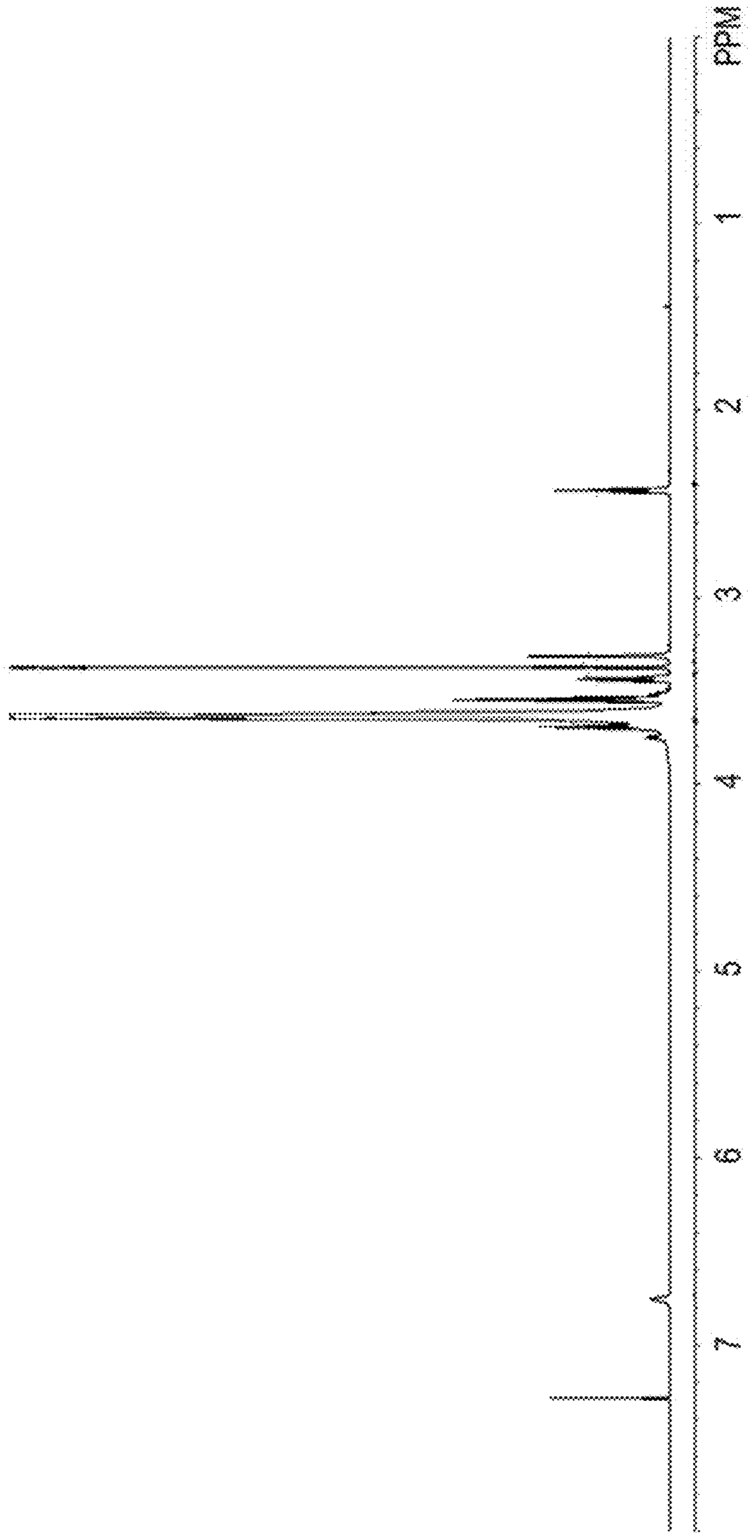
FIG. 4C provides the $^1$H NMR and HPLC spectrum obtained for conjugate 53 of FIG. 4B.
Figure 4C:
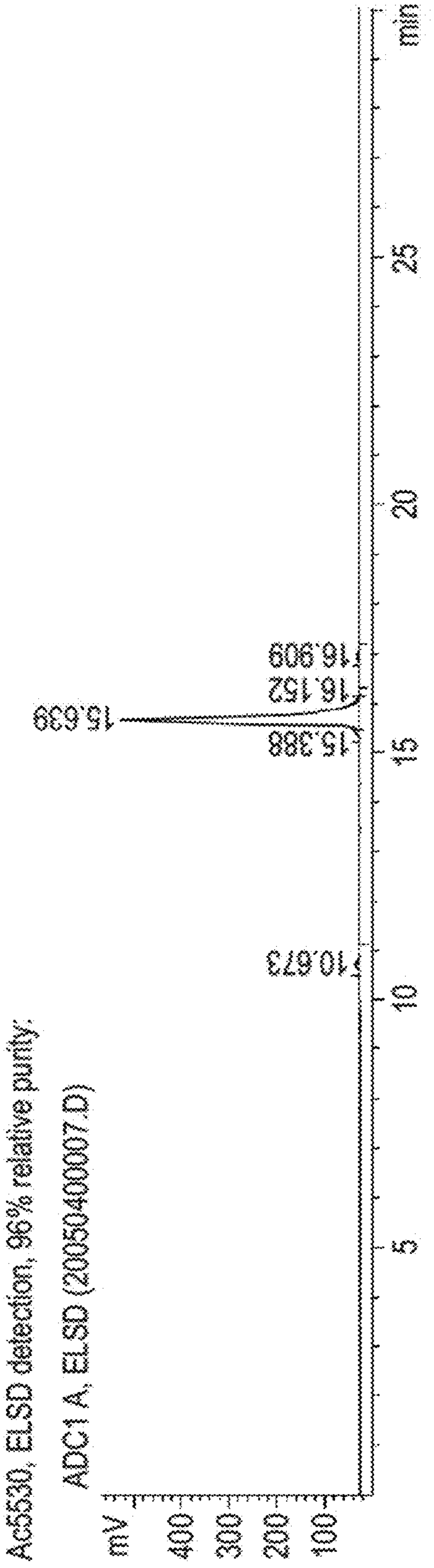

A 25 mL flask was charged with Compound 52 (0.312 g, 0.148 mmol) and dichloromethane (5 mL). In a separate flask, Compound 13 (0.116 g, 0.170 mmol) was dissolved in DMF (3 mL) and added dropwise. The reaction was stirred at ambient temperature for 24 hours. Both TLC (85:15 DCM:MeOH) and HPLC indicated complete reaction. The solvent was removed under vacuum to give a viscous DMF solution. Hexanes was added and then decanted from the oil, which was rinsed once more with hexanes. The oil was pre-absorbed onto 2 g of silica gel and purified on a 12 g column with dichloromethane and methanol. Tubes 8-14 were pooled, concentrated, and dried under vacuum to provide 261 mg (67%) of Compound 53 as a clear pale-yellow oil. TLC (85:15 DCM:MeOH, visualized with UV and iodine) was a single spot $R_f$=0.25. The product was characterized by ESI (calculated: 2623.3745, observed: 2624.3818 $[M+H]^+$), HPLC, and $^1H$NMR ($d_6$-DMSO) (FIG. 4C).

Synthesis of Compound 87 (FIG. 4B)

Synthesis of Compound 82

A 200 mL flask was charged with Compound 23 (2.463 g, 5.07 mmol) and dichloromethane (35 mL). Compound 47 (15 g, 4.23 mmol) was dissolved in dichloromethane (100 mL) and N,N-diisopropylethylamine (0.886 mL, 5.07 mmol) was added via syringe. The mixture was placed in an addition funnel and added dropwise. The reaction was stirred at ambient temperature for 72 hours. Both TLC (80:20 DCM:EtOH) and HPLC indicated formation of a major product. The reaction was diluted to 500 mL with dichloromethane and washed with 0.5M HCl (3×50 mL). The solvent was removed and the oil taken up in 600 mL water and washed with MTBE (2×100 mL), washed with 1:1 MTBE/ethyl acetate (100 mL), and washed with hexanes (100 mL). The aqueous phase was extracted with dichloromethane (3×500 mL). The combined organics were washed with brine, dried over $MgSO_4$, filtered over celite, and concentrated to give of a white solid. The solid was pre-absorbed onto 25 g of silica gel and purified on a 330 g column with dichloromethane and ethanol. Tubes 4-24 were pooled and concentrated to provide 9.226 g (56%) of Compound 82 as a white solid. TLC (85:15 DCM:EtOH, visualized with UV and iodine) was a single spot $R_f$=0.53. The product was characterized by MALDI (calculated: 3865.2616, observed: 3888.784 $[M+H+Na]^+$), HPLC, and $^1H$ NMR ($CDCl_3$).

Synthesis of Compound 83

A 100 mL flask was charged with Compound 82 (9.226 g, 2.385 mmol) and formic acid (45.7 ml, 1193 mmol). The flask was heated to 35° C. and stirred for 18 hours. Both TLC (85:15 DCM:EtOH) and HPLC indicated the reaction was complete. The reaction was diluted with dichloromethane, washed with 0.5M HCl (3×50 mL), washed with brine (50 mL), dried over $MgSO_4$, filtered over celite, and concentrated under reduced pressure to give a white solid. The solid was suspended in ether with vigorous stirring for 15 minutes, the solvent decanted and the solid dried. This was repeated once more. Drying under high vacuum provided 8.578 g (94%) of Compound 83 as a white solid. TLC (85:15 DCM:EtOH, visualized with UV and iodine) was a single spot $R_f$=0.38. The product was characterized by MALDI (calculated: 3809.1990, observed: 3832.633 $[M+H+Na]^+$), HPLC, and $^1H$ NMR ($CDCl_3$).

Synthesis of Compound 84

A 200 mL 3-neck flask was charged with methanol-wet 10% palladium on activated charcoal (0.838 g) and methanol (110 mL) and a hydrogen purge was started. Compound 83 (8.578 g, 2.251 mmol) was dissolved in a small amount of methanol and added to the flask and the reaction was stirred vigorously under a hydrogen purge for two hours. Both TLC (85:15 DCM:EtOH) and HPLC indicated consumption of sm. The reaction was filtered over a methanol-wet bed of celite and concentrated under reduced pressure to provide a white solid. The solid was stirred in ether for 15 minutes, allowed to settle, and the solvent decanted. Drying under high vacuum provided 7.142 g (86%) of Compound 84 as a white powdery solid. The product was characterized by MALDI (calculated: 3675.1622, observed: 3698.469 $[M+H+Na]^+$), HPLC, and $^1H$ NMR ($CDCl_3$).

Synthesis of Compound 85

A 50 mL flask was charged with Mal-dPEG®$_4$-TFP ester (0.138 g, 0.245 mmol) and dichloromethane (10 mL) and chilled in an ice bath. In a separate flask, Compound 84 (0.75 g, 0.204 mmol) was dissolved in dichloromethane (10 mL) and N,N-diisopropylethylamine (0.085 ml, 0.489 mmol) was added via syringe. The mixture was placed in an addition funnel and added dropwise. The ice bath was removed and the reaction was stirred at ambient temperature for 16 hours. Both TLC (85:15 DCM:MeOH) and HPLC indicated formation of a single major product. The reaction was diluted to 150 mL with dichloromethane, washed with 10% HCl (5×10 mL), washed with brine, dried over $MgSO_4$, filtered over celite, and concentrated under reduced pressure to provide an oil. The oil was suspended in MTBE and the solvent was decanted to give a solid. The solid was rinsed with MTBE and then suspended in MTBE with vigorous stirring for 10 minutes. The MTBE was decanted and the solid dried under high vacuum to provide 0.730 g (88%) of Compound 85 as a white powdery solid. TLC (85:15 DCM:MeOH, visualized with iodine) was a single major spot $R_f$=0.28. The purity was verified by HPLC and the product was used in the subsequent step without further purification or characterization.

Synthesis of Compound 86

A 50 mL 3-neck flask was charged with 2,3,5,6-tetrafluorophenol (0.059 g, 0.358 mmol) and dichloromethane (10 mL). DCC (0.055 g, 0.269 mmol) was added in a single portion and the mixture was stirred for ten minutes. (85) (0.730 g, 0.179 mmol) was dissolved in dichloromethane (10 mL) and added dropwise. The reaction was stirred at ambient temperature for 18 hours. Both TLC (85:15 DCM:MeOH) and HPLC indicated a single major product. The reaction was chilled in an ice bath and the DCU was filtered off using a syringe filter. The solvent was removed and the oil was taken up in acetonitrile and chilled in an ice bath. The DCU was filtered off via syringe filter. Removal of the solvent provided an orange oil that was suspended in ether and the solvent decanted. Drying under high vacuum gave a pale orange solid. The solid was suspended in ether and the solvent decanted (2×). Drying under high vacuum provided 0.718 g (95%) of Compound 86 as a pale orange solid. TLC (85:15 DCM:MeOH, visualized with UV and iodine) was a single major spot $R_f$=0.55. The purity was verified by HPLC and the product was used in the subsequent step without further purification or characterization.

Synthesis of Compound 87-(P)

Figure 4D:
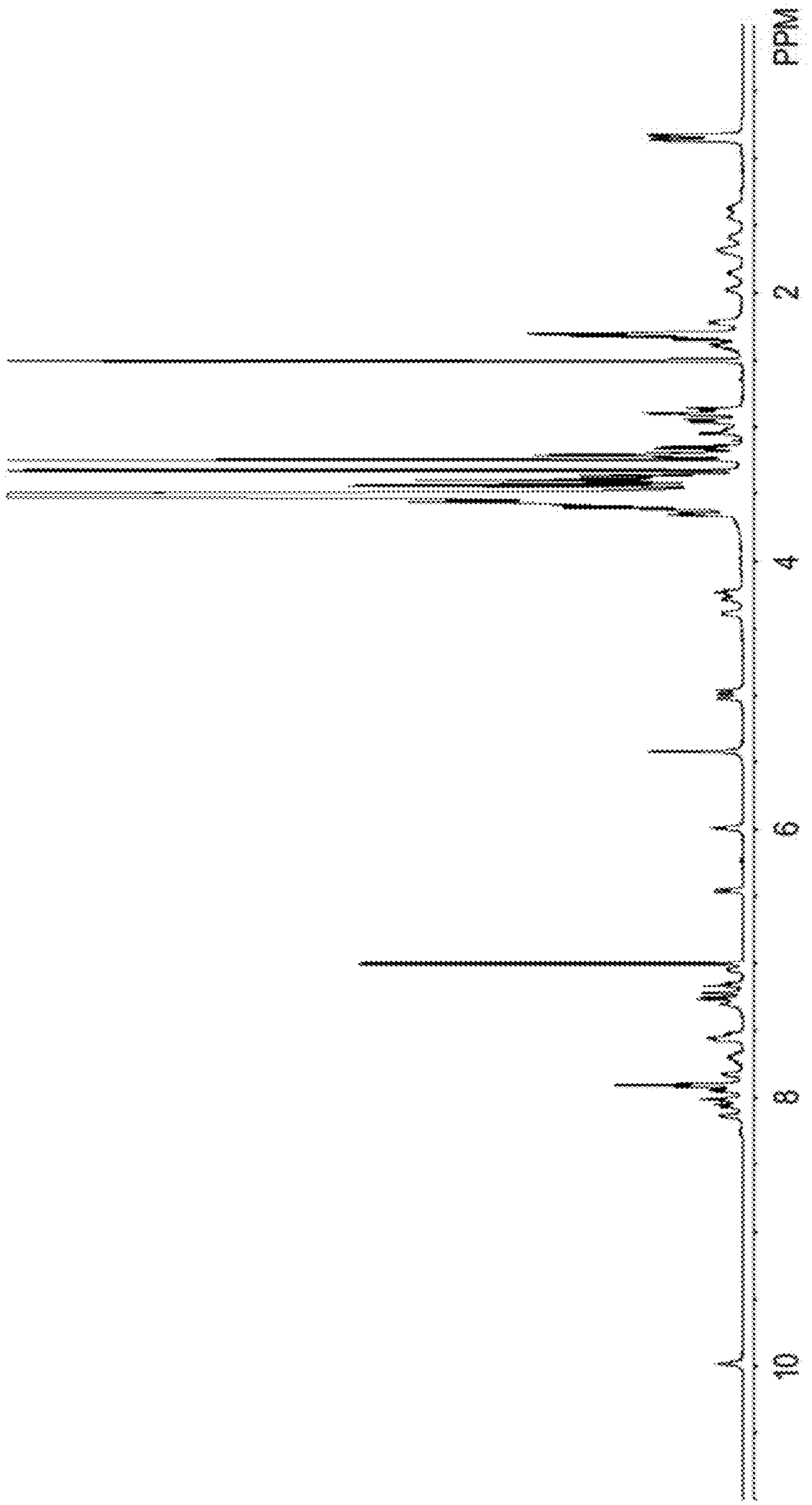
FIG. 4D provides the $^1$H NMR and HPLC spectrum obtained for conjugate 87 of FIG. 4B.
Figure 4D:
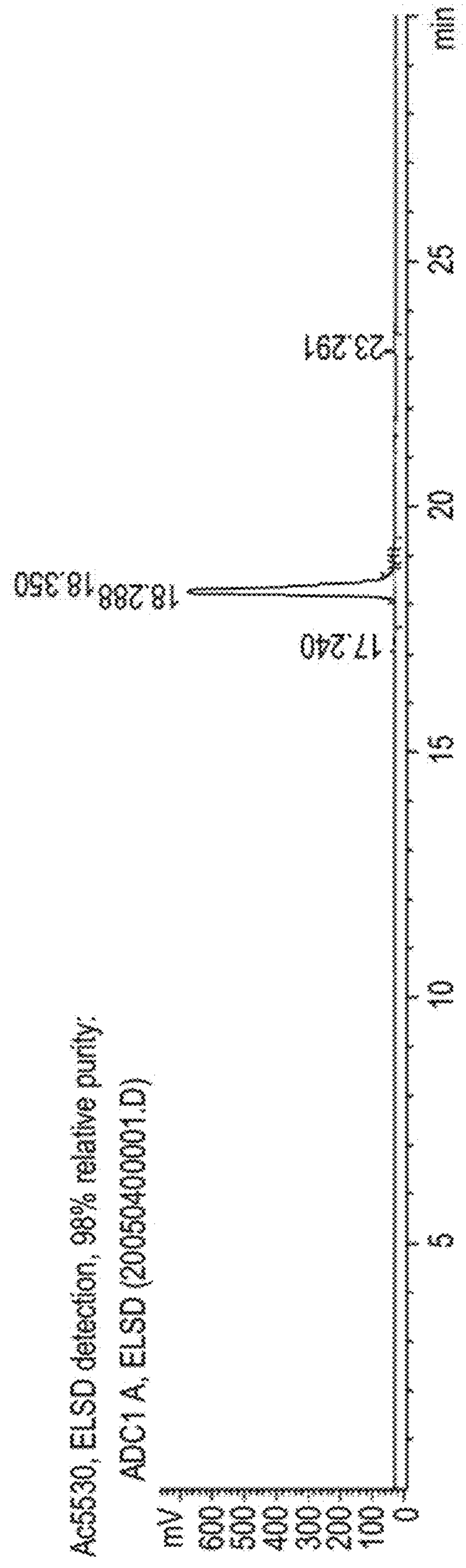

A 25 mL flask was charged Compound 86 (0.45 g, 0.107 mmol) and dichloromethane (7 mL). (13) (0.084 g, 0.123 mmol) was dissolved in DMF (4 mL) and added dropwise. The reaction was stirred at ambient temperature for 24 hours. Both TLC (85:15 DCM:MeOH) and HPLC indicated complete reaction. The solvent was removed under vacuum and the resultant oil was triturated with hexanes to give an oily solid. The solid was crushed under ether and the solvent decanted (2×). The residue was pre-absorbed onto 2 g of silica gel and purified on a 12 g column with dichloromethane and methanol. Tubes 6-15 were pooled, concentrated, and dried under vacuum to provide 354 mg (70%) of Compound 87 as an off-white powdery solid. TLC (85:15 DCM:MeOH, visualized with UV and iodine) was a single spot $R_f$=0.63. The product was characterized by HRMS (calculated: 4736.6328, observed: 4737.6401 $[M+H]^+$), HPLC, and $^1H$ NMR ($d_6$-DMSO) (FIG. 4D).

Figure 4E:
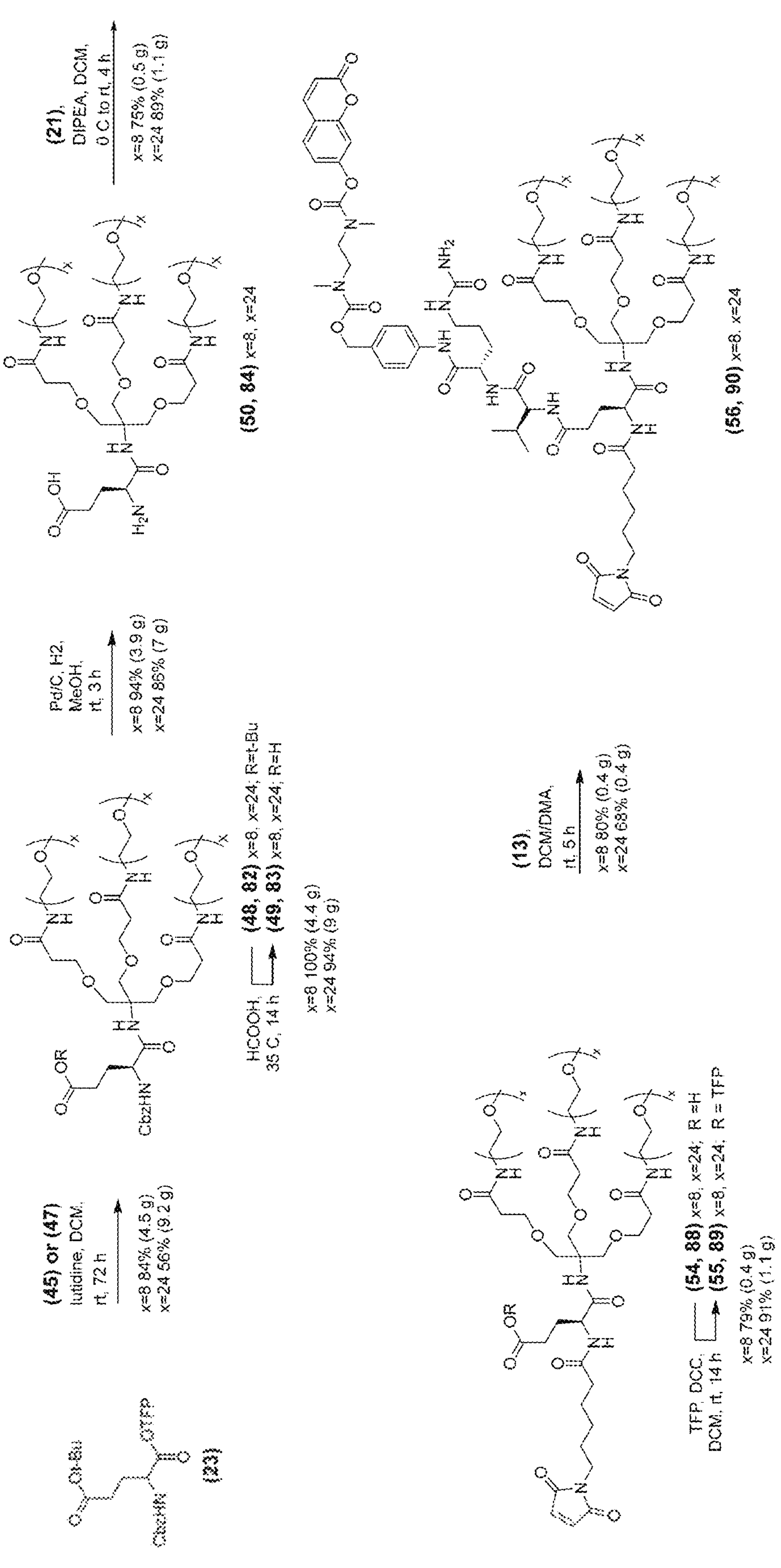
FIG. 4E shows the synthesis of conjugates 56 (K, x=8, y=3) and 90 (Q, x=24, y=3) of Formula (II) disclosed herein.

Synthesis of Compound 56 (FIG. 4E)

Synthesis of Compound 54

A 50 mL flask was charged with Compound 21 (FIG. 2C, 0.166 g, 0.461 mmol) and dichloromethane (12 mL) and chilled in an ice bath. In a separate flask, (50) (0.6 g, 0.384 mmol) was dissolved in dichloromethane (12 mL) and N,N-diisopropylethylamine (0.268 ml, 1.536 mmol) was added via syringe. The mixture was placed in an addition funnel and added dropwise. The ice bath was removed and the reaction was stirred for 3 hours. Both TLC (85:15 DCM:MeOH) and HPLC indicated complete reaction. The reaction was diluted to 75 mL with dichloromethane, washed with 10% HCl (3×5 mL), and concentrated under reduced pressure. The residue was taken up in 75 mL water, washed with MTBE (3×10 mL), washed with hexanes (10 mL), salt was added, the solution was acidified, and the aqueous phase was extracted with dichloromethane (3×30 mL). The combined organics were washed with brine, dried over $MgSO_4$, filtered over celite, and concentrated under reduced pressure to provide 507 mg (75%) of Compound 54 as a viscous oil. TLC (85:15 DCM:MeOH, visualized with iodine) was a single major spot $R_f$=0.51. The purity was verified by HPLC and the product was used in the subsequent step without further purification or characterization.

Synthesis of Compound 55

A 50 mL 3-neck flask was charged with 2,3,5,6-tetrafluorophenol (0.096 g, 0.577 mmol) and dichloromethane (20 mL). DCC (0.089 g, 0.433 mmol) was added in a single portion and after dissolution the flask was chilled in an ice bath. Compound 54 (0.507 g, 0.289 mmol) was dissolved in dichloromethane (10 mL) and added dropwise via addition funnel. The reaction was stirred at ambient temperature overnight. Both TLC (85:15 DCM:MeOH) and HPLC indicated complete consumption of starting material. The reaction was chilled in an ice bath and the DCU was filtered off. The solvent was removed and the oil was taken up in acetonitrile and chilled in an ice bath. The DCU was filtered off via syringe filter. Removal of the solvent provided an orange oil that was suspended in ether and the solvent decanted. The oil was dried under high vacuum and again suspended in ether and the solvent decanted. This was repeated once more. Drying under high vacuum provided 437 mg (79%) of Compound 55 as a pale yellow powdery solid. TLC (85:15 DCM:MeOH, visualized with UV and iodine) was a single major spot $R_f$=0.59. The purity was verified by HPLC and the product was used in the subsequent step without further purification or characterization.

Synthesis of Compound 56-(K)

Figure 4F:
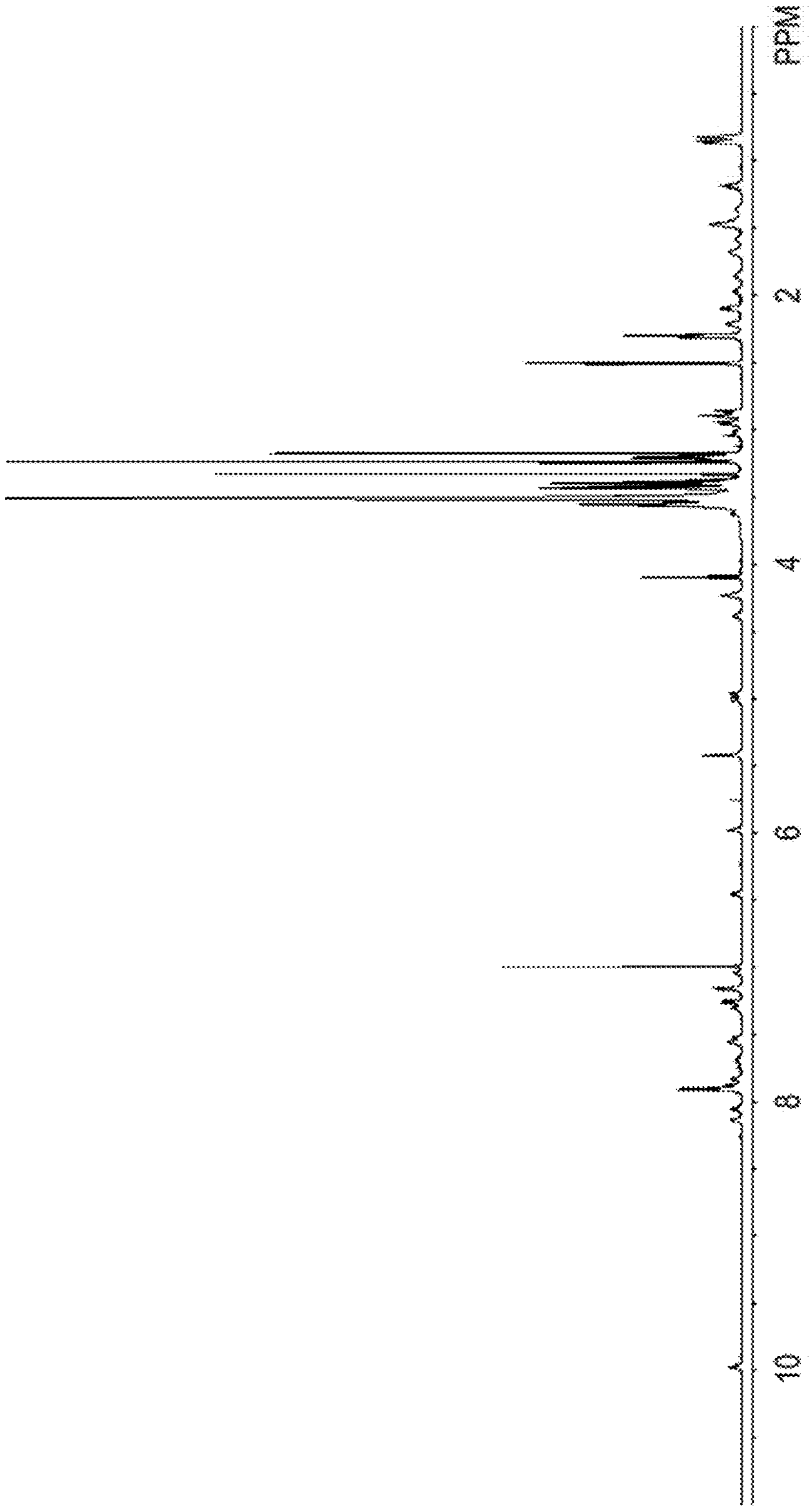
FIG. 4F provides the $^1$H NMR and HPLC spectrum obtained for conjugate 56 of FIG. 4D.
Figure 4F:
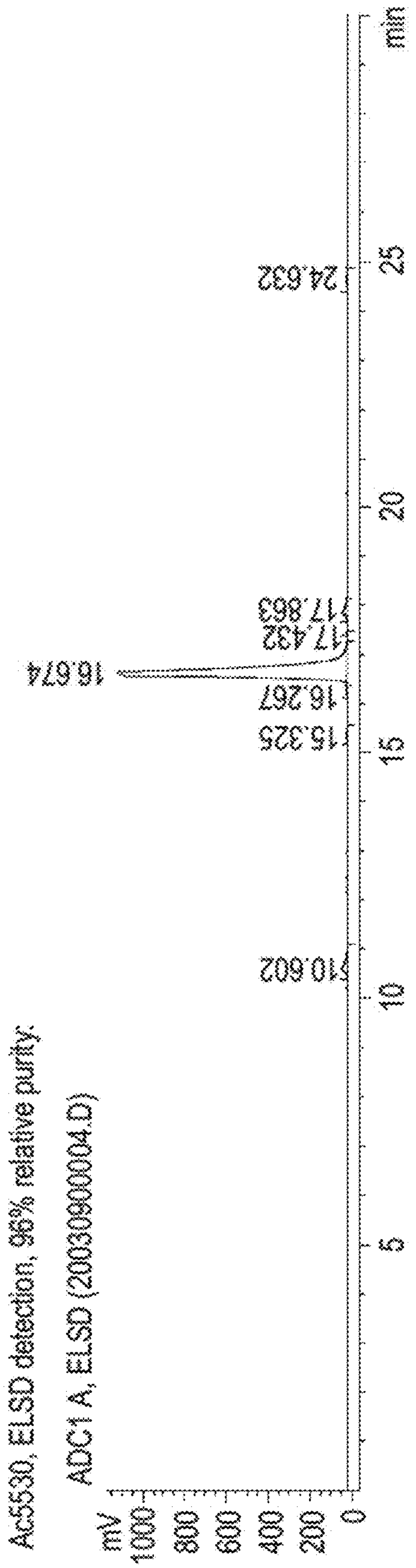
Figure 4G:
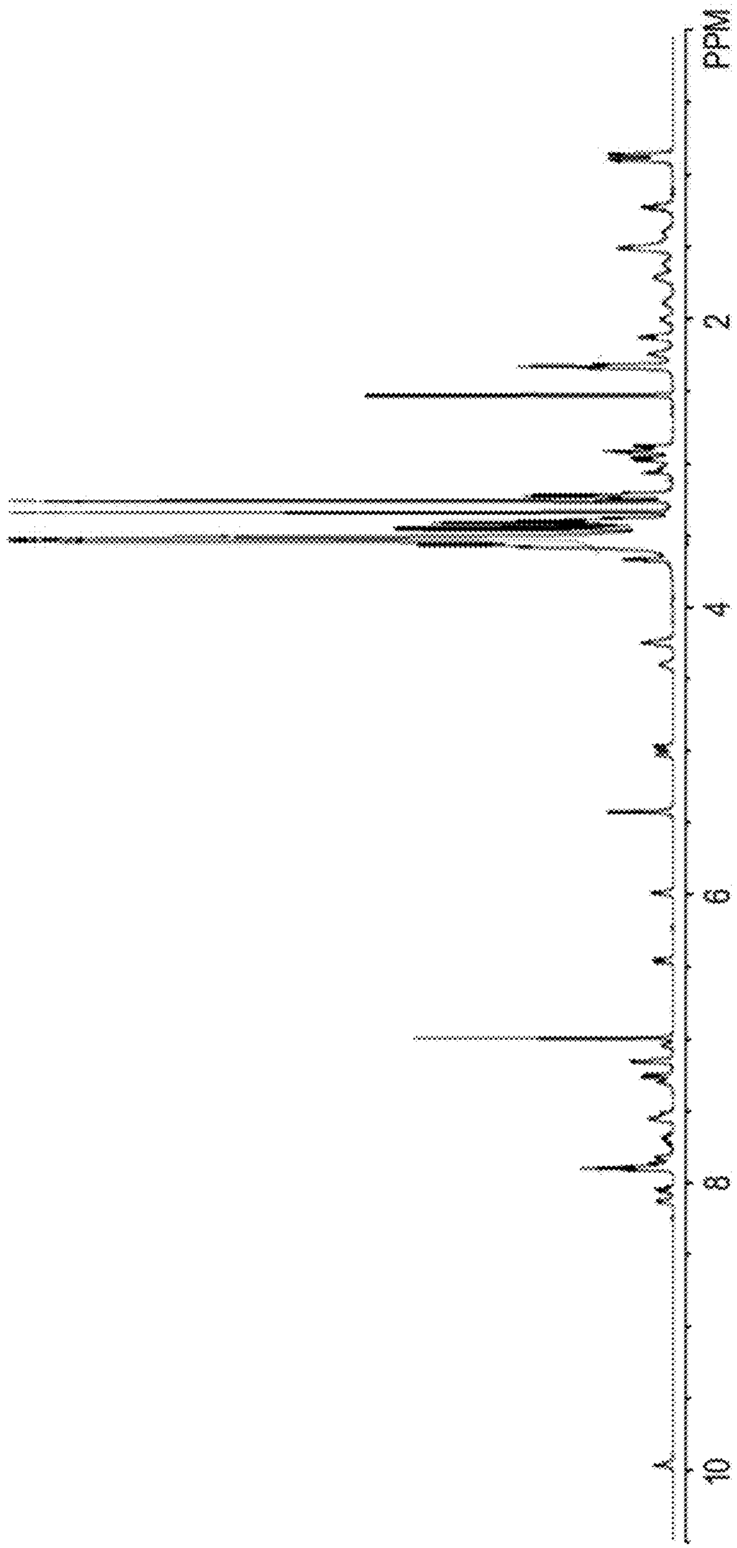
FIG. 4G provides the $^1$H NMR and HPLC spectrum obtained for conjugate 90 of FIG. 4D.
Figure 4G:
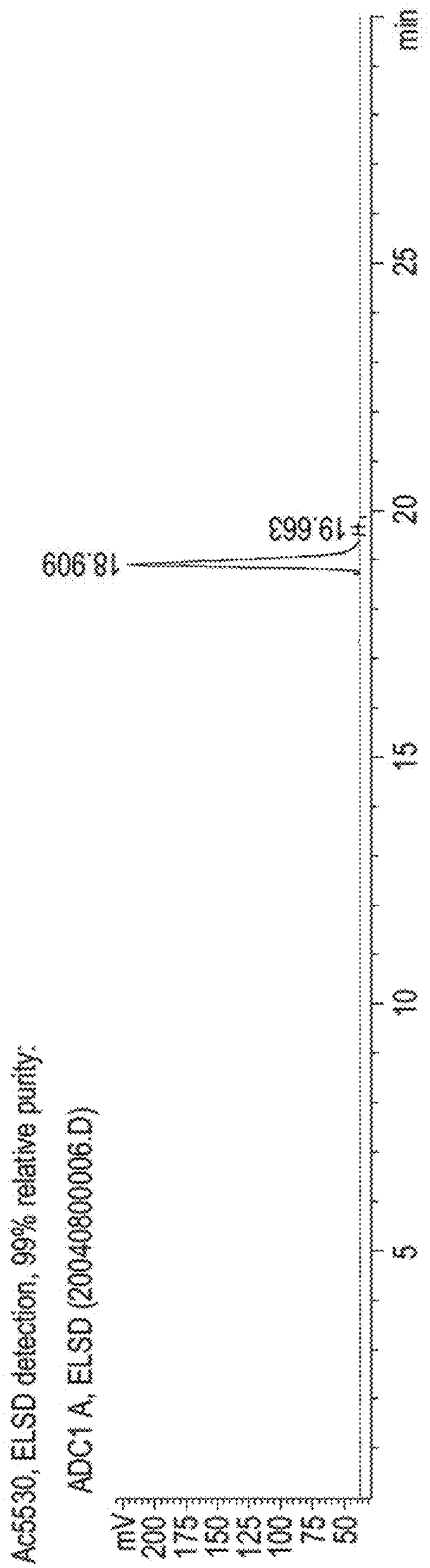

A 25 mL flask was charged with (55) (0.437 g, 0.230 mmol) and dichloromethane (7 mL). In a separate flask, Compound 13 (0.188 g, 0.275 mmol) was dissolved in DMF (4 mL) and then added dropwise. The reaction was stirred for at ambient temperature for two hours. Both TLC (85:15 DCM:MeOH) and HPLC indicated complete reaction. The solvent was removed under vacuum to give a viscous DMF solution. Hexanes was added and then decanted from the oil, which was rinsed once more with hexanes. The oil was dried under high vacuum and then ether was added to give an oily solid. The solid was crushed under ether and the solvent decanted. The oil was pre-absorbed onto 2 g of silica gel and purified on a 12 g column with dichloromethane and methanol. Tubes 9-14 were pooled and concentrated to give an oily solid that was triturated with ether and dried under vacuum to provide 445 mg (80%) of (56) as a pale yellow viscous oil. TLC (85:15 DCM:MeOH, visualized with UV and iodine) was a single spot $R_f$=0.39. The product was characterized by ESI (calculated: 2418.2795, observed: 2419.3 $[M+H]^+$), HPLC, and $^1H$ NMR ($d_6$-DMSO) (FIG. 4F).

Synthesis of Compound 90 (FIG. 4E)

Synthesis of Compound 88

A 50 mL flask was charged with (21) (0.141 g, 0.392 mmol) and dichloromethane (15 mL) and chilled in an ice bath. In a separate flask, Compound 84 (1.2 g, 0.326 mmol) was dissolved in dichloromethane (15 mL) and N,N-diisopropylethylamine (0.137 ml, 0.783 mmol) was added via syringe. The mixture was placed in an addition funnel and added dropwise. The ice bath was removed and the reaction was stirred at ambient temperature for 14 hours. Both TLC (85:15 DCM:MeOH) and HPLC indicated formation of a single major product. The reaction was diluted to 200 mL with dichloromethane, washed with 10% HCl (5×10 mL), washed with brine, dried over $MgSO_4$, filtered over celite, and concentrated under reduced pressure to provide a white solid. The solid was suspended in ether and stirred vigorously for 10 minutes. The solvent was decanted. This was repeated once more and the solid was dried under high vacuum to give 1.122 g (89%) of Compound 88 as a white powdery solid. TLC (85:15 DCM:MeOH, visualized with iodine) was a single major spot $R_f$=0.58. The purity was verified by HPLC and the product was used in the subsequent step without further purification or characterization.

Synthesis of Compound 89

A 50 mL 3-neck flask was charged with 2,3,5,6-tetrafluorophenol (0.096 g, 0.580 mmol) and dichloromethane (15 mL). DCC (0.090 g, 0.435 mmol) was added in a single portion and the mixture was stirred for ten minutes. Compound 88 (1.122 g, 0.290 mmol) was dissolved in dichloromethane (15 mL) and added dropwise. The reaction was stirred at ambient temperature for 16 hours. Both TLC (85:15 DCM:MeOH) and HPLC indicated formation of a single major product. The reaction was chilled in an icebath and the DCU was filtered off using a syringe filter. The solvent was removed and the oil was taken up in acetonitrile and chilled in an ice bath. The DCU was filtered off via syringe filter. Removal of the solvent provided an orange oil that was triturated with ether and dried under high vacuum to give a pale orange solid. The solid was suspended in ether and the solvent decanted (2×). Drying under high vacuum provided 1.08 g (93%) of Compound 89 as a white powdery solid. TLC (85:15 DCM:MeOH, visualized with UV and iodine) was a single major spot $R_f$=0.56. The purity was verified by HPLC and the product was used in the subsequent step without further purification or characterization.

Synthesis of Compound 90-(Q)

A 25 mL flask was charged Compound 89 (0.45 g, 0.112 mmol) and dichloromethane (7 mL). Compound 13 (0.092 g, 0.134 mmol) was dissolved in DMF (3 mL) and added dropwise. The reaction was stirred at ambient temperature for 24 hours. Both TLC (85:15 DCM:MeOH) and HPLC indicated complete reaction. The solvent was removed under vacuum to give a viscous oil. Hexanes was added and then decanted from the oil, which was rinsed once more with hexanes. The oil was dried under high vacuum and then triturated with ether to give an oily solid. The solid was crushed under ether and the solvent decanted. The solid was pre-absorbed onto 2 g of silica gel and purified on a 12 g column with dichloromethane and methanol. Tubes 5-11 were pooled, concentrated, and dried under vacuum to provide 0.347 g (68%) of Compound 90 as an off-white powdery solid. TLC (85:15 DCM:MeOH, visualized with UV and iodine) was a single spot $R_f$=0.52. The product was characterized by HRMS (calculated: 4531.5378, observed: 2288.7629 $[M-2H]^{2-}$), HPLC, and $^1H$ NMR ($d_6$-DMSO) (FIG. 4F).

Figure 5A:
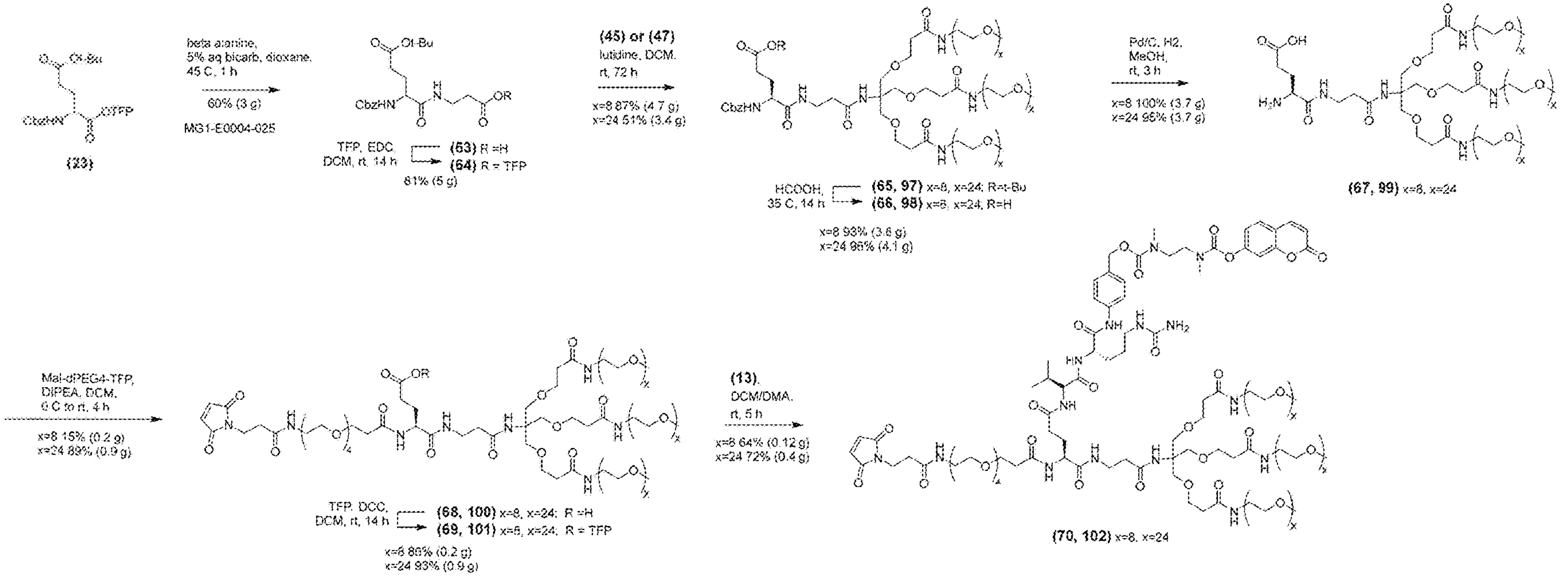
FIG. 5A shows the synthesis of conjugates 70 (G, x=8, y=3) and 102 (M, x=24, y=3) of Formula (II) disclosed herein.
Figure 5A:
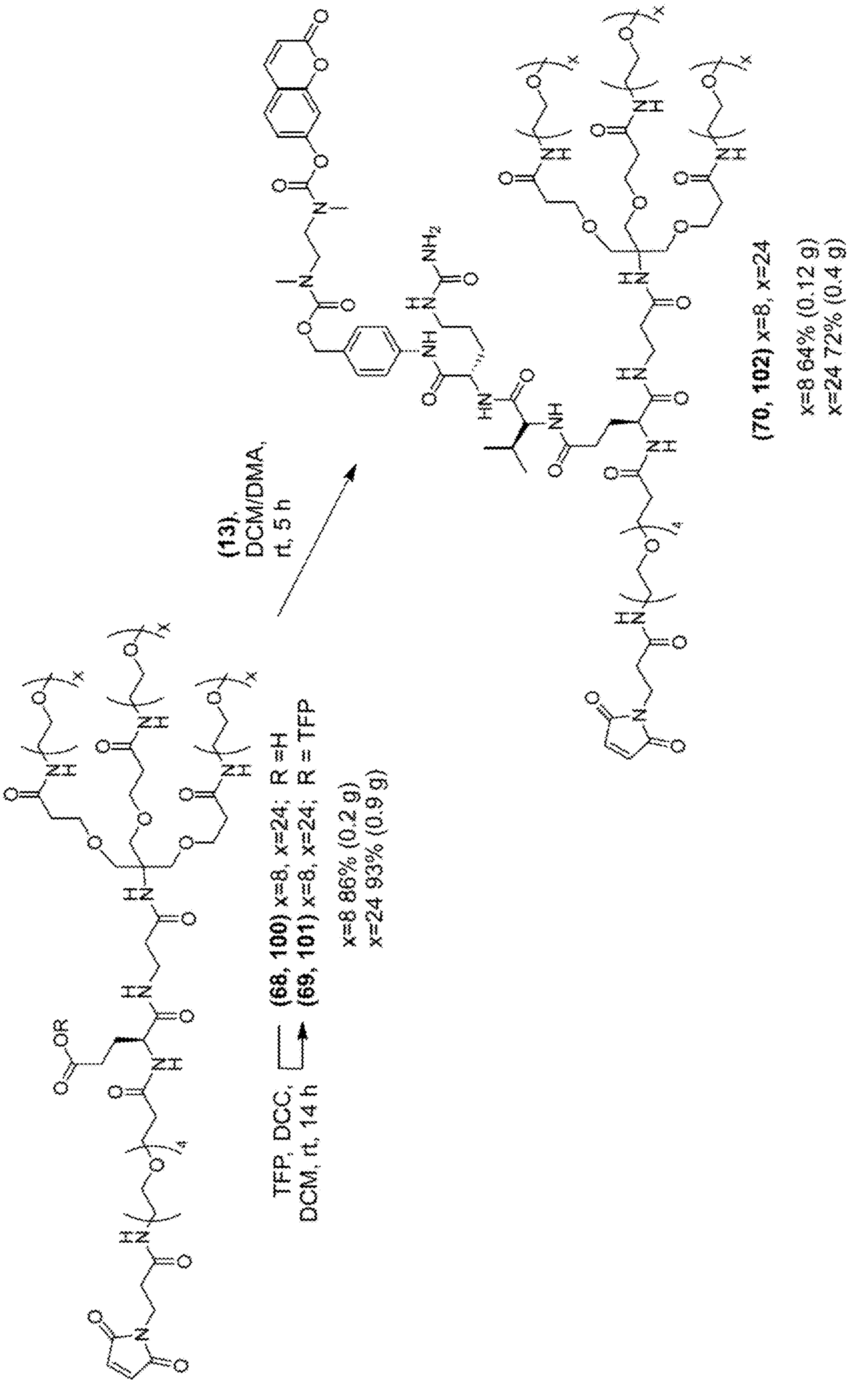

Synthesis of Compound 70 (FIG. 5A)

Synthesis of Compound 64

A 250 mL flask was charged with 2,3,5,6-tetrafluorophenol (2.463 g, 14.83 mmol) and dichloromethane (25 mL). EDC (2.84 g, 14.83 mmol) was added in a single portion and after dissolution the solution was chilled in an ice bath. Compound 63 (4.66 g, 11.41 mmol) was dissolved in dichloromethane (50 mL) and added dropwise via addition funnel. The ice bath was removed and the reaction was stirred at ambient temperature overnight. Both TLC (60:40 hexanes:ethyl acetate) and HPLC indicted a single product and tetrafluorophenol. The reaction was diluted with dichloromethane, washed with water, washed with brine, dried, filtered, and concentrated to give a pale yellow oil. The oil was pre-absorbed onto 15 g of silica gel and purified on an 80 g column with hexanes and ethyl acetate. Tubes 11-18 were pooled and concentrated to give 5.13 g (81%) of Compound 64 as a white solid. TLC (60:40 hexanes:ethyl acetate, visualized with UV) was a single spot $R_f$=0.34. The product was characterized by LRMS (calculated: 556.1833, observed: 579.3 $[M+H+Na]^+$, 595.2 $[M+H+K]^+$), HPLC, and $^1H$ NMR ($CDCl_3$).

Synthesis of Compound 65

A 250 mL flask was charged with Compound 64 (2.170 g, 3.90 mmol) and dichloromethane (25 mL). Compound 45 (4.3 g, 3.00 mmol) was dissolved in dichloromethane (45 mL) and N,N-diisopropylethylamine (0.681 ml, 3.90 mmol) was added via syringe. The mixture was placed in an addition funnel and added dropwise. The reaction was stirred at ambient temperature for 48 hours. Both TLC (90:10 DCM:MeOH) and HPLC indicated a single major product spot and consumption of starting material. The reaction was diluted to 200 mL with dichloromethane and washed with 0.5M HCl (3×20 mL). The organic phase was washed with brine, dried over $MgSO_4$, filtered over celite, and concentrated to give a viscous oil. The oil was pre-absorbed onto 15 g of silica gel and purified on an 80 g column with dichloromethane and methanol. Tubes 14-40 were pooled and concentrated to give 4.74 g (87%) of Compound 65 as a colorless viscous oil. TLC (90:10 DCM:MeOH, visualized with UV and iodine) was a single spot $R_f$=0.46. The product was characterized by MALDI (calculated: 1823.0404, observed: 1846.107 $[M+H+Na]^+$, 1862.077 $[M+H+K]^+$), HPLC, and $^1H$ NMR ($CDCl_3$).

Synthesis of Compound 66

A 100 mL 3-neck flask was charged with Compound 65 (4.54 g, 2.59 mmol) and formic acid (49.7 ml, 1295 mmol) and heated to 35° C. for 16 hours. Both TLC (85:15 DCM:MeOH) and HPLC indicated complete consumption of starting material. The formic acid was removed on a rotary evaporator, the oil suspended in ether, allowed to settle, and the solvent decanted. This was repeated once more. Drying under high vacuum provided 3.88 g (93%) of Compound 66 as a clear colorless oil. TLC (85:15 DCM:MeOH, visualized with iodine) was a single spot $R_f$=0.41. The product was characterized by MALDI (calculated: 1766.9778, observed: 1767.9756 $[M+H]^+$), HPLC, and $^1H$ NMR ($CDCl_3$).

Synthesis of Compound 67

A 250 mL flask was charged with methanol-wet 10% palladium on activated charcoal (0.350 g) and methanol (75 mL) and hydrogen purge was started. Compound 66 (3.882 g, 2.196 mmol) was dissolved in a small amount of methanol and added to the flask. The reaction was stirred under a hydrogen purge for 3 hours. Both TLC (85:15 DCM:MeOH) and HPLC indicated complete conversion of starting material. The reaction was filtered over a methanol-wet bed of celite and concentrated under reduced pressure to provide 3.69 g (100%) of Compound 67 as a clear pale yellow oil. The purity was verified by HPLC and the product was used in the subsequent step without further purification or characterization.

Synthesis of Compound 68

A 50 mL flask was charged with Mal-dPEG 4-TFP ester (0.230 g, 0.408 mmol) and dichloromethane (10 mL) and chilled in an ice bath. In a separate flask, Compound 67 (0.513 g, 0.314 mmol) was dissolved dichloromethane (10 mL) and N,N-diisopropylethylamine (0.143 ml, 0.816 mmol) was added via syringe. The mixture was placed in an addition funnel and added dropwise. The ice bath was removed and the reaction was stirred at ambient temperature for 4 hours. Both TLC (85:15 DCM:MeOH) and HPLC indicated a single major spot and some minor impurities. The reaction was diluted to 200 mL with dichloromethane, washed with 10% HCl (5×10 mL), washed with brine, dried over $MgSO_4$, filtered over celite, and concentrated under reduced pressure to provide an oil. The oil was pre-absorbed onto 2 g of silica gel and purified on a 24 g column with dichloromethane and methanol. Tubes 11-22 were pooled and concentrated to provide 230 mg (36%) of (68) as a clear colorless oil. TLC (85:15 DCM:MeOH) was a single major spot $R_f$=0.37. The purity was verified by HPLC and the product was used in the subsequent step without further purification or characterization.

Synthesis of Compound 69

A 50 mL 3-neck flask was charged with 2,3,5,6-tetrafluorophenol (0.027 g, 0.163 mmol) and dichloromethane (4 mL). DCC (0.025 g, 0.123 mmol) was added in a single portion and the mixture was stirred for ten minutes. Compound 68 (0.166 g, 0.082 mmol) was dissolved in dichloromethane (4 mL) and added dropwise. The reaction was stirred at ambient temperature for 3 hours. Both TLC (85:15 DCM:MeOH) and HPLC indicated consumption of starting material. The reaction was chilled in an ice bath and the DCU was filtered off using a syringe filter. The solvent was removed and the oil was taken up in acetonitrile and chilled in an ice bath. The DCU was filtered off via syringe filter. Removal of the solvent provided an orange oil that was suspended in ether and the solvent decanted. Drying under high vacuum gave a pale orange oil that was again suspended in ether and the solvent decanted. This was repeated once more. Drying under high vacuum provided 153 mg (86%) of Compound 69 as a pale orange oil. TLC (85:15 DCM:MeOH) was a single major spot $R_f$=0.48 with a minor impurity. The purity was verified by HPLC and the product was used in the subsequent step without further purification or characterization.

Synthesis of Compound 70-(G)

Figure 5B:
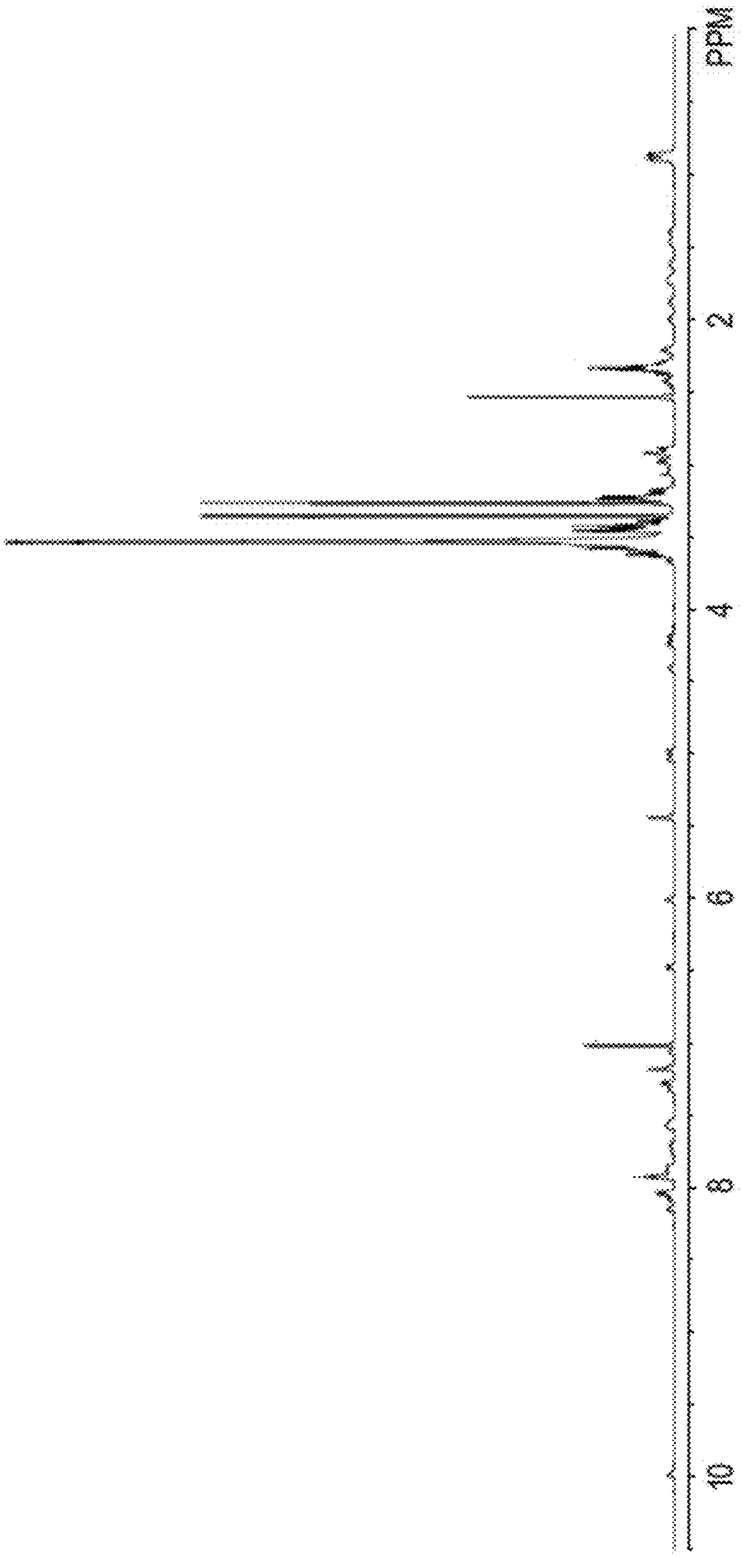
FIG. 5B provides the $^1$H NMR and HPLC spectrum obtained for conjugate 70 of FIG. 5A.
Figure 5B:
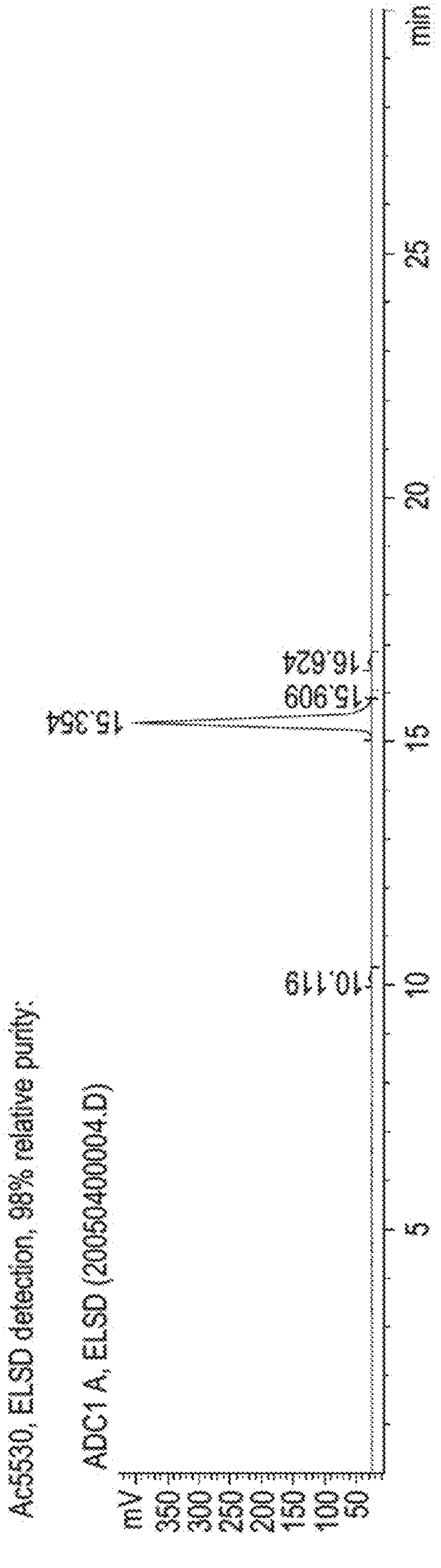

A 25 mL flask was charged Compound 69 (0.153 g, 0.070 mmol) and dichloromethane (5 mL). (13) (0.055 g, 0.081 mmol) was dissolved in DMF (2 mL) and added dropwise. The reaction was stirred at ambient temperature for 24 hours. Both TLC (85:15 DCM:MeOH) and HPLC indicated complete reaction. The solvent was removed under vacuum to give a viscous oil. Hexanes was added and then decanted from the oil, which was rinsed once more with hexanes. The oil was pre-absorbed onto 1 g of silica gel and purified on a 12 g column with dichloromethane and methanol. Tubes 10-15 were pooled, concentrated, and dried under vacuum to provide 121 mg (64%) of Compound 70 as a clear pale yellow oil. TLC (85:15 DCM:MeOH, visualized with UV and iodine) was a single spot $R_f$=0.37. The product was characterized by HRMS (calculated: 2278.1845, observed: 2279.1918 $[M+H]^+$), HPLC, and $^1H$ NMR ($d_6$-DMSO) (FIG. 5B).

Synthesis of Compound 102 (FIG. 5A)

Synthesis of Compound 97

A 250 mL flask was charged with Compound 64 (1.232 g, 2.213 mmol) and dichloromethane (8 mL). Compound 47 (6.04 g, 1.702 mmol) was dissolved in dichloromethane (25 mL) and N,N-diisopropylethylamine (0.386 ml, 2.213 mmol) was added via syringe. The mixture was placed in an addition funnel and added dropwise. The reaction was stirred at ambient temperature for 72 hours. Both TLC (85:15 DCM:MeOH) and HPLC showed formation of a major product. The reaction was diluted to 200 mL with dichloromethane and washed with 0.5M HCl (3×20 mL). The organic phase was washed with brine, dried over $MgSO_4$, filtered over celite, and concentrated to give a viscous oil. The oil was pre-absorbed onto 12 g of silica gel and purified on a 120 g column with dichloromethane and methanol. Tubes 9-18 were pooled, concentrated, and dried under high vacuum to provide 3.44 g (51%) of (97) as a white solid. TLC (85:15 DCM:MeOH, visualized with UV and iodine) was a single spot $R_f$=0.59. The product was characterized by MALDI (calculated: 3936.2987, observed: 3939.2579 $[M+H]^+$, 3961.241 $[M+H+Na]^+$), HPLC, and $^1H$NMR ($CDCl_3$).

Synthesis of Compound 98

A 100 mL flask was charge with Compound 97 (4.323 g, 1.098 mmol) and formic acid (42.1 ml, 1098 mmol) and warmed to 35° C. for 16 hours. Both TLC (85:15 DCM:MeOH) and HPLC indicated complete reaction. The solvent was removed and the residue triturated with ether to give an off-white solid. The solid was stirred vigorously under ether for 15 minutes, the solvent decanted, and the residue dried under high vacuum to give 4.106 g (96%) of Compound 98 as a white powdery solid. The product was characterized by MALDI (calculated: 3880.2361, observed: 3903.523 $[M+H+Na]^+$, 3919.515 $[M+H+K]^+$), HPLC, and $^1H$NMR ($CDCl_3$).

Synthesis of Compound 99

A 100 mL 3-neck flask was charged with methanol-wet 10% palladium on activated charcoal (0.450 g) and methanol (50 mL) and a hydrogen purge was started. Compound 98 (4.1 g, 1.056 mmol) was dissolved in a small amount of methanol and added to the flask. The reaction was stirred under a hydrogen purge for five hours. Both TLC (85:15 DCM:MeOH) and HPLC indicated complete consumption of starting material. The reaction was filtered over a methanol-wet bed of celite, concentrated, and dried under high vacuum to 3.742 g (95%) of Compound 99 as a white solid. The purity was verified by HPLC and the product was used in the subsequent step without further purification or characterization.

Synthesis of Compound 100

A 50 mL flask was charged with Mal-dPEG 4-TFP ester (0.163 g, 0.288 mmol) and dichloromethane (12 mL) and chilled in an ice bath. In a separate flask, Compound 99 (0.9 g, 0.240 mmol) was dissolved in and dichloromethane (12 mL) and N,N-diisopropylethylamine (0.101 ml, 0.576 mmol) was added via syringe. The mixture was placed in an addition funnel and added dropwise. The ice bath was removed and the reaction was stirred at ambient temperature for 16 hours. Both TLC (85:15 DCM:MeOH) and HPLC indicated complete consumption of starting material and formation of a single major product. The reaction was diluted to 150 mL with dichloromethane, washed with 10% HCl (5×10 mL), washed with brine, dried over $MgSO_4$, filtered over celite, and concentrated under reduced pressure to provide an oil. The oil was suspended in MTBE and the solvent was decanted to give a solid. The solid was rinsed with MTBE and then suspended in MTBE with vigorous stirring for 10 minutes. The MTBE was decanted and the solid dried under high vacuum to give 0.886 g (89%) of Compound 100 as a white powdery solid. TLC (85:15 DCM:MeOH, visualized with iodine) was a single major spot $R_f$=0.21. The purity was verified by HPLC and the product was used in the subsequent step without further purification or characterization.

Synthesis of Compound 101

A 50 mL 3-neck flask was charged with 2,3,5,6-tetrafluorophenol (0.071 g, 0.427 mmol) and dichloromethane (10 mL). DCC (0.066 g, 0.320 mmol) was added in a single portion and the mixture was stirred for ten minutes. Compound 100 (0.886 g, 0.214 mmol) was dissolved in dichloromethane (10 mL) and added dropwise. The reaction was stirred at ambient temperature for 24 hours. Both TLC (85:15 DCM:MeOH) and HPLC indicated formation of a major product. The reaction was chilled in an ice bath and the DCU was filtered off using a syringe filter. The solvent was removed and the oil was taken up in acetonitrile and chilled in an ice bath. The DCU was filtered off via syringe filter. Removal of the solvent provided an orange oil that was suspended in ether and the solvent decanted. Drying under high vacuum gave a pale orange solid. The solid was suspended in ether and stirred vigorously for ten minutes and then the solvent decanted. This was repeated once more. Drying under high vacuum provided 0.854 g (93%) of Compound 101 as a pale orange solid. TLC (85:15 DCM:MeOH, visualized with UV and iodine) was a single major spot $R_f$=0.39. The purity was verified by HPLC and the product was used in the subsequent step without further purification or characterization.

Synthesis of Compound 102-(M)

Figure 5C:
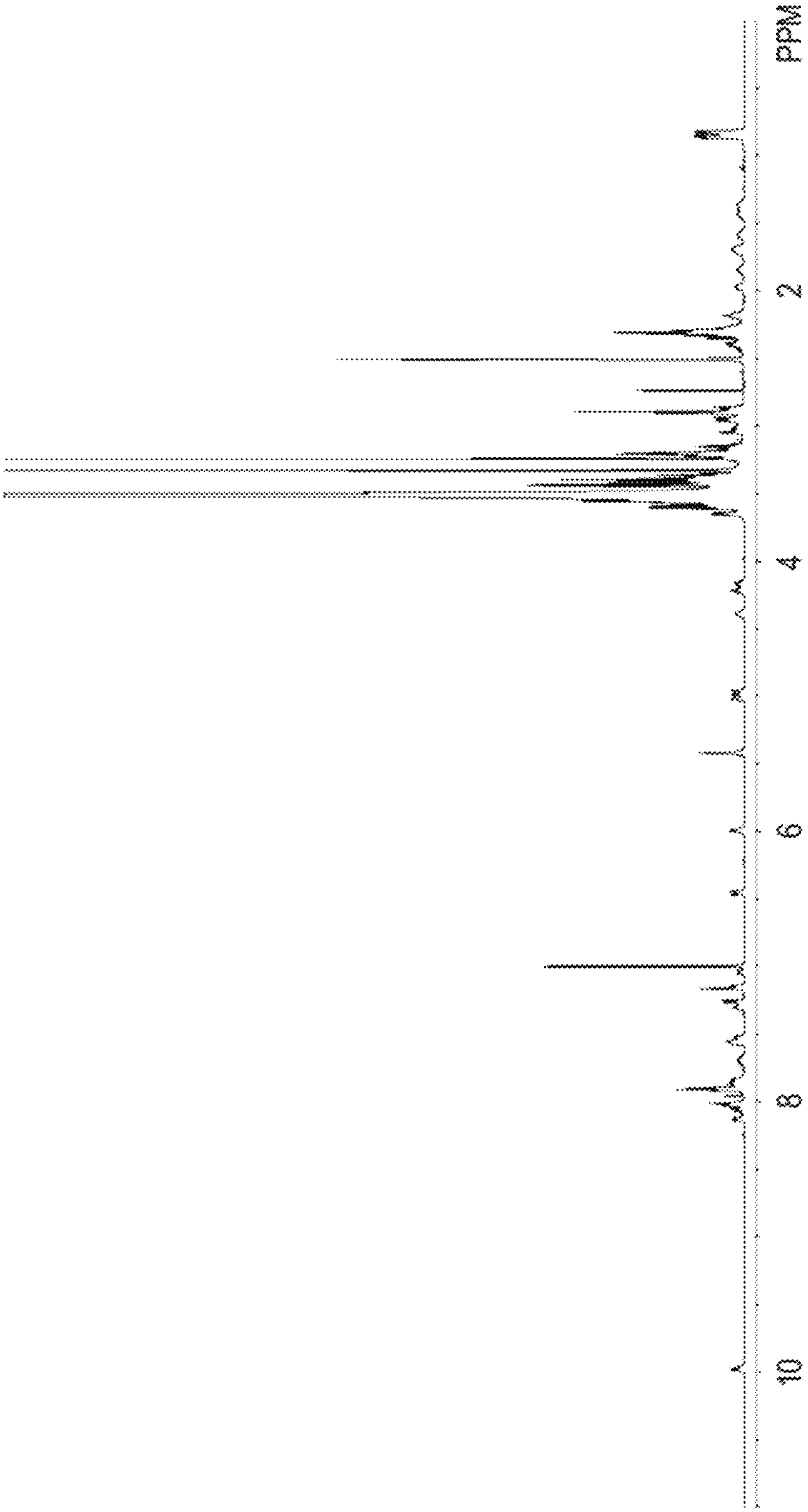
FIG. 5C provides the $^1$H NMR and HPLC spectrum obtained for conjugate 102 of FIG. 5A.
Figure 5C:
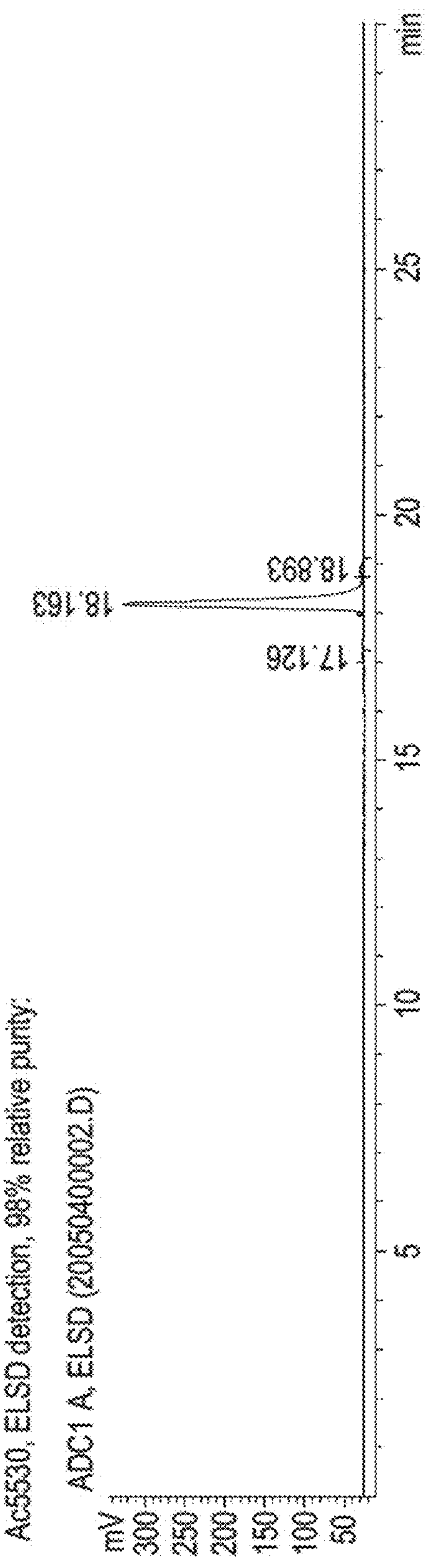

A 25 mL flask was charged Compound 101 (0.45 g, 0.105 mmol) and dichloromethane (8 mL). (13) (0.082 g, 0.120 mmol) was dissolved in DMF (4 mL) and added dropwise. The reaction was stirred at ambient temperature for 24 hours. Both TLC (85:15 DCM:MeOH) and HPLC indicated complete reaction. The solvent was removed under vacuum to give a viscous oil. Hexanes was added and then decanted from the oil, which was rinsed once more with hexanes. The oil was dried under high vacuum and triturated with ether to give an oily solid. The oil was pre-absorbed onto 2 g of silica gel and purified on a 12 g column with dichloromethane and methanol. Tubes 6-15 were pooled, concentrated, and dried under high vacuum to provide 0.365 g (72%) of Compound 102 as an off-white powdery solid. TLC (85:15 DCM:MeOH, visualized with UV and iodine) was a single spot $R_f$=0.55. The product was characterized by HRMS (calculated: 4807.6699, observed: 2422.3154 $[M+K-2H]^{2-}$), HPLC, and $^1$H NMR ($d_6$-DMSO) (FIG. 5C).

Figure 5D:
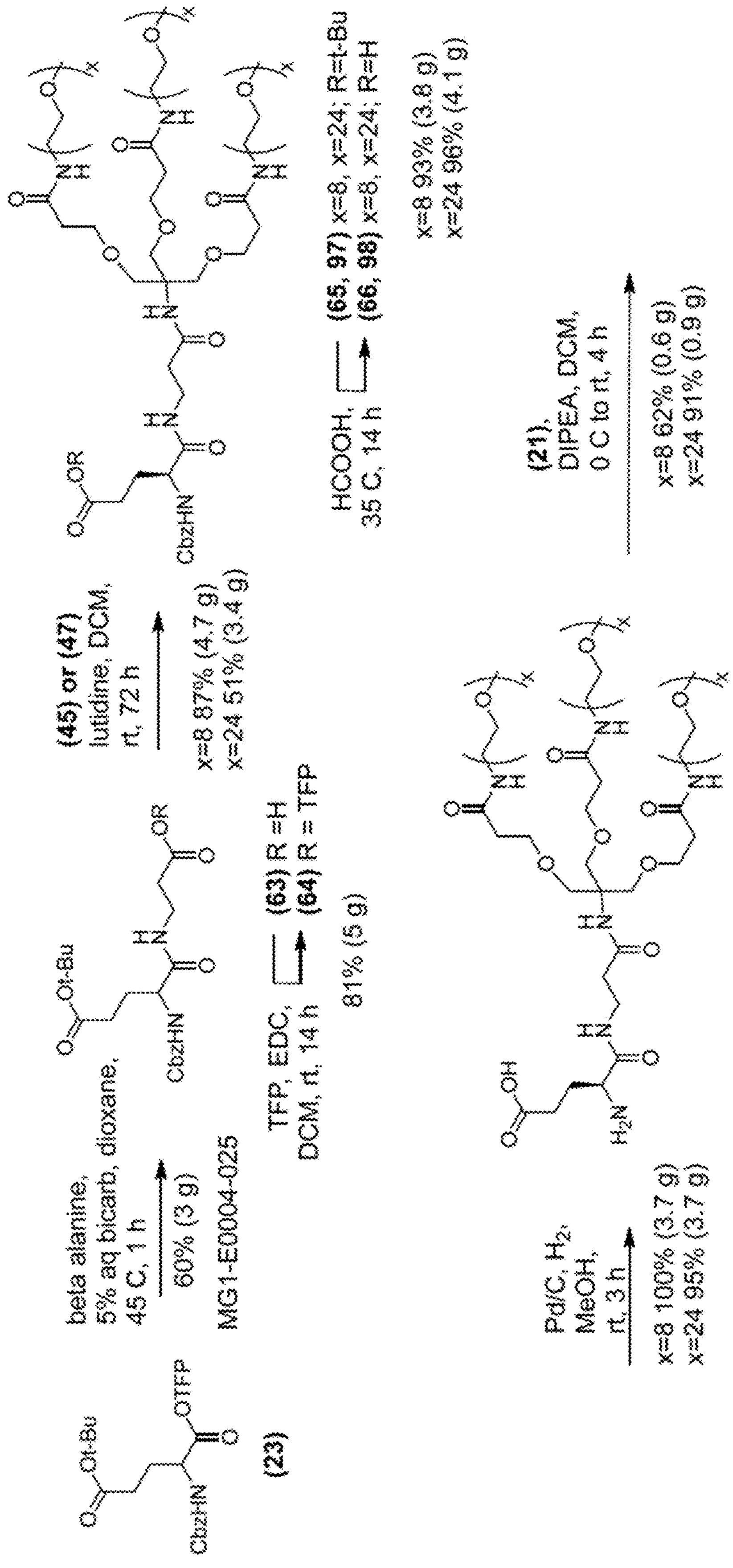
FIG. 5D shows the synthesis of conjugates 73 (H, x=8, y=3) and 105 (N, x=24, y=3) of Formula (II) disclosed herein.
Figure 5D:
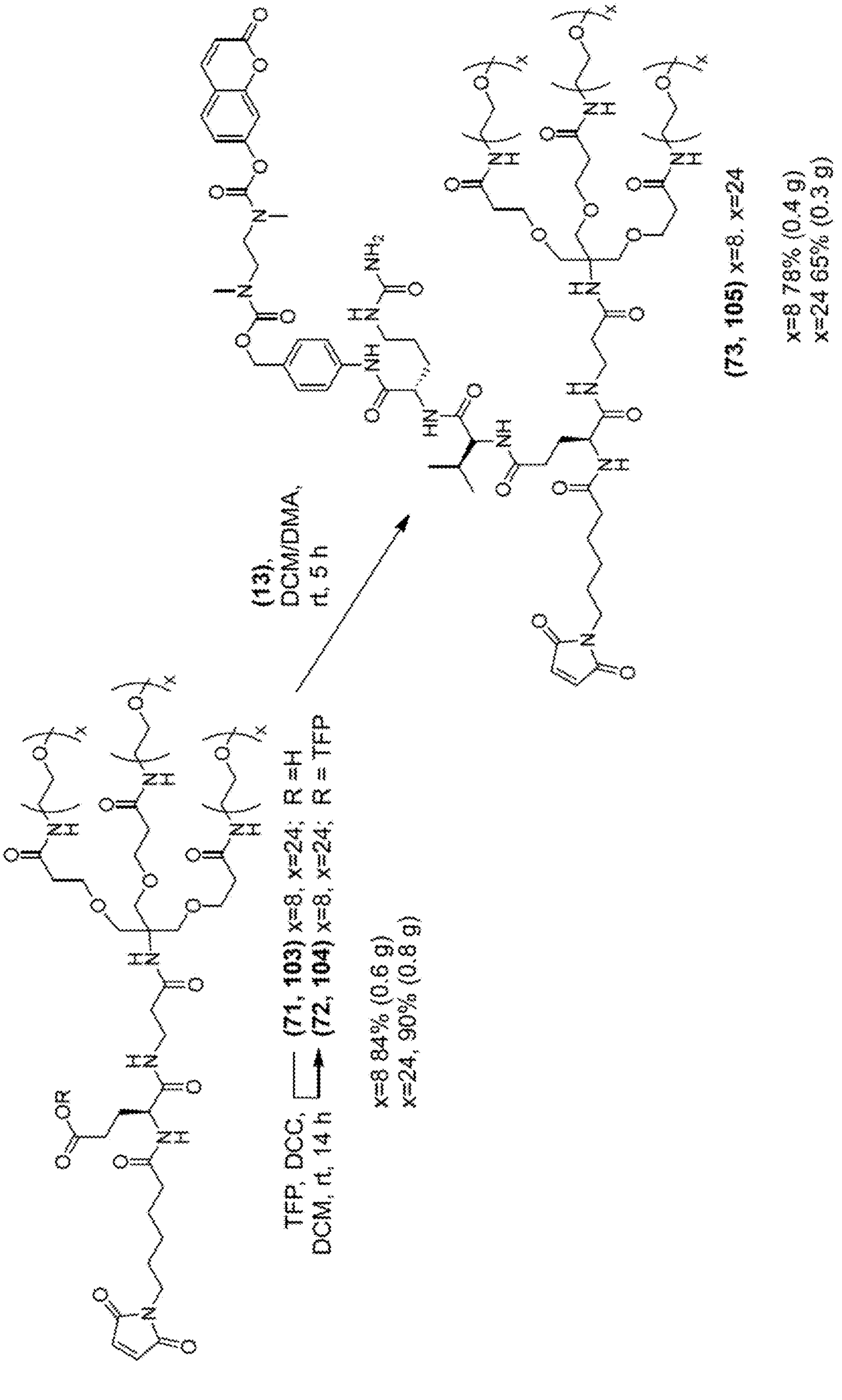

Synthesis of Compound 73 (FIG. 5D)

Synthesis of Compound 71

A 50 mL flask was charged with Compound 21 (0.243 g, 0.676 mmol) and dichloromethane (14 mL) and chilled in an ice bath. In a separate flask, Compound 67 (0.92 g, 0.563 mmol) was dissolved in dichloromethane (14 mL) and N,N-diisopropylethylaine (0.393 ml, 2.252 mmol) was added via syringe. The mixture was placed in an addition funnel and added dropwise. The ice bath was removed and the reaction was stirred at ambient temperature for 3 hours. Both TLC (85:15 DCM:MeOH) and HPLC indicated complete consumption of starting material and formation of a single product. The reaction was diluted to 200 mL with dichloromethane, washed with 10% HCl (3×5 mL), and concentrated under reduced pressure. The residue was taken up in 50 mL water, washed with MTBE (3×10 mL), washed with hexanes (10 mL), salt was added, and the aqueous phase was extracted with dichloromethane (3×100 mL). The organics were washed with brine, dried over $MgSO_4$, filtered over celite, and concentrated under reduced pressure to provide 640 mg (62%) of Compound 71 as a viscous oil. TLC (85:15 DCM:MeOH, visualized with iodine) was a single major spot $R_f$=0.52. The purity was verified by HPLC and the product was used in the subsequent step without further purification or characterization.

Synthesis of Compound 72

A 50 mL 3-neck flask was charged with 2,3,5,6-tetrafluorophenol (0.116 g, 0.701 mmol) and dichloromethane (25 mL). DCC (0.108 g, 0.525 mmol) was added in a single portion and the mixture was stirred for ten minutes. Compound 71 (0.350 g, 0.640 mmol) was dissolved in dichloromethane (12 mL) and added dropwise. The reaction was stirred at ambient temperature for 16 hours. Both TLC (85:15 DCM:MeOH) and HPLC indicated a single major product. The reaction was chilled in an ice bath and the DCU was filtered off over via syringe filter. The solvent was removed and the oil was taken up in acetonitrile and chilled in an ice bath. The DCU was filtered off via syringe filter. Removal of the solvent provided an orange oil that was suspended in hexanes and the solvent decanted. Drying under high vacuum gave an orange oil. The oil was suspended in ether and the solvent decanted. This was repeated once more. Drying under high vacuum provided 583 mg (84%) of (72) as an orange viscous oil. TLC (85:15 DCM:MeOH, visualized with UV and iodine) was a single major spot $R_f$=0.61. The purity was verified by HPLC and the product was used in the subsequent step without further purification or characterization.

Synthesis of Compound 73-(H)

Figure 5E:
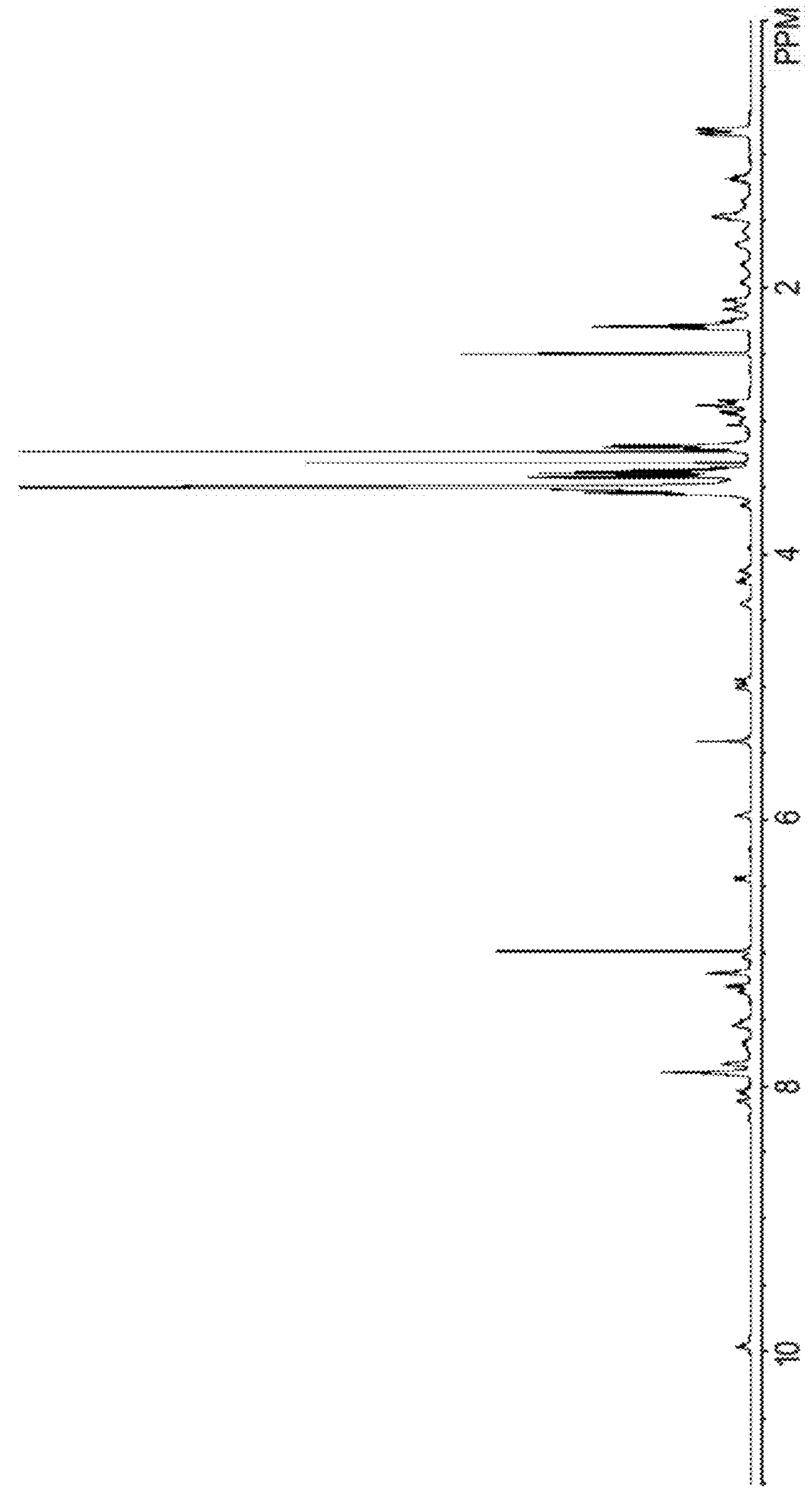
FIG. 5E provides the $^1$H NMR and HPLC spectrum obtained for conjugate 73 of FIG. 5D.
Figure 5E:
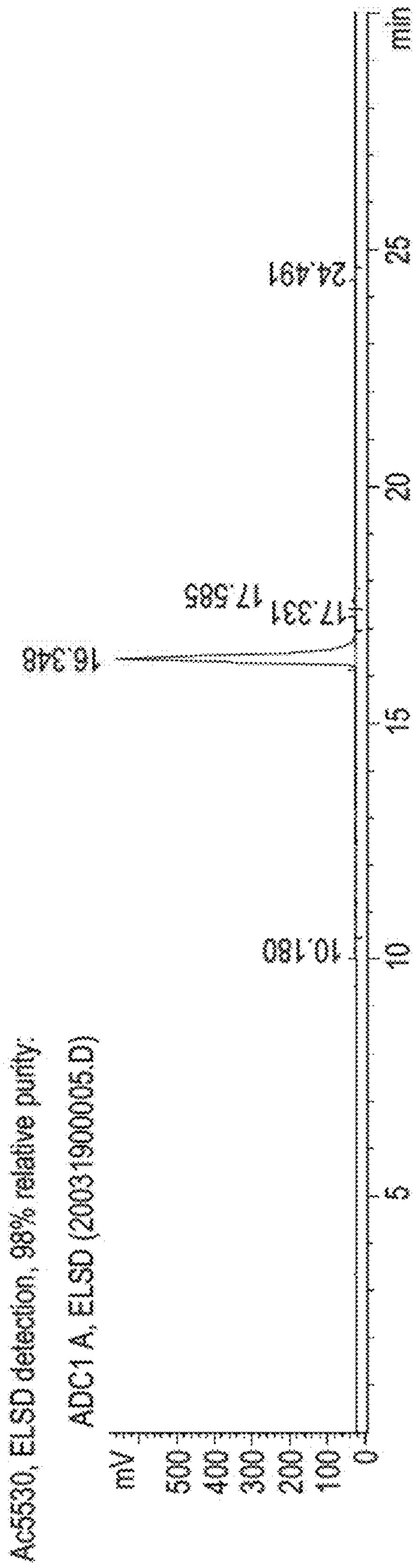

A 25 mL flask was charged with Compound 72 (0.42 g, 0.213 mmol) and dichloromethane (10 mL). Compound 13 (0.174 g, 0.255 mmol) was dissolved in DMF (4 mL) and added dropwise. The reaction was stirred at ambient temperature for three hours. Both TLC (85:15 DCM:MeOH) and HPLC indicated complete reaction. The solvent was removed under vacuum to give a viscous oil. Hexanes was added and then decanted from the oil, which was rinsed once more with hexanes. The oil was dried under high vacuum and then ether was added to give an oily residue. The residue was stirred under ether and the solvent decanted. The oil was pre-absorbed onto 2 g of silica gel and purified on a 12 g column with dichloromethane and methanol. Tubes 11-19 were pooled, concentrated, and dried under vacuum to provide 412 mg (78%) of Compound 73 as a pale yellow viscous oil. TLC (85:15 DCM:MeOH, visualized with UV and iodine) was a single spot $R_f$=0.42. The product was characterized by LRMS (calculated: 2489.3166, observed: 2490.3 $[M+H]^+$), HPLC, and $^1H$ NMR ($d_6$-DMSO) (FIG. 5E).

Synthesis of Compound 105 (FIG. 5D)

Synthesis of Compound 103

A 50 mL flask was charged with Compound 21 (0.108 g, 0.299 mmol) and dichloromethane (13 mL) and chilled in an ice bath. In a separate flask, Compound 99 (0.935 g, 0.249 mmol) was dissolved in dichloromethane (13 mL) and N,N-diisopropylethylamine (0.105 ml, 0.599 mmol) was added via syringe. The mixture was placed in an addition funnel and added dropwise. The ice bath was removed and the reaction was stirred at ambient temperature for three hours. Both TLC (85:15 DCM:MeOH) and HPLC indicated complete consumption of starting material and formation of a single major product. The reaction was diluted to 200 mL with dichloromethane, washed with 10% HCl (3×5 mL), washed with brine, dried over $MgSO_4$, filtered over celite, and concentrated under reduced pressure to provide a white solid. The solid was suspended in ether, stirred vigorously for 10 minutes, and the solvent was decanted. This was repeated once more and the solid was dried under high vacuum to give 0.895 g (91%) of Compound 103 as a white powdery solid. TLC (85:15 DCM:MeOH, visualized with iodine) was a single major spot $R_f$=0.45. The purity was verified by HPLC and the product was used in the subsequent step without further purification or characterization.

Synthesis of Compound 104

A 50 mL 3-neck flask was charged with 2,3,5,6-tetrafluorophenol (0.075 g, 0.454 mmol) and dichloromethane (10 mL). DCC (0.070 g, 0.341 mmol) was added in a single portion and the mixture was stirred for ten minutes. Compound 103 (0.895 g, 0.227 mmol) was dissolved in dichloromethane (10 mL) and added dropwise. The reaction was stirred at ambient temperature for 16 hours. Both TLC (85:15 DCM:MeOH) and HPLC indicated complete consumption of starting material. The reaction was chilled in an ice bath and the DCU was filtered off using a syringe filter. The solvent was removed and the oil was taken up in acetonitrile and chilled in an ice bath. The DCU was filtered off via syringe filter. Removal of the solvent provided an orange oil that was triturated with ether to give a pale orange solid. The solid was suspended in Et2O, stirred vigorously for ten minutes, and the solvent decanted. This was repeated once more. Drying under high vacuum provided 0.838 g (90%) of a pale orange solid. TLC (85:15 DCM:MeOH, visualized with UV and iodine) was a single major spot $R_f$=0.48. The purity was verified by HPLC and the product was used in the subsequent step without further purification or characterization.

Synthesis of Compound 105-(N)

Figure 5F:
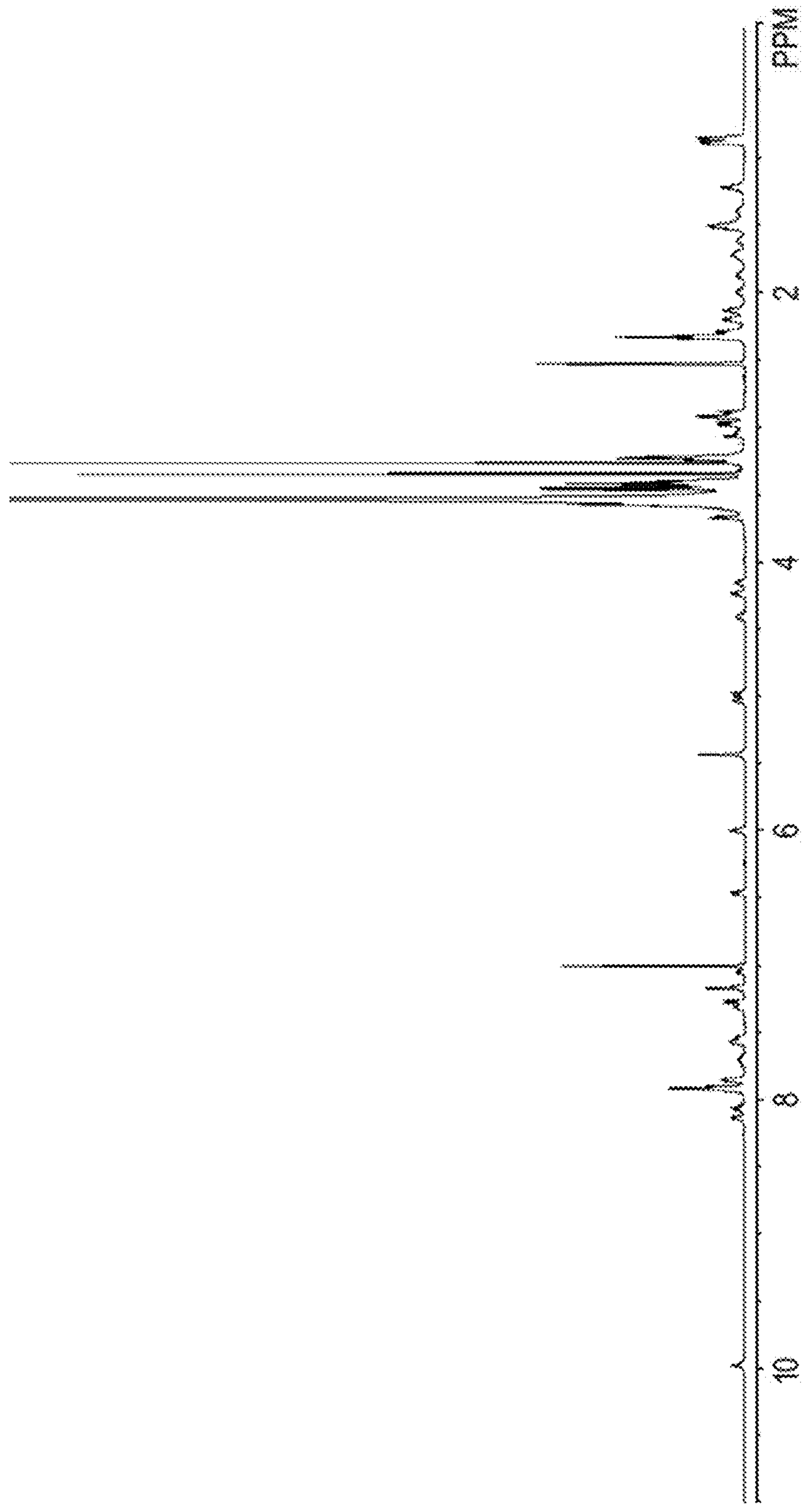
FIG. 5F provides the $^1$H NMR and HPLC spectrum obtained for conjugate 105 of FIG. 5D.
Figure 5F:
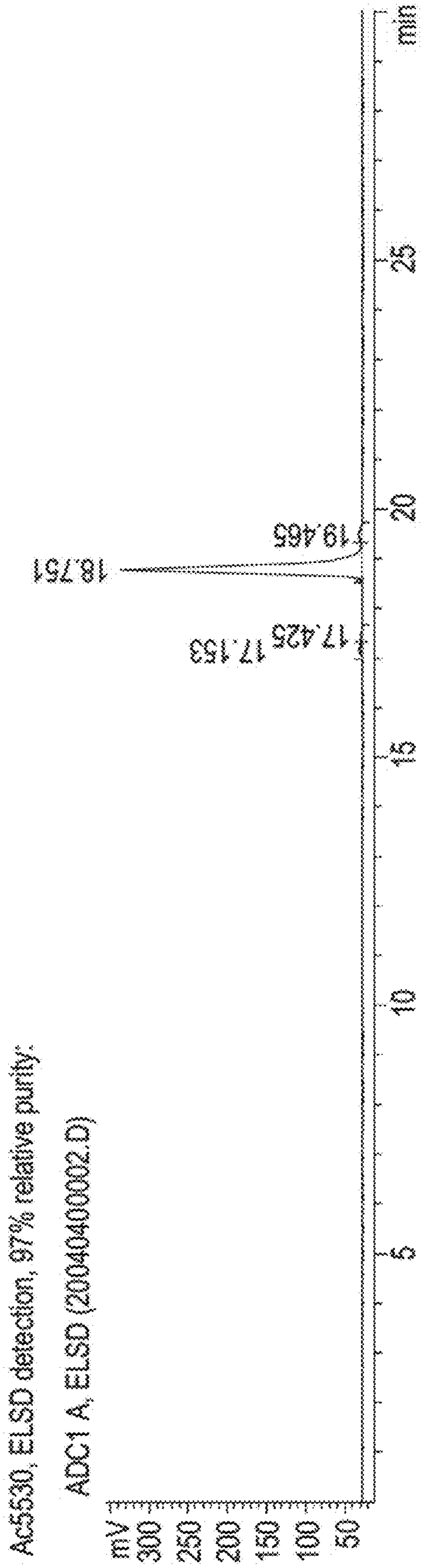

A 25 mL flask was charged with Compound 104 (0.45 g, 0.110 mmol) and dichloromethane (5 mL). Compound 13 (0.090 g, 0.132 mmol) was dissolved in DMF (2 mL) and added dropwise. The reaction was stirred at ambient temperature for three hours. Both TLC (85:15 DCM:MeOH) and HPLC indicated complete reaction. The solvent was removed under vacuum to give a viscous oil. The oil was rinsed twice with hexanes, dried under high vacuum and then triturated with ether to give an oily solid. The residue was pre-absorbed onto 2 g of silica gel and purified on a 12 g column with dichloromethane and methanol. Tubes 7-15 were pooled, concentrated, and dried under vacuum to provide 0.328 g (65%) of Compound 105 as a white powdery solid. TLC (85:15 DCM:MeOH, visualized with UV and iodine) was a single spot $R_f$=0.45. The product was characterized by HRMS (calculated: 4602.5752, observed: 2323.2842 $[M+CHO2^{-}-H]^{2-}$), HPLC, and $^1H$ NMR ($d_6$-DMSO) (FIG. 5F).

Synthesis of Compound 62 (FIG. 6A)

Synthesis of Compound 57

A 100 mL flask was charged with Compound 33 (0.921 g, 1.953 mmol) and dichloromethane (17 mL). In a separate flask, Compound 45 (2 g, 1.395 mmol) was dissolved in dichloromethane (50 mL) and N,N-diisopropylethylamine (0.731 ml, 4.18 mmol) was added via syringe. The mixture was placed in an addition funnel and added dropwise. The reaction was stirred at ambient temperature for 48 hours. Both TLC (85:15 DCM:MeOH) and HPLC indicated complete consumption of starting material. The reaction was diluted to 200 mL with dichloromethane and washed with 10% HCl (3×20 mL), washed with brine, dried over $MgSO_4$, filtered over celite, and pre-absorbed onto 8 g of silica gel. The residue was purified on a 40 g column with dichloromethane and methanol. Tubes 10-21 were pooled and concentrated to give 2.21 g (91%) of Compound 57 as a clear pale yellow oil. TLC (85:15 DCM:MeOH, visualized with UV and iodine) was a single spot $R_f$=0.69. The product was characterized by FT-ICR (calculated: 1737.9877, observed: 1738.9987 $[M+H]^+$), HPLC, and $^1H$ NMR ($CDCl_3$).

Synthesis of Compound 58

A flask was charged with Compound 57 (2.2 g, 1.265 mmol) and formic acid (24.3 mL, 633 mmol) and heated to 35° C. for 12 hours. Both TLC (85:15 DCM:MeOH) and HPLC indicated reaction was complete. The solvent was removed on a rotary evaporator and the residue pre-absorbed onto 4 g of silica gel and purified on a 40 g column with dichloromethane and methanol. Tubes 4-25 were pooled and concentrated to provide 1.722 g (81%) of Compound 58 as a clear pale yellow viscous oil. TLC (85:15 DCM:MeOH, visualized with iodine) was a single major spot $R_f$=0.35. The product was characterized by MALDI (calculated: 1681.9251, observed: 1704.991 $[M+H+Na]^+$), HPLC, and $^1H$ NMR ($CDCl_3$).

Synthesis of Compound 59

A 100 mL 3-neck flask was charged with methanol-wet 10% palladium on activated charcoal (0.163 g) and methanol (20 mL) and a hydrogen purge was started. Compound 58 (1.722 g, 1.023 mmol) was dissolved in a small amount of methanol and added to the flask. The reaction was stirred under a hydrogen purge for 2 hours. HPLC indicated complete consumption of the starting material. The reaction was filtered over a methanol-wet bed of celite and concentrated under reduced pressure to provide 1.64 g (100%) of Compound 59 as a clear viscous oil. The product was characterized by MALDI (calculated: 1547.8883, observed: 1548.842 $[M+H]^+$, 1570.827 $[M+H+Na]^+$, 1586.804 $[M+H+K]^+$), HPLC, and $^1H$ NMR ($CDCl_3$).

Synthesis of Compound 60

A 50 mL flask was charged with MP-TFP (0.201 g, 0.635 mmol) and dichloromethane (13 mL) and chilled in an ice bath. In a separate flask, Compound 59 (0.819 g, 0.529 mmol) was dissolved in dichloromethane (13 mL) and N,N-diisopropylethylamine (0.222 ml, 1.269 mmol) was added via syringe. The mixture was placed in an addition funnel and added dropwise. The ice bath was removed and the reaction was stirred at ambient temperature for two hours. Both TLC (85:15 DCM:MeOH) and HPLC indicated a single product. The reaction was diluted to 75 mL with dichloromethane, washed with 10% HCl (3×5 mL), and concentrated under reduced pressure. The residue was taken up in 75 mL water, washed with MTBE (3×10 mL), washed with hexanes (10 mL), salt was added, and the aqueous phase was extracted with dichloromethane (3×50 mL). The organics were washed with brine, dried over $MgSO_4$, filtered over celite, and concentrated under reduced pressure to provide 615 mg (68%) of Compound 60 as a pale orange oil. TLC (85:15 DCM:MeOH, visualized with iodine) was a single major spot $R_f$=0.39. The purity was verified by HPLC and the product was used in the subsequent step without further purification or characterization.

Synthesis of Compound 61

A 50 mL 3-neck flask was charged with 2,3,5,6-tetrafluorophenol (0.120 g, 0.724 mmol) and dichloromethane (25 mL). DCC (0.112 g, 0.543 mmol) was added in a single portion and after dissolution the flask was chilled in an ice bath. Compound 60 (0.615 g, 0.362 mmol) was dissolved in dichloromethane (12 mL) and added dropwise via addition funnel. The ice bath was removed and the reaction was stirred at 22° C. overnight. Both TLC (85:15 DCM:MeOH) and HPLC indicated complete consumption of starting material and a single major product. The reaction was chilled in an ice bath and the DCU was filtered off using a syringe filter. The solvent was removed and the oil was taken up in acetonitrile and chilled in an ice bath. The DCU was filtered off via syringe filter. Removal of the solvent provided an orange oil that was suspended in ether and the solvent decanted. The oil was again suspended in ether and the solvent decanted. Drying under high vacuum provided 530 mg (79%) of Compound 61 as an orange viscous oil. TLC (85:15 DCM:MeOH, visualized with UV and iodine) was a single major spot $R_f$=0.62. The purity was verified by HPLC and the product was used in the subsequent step without further purification or characterization.

Synthesis of Compound 62-(L)

A 25 mL flask was charged with Compound 61 (0.45 g, 0.244 mmol) and dichloromethane (8 mL). Compound 13 (0.199 g, 0.292 mmol) was dissolved in DMF (4 mL) and added dropwise. The reaction was stirred at ambient temperature for three hours. Both TLC (85:15 DCM:MeOH) and HPLC indicated complete reaction. The solvent was removed under vacuum to give a viscous oil. Hexanes was added and then decanted from the oil, which was rinsed once more with hexanes. The oil was dried under high vacuum and then ether was added to give an oily residue. The residue was suspended in ether and the solvent decanted. The oil was pre-absorbed onto 2 g of silica gel and purified on a 12 g column with dichloromethane and methanol. Tubes 9-17 were pooled, concentrated, and dried under vacuum to provide 480 mg (83%) of Compound 62 as a pale yellow viscous oil. TLC (85:15 DCM:MeOH, visualized with UV and iodine) was a single spot $R_f$=0.42. The product was characterized by LRMS (calculated: 2362.2169, observed: 2363.2 $[M+H]^+$), HPLC, and $^1H$ NMR ($d_6$-DMSO) (FIG. 6B).

Synthesis of Compound 96 (FIG. 6A)

Synthesis of Compound 91

A 100 mL flask was charged with Compound 33 (0.539 g, 1.144 mmol) and dichloromethane (10 mL). Compound 47 (2.9 g, 0.817 mmol) was dissolved in dichloromethane (30 mL) and N,N-diisopropylethylamine (0.285 ml, 1.635 mmol) was added via syringe. The mixture was placed in an addition funnel and added dropwise. The reaction was stirred at ambient temperature for 72 hours. Both TLC (85:15 DCM:MeOH) and HPLC indicated formation of a single major product. The reaction was diluted to 200 mL with dichloromethane and washed with 10% HCl (3×20 mL), washed with brine, dried over $MgSO_4$, filtered over celite, and concentrated onto 8 g of silica gel. The residue was purified on a 40 g column with dichloromethane and methanol. Tubes 9-20 were pooled, concentrated, and dried under high vacuum to give 2.731 g (87%) of a white powdery solid. TLC (85:15 DCM:MeOH, visualized with UV and iodine) was a single spot $R_f$=0.58. The product was characterized by FT-ICR (calculated: 3851.2460, observed: 3876.3038 $[M+Na+H]^+$, 3892.2899 $[M+K+H]^+$), HPLC, and $^1H$ NMR ($CDCl_3$).

Synthesis of Compound 92

A 50 mL flask was charged with Compound 91 (2.7 g, 0.701 mmol) and formic acid (18.81 ml, 490 mmol) and heated to 35° C. for 24 hours. Both TLC (85:15 DCM:MeOH) and HPLC indicated complete consumption of starting material. The formic acid was removed on a rotary evaporator and the residue was taken up in dichloromethane, washed with 10% HCl, washed with brine, dried over $MgSO_4$, filtered, and concentrated on to 8 g of silica gel. The residue was flashed on a 40 g column with dichloromethane and methanol. Tubes 1-7 were pooled, concentrated, and dried under high vacuum to give 1.62 g (61%) of Compound 92 as a white powdery solid. TLC (85:15 DCM:MeOH, visualized with UV and iodine) was a single spot $R_f$=0.65. The product was characterized by FT-ICR (calculated: 3795.1834, observed: 3796.1989 $[M+H]^+$, 3820.1826 $[M+Na+H]^+$), HPLC, and $^1H$ NMR ($CDCl_3$).

Synthesis of Compound 93

A 100 mL 3-neck flask was charged with methanol-wet 10% palladium on activated charcoal (0.159 g) and methanol (45 mL) and a hydrogen purge was started. Compound 92 (1.62 g, 0.427 mmol) was dissolved in a small amount of methanol and added to the flask. The reaction was stirred under a hydrogen purge for 3 hours. Both TLC (85:15 DCM:MeOH) and HPLC indicated complete consumption of starting material. The reaction was filtered over a methanol-wet bed of celite and concentrated under reduced pressure to give 1.511 g (97%) of Compound 93 as a white powdery solid. The product was characterized by MALDI (calculated: 3661.1466, observed: 3662.41 $[M+H]^+$, 3684.603 $[M+H+Na]^+$, 3700.591 $[M+H+K]^+$), HPLC, and $^1H$ NMR ($CDCl_3$).

Synthesis of Compound 94

A 50 mL flask was charged with MP-TFP (0.078 g, 0.246 mmol) and dichloromethane (10 mL) and chilled in an ice bath. In a separate flask, Compound 93 (0.75 g, 0.205 mmol) was dissolved in dichloromethane (10 mL) and N,N-diisopropylethylamine (0.086 ml, 0.491 mmol) was added via syringe. The mixture was placed in an addition funnel and added dropwise. The ice bath was removed and the reaction was stirred at ambient temperature for five hours. Both TLC (85:15 DCM:MeOH) and HPLC indicated a single major product. The reaction was diluted to 150 mL with dichloromethane, washed with 10% HCl (5×10 mL), and concentrated under reduced pressure. The residue was taken up in 75 mL water, washed with MTBE (2×10 mL), washed with hexanes (10 mL), salt was added, and the aqueous phase was extracted with dichloromethane (3×100 mL). The combined organics were washed with brine, dried over $MgSO_4$, filtered over celite, and concentrated under reduced pressure to provide 0.619 g (79%) of Compound 94 as a pale orange solid. TLC (85:15 DCM:MeOH, visualized with iodine) was a single major spot $R_f$=0.5. The purity was verified by HPLC and the product was used in the subsequent step without further purification or characterization.

Synthesis of Compound 95

A 50 mL 3-neck flask was charged with 2,3,5,6-tetrafluorophenol (0.054 g, 0.325 mmol) and dichloromethane (8 mL). DCC (0.050 g, 0.243 mmol) was added in a single portion and the mixture was stirred for ten minutes. Compound 94 (0.619 g, 0.162 mmol) was dissolved in dichloromethane (8 mL) and added dropwise. The reaction was stirred at ambient temperature for 14 hours. Both TLC (85:15 DCM:MeOH) and HPLC indicated a single major product. The reaction was chilled in an ice bath and the DCU was filtered off with a syringe filter. The solvent was removed and the oil was taken up in acetonitrile and chilled in an ice bath. The DCU was filtered off via syringe filter. Removal of the solvent provided an orange oil that was suspended in hexanes and the solvent decanted. The oil was repeatedly suspended in ether and the solvent decanted to provide a pale orange solid. Drying under high vacuum provided 0.572g (89%) of Compound 95 as a pale orange solid. TLC (85:15 DCM:MeOH, visualized with UV and iodine) was a single major spot $R_f$=0.54. The purity was verified by HPLC and the product was used in the subsequent step without further purification or characterization.

Synthesis of Compound 96-(R)

A 25 mL flask was charged with Compound 95 (0.572 g, 0.144 mmol) and dichloromethane (5 mL). Compound 13 (0.118 g, 0.173 mmol) was dissolved in DMF (2 mL) and added dropwise. The reaction was stirred at ambient temperature for four hours. Both TLC (85:15 DCM:MeOH) and HPLC indicated complete reaction. The solvent was removed under vacuum to give an oil. Hexanes was added and then decanted from the oil, which was rinsed once more with hexanes. The oil was dried under high vacuum and then triturated with ether to give an oily solid. The residue was pre-absorbed onto 2 g of silica gel and purified on a 12 g column with dichloromethane and methanol. Tubes 8-17 were pooled and concentrated and dried under vac to provide 0.571 g (88%) of Compound 96 as a pale yellow solid. TLC (85:15 DCM:MeOH, visualized with UV and iodine) was a single spot $R_f$=0.46. The product was characterized by HRMS (calculated: 4475.4752, observed: 2237.7319 $[M-2H]^{2-}$), HPLC, and $^1H$ NMR ($d_6$-DMSO) (FIG. 6C).

Synthesis of Compound 81 (FIG. 6D)

Synthesis of Compound (74)

A 100 mL flask was charged with 3-aminopropanoic acid (2.83 g, 31.8 mmol), 5% aqueous sodium bicarbonate (40 mL), and 1,4-dioxane (20 mL). The flask was warmed to 45° C. Compound 33 (5 g, 10.61 mmol) was dissolved in 1,4-dioxane (20 mL) and added to the flask to give a suspension. The cloudy solution was warmed to 55° C. and it turned clear pale yellow. After 1 hour both TLC (85:15 DCM:MeOH) and HPLC indicated complete consumption of sm. The reaction was diluted with water and adjusted to pH 3 by the addition of solid citric acid. The aqueous phase was saturated with salt and extracted with dichloromethane (3×100 mL). The oil was pre-absorbed onto 10 g of silica gel and flashed on an 80g column with dichloromethane and methanol. Tubes 11-16 were pooled and concentrated to give 3.65 g (87%) of Compound 74 as a white sticky foam. TLC (85:15 DCM:MeOH, visualized with UV) was a single spot $R_f$=0.63. The product was characterized by LRMS (calculated: 394.1740, observed: 417.3 $[M+H+Na]^+$, 433.3 $[M+H+K]^+$), HPLC, and $^1H$ NMR ($CDCl_3$).

Synthesis of Compound 75

A 250 mL flask was charged with 2,3,5,6-tetrafluorophenol (1.844 g, 11.10 mmol) and dichloromethane (30 mL). EDC (2.129 g, 11.10 mmol) was added and after dissolution the flask was chilled in an ice bath. Compound 74 (3.65 g, 9.25 mmol) was dissolved in dichloromethane (30 mL) and added dropwise via addition funnel. The reaction was stirred at ambient temperature overnight. Both TLC (70:30 hexanes:ethyl acetate) and HPLC indicted a single major product. The solvent was removed on a rotary evaporator, the residue taken up in ethyl acetate, washed with water, washed with brine, dried over $MgSO_4$, filtered, and concentrated onto 12 g of silica gel. The crude was purified on an 80 g column with hexanes and ethyl acetate. Tubes 18-26 were pooled and concentrated to provide 4.595 g (92%) of Compound 75 as a clear colorless viscous oil. TLC (70:30 hexanes:ethyl acetate, visualized with UV) was a single spot $R_f$=0.26. The product was characterized by LRMS (calculated: 542.1676, observed: 565.2 $[M+H+Na]^+$, 581.2 $[M+H+K]^+$), HPLC, and $^1H$ NMR ($CDCl_3$).

Synthesis of Compound 76

A 100 mL flask was charged with Compound 75 (1.042 g, 1.922 mmol) and dichloromethane (18 mL). Compound 45 (1.968g, 1.373 mmol) was dissolved in dichloromethane (50 mL) and N,N-diisopropylethylamine (0.719 ml, 4.12 mmol) was added via syringe. The mixture was placed in an addition funnel and added dropwise. The reaction was stirred at ambient temperature for 48 hours. Both TLC (85:15 DCM:MeOH) and HPLC indicated complete consumption of the starting material. The reaction was diluted to 200 mL with dichloromethane and washed with 10% HCl (3×20 mL), washed with brine, dried over $MgSO_4$, filtered over celite, and concentrated onto 8 g of silica gel. The residue was purified on a 40 g column with dichloromethane and methanol. Tubes 13-25 were pooled and concentrated to give 2.123 g (85%) of Compound 76 as a clear viscous oil. TLC (85:15 DCM:MeOH, visualized with UV and iodine) was a single spot $R_f$=0.64. The product was characterized by MALDI (calculated: 1809.0248, observed: 1832.053 $[M+H+Na]^+$, 1848.040 $[M+H+K]^+$), HPLC, and $^1H$ NMR ($CDCl_3$).

Synthesis of Compound 77

A 50 mL flask was charged with Compound 76 (2.123 g, 1.173 mmol) and formic acid (22.49 ml, 586 mmol) and warmed to 35° C. for 16 hours. Both TLC (85:15 DCM:MeOH) indicated consumption of starting material. The solvent was removed and the residue triturated with ether, placed in a dry ice/acetone bath, and the solvent decanted. This was repeated once more. Drying under high vacuum gave a pale yellow viscous oil. The residue was pre-absorbed onto 6 g of silica gel and purified on a 40 g column with dichloromethane and methanol. Tubes 7-20 were pooled and concentrated to provide 1.687 g (82%) of Compound 77 as a pale yellow oil. TLC (85:15 DCM:MeOH, visualized with iodine) was a single major spot $R_f$=0.42 with a minor impurity spot. The purity was verified by HPLC and the product was used in the subsequent step without further purification or characterization.

Synthesis of Compound 78

A 100 mL flask was charged with methanol-wet 10% palladium on activated charcoal (0.174 g) and methanol (30 mL). A hydrogen purge was started and Compound 77

(1.687 g, 0.962 mmol) was dissolved in a little methanol and added to the flask. The reaction was stirred under a hydrogen purge for three hours. Both TLC (85:15 DCM:MeOH) and HPLC indicated consumption of starting material. The reaction was filtered over a methanol-wet bed of celite and concentrated under reduced pressure to provide 1.365 g (88%) of Compound 78 as a pale yellow viscous oil. The purity was verified by HPLC and the product was used in the subsequent step without further purification or characterization.

Synthesis of Compound 79

A 50 mL flask was charged with MP-TFP (0.160 g, 0.506 mmol) and dichloromethane (10 mL) and then chilled in an ice bath. In a separate flask, Compound 78 (0.683 g, 0.422 mmol) was dissolved in dichloromethane (10 mL) and N,N-diisopropylethylamine (0.177 ml, 1.012 mmol) was added via syringe. The mixture was placed in an addition funnel and added dropwise. The ice bath was removed and the reaction was stirred at ambient temperature for 2 hours. Both TLC (85:15 DCM:MeOH) and HPLC indicated complete consumption of starting material. The reaction was diluted to 75 mL with dichloromethane, washed with 10% HCl (3×5 mL), and concentrated under reduced pressure. The residue was taken up in 75 mL water, washed with MTBE (3×10 mL), washed with hexanes (10 mL), salt was added, and the aqueous phase was extracted with dichloromethane (3×100 mL). The organics were washed with brine, dried over $MgSO_4$, filtered over celite, and concentrated under reduced pressure to provide 488 mg (65%) of Compound 79 as a pale orange oil. TLC (85:15 DCM:MeOH, visualized with iodine) was a single major spot $R_f$=0.32. The purity was verified by HPLC and the product was used in the subsequent step without further purification or characterization.

Synthesis of Compound 80

A 50 mL 3-neck flask was charged with 2,3,5,6-tetrafluorophenol (0.092 g, 0.551 mmol) and dichloromethane (20 mL). DCC (0.085 g, 0.413 mmol) was added in a single portion and after dissolution the flask was chilled in an ice bath. Compound 79 (0.488 g, 0.276 mmol) was dissolved in dichloromethane (10 mL) and added dropwise via addition funnel. The ice bath was removed and the reaction was stirred at ambient temperature for 16 hours. Both TLC (85:15 DCM:MeOH) and HPLC indicated complete consumption of starting material and formation of a single major product. The reaction was chilled in an ice bath and the DCU was filtered off via syringe filter. The solvent was removed and the oil was taken up in acetonitrile and chilled in an ice bath. The DCU was filtered off via syringe filter. Removal of the solvent provided an orange oil that was triturated with ether and dried under high vacuum to provide 440 mg (83%) of Compound 80 as an orange oil. TLC (85:15 DCM:MeOH, visualized with UV and iodine) was a single major spot $R_f$=0.60. The purity was verified by HPLC and the product was used in the subsequent step without further purification or characterization.

Synthesis of Compound 81-(I)

A 25 mL flask was charged with Compound 80 (0.440 g, 0.229 mmol) and dichloromethane (8 mL). Compound 13 (0.188 g, 0.275 mmol) was dissolved in DMF (4 mL) and added dropwise. The reaction was stirred at ambient temperature for three hours. Both TLC (85:15 DCM:MeOH) and HPLC indicated complete reaction. The solvent was removed under vacuum and the resulting oil was triturated multiple times with hexanes. The oil was dried under high vacuum and then triturated multiple times with ether. The resulting oil was pre-absorbed onto 2 g of silica gel and purified on a 12 g column with dichloromethane and methanol. Tubes 9-17 were pooled, concentrated, and dried under vacuum to provide 417 mg (75%) of Compound 81 as a pale yellow viscous oil. TLC (85:15 DCM:MeOH, visualized with UV and iodine) was a single spot $R_f$=0.49. The product was characterized by LRMS (calculated: 2433.2540, observed: 2434.3 $[M+H]^+$), HPLC, and $^1H$ NMR ($d_6$-DMSO) (FIG. 6E).

Synthesis of Compound 111 (FIG. 6D)

Synthesis of Compound 106

A 100 mL flask was charged with Compound 75 (0.621 g, 1.144 mmol) and dichloromethane (10 mL). Compound 47 (2.9 g, 0.817 mmol) was dissolved in dichloromethane (30 mL) and N,N-diisopropylethylamine (0.428 ml, 2.452 mmol) was added via syringe. The mixture was placed in an addition funnel and added dropwise. The reaction was stirred at ambient temperature for 72 hours. The reaction was diluted to 200 mL with dichloromethane and washed with 10% HCl (3×20 mL), washed with brine, dried over $MgSO_4$, filtered over celite, and concentrated onto 7 g of silica gel. The residue was purified on a 40 g column with dichloromethane and methanol. Tubes 6-15 were pooled and concentrated to give 2.299 g (72%) of Compound 106 as a white powdery solid. TLC (85:15 DCM:MeOH, visualized with UV and iodine) was a single spot $R_f$=0.45. The product was characterized by MALDI (calculated: 3922.2831, observed: 3945.469 $[M+H+Na]^+$, 3961.451 $[M+H+K]^+$), HPLC, and $^1H$ NMR ($CDCl_3$).

Synthesis of Compound 107

A 50 mL flask was charged with Compound 106 (2.299 g, 0.586 mmol) and formic acid (17.97 ml, 469 mmol) and heated to 35° C. for 16 hours. Both TLC (85:15 DCM:MeOH) and HPLC indicated formation of a single major product. The solvent was removed and the residue triturated with ether, placed in an ice bath, and the solvent decanted. This was repeated once more. Drying under high vacuum gave a white solid. The solid was pre-absorbed onto 4 g of silica gel and purified on a 24 g column with dichloromethane and methanol. Tubes 6-25 were pooled, concentrated, and dried under high vacuum to provide 1.92 g (87%) of Compound 107 as a white solid. TLC (85:15 DCM:MeOH, visualized with UV and iodine) was a single major spot $R_f$=0.33. The purity was verified by HPLC and the product was used in the subsequent step without further purification or characterization.

Synthesis of Compound 108

A 100 mL flask was charged with ethanol-wet 10% palladium on activated charcoal (0.183 g) and ethanol (25 mL) and a hydrogen purge was started. Compound 107 (1.9 g, 0.491 mmol) was dissolved in a little ethanol and added to the flask. The reaction was stirred under a hydrogen purge for three hours. Both TLC (85:15 DCM:MeOH) and HPLC indicated consumption of starting material. The reaction was filtered over a ethanol-wet bed of celite, and concentrated under reduced pressure to give an oily solid. The solid was suspended in MTBE with stirring, allowed to settle, and the solvent decanted. Drying under high vacuum provided 1.803 g (98%) of Compound 108 as a white solid. The purity was verified by HPLC and the product was used in the subsequent step without further purification or characterization.

Synthesis of Compound 109

A 50 mL flask was charged with MP-TFP (0.092 g, 0.289 mmol) and dichloromethane (6 mL) and chilled in an ice bath. In a separate flask, Compound 107 (0.9 g, 0.241 mmol) was dissolved in dichloromethane (6 mL) and N,N-diisopropylethylamine (0.101 ml, 0.578 mmol) was added via syringe. The mixture was placed in an addition funnel and added dropwise. The ice bath was removed and the reaction was stirred at ambient temperature for three hours. Both TLC (85:15 DCM:MeOH) and HPLC indicated formation of a single major product. The reaction was diluted to 150 mL with dichloromethane, washed with 10% HCl (5×10 mL), and concentrated under reduced pressure. The residue was taken up in 75 mL water, washed with MTBE (2×10 mL), washed with hexanes (10 mL), salt was added, the solution was acidified, and the aqueous phase was extracted with dichloromethane (3×100 mL). The combined organics were washed with brine, dried over $MgSO_4$, filtered over celite, and concentrated under reduced pressure to provide 0.701 g (75%) of Compound 108 as a pale orange solid. TLC (85:15 DCM:MeOH, visualized with iodine) was a single major spot $R_f$=0.42. The purity was verified by HPLC and the product was used in the subsequent step without further purification or characterization.

Synthesis of Compound 110

A 50 mL 3-neck flask was charged with 2,3,5,6-tetrafluorophenol (0.052 g, 0.315 mmol) and dichloromethane (8 mL). DCC (0.049 g, 0.236 mmol) was added in a single portion and the mixture was stirred for ten minutes. Compound 109 (0.6 g, 0.157 mmol) was dissolved in dichloromethane (8 mL) and added dropwise. The reaction was stirred at ambient temperature overnight. Both TLC (85:15 DCM:MeOH) and HPLC indicated a single major product. The reaction was chilled in an ice bath and the DCU was filtered off via syringe filter. The solvent was removed and the oil was taken up in acetonitrile and chilled in an ice bath. The DCU was filtered off via syringe filter. Removal of the solvent provided an orange oil that was rinsed with hexanes and then dried under high vacuum. The oily solid was suspended in ether, stirred vigorously for ten minutes, and the solvent was decanted. This was repeated once more. Drying under high vacuum provided 0.649 g (89%) of Compound 110 as a pale orange solid. TLC (85:15 DCM:MeOH, visualized with UV and iodine) was a single major spot $R_f$=0.53. The purity was verified by HPLC and the product was used in the subsequent step without further purification or characterization.

Synthesis of Compound 111-(O)

A 25 mL flask was charged with Compound 110 (0.649 g, 0.161 mmol) and dichloromethane (5 mL). Compound 13 (0.121 g, 0.177 mmol) was dissolved in DMF (2 mL) and added dropwise. The reaction was stirred at ambient temperature for four hours. Both TLC (85:15 DCM:MeOH) and HPLC indicated formation of a major product. The solvent was removed under vacuum to give a viscous oil. The oil was rinsed with hexanes and then triturated with ether to give an oily solid. The solid was crushed under ether and the solvent decanted. The solid was pre-absorbed onto 2 g of silica gel and purified on a 12 g column with dichloromethane and methanol. Tubes 10-20 were pooled, concentrated, and dried under vacuum to provide 0.421 g (58%) of Compound 111 as a white powdery solid. TLC (85:15 DCM:MeOH, visualized with UV and iodine) was a single spot $R_f$=0.43. The product was characterized by HRMS (calculated: 4546.5123, observed: 2272.7456 $[M-2H]^{2-}$), HPLC, and $^1H$ NMR ($d_6$-DMSO) (FIG. 6F).

Example 2

Figure 7:
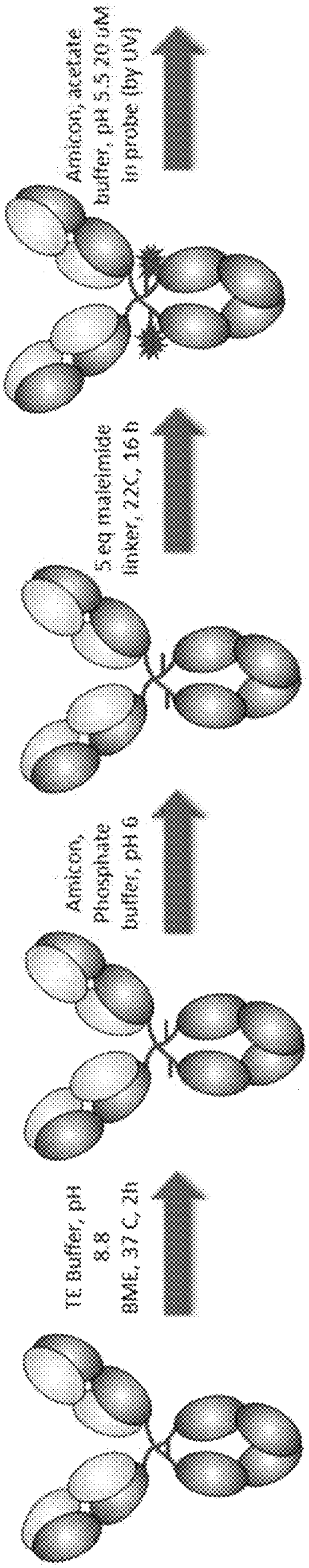
FIG. 7 shows the synthesis of DAR2 conjugates of Formula (III) disclosed herein.

Linear IgG conjugates and DAR 2IgG conjugates of Formula (III) were prepared from the compounds in Table 1 according to the process depicted in FIG. 7, which is described in detail below.

TABLE 1

| Synthesized and Evaluated Compounds of the Present Disclosure. | | |
|---|---|---|
| Cmpd No. | Code | Structure |
| 18 | A | 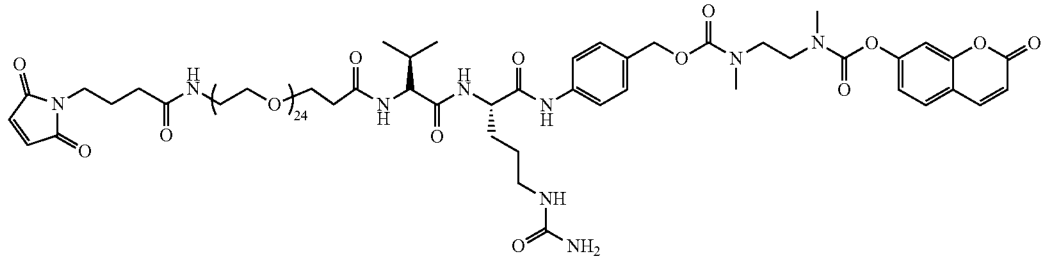 (Linear Control) |
| 19 | B | 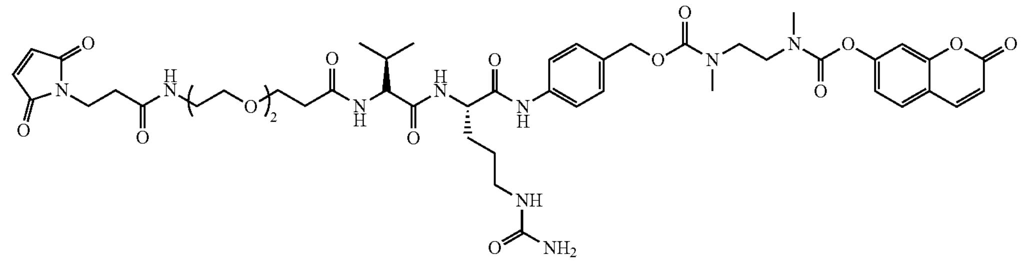 (Linear Control) |

TABLE 1-continued
| Synthesized and Evaluated Compounds of the Present Disclosure. | | |
|---|---|---|
| Cmpd No. | Code | Structure |
| 22 | C | 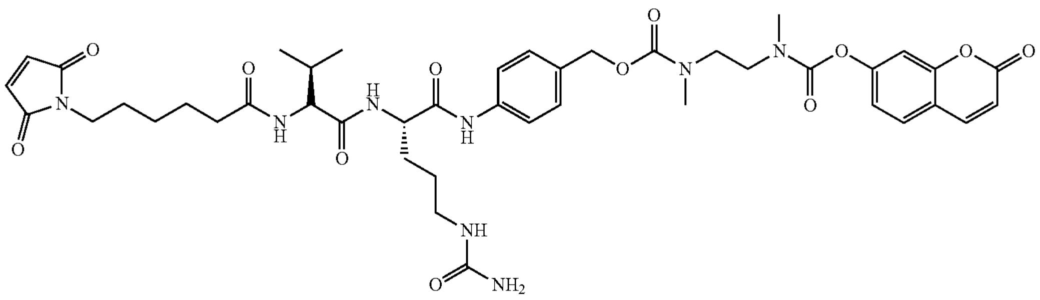 (Linear Control) |
| 29 | D | 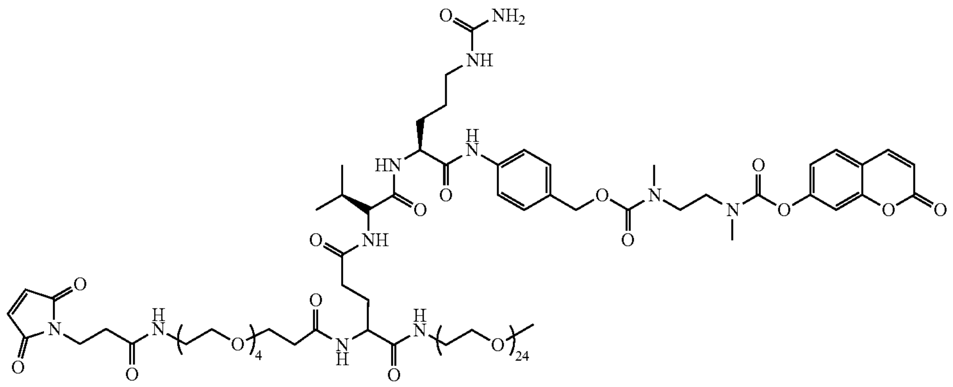 (Sidewinder 24) |
| 32 | E | 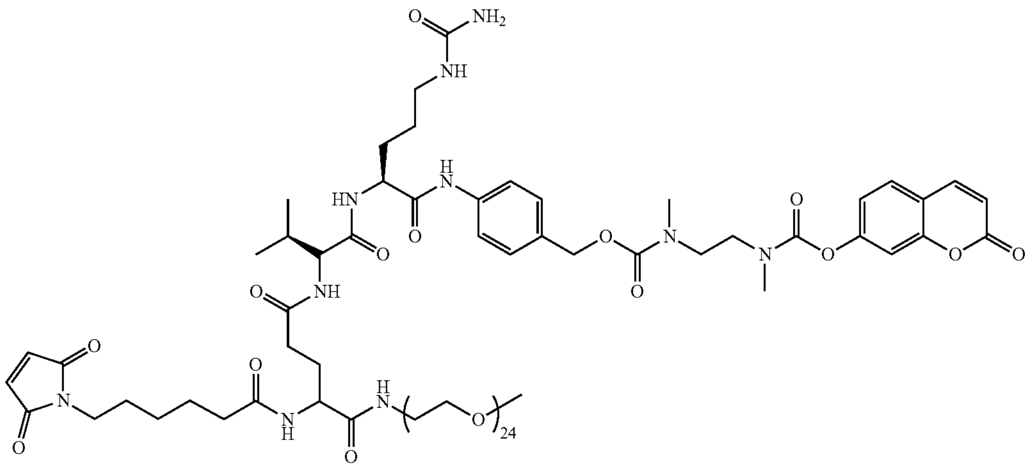 (Sidewinder 24) |

TABLE 1-continued
| Synthesized and Evaluated Compounds of the Present Disclosure. | | |
|---|---|---|
| Cmpd No. | Code | Structure |
| 39 | F | 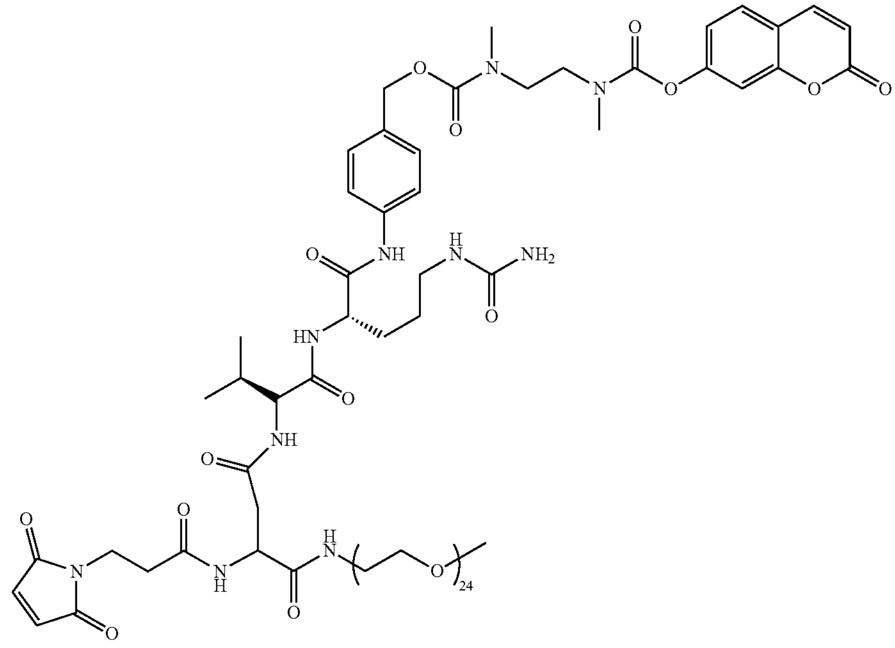 (Sidewinder 24) |
| 53 | J | 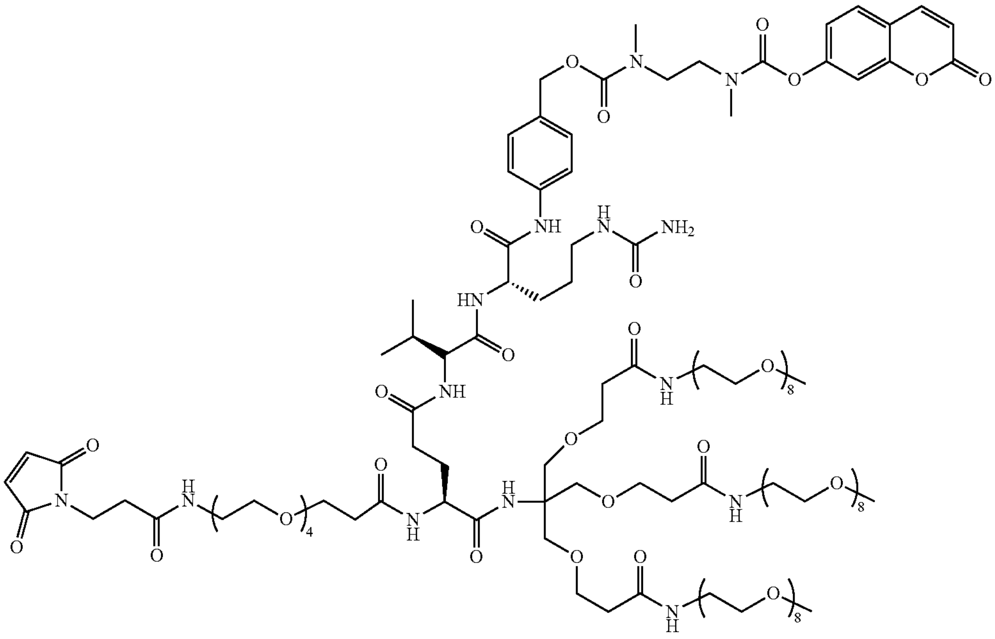 (C2-Tris 8) |

TABLE 1-continued
| Synthesized and Evaluated Compounds of the Present Disclosure. | | |
|---|---|---|
| Cmpd No. | Code | Structure |
| 56 | K | 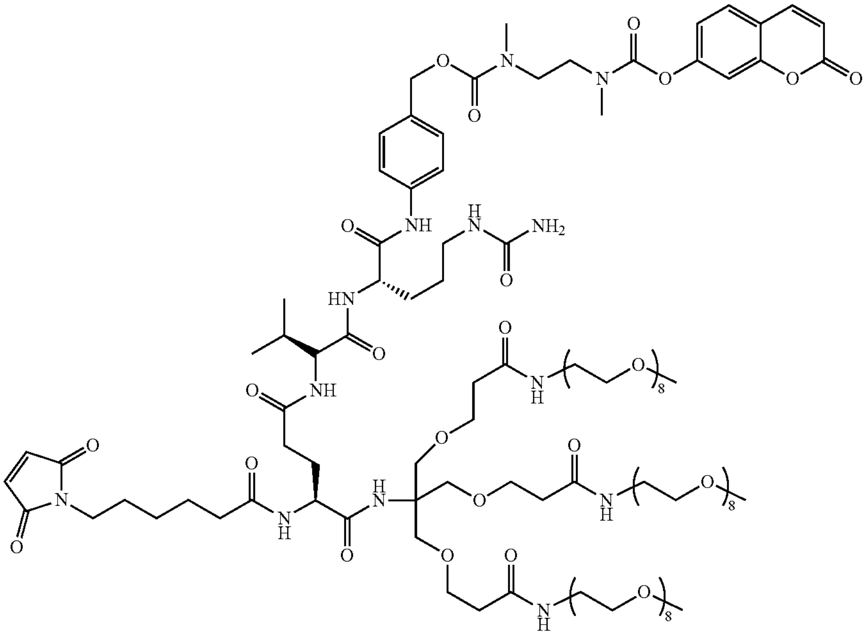 (C2-Tris 8) |
| 62 | L | 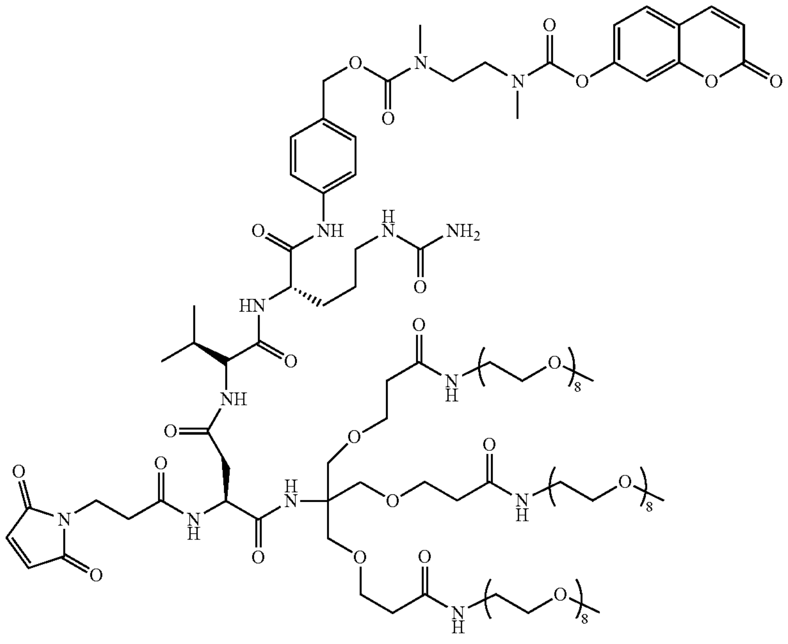 (Tris 8) |

TABLE 1-continued
| Synthesized and Evaluated Compounds of the Present Disclosure. | | |
|---|---|---|
| Cmpd No. | Code | Structure |
| 70 | G | 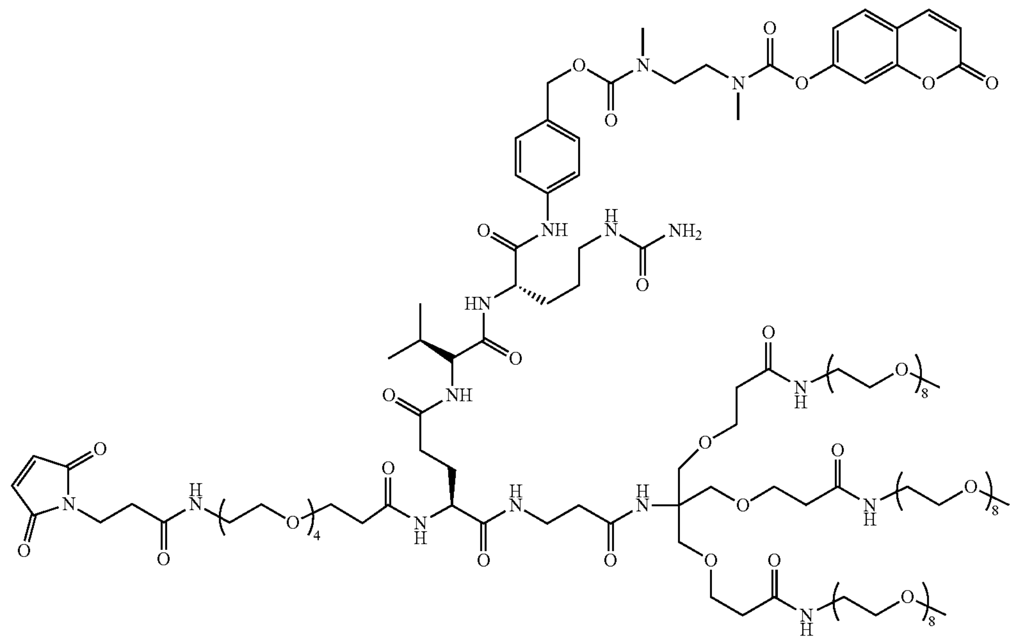 (C2-Tris 8) |
| 73 | H | 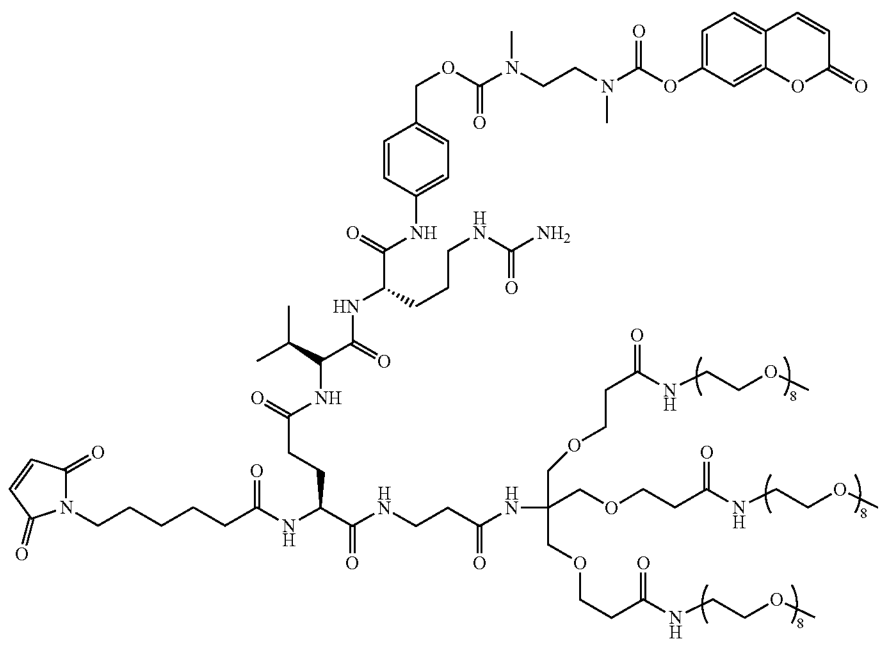 (C2-Tris 8) |

TABLE 1-continued
| Cmpd No. | Code | Structure |
| --- | --- | --- |
| | | Synthesized and Evaluated Compounds of the Present Disclosure. |
| 81 | I | 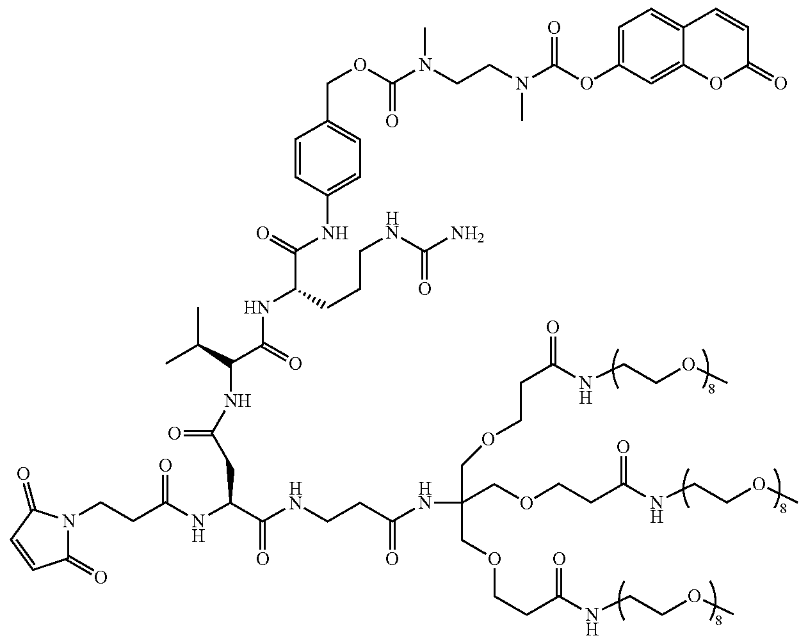 (Tris 8) |
| 87 | P | 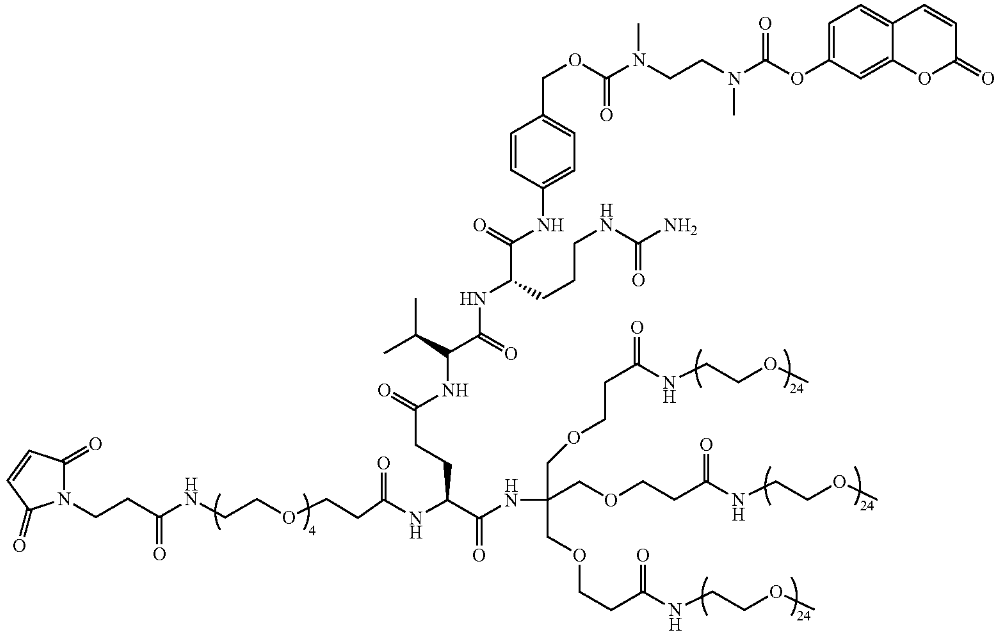 (C2-Tris 24) |

TABLE 1-continued
| Cmpd No. | Code | Structure |
|---|---|---|
| | | Synthesized and Evaluated Compounds of the Present Disclosure. |
| 90 | Q | 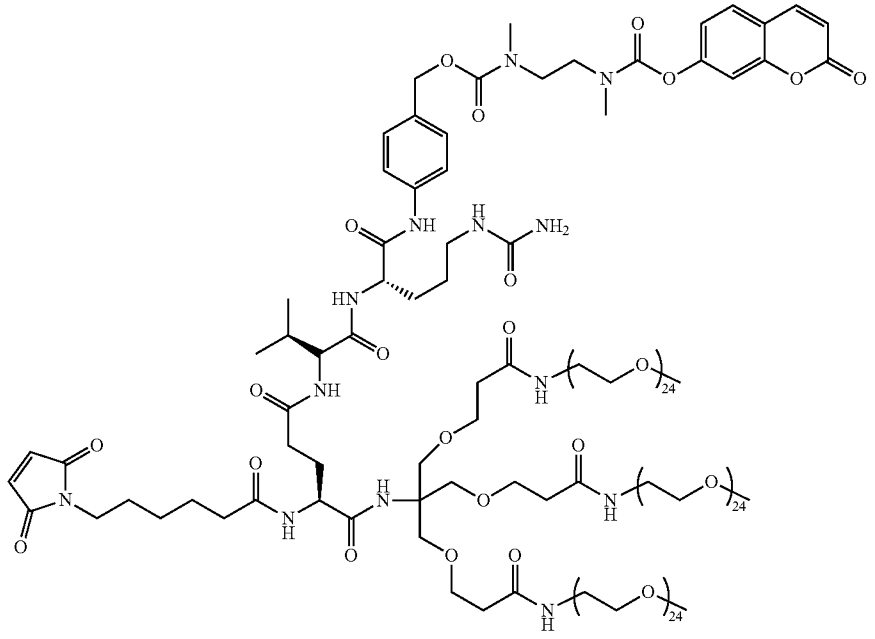 (C2-Tris 24) |
| 96 | R | 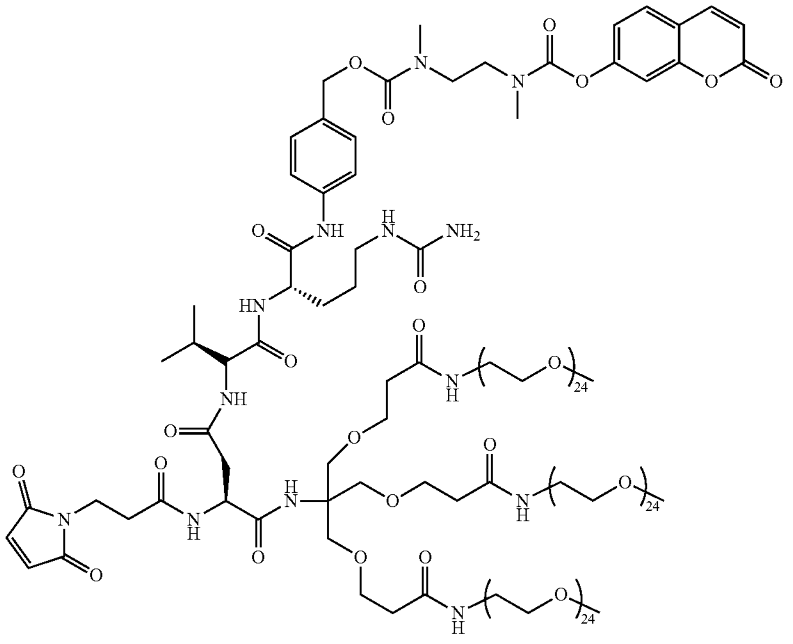 (Tris 24) |

TABLE 1-continued
| Cmpd No. | Code | Structure |
|---|---|---|
| 102 | M | 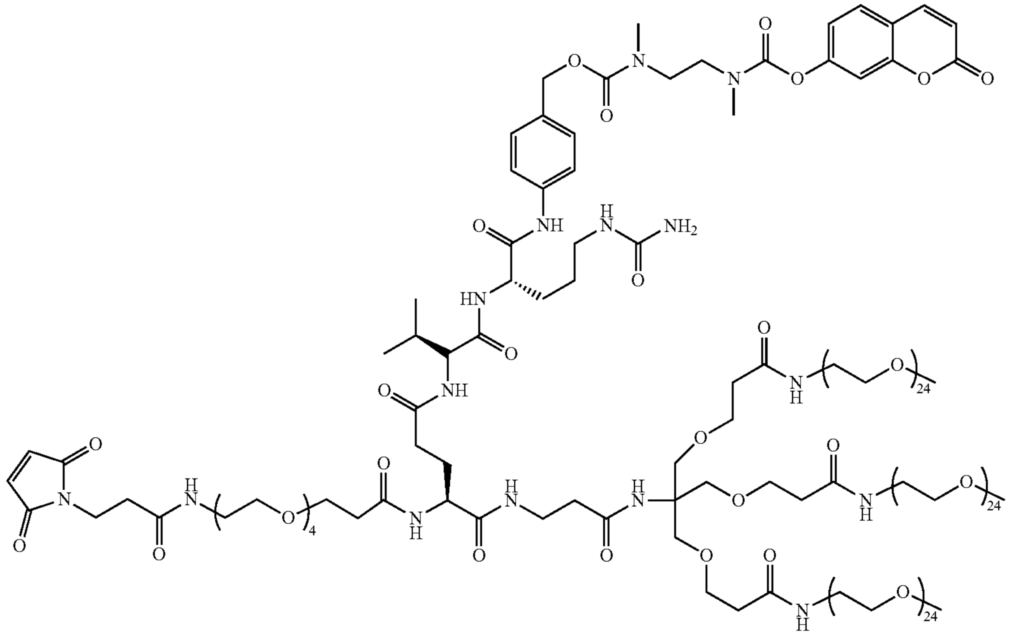 (C2-Tris 24) |
| 105 | N | 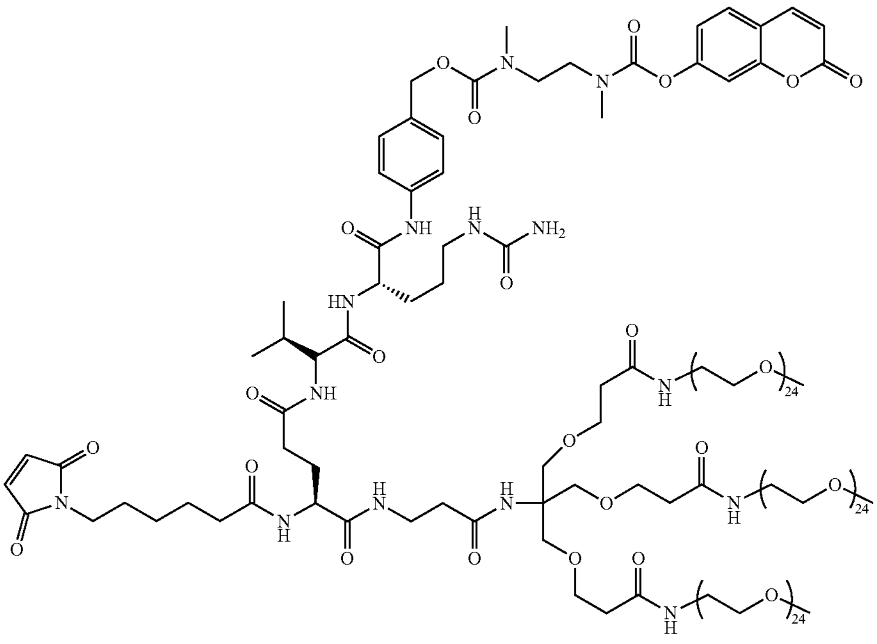 (C2-Tris 24) |
Synthesized and Evaluated Compounds of the Present Disclosure.

TABLE 1-continued

| Synthesized and Evaluated Compounds of the Present Disclosure. | | |
|---|---|---|
| Cmpd No. | Code | Structure |
| 111 | O | 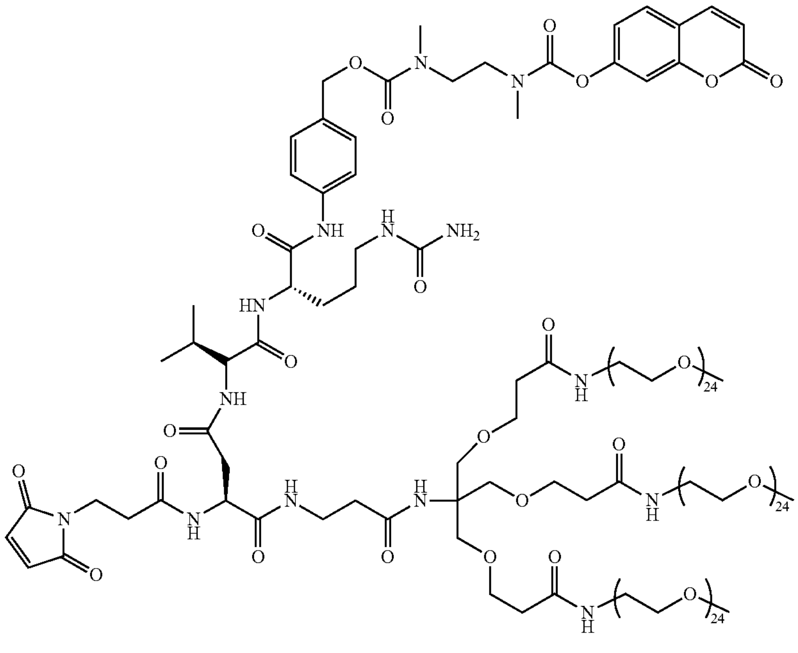 (Tris 24) |

Bioconjugation

Materials and Methods

Purified rabbit antibody was obtained from ImmunoReagents, Inc. (PN Rb-003-C.01) at a concentration of 11.1 mg/mL. All other reagents and solvents were purchased from commercial sources and used as provided. All buffer solutions were prepared with MilliQ water, sterile filtered, and degassed by purging with argon. Reduction was carried out in a polypropylene 50 mL VWR centrifuge tube, and conjugations were performed in polypropylene 1.5 mL Eppendorf safe-lock tubes. Ultrafiltration was carried out in Amicon Ultra centrifugal filter units (4 mL 50 kDa MWCO or 14 mL 10 kDa MWCO) on a Sorvall Legend RT+ swinging bucket rotor operating at 4000 rpm at 20° C. Reduced antibody and conjugates were characterized by SDS-PAGE with Bio-Rad 4-20% Mini-PROTEAN TGX precast gels under non-reducing conditions. Aliquots of reduced and buffer exchanged antibody were quenched with excess maleimide before sample preparation. Samples were mixed 1:1 with Bio-Rad Laemmli buffer and heated at 100° C. for two minutes before applying to the gel (approximate sample concentration of 0.125 mg/mL). Samples were run at 100 V for ten minutes followed by 200 V for twenty minutes in Bio-Rad 1× Tris/Glycine/SDS running buffer. Gels were stained with Bio-Rad Bio-Safe Coomassie G-250 stain. Absorbance measurements were carried out on a Shimadzu UV-1800 UV/Vis spectrophotometer in quartz cuvettes (1 cm path length, 200 μL volume).

Synthesis of Conjugates

Purified rabbit antibody (11.1 mg/mL, 3604 μL, 40 mg) was buffer exchanged into Tris-EDTA buffer (20 mM Tris, 1 mM EDTA, pH 8.8) using a 4 mL Amicon and the antibody was reconstituted to a final volume of 20 mL Tris-EDTA buffer. To the antibody (0.274 μmol, 40 mg, 20 mL, 2 mg/mL) in Tris-EDTA buffer was added 1:2 2-mercaptoethanol:Tris-EDTA buffer (3500 eq, 0.959 mmol, 203 μL) and the mixture was incubated at 37° C. for 2.5 hours. The solution was divided into two 10 mL portions and buffer exchanged into phosphate buffer (40 mM phosphate, 20 mM NaCl, 6 mM EDTA, pH 6.0) using two 14 mL Amicons. After exchange, the portions were combined and reconstituted to a final volume of 20 mL phosphate buffer, and this was divided into 20 1 mL aliquots for conjugation reactions. To each of the aliquots of reduced rabbit antibody (0.014 μmol, 2 mg, 1 mL, 2 mg/mL) was added one of the eighteen linker-payloads (10 eq, 0.137 μmol, 1 mM in DMF, 137 μL). Two control samples were also prepared by adding either a larges excess of maleimide (137 μL of 200 mM maleimide in PBS) or only 137 μL of DMF. The conjugations were incubated overnight at room temperature and then the excess reagents were removed via buffer exchange into acetate buffer (50 mM acetate, 10% DMSO, pH 5.5) using 4 mL Amicons. Samples were each recovered from the centrifugal filter units and diluted to final volumes of 500 μL to determine DAR. The volume of each of the samples was then adjusted to provide a final trigger-payload concentration of 20 uM ($A_{310}$=0.165) for each conjugate regardless of the DAR. These conjugate solutions were used in the payload release assays.

Figure 8:
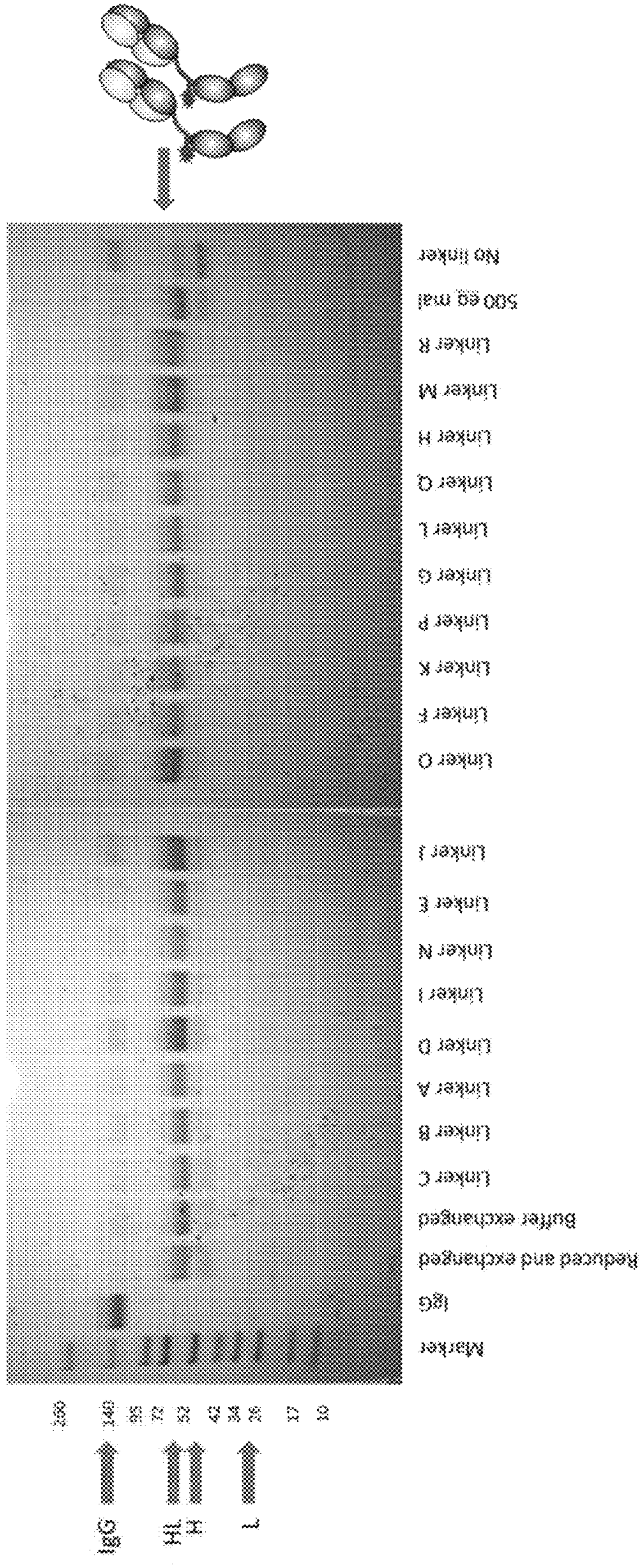
FIG. 8 provides an SDS-PAGE analysis for the conjugation of payloads with linkers of the present disclosure.

The reduction and conjugation process for each conjugate was monitored via SDS-PAGE (FIG. 8). Aliquots of the IgG were sampled before reduction, after reduction, after buffer-swap into the conjugation buffer, after conjugation with the maleimide-based linker-payload, and after incubation with a 100× excess of maleimide. In all cases SDS-PAGE displayed molecular weights corresponding to 150 kDa for the starting IgG, 75 kDa after fairly clean reduction to the 1/2/IgG, 75 kDa after buffer swap into the conjugation buffer with a small amount of re-oxidation to the full IgG occurring, and 75 kDa after both conjugation with the linker payload as well as after quenching with a large excess of maleimide. The SDS-PAGE profiles of reduced IgG conjugated with all the various linker-payload as well as quenched with excess maleimide were nearly identical and showed mainly 1/2 IgG (75 kDa) with a small amount of full IgG (150 kDa).

SDS-PAGE analysis of the prepared conjugates in Table 1 indicated that all linker payloads conjugated similarly. With only a single hinge disulfide, the conjugate denatures into two 1/2 IgG under gel conditions due to capping by the maleimide linker (FIG. 8).

These optimized reduction and conjugation protocols for selective reduction of rabbit IgG hinge disulfides and conjugation with maleimide provided substantially pure DAR2 conjugates.

DAR2 conjugates were used because they tend to minimize complications from solubility/aggregation of high DAR species and minimize differences in payload release rates due to DAR distribution (isolates the variable of linker architecture).

UV/Vis Analysis: the uncorrected fluorophore-antibody ratio (FAR) for each conjugate in Table 2 was determined by UV/Vis absorption spectroscopy ($A_{280}/A_{310}$) by the formula:

$$FAR = \frac{(\mathrm{Abs}_{310}A/\varepsilon_{310})}{((\mathrm{Abs}_{280} - CFx\mathrm{Abs}_{310})/\varepsilon_{280})}$$

where $\varepsilon_{280}$=for rabbit IgG (reported as E1%=13 by supplier), $\varepsilon_{280}$=215380 M−1 cm−1 for rabbit IgG, $\varepsilon_{310}$=0.0081 M−1 cm−1 for the trigger-coumarin probe, CF=1.13 as a correction factor for the trigger-probe absorption at 280 nm.

The final corrected FAR was then determined by subtracting the FAR of a control IgG, which was reduced and quenched with an excess of maleimide and run in parallel to each IgG conjugated to the linker-payload. These blanks generally provided a FAR of 0.24-0.29.

Figure 9:
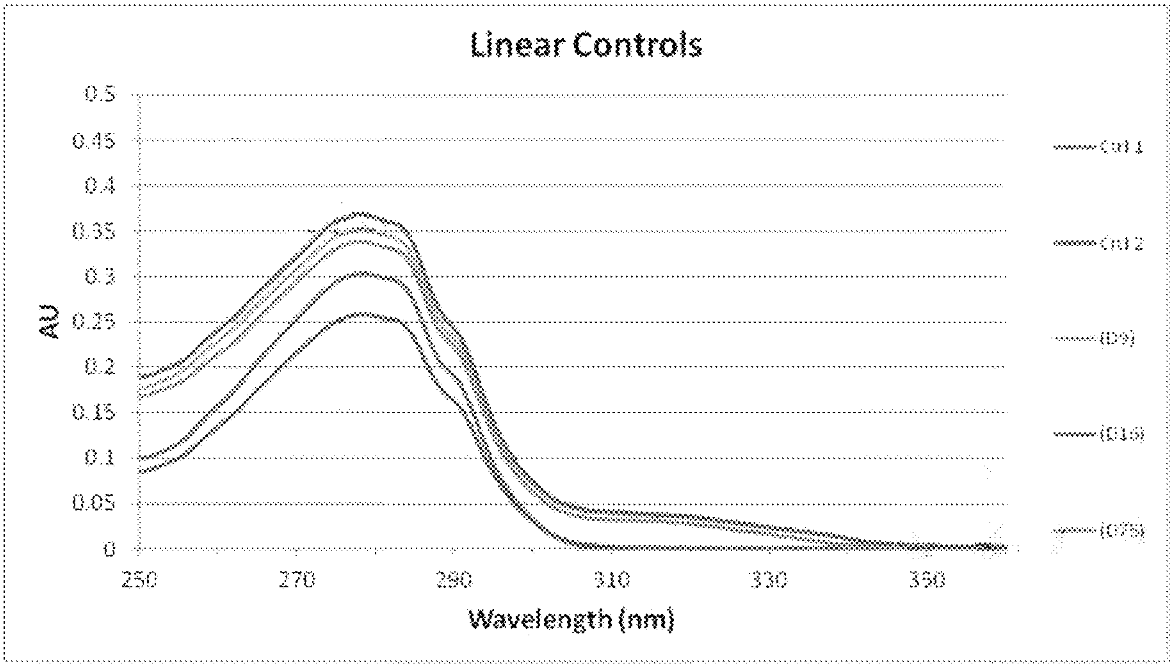
FIG. 9 provides UV/Vis absorption spectra for controls, linear conjugates, and DAR2 conjugates of the present disclosure.
Figure 9:
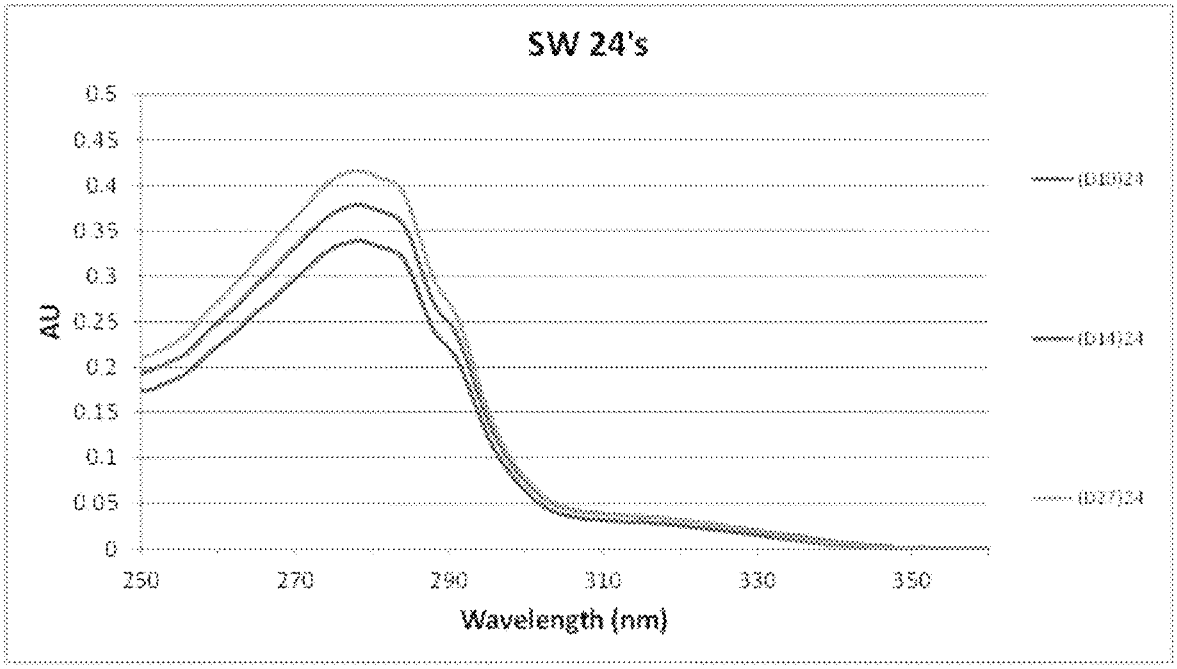
Figure 9:
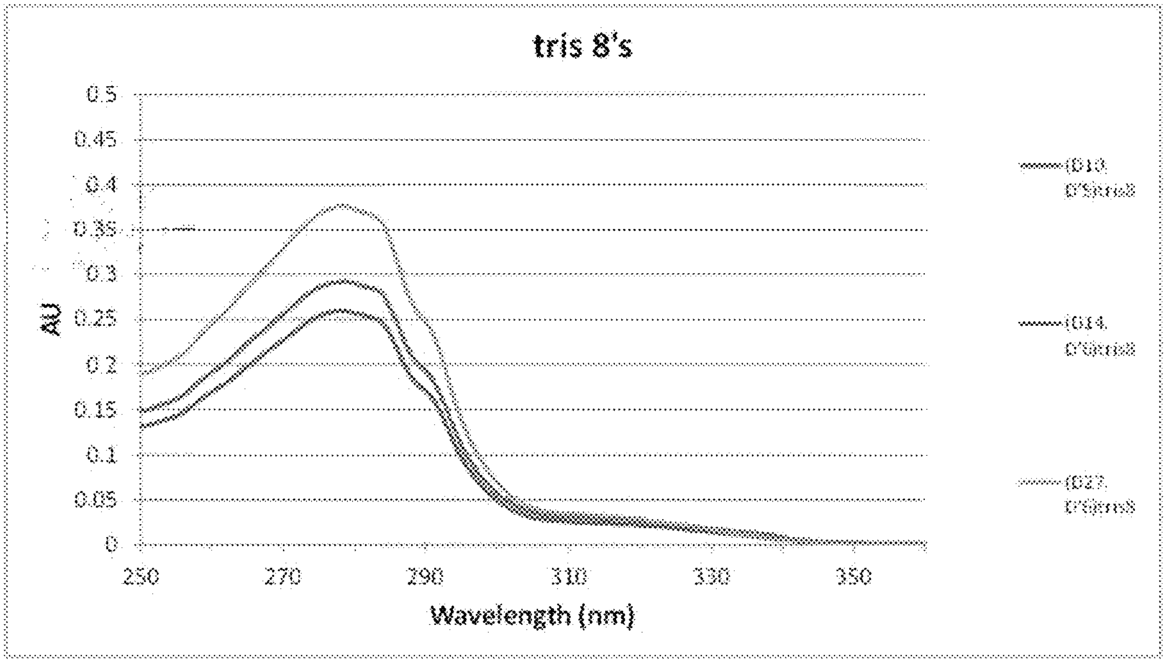
Figure 9:
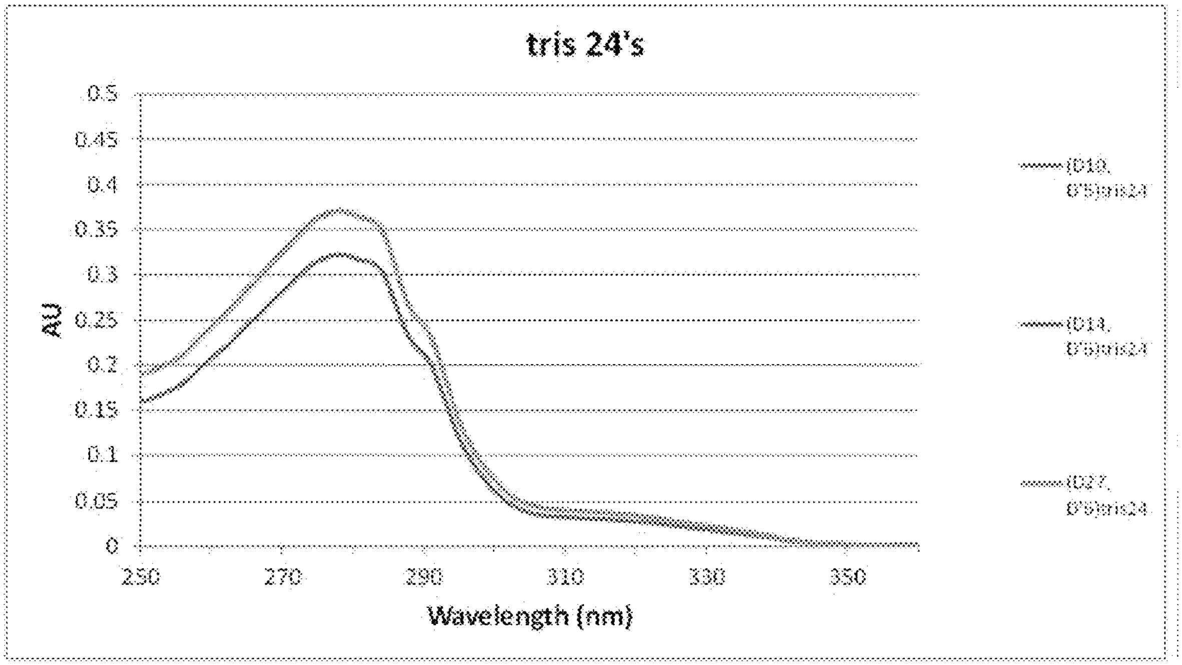
Figure 9:
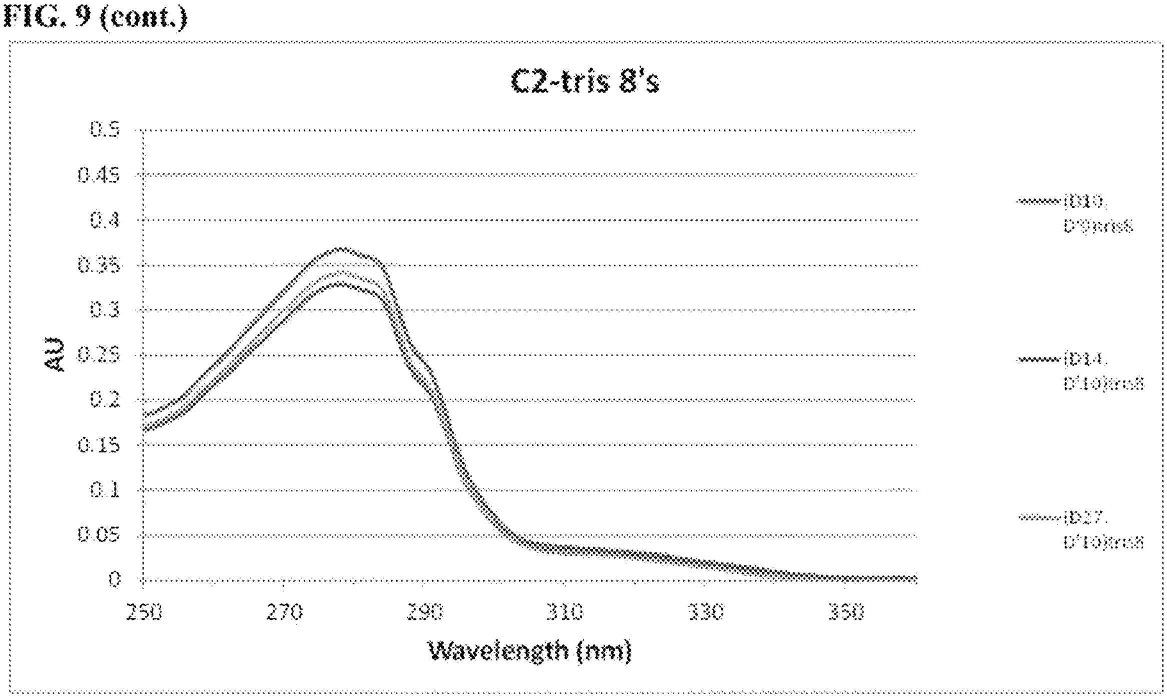
Figure 9:
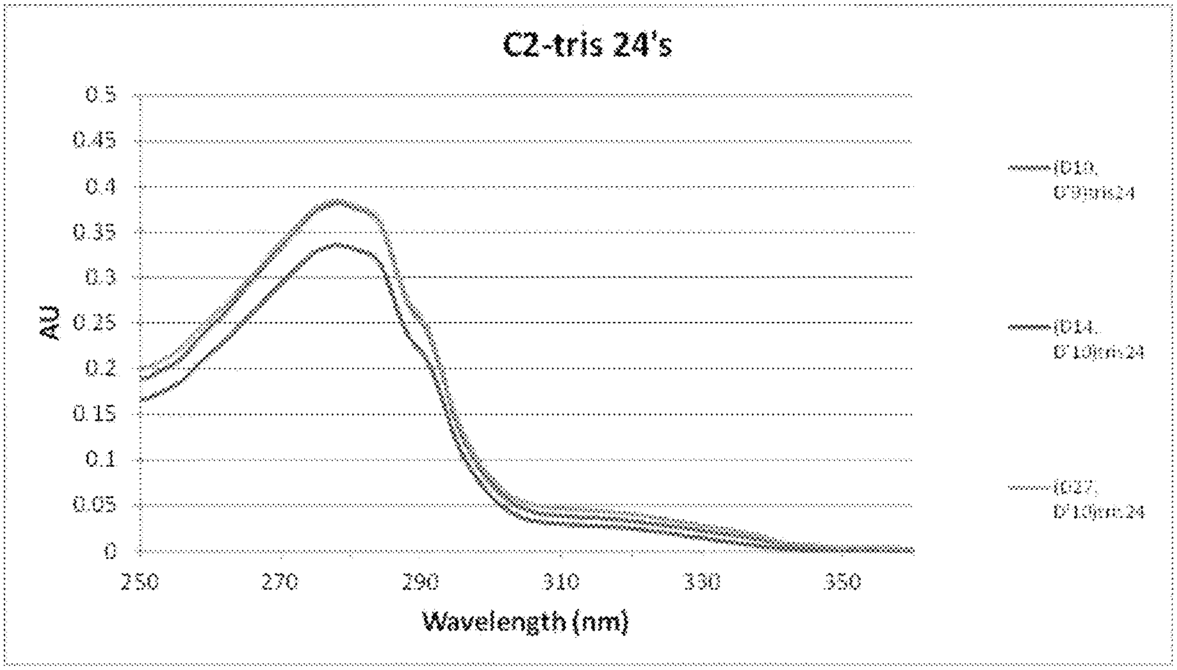

Results:

According to the data, the prepared conjugates showed reasonably homogeneous DAR2 regardless of widely varying linker architectures (FIG. 9). The data in Table 2 indicates there is systemic bias towards higher DAR, but the variation is reasonable and likely minimizes the impact of DAR as a variable.

TABLE 2

Determination of Drug-Antibody Ratio (DAR) Across Various Linker Architectures.

| Conjugate | D (atoms) | Linker-Payload (y, n, D') | $A_{280}$ | $A_{310}$ | DAR |
|---|---|---|---|---|---|
| A | 75 | 18-Linear | 0.336 | 0.032 | 2.5 |
| B | 16 | 19-Linear | 0.365 | 0.041 | 3.0 |
| C | 9 | 22-Linear | 0.349 | 0.039 | 3.0 |
| D | 27 | 29-1, 24, NA | 0.412 | 0.039 | 2.5 |
| E | 14 | 32-1, 24, NA | 0.335 | 0.032 | 2.5 |
| F | 10 | 39-1, 24, NA | 0.375 | 0.039 | 2.8 |
| G | 27 | 102-3, 8, 10 | 0.338 | 0.031 | 2.4 |
| H | 14 | 105-3, 8, 10 | 0.326 | 0.033 | 2.7 |
| I | 10 | 111-3, 8, 9 | 0.364 | 0.037 | 2.7 |
| J | 27 | 70-3, 8, 6 | 0.373 | 0.035 | 2.5 |
| K | 14 | 73-3, 8, 6 | 0.257 | 0.026 | 2.7 |
| L | 10 | 81-3, 8, 5 | 0.29 | 0.031 | 2.8 |
| M | 27 | 87-3, 24, 10 | 0.381 | 0.047 | 3.4 |
| N | 14 | 90-3, 24, 10 | 0.333 | 0.03 | 2.4 |
| O | 10 | 96-3, 24, 9 | 0.378 | 0.039 | 2.7 |
| P | 27 | 53-3, 24, 6 | 0.366 | 0.04 | 2.9 |
| Q | 14 | 56-3, 24, 6 | 0.367 | 0.041 | 3.0 |
| R | 10 | 62-3, 24, 5 | 0.319 | 0.033 | 2.7 |
| | | | | Average | 2.7 |
| | | | | St Dev | 0.26 |
| | | | | RSD | 10% |

Example 3: Examining the Effect of Linker Architecture and D' on Payload Release with Minimal Shielding from the Antibody Materials and Methods Human liver lysosome preparations were obtained from XenoTech (CAT #H0610.L). Cathepsin B, cathepsin K, and cathepsin L were obtained from Millipore Sigma (CAT #C8571-25UG, CAT #219461, and CAT #219402). Cathepsin S was obtained from Abcam (CAT #191650). Mouse serum was obtained from Invitrogen (CAT #10410). All other reagents and solvents were purchased from commercial sources and used as provided. All buffer solutions were prepared with MilliQ water, sterile filtered, and degassed by purging with argon. Pre-activation of the enzymes was performed in polypropylene 1.5 mL Eppendorf safe-lock tubes at 37° C. Payload release assays were performed at 37° C. in opaque white 96-well plates fitted with polyester adhesive film (VWR), which was removed for fluorescence readings. Fluorescence measurements were made on a Molecular Devices Gemini XPS microplate reader ($\lambda_{Ex}$ 325, $\lambda_{Em}$ 455). For all experiments the conjugates were added as solutions in pH 5.5 acetate buffer with 10% DMSO and at a probe concentration of 20 μM. A 20 μM solution of the free coumarin fluorophore in pH 5.5 acetate buffer with 10% DMSO was also prepared gravimetrically.

Previous investigations have tried to leverage steric hindrance from the biologic to afford protection to the cleavable trigger and reduce off-target extracellular payload release. It has been demonstrated that short linkers between a targeting vector and a glu-PABC trigger can slow BG-mediated payload release. It has also been shown previously that linker length and conjugation site can be manipulated to increase steric hindrance around dipeptide triggers and reduce systemic payload release in mouse models, likely due to CES1c-mediated cleavage of the dipeptide trigger. This same strategy of reducing linker length to increase steric hindrance by the antibody has been applied to preventing deactivation of metabolically labile payloads by a variety of esterases and hydrolases. While this general strategy has proven successful for some enzymes, this has not been a successful approach to regulating cathepsin-mediated payload release.

Figure 10:
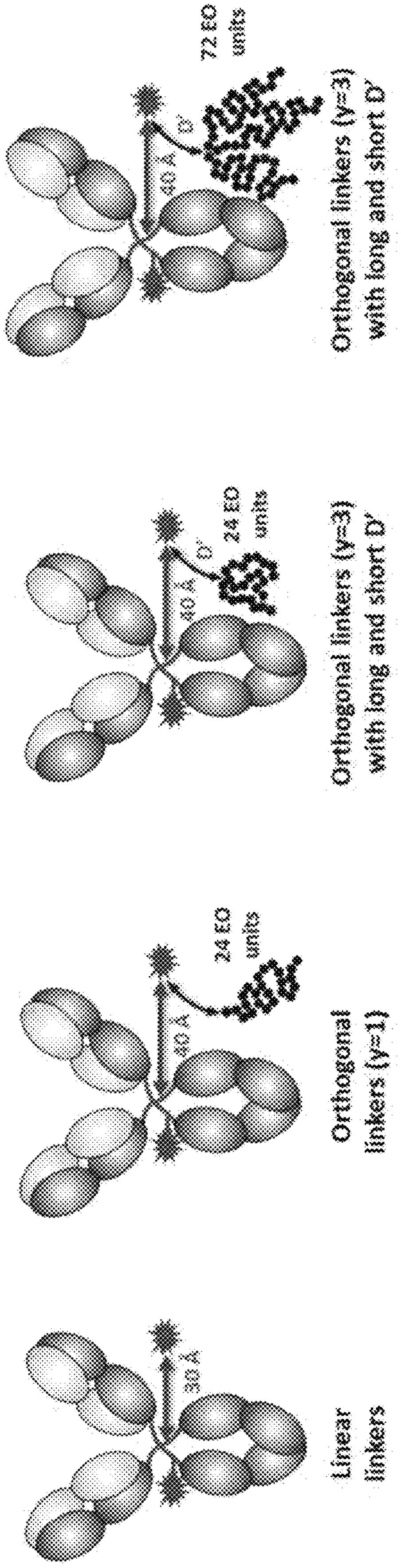
FIG. 10 is a schematic showing conjugates with minimal shielding from the antibody and different linker architectures.

Objective: To explore the effect of the linker architectures on payload release when the steric shielding from the antibody is minimized (see FIG. 10), and therefore not a factor in facilitating payload release.

Figure 11:
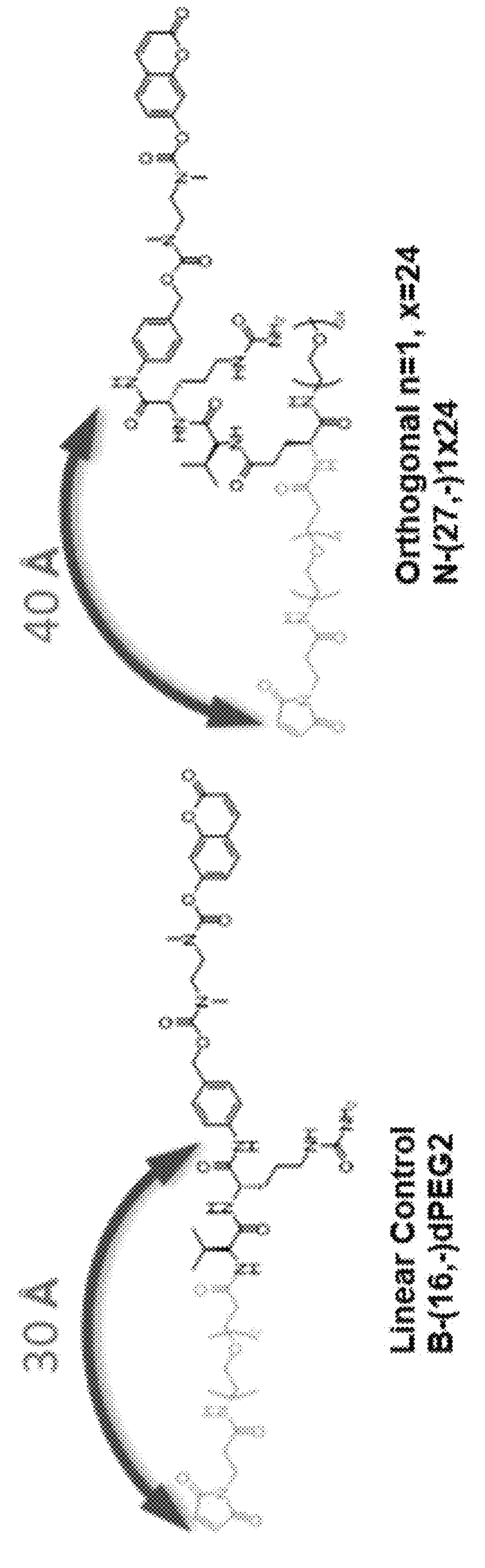
FIG. 11 provides various conjugates with linear or orthogonal linker architectures having large antibody-payload distances.
Figure 11:
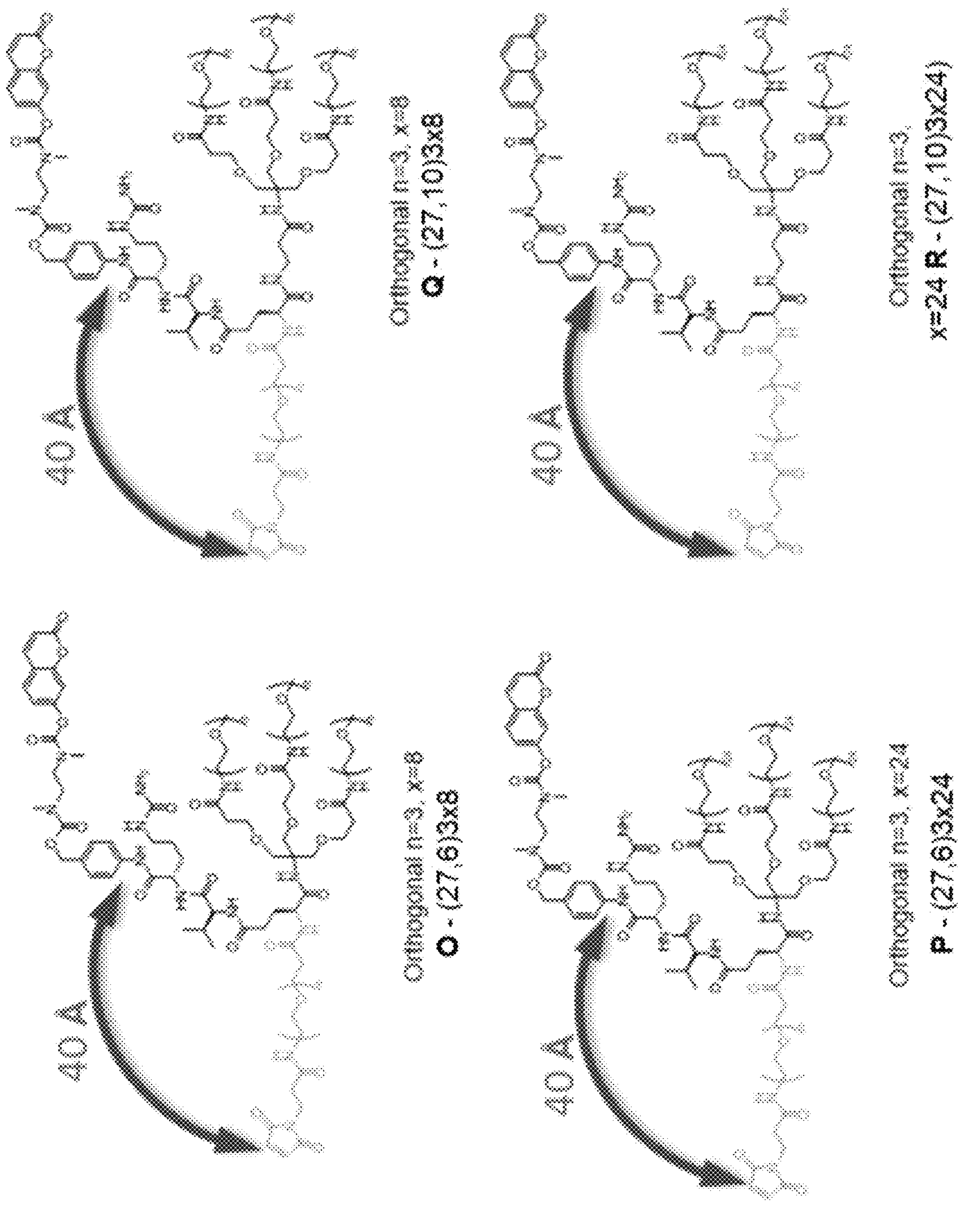

Study Design: A set of linker architectures was prepared that varied the number of atoms between the first heteroatom of the P2 residue, which is the first residue displaying selectivity and recognized by the S2 enzyme site, and the branch point (FIG. 11). This structural variable is defined as D'. This variable could also be defined as the distance between the site on the dipeptide cleaved by the enzyme and the quaternary branch point (the distance $D_2$, $D_3$, and A in Formula (I) or the present claims), which in this case would be D'+7. The set of linkers in FIG. 11 have either 6 or 10 atoms between the first heteroatom of the P2 residue and the branch point (D'), and also increase the number of EO units in each of the dPEG (discrete PEG) arms from x=8 (2 kDa) to x=24 (6 kDa).

As shown in FIG. 11, the linear control B has a 30 Å distance between the antibody and payload, while the other conjugates (D, J, G, P, and M; see Table 1) maintain a 40 Å (27 atom) distance. Percent payload release of the conjugates with dipeptide linkers was evaluated at the 22 hour timepoint using a pro-fluorophore probe to monitor payload release by fluorescence.

In Vitro Payload Release Assays

Preliminary experiments with Conjugate A were used to determine the amount of enzyme used in each of the assays. Payload release from Conjugate A was anticipated to be unaffected by steric hindrance, so this conjugate was incubated with varying amounts of each of the enzymes, and the quantities that provided nearly complete payload release over similar time courses were chosen and fixed for the entire set of experiments.

Figure 12:
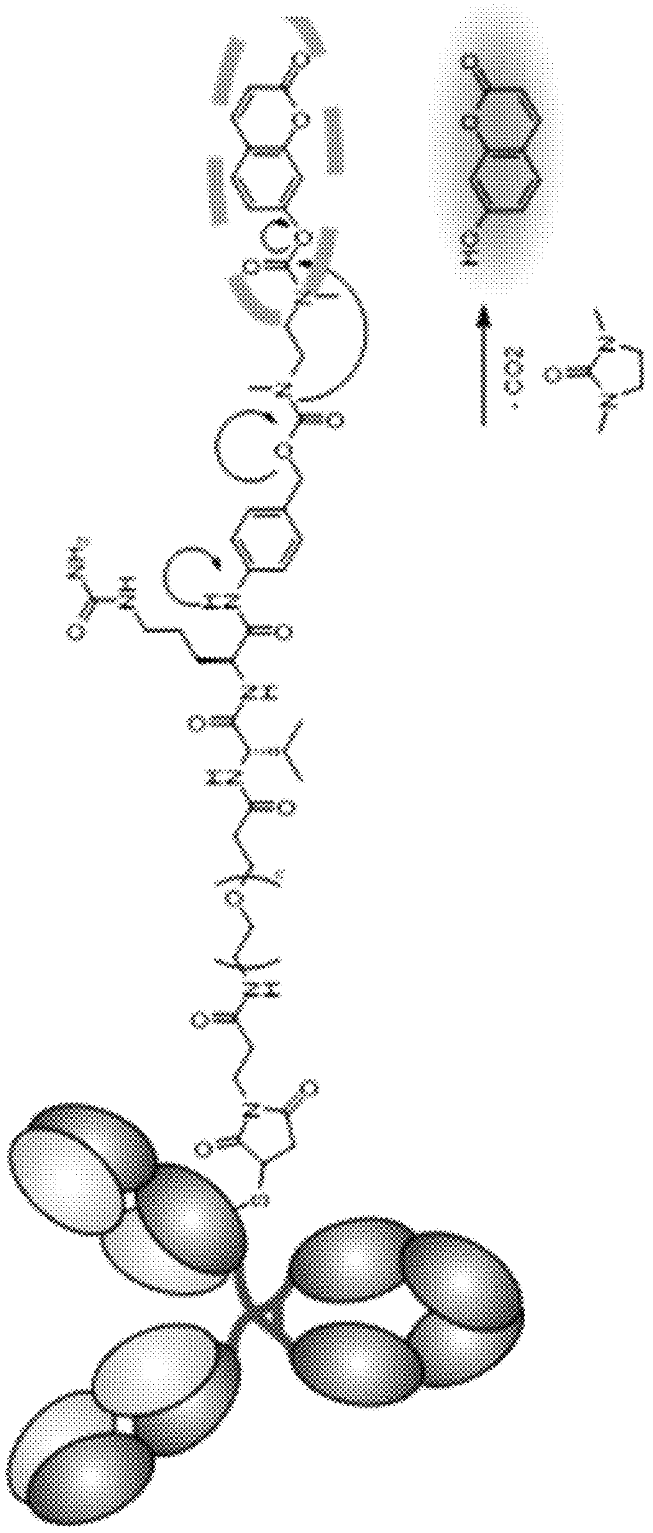
FIG. 12 shows a conjugate having a pro-fluorophore probe and the assay used to monitor fluorescence.
Figure 12:
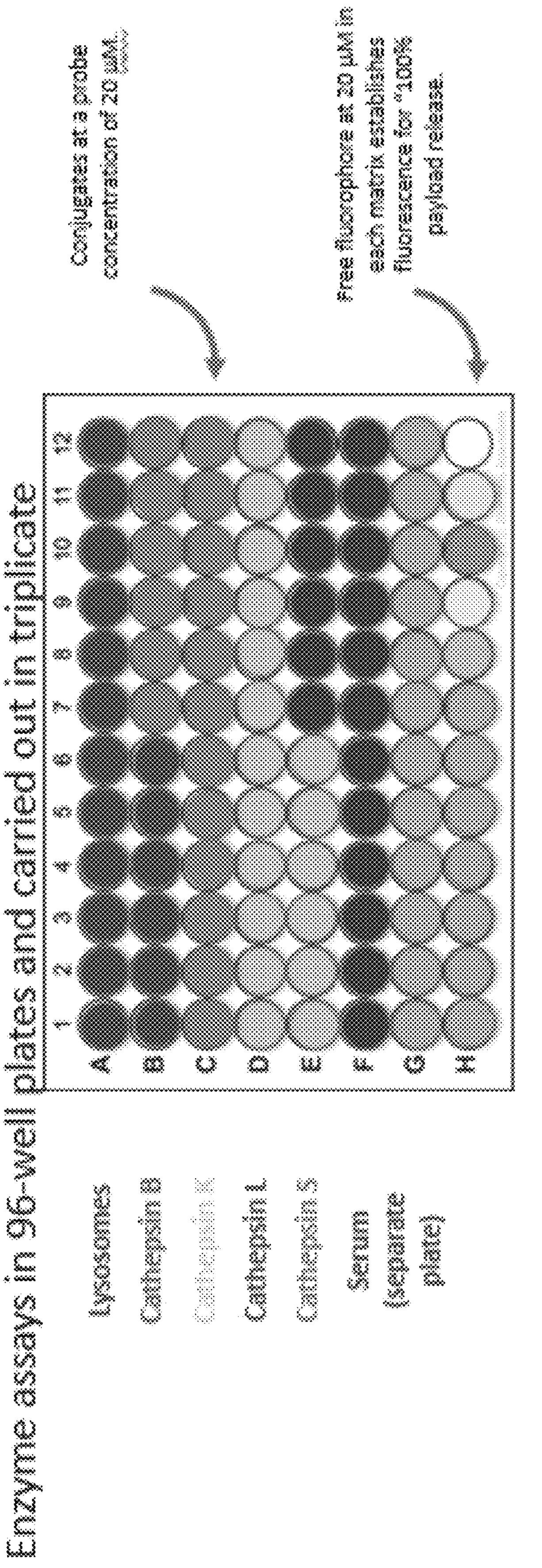
Figure 13:
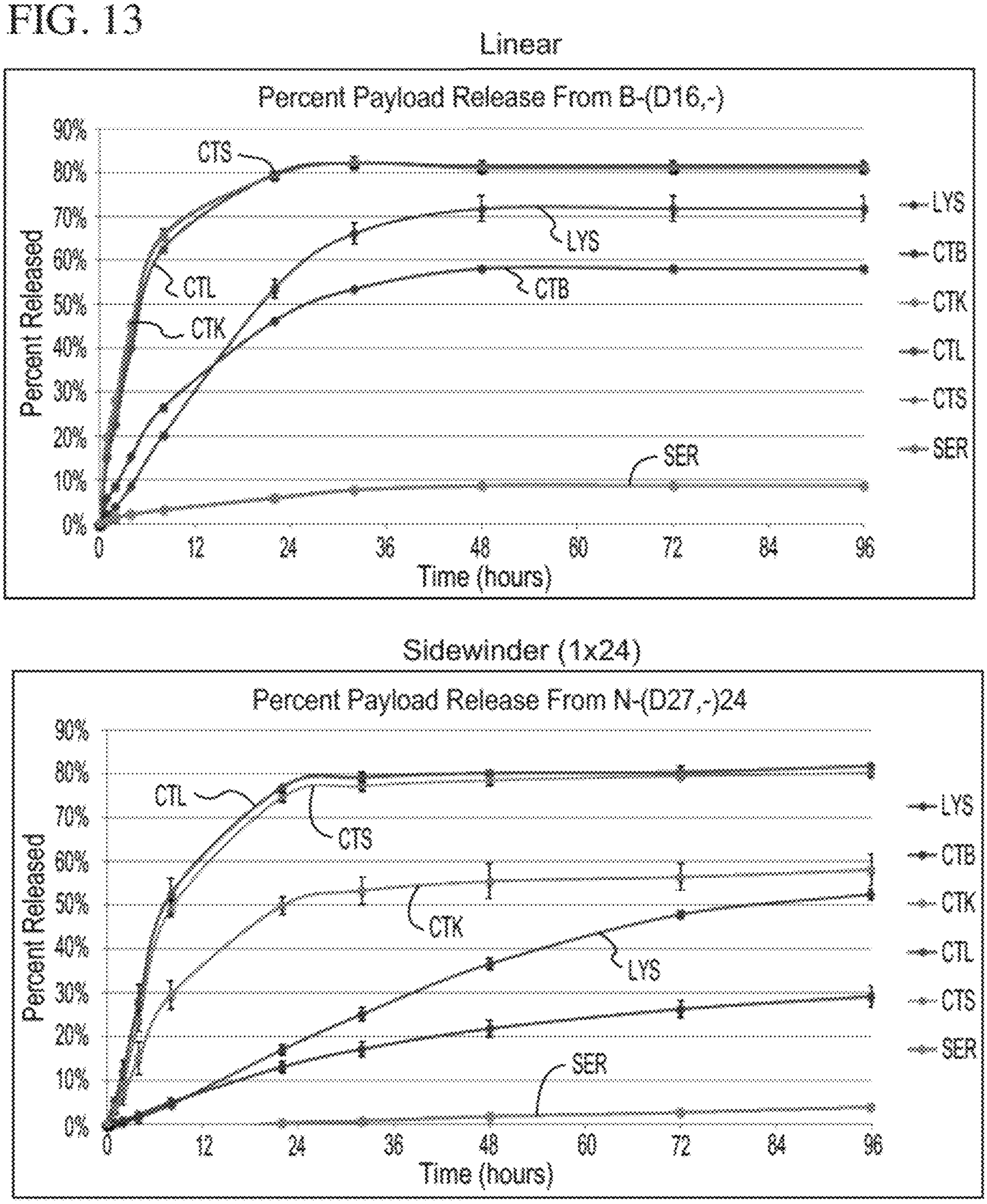
FIG. 13 shows the raw data for payload release from control conjugates and conjugates of the present disclosure with minimal shielding from antibody.
Figure 13:
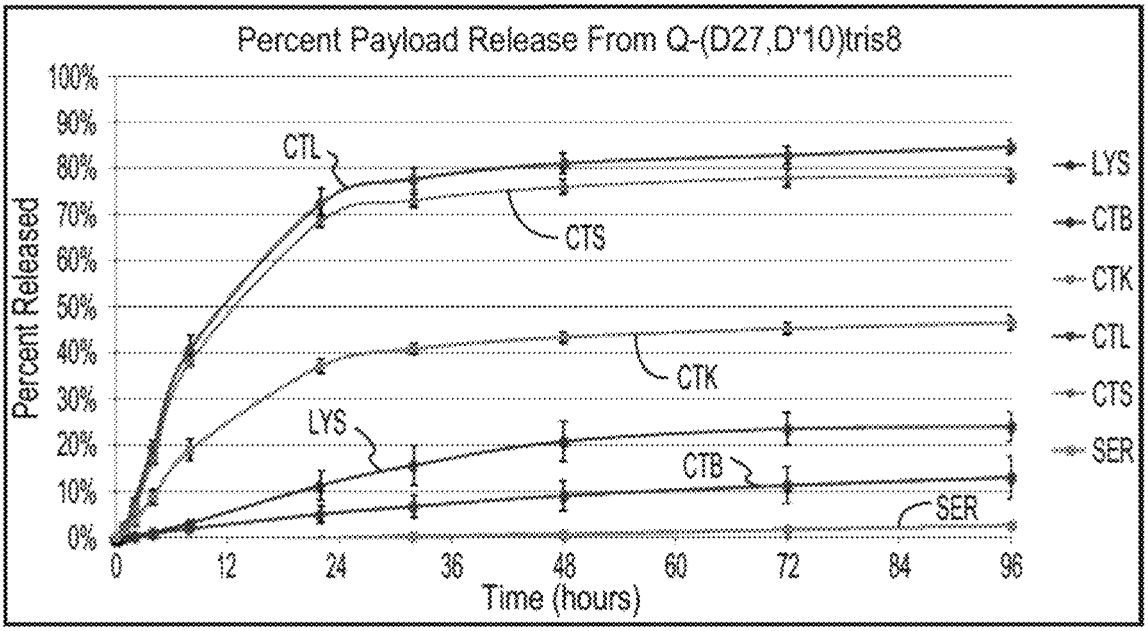
Figure 13:
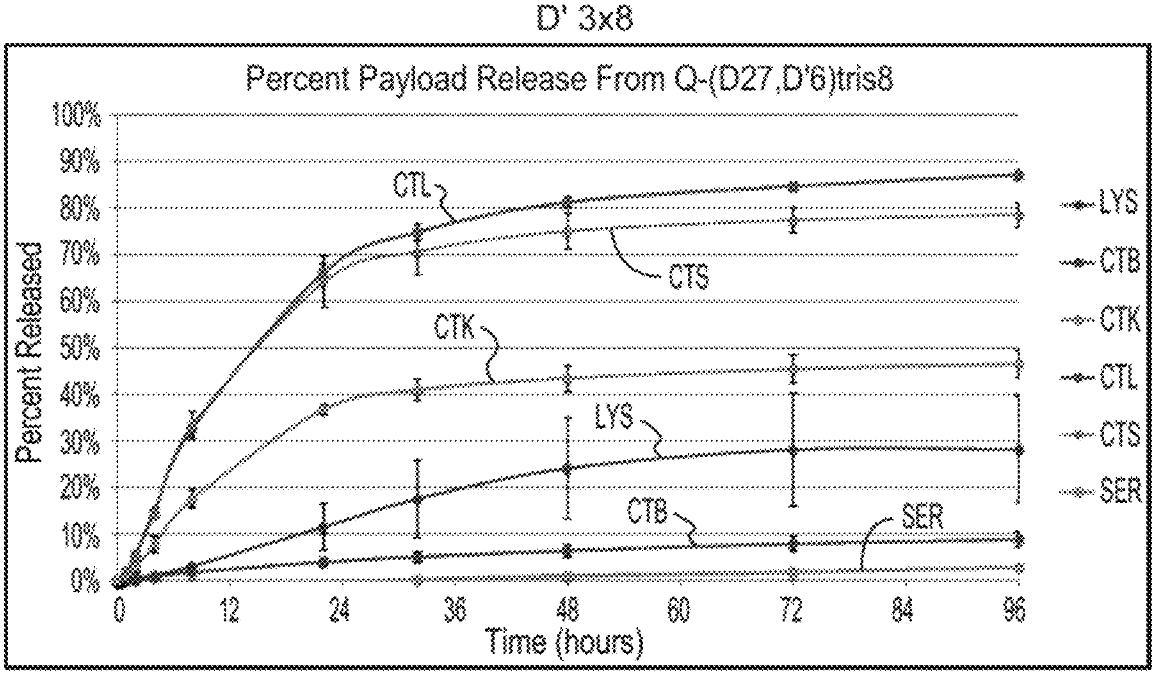
Figure 13:
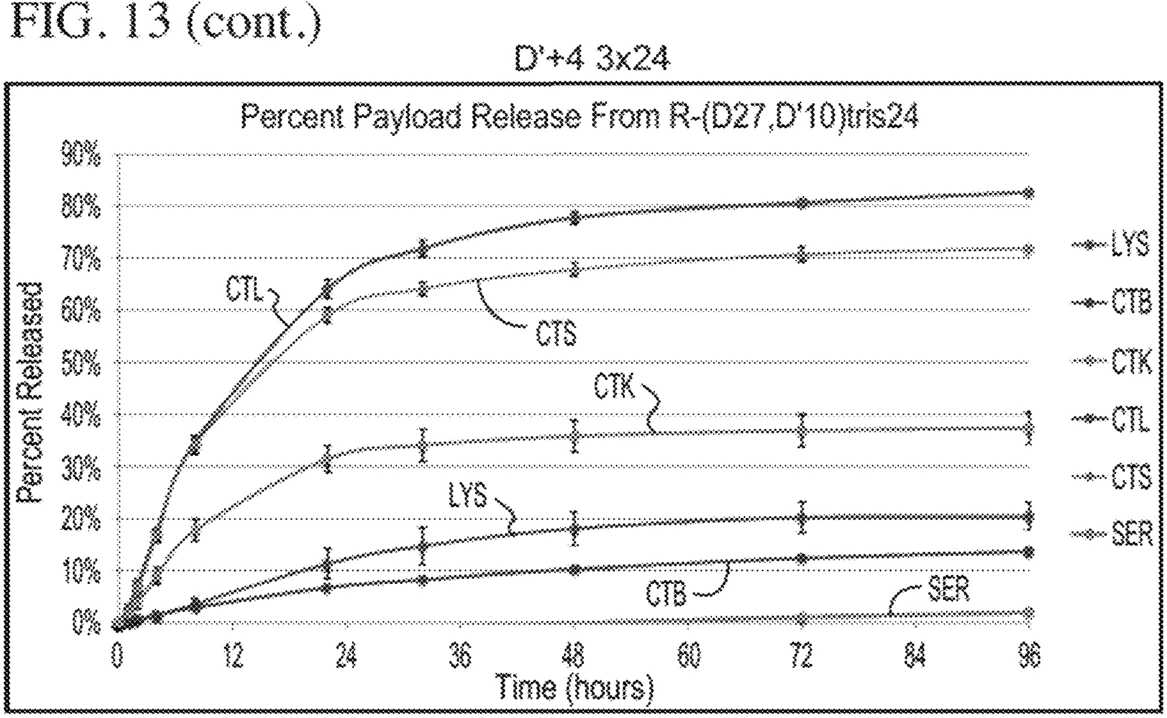
Figure 13:
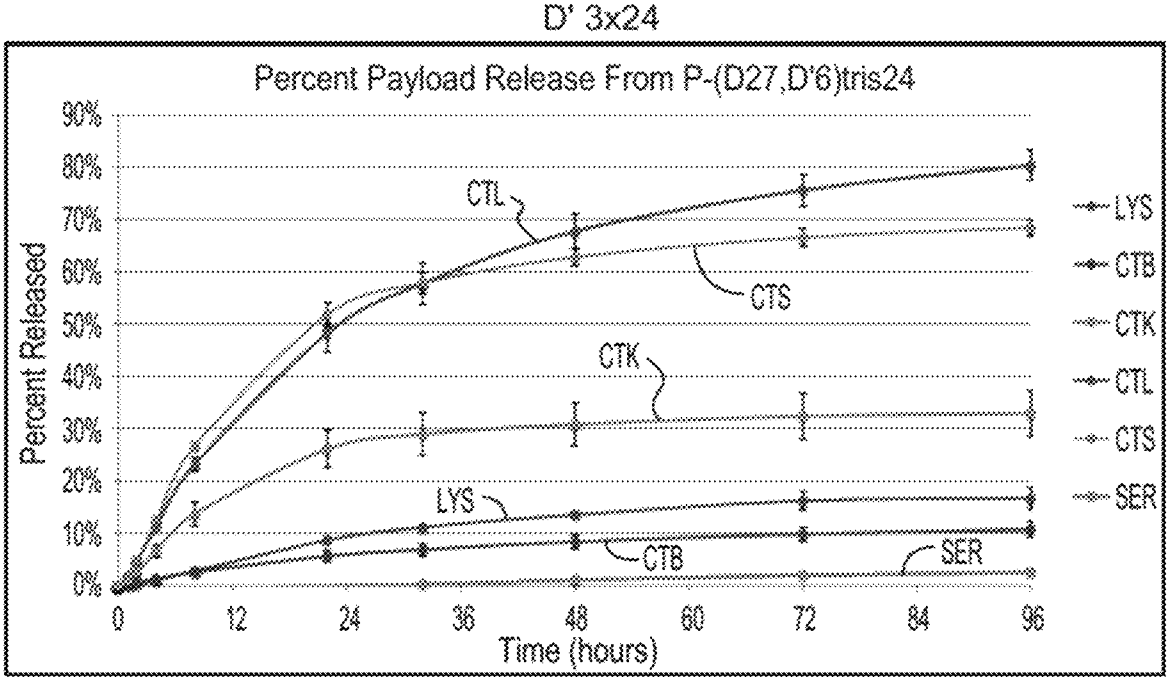

For all experiments, the null conjugates, the IgG conjugates, and the free coumarin were prepared as solutions in pH 5.5 acetate buffer with 10% DMSO and at a probe concentration of 20 uM. Solutions of the null conjugates were determined by mass. The concentrations of the IgG conjugates were determined by A310, and they were diluted to a concentration of 20 uM. For DAR 2 conjugates this is a conjugate concentration of 10 uM, however all solutions were normalized to a maximum possible coumarin concentration of 20 uM. The general layout for assays in a 96-well plate is shown in FIG. 12.

Payload release of the conjugates by lysosomes was determined as follows. 200 uL of human liver lysosomes (XenoTech CAT #H0610.L) was diluted with 200 uL of 50 mM NaAc, with 4 mM TCEP and adjusted to pH 5.0, and incubated at 37 C for 15 minutes. To each of the wells in a 96-well plate (according to FIG. 12) was added 20 uL of lysosome solution, 60 uL of assay buffer (50 mM NaAc, with 2 mM TCEP and adjusted to pH 5.0), and 20 uL of the linker-payload to give a final volume of 100 uL and a final conjugate concentration of 4 uM in each well. The plate was placed in an incubator at 37 C and at the given time points the emission spectra were obtained from 400-500 nm at an excitation wavelength of 325 nm. Payload release was monitored by plotting fluorescence versus time. A control sample representing 100% payload release was also monitored in parallel, which substituted the 20 uL of the conjugate with 20 uL of the free coumarin.

Payload release of the conjugates by each of the cathepsins was determined as follows. 33.6 uL of cathepsin B (Millipore Sigma CAT #C8571-25UG), 0.9 uL of cathepsin K (Millipore Sigma CAT #219461), 63.5 uL of cathepsin L (Millipore Sigma CAT #219402), and 69.8 uL of cathepsin S (Abcam CAT #191650) were diluted with 365.4 uL, 398.1 uL, 335.5 uL, and 329.2 uL of 50 mM NaAc with 4 mM TCEP at pH 5.0, respectively. The mixtures were incubated at 37 C for 15 minutes. To each of the wells in a 96-well plate (according to FIG. 12) was added 60 uL of assay buffer, 20 uL of the pre-activated enzyme, and 20 uL of the conjugate solution to give a final volume of 100 uL in each well with a linker-probe concentration of 4 μM. The plate was placed in an incubator at 37 C and at the given time points the emission spectra were obtained from 400-500 nm at an excitation wavelength of 325 nm. Payload release was monitored by plotting fluorescence versus time. Control samples in each of the enzymes representing 100% payload release were also monitored in parallel, which substituted 20 uL of the conjugate with 20 uL of the free coumarin.

Payload release of the conjugates in mouse serum was determined as follows. 418 uL of mouse serum (Invitrogen CAT #10410) was diluted with 1254 uL of phosphate buffered saline at pH 7.4. The mixture was incubated at 37 C for 15 minutes. To each of the wells in a 96-well plate (according to FIG. 12) was added 80 uL of serum and 20 uL of the conjugate solution to give a final volume of 100 uL in each well with a linker-probe concentration of 4 μM in each well. A control sample representing 100% payload release was also analyzed, which substituted the 20 μL of the conjugate with 20 μL of the free coumarin.

The plate was placed in an incubator at 37° C. and at the given time points the emission spectra were obtained from 400-500 nm at an excitation wavelength of 325 nm. Payload release was monitored by plotting fluorescence versus time. A control sample representing 100% payload release was also monitored in parallel, which substituted 20 uL of the conjugated with 20 uL of the free coumarin. The fluorescence versus time data was then converted to percent release for direct comparison of the different assays. Each conjugate (profluorophore probe) was assayed in parallel with a control (free fluorescent coumarin) at the same concentration (4 uM) and in the same matrix, thus the control provides the fluorescent signal corresponding to complete payload release and accounts for the varying backgrounds in the different matrices. In each of the assays the percent release can be given by the formula:

$$\%\ \text{Paylod Release} = \frac{\text{Conjugate } Em_{455}}{\text{Coumarin } Em_{455}}$$

Results:

The above procedures were carried out in three separate plates with three independent enzyme preparations and the average value was determined. Error bars for raw data measurements are given as the standard deviations, while error bars for derived values (such as % Payload Release) are determined by standard formulas for propagation of uncertainty.

Figure 14A:
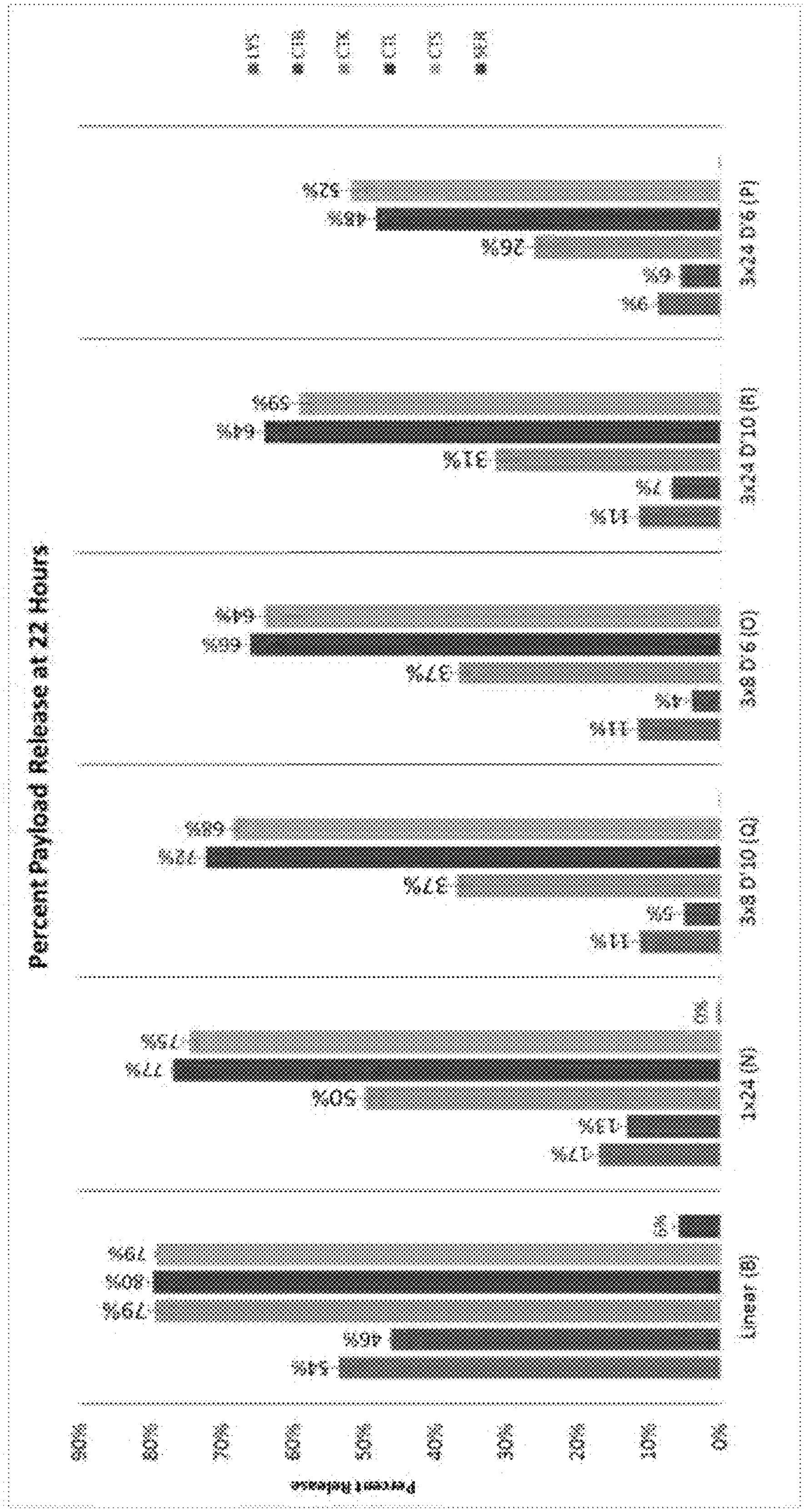
FIG. 14A shows a graph of percent release of payload from conjugates subjected to LYS, CTB, CTK, CTL, CTS, or SER.
Figure 14B:
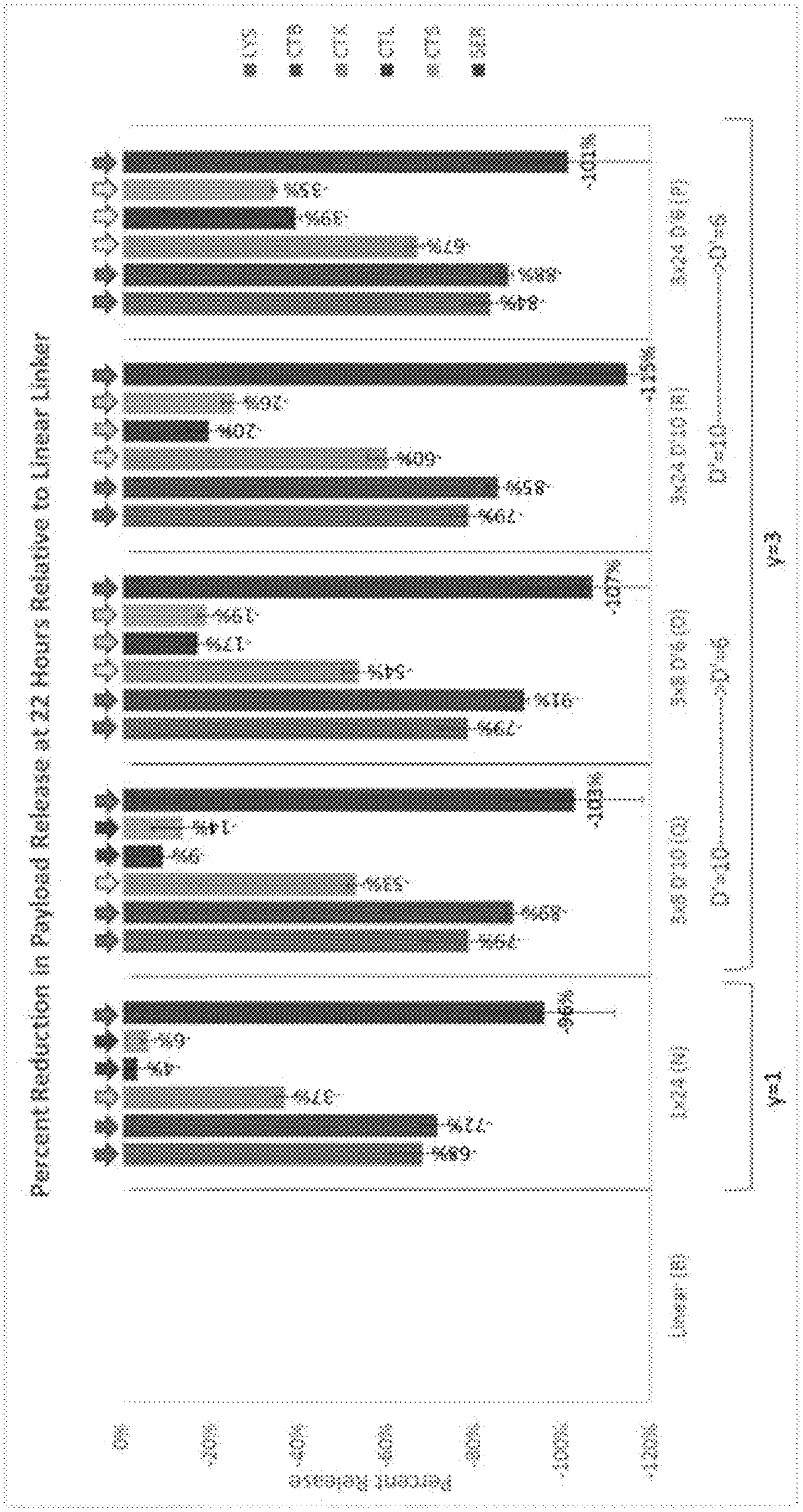
FIG. 14B shows a graph of the percent reduction in payload release from conjugates relative to a linear linker (control) when subjected to LYS, CTB, CTK, CTL, CTS, or SER.

Despite no steric shielding from the 150 kDa antibody, there is a global reduction in cathepsin-mediated payload release that correlates with increasing y, decreasing D', and increasing x (FIGS. 14A and 14B).

In particular, it was found that attenuation of payload release by both endo and exopeptidases, within error bars, was only observed for y=3 architectures (cf. conjugate D and conjugate J, where y=1 and y=3, respectively, but the same number of EO units 24).

It was also found that the extent of payload release is dependent on D'. As shown in FIGS. 14A and 14B, for both x=8 and x=24, payload release at 22 h was diminished as D' increased from 6 atoms to 10 atoms. In fact, the architecture with the smaller x=8 arms (e.g., conjugate G) provided little to no reduction in release rates by the endopeptidases CTL and CTS when D'=10. Architectures with x=24 arms exhibited an attenuation of payload release at both D' values (6 and 10 atoms). However, even with the large dPEG structure (6 kDa), there was still a noticeable reduction in effect when D' increased by four atoms.

This suggests that as D' increases, the linker architecture behaves more like a linear linker and affords no protection from enzymes with readily accessible active sites. While the distance between the heteroatom of the first residue and the branch point required for attenuation of payload release by the entire panel of cathepsins is unknown, extending D' by only four atoms from 6 to 10 diminished this effect by 38-57% for both x=8 and x=24 dPEG arms.

Summary

As described above, the conjugates in FIG. 11 used longer linkers that placed the trigger at a distance of 40 Å (27 atoms) from the antibody to minimize steric shielding from the biologic. All orthogonal y=1 and y=3 architectures show significant reductions in payload release by CES1c, CTB, and LYS relative to the linear linker (see FIGS. 14A-14B). This is consistent with the known function of CES1c, which has been shown to be sensitive to steric hindrance due to the location of the active site and CTB is an exopeptidase at this pH and somewhat intolerant of extended substrates. The reductions in CTB and LYS rates in vitro are not expected to negatively impact the overall in vivo efficacy and these linkers. Indeed, several studies have shown that even linkers that exhibit in vitro payload release resistance in vitro (e.g. for enzymes expected to exist extracellularly, or outside of the lysosome) are still ultimately processed and release their payloads when they reach target cells in vivo. Presumably this is due to the fact that once the ADC is internalized it is sequestered in the endolysosomal compartments, where it will eventually undergo proteolytic degradation. As long as a threshold level of cytotoxin is released, the appropriate end-point is observed. In contrast, excess payload release from prior art linkers (i.e., lacking the orthogonal multi-branched moieties of the present disclosure), has been shown to result in a plateau effect in the therapeutic window without a concomitant increase in efficacy.

A surprising and unexpected finding is with the endopeptidases, CTK, CTL, and CTS, which cleave internal peptide bonds and are typically tolerant of extended substrates. Simply switching from an orthogonal (y=1, x=24) architecture to a (y=3, x=8) architecture results in much greater decreases in payload release despite the same number of EO units and shorter dPEG arms (85 Å versus 30 Å). The difference in payload release due to architecture is especially noticeable with CTL and CTS (see FIGS. 14A-14B). While the orthogonal y=1 architecture releases the same amount of payload as the typical linear linker, the analogous y=3 architecture results in ~15% less payload release. Given the implication of these enzymes in extracellular processes such as in bone (CTK), intestine (CTK, CTL), and smooth muscle in response to proinflammatory stimuli (CTS), these orthogonal y=3 architectures are expected to reduce extracellular payload release. It should be noted that CTB is an exopeptidase in the acidic environment of the lysosome (the pH used in these assays), but it functions as an endopeptidase at neutral pH. Thus, in some embodiments, the orthogonal y=3 architectures provide additional attenuation of extracellular CTB-mediated payload release in both physiological and pathological conditions involving secretion of CTB in the extracellular milieu.

Example 4: Examining the Effects of Increasing Steric Hindrance from Targeting Vector on Conjugates with Different Linker Architectures Background: For linear conjugates disclosed in the art, cathepsin-mediated payload release is generally unaffected by proximity of the antibody to the cleavable trigger.

Figure 15:
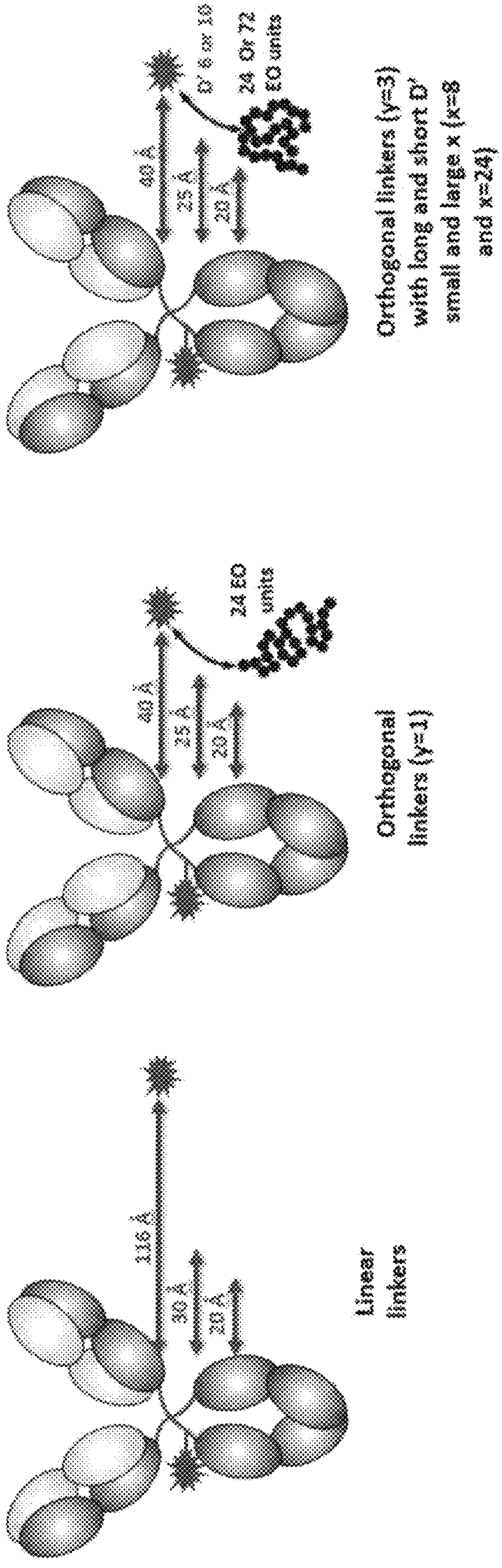
FIG. 15 is a schematic showing linear and orthogonal linker-containing conjugates having varying distances between the payload and targeting vector (e.g., an antibody).

Objective: To examine the effect of increasing steric hindrance from the antibody on payload release with D'=6 and D'=10 conjugates having y=3 linker architectures (see FIG. 15). The results obtained were compared to conjugates where y=1.

Study Design: Payload release was evaluated for the conjugates in FIGS. 16-18 having decreasing values for D, which measures the distance between the targeting vector X (e.g., an antibody) and the cleavable trigger T.

Figure 16:
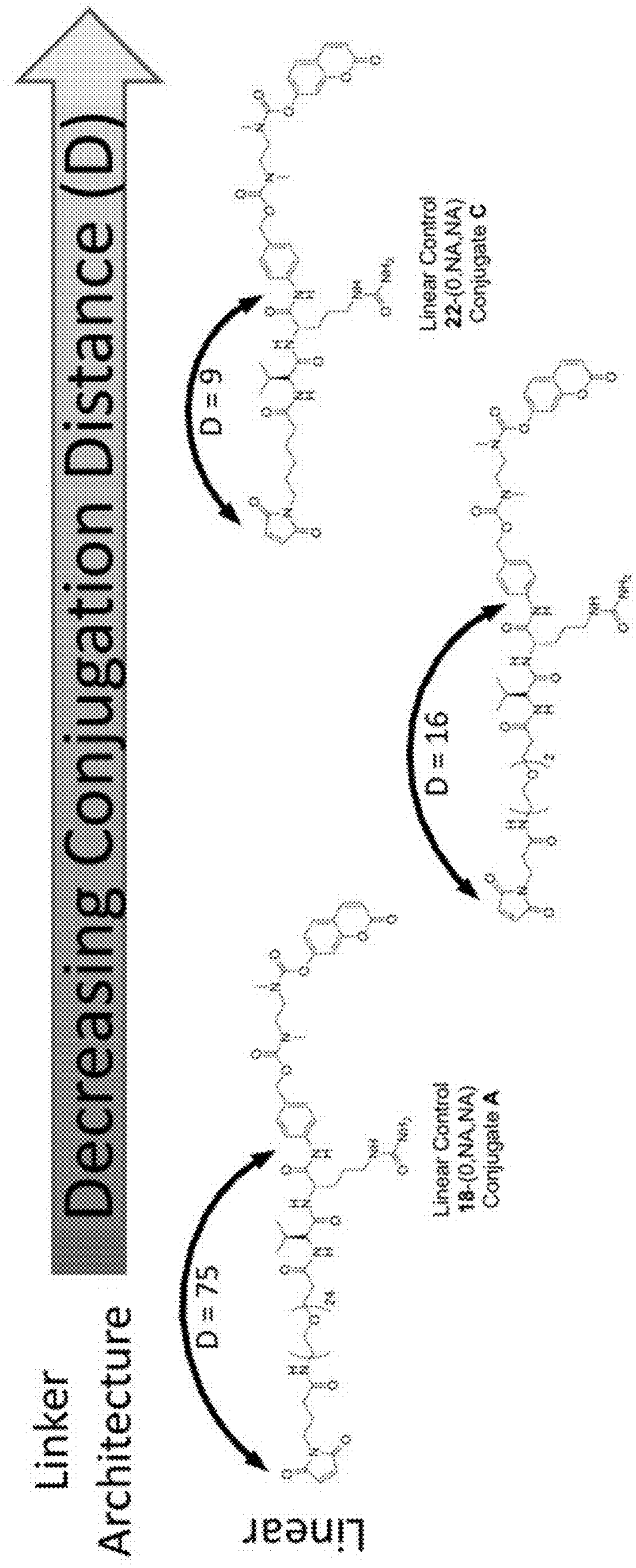
FIG. 16 shows examples of linear and 1×24 control conjugates having various distances between the payload and targeting vector (e.g., an antibody).
Figure 16:
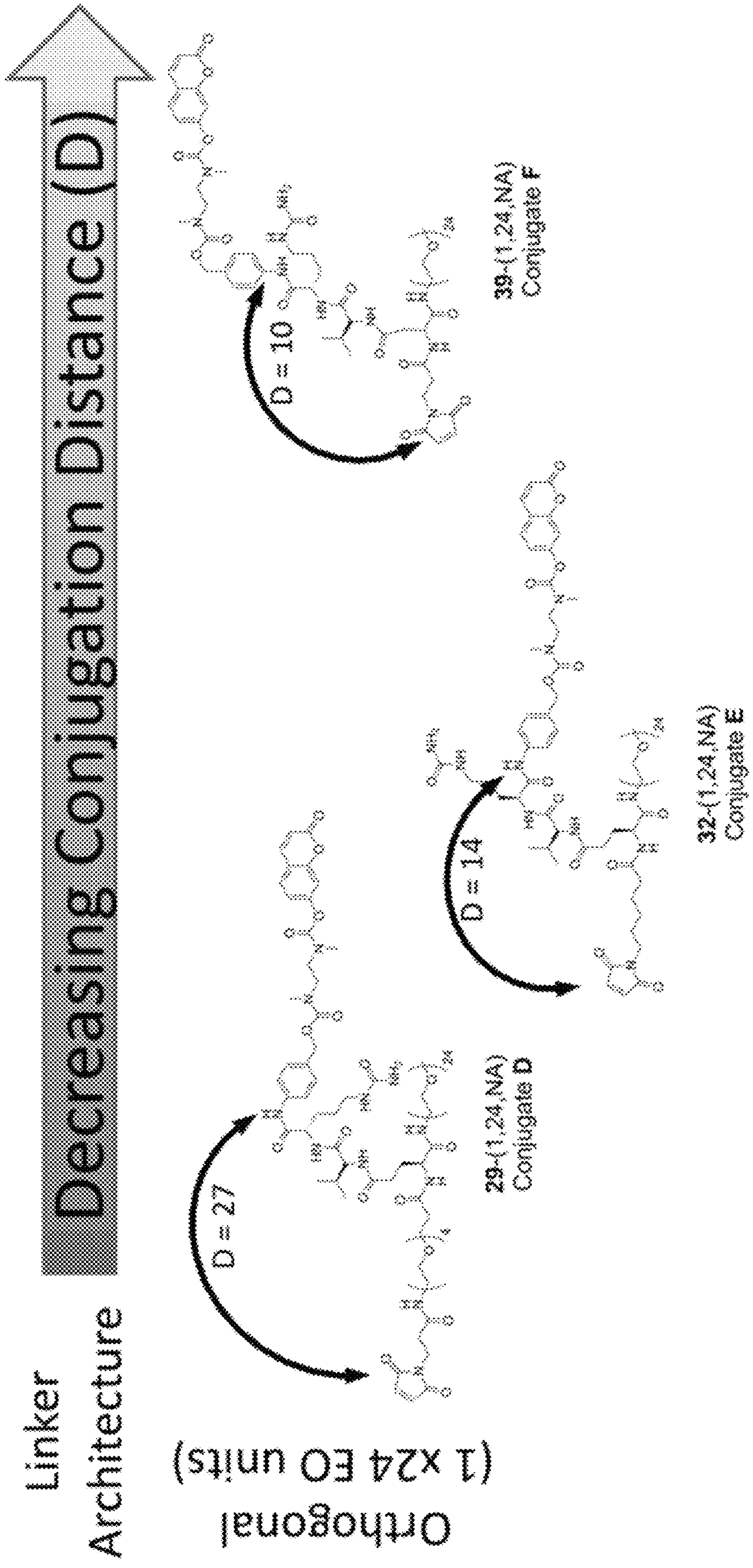

The conjugates of FIG. 16 explore the effects of steric shielding from the antibody on payload release for linear and y=1 orthogonal linker architectures disclosed in the prior art. The conjugates of FIG. 17 explore the effects of steric shielding from the antibody on payload release for linker architectures where y=1 or 3, D'=6 or 10, and the dPEG has 24 EO units. The conjugates of FIG. 18 explore the effects of steric shielding from the antibody on payload release for linker architectures where y=3, D'=6 or 10, and the dPEG has 72 EO units. The linear series of conjugates was evaluated at antibody-trigger distances (D) of 116 Å, 30 Å, and 20 Å. The 1×24 dPEG, 3×8 dPEG, and 3×24 dPEG series of conjugates were evaluated at antibody-trigger distances (D) of 40 Å (27 atoms), 25 Å (14 atoms), and 20 Å (10 atoms).

Results:

While shortening distances (116 Å, 30 Å, or 20 Å) between a 150 kDa antibody and the cleavable trigger did not affect payload release for linear conjugates A, B, and C, orthogonal positioning of a relatively small (2 kDa) dPEG with 24 EO units in a single dPEG chain (x=24, n=1) was found to reduce payload release by cathepsin B and cathepsin K. Despite the fact the distance to the large 150 kDa antibody was increased from 20 Å (10 atoms) to 40 Å (14 atoms) the addition of a relatively small 2 kDa dPEG in an orthogonal was able to attenuate payload release rates (e.g., see conjugate C and D). It was also surprising to see that changing the 2 kDa dPEG to maintain the same number of 24 EO units, but distributed among three smaller chains (x=8, n=3) provided additional attenuation of the other endopeptidases cathepsin L and cathepsin S (e.g., see conjugate D and 0.1).

As shown by the data in FIGS. 19-21 and FIGS. 22A-22B, cathepsin-mediated payload release within each series of conjugates is reduced as the antibody-trigger distance D decreases from 40 Å (27 atoms) to 25 Å (14 atoms) to 20 Å (10 atoms). Moreover, and consistent with the findings outlined in Example 3, percent payload release is attenuated in both the 3×8 (FIG. 20) and 3×24 (FIG. 21) series when D'=6. In the present study, optimal results were achieved with conjugate R (D'=6, 3×24 dPEG).

Thus, in summary, it can be concluded that there is generally a global reduction in cathepsin-mediated payload release for y=3 conjugates having smaller D' and increasing x.

Ratios of payload release at decreasing IgG-payload distances (D) were calculated for each linker architecture by comparing the percent payload release for a given conjugate to the percent payload release for the conjugate in the same series having the longest D value. As shown in FIG. 22B, the linear linkers of the prior art have the same cathepsin-mediated payload release regardless of shielding from the antibody due to decreasing D. This translated to payload release ratios of ~1.0 for all distances, which highlights the lack of steric shielding by the antibody. In contrast, while y=3 architectures of FIGS. 17-18 result in an overall reduction in payload release, the smaller ratios show the reduction is greater at small antibody-trigger distances (i.e., 10 atoms) relative to larger distances (i.e., 27 atoms).

Figure 22A:
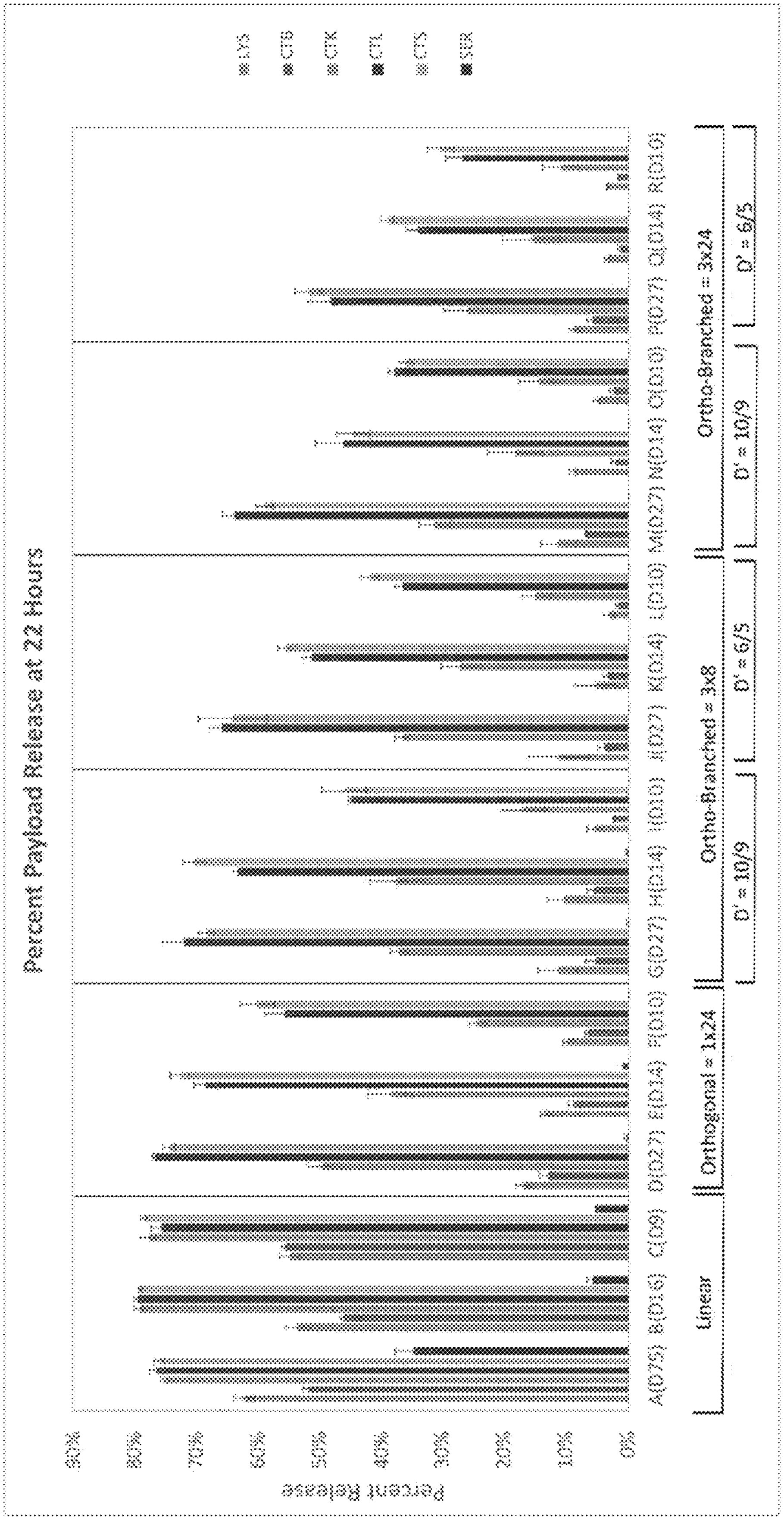
FIG. 22A shows a graph comparing percent payload release from the linear, y=1, and y=3 conjugates of FIGS. 16-18 as antibody-payload distance decreases.
Figure 22B:
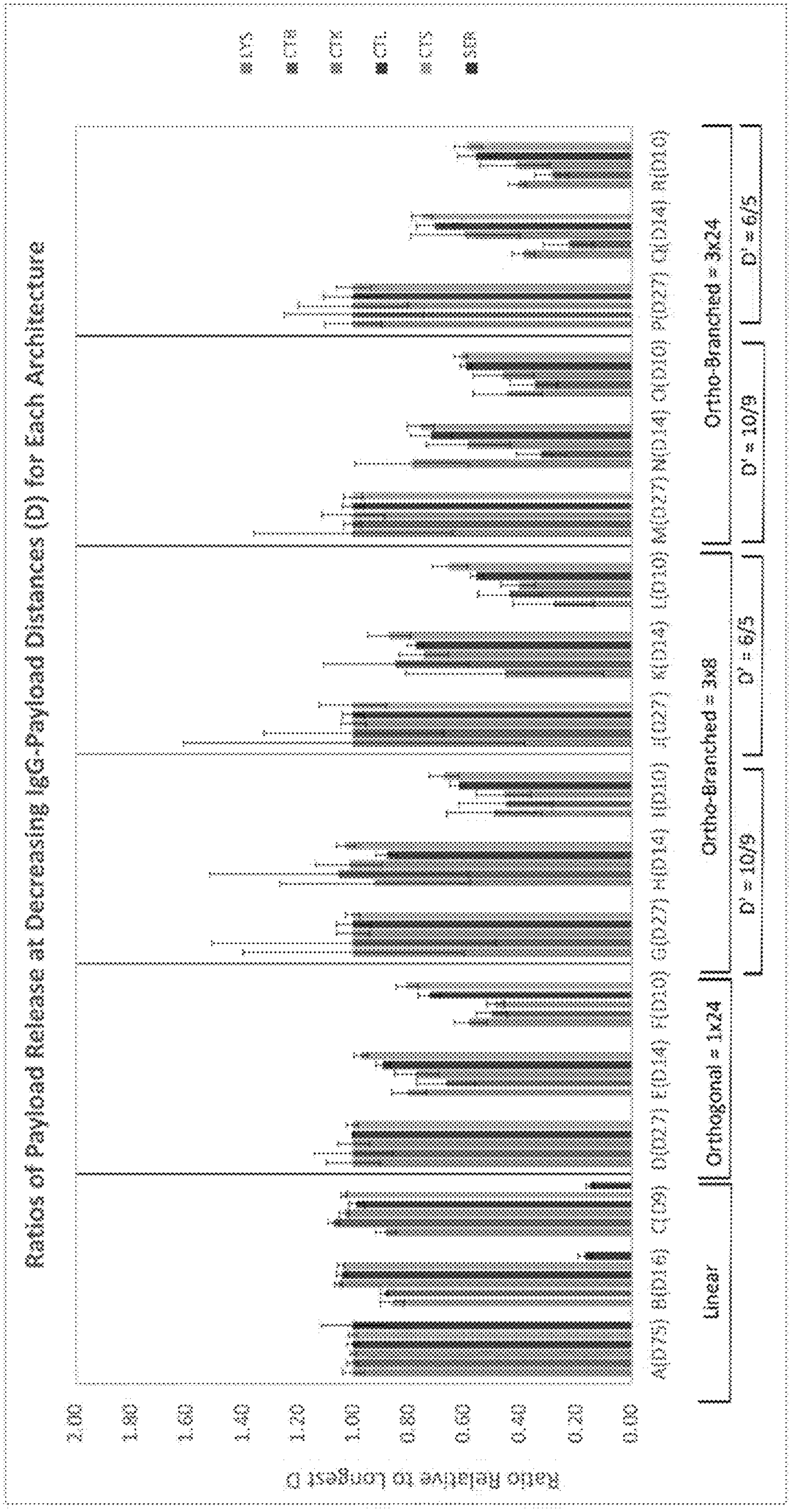
FIG. 22B shows a graph comparing ratios of payload release from the linear, y=1, and y=3 conjugates of FIGS. 16-18 as antibody-payload distance decreases.

To further evaluate the selectivity of payload release from each of the conjugates, the results summarized in FIGS. 22A-22B were isolated for serum, lysosomes and each of the cathepsins.

Figure 23A:
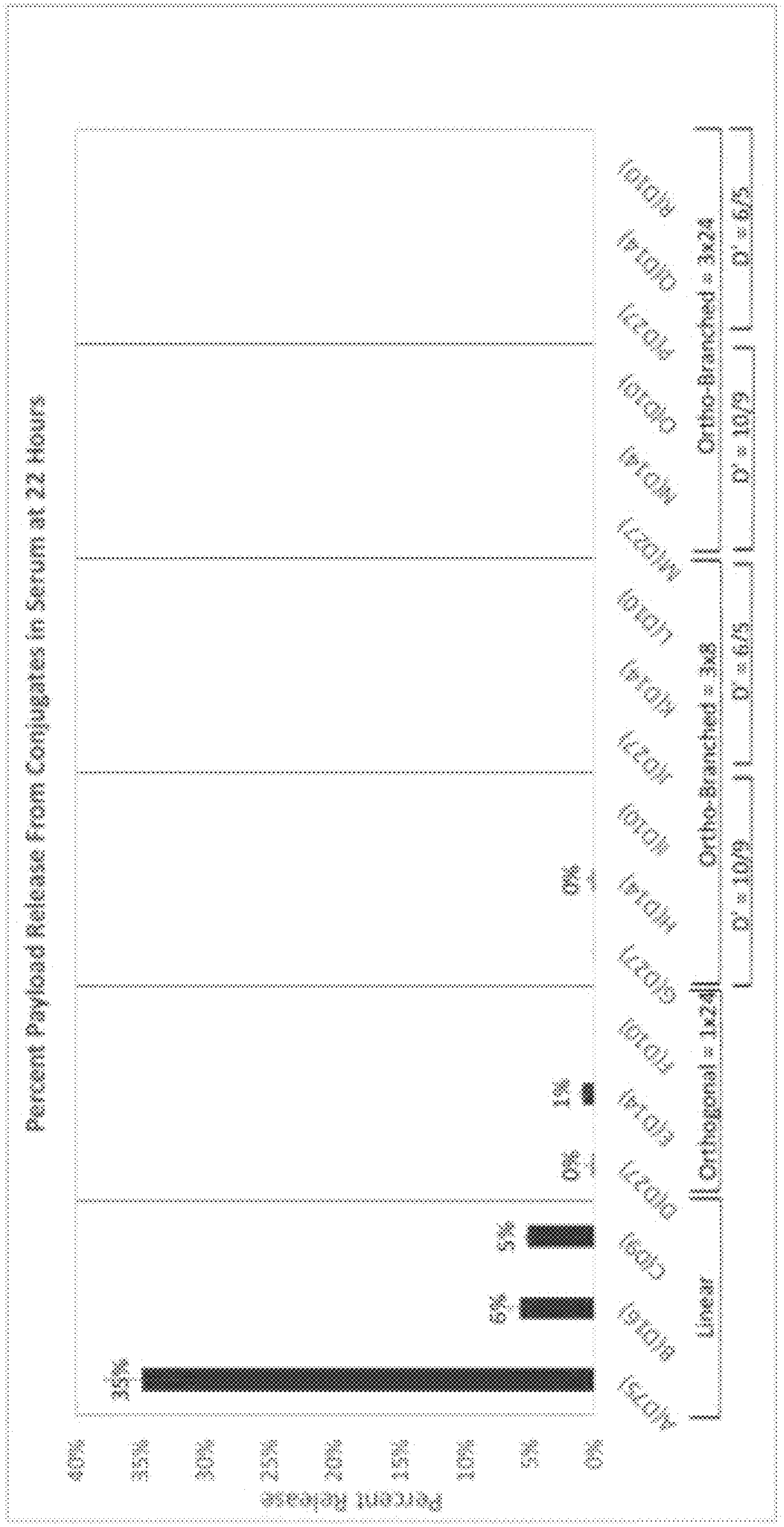
FIG. 23A shows a graph comparing percent payload release in serum from the linear, y=1, and y=3 conjugates of FIGS. 16-18 as antibody-payload distance decreases.
Figure 23B:
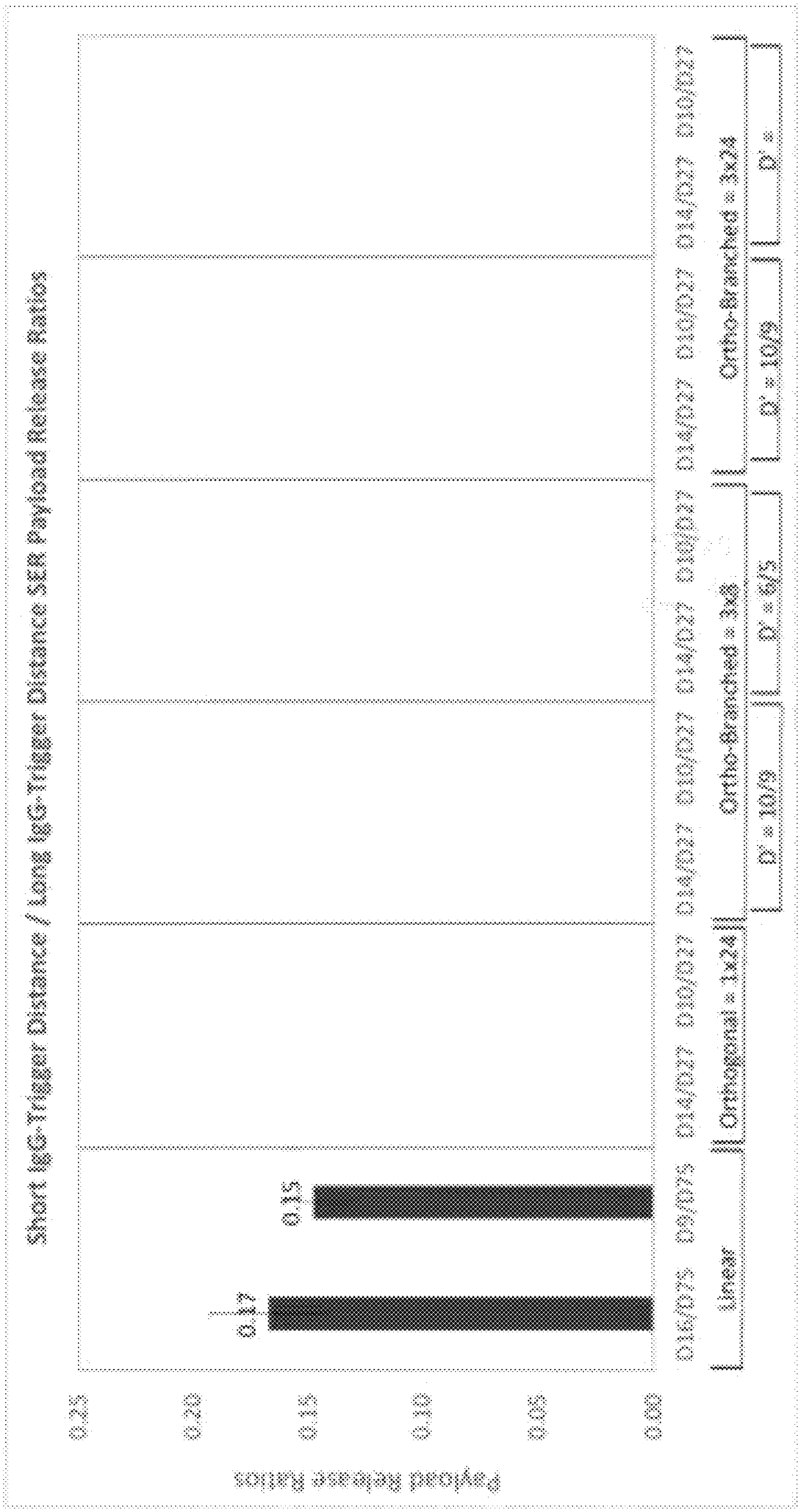
FIG. 23B shows a graph comparing ratios of payload release in serum from the linear, y=1, and y=3 conjugates of FIGS. 16-18 as antibody-payload distance decreases.

As shown in FIGS. 23A-23B, all orthogonal architectures (both y=1 and y=3) completely eliminate CES1c-mediated release in mouse serum. Payload release is influenced by antibody-payload distance with linear linkers. CES1c, in these cases, is very sensitive to steric hindrance.

Figure 24A:
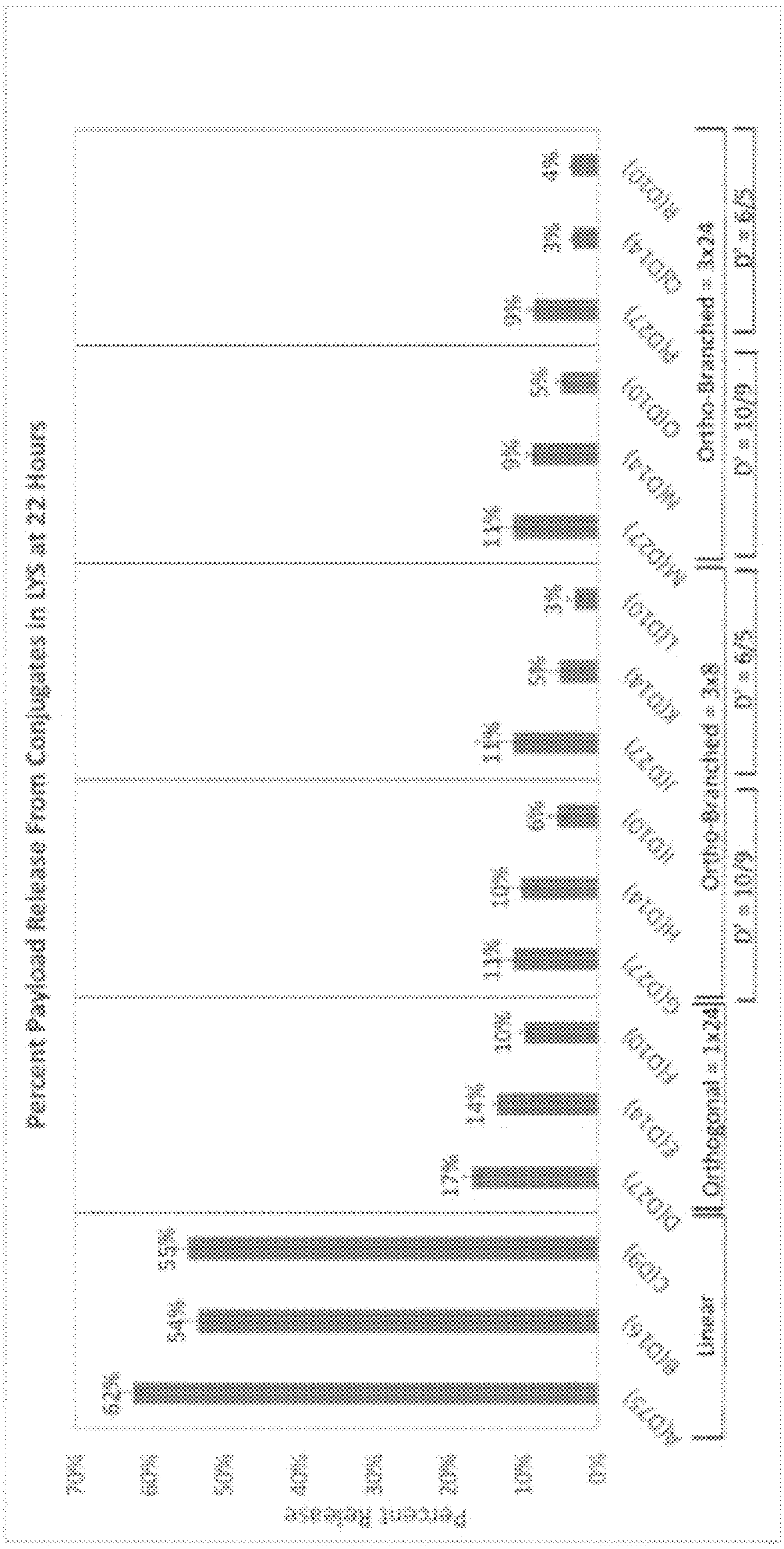
FIG. 24A shows a graph comparing percent payload release from the linear, y=1, and y=3 conjugates of FIGS. 16-18 subjected to lysosomes as antibody-payload distance.
Figure 24B:
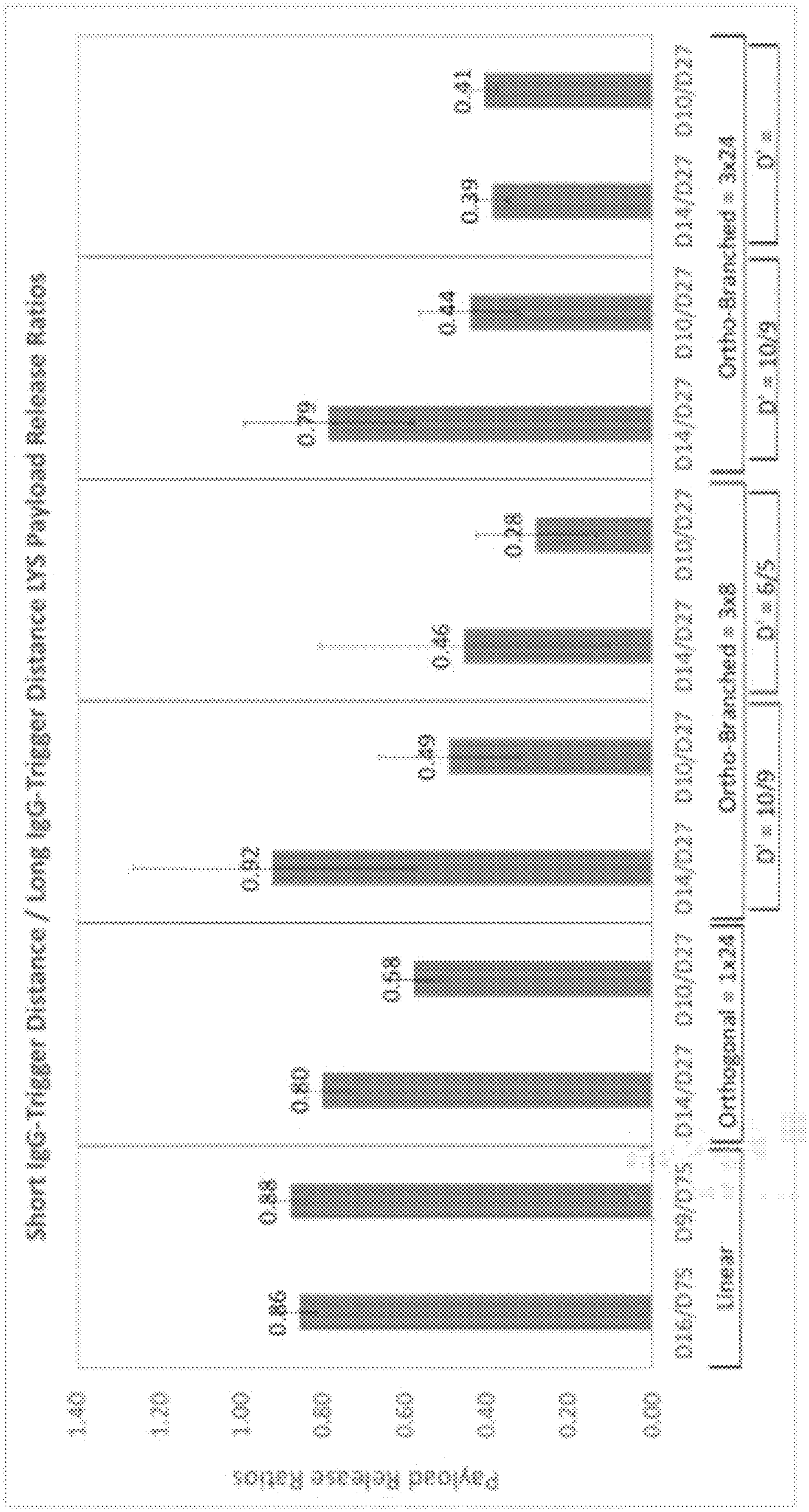
FIG. 24B shows a graph comparing ratios of payload release from the linear, y=1, and y=3 conjugates of FIGS. 16-18 subjected to lysosomes as antibody-payload distance decreases.

FIGS. 24A-24B show payload release and ratios of payload release in lysosomes, respectively. There is a broad array of enzymes present in lysosomal preparation, but release is primarily driven by CTB. According to the data, all orthogonal architectures (y=1 and y=3) show reductions in release, but still release payload in lysosomes. The smaller ratios for y=3 architectures highlight the greater impact of steric shielding from the antibody with these linkers.

Figure 25A:
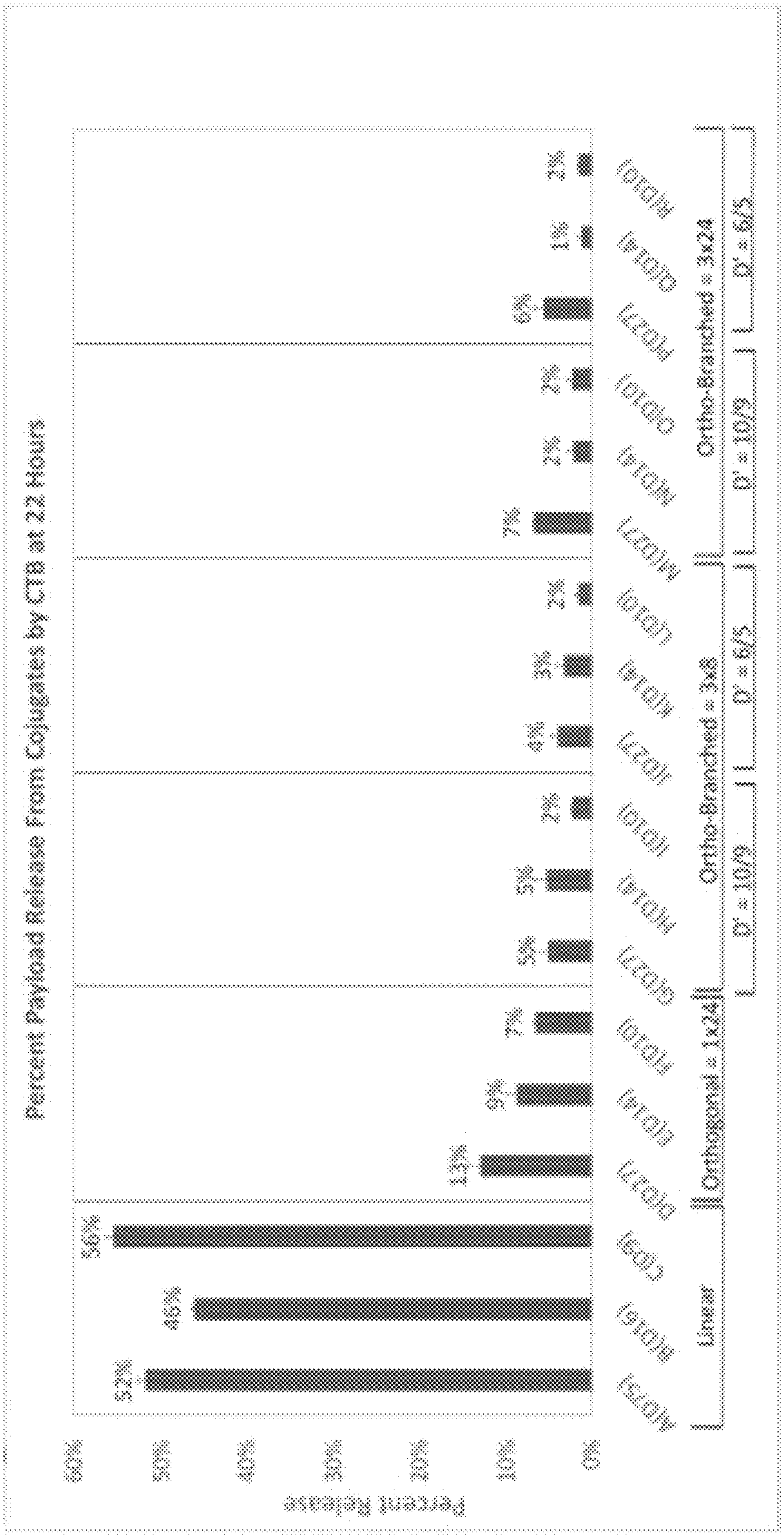
FIG. 25A shows a graph comparing percent payload release from the linear, y=1, and y=3 conjugates of FIGS. 16-18 subjected to CTB as antibody-payload distance decreases.
Figure 25B:
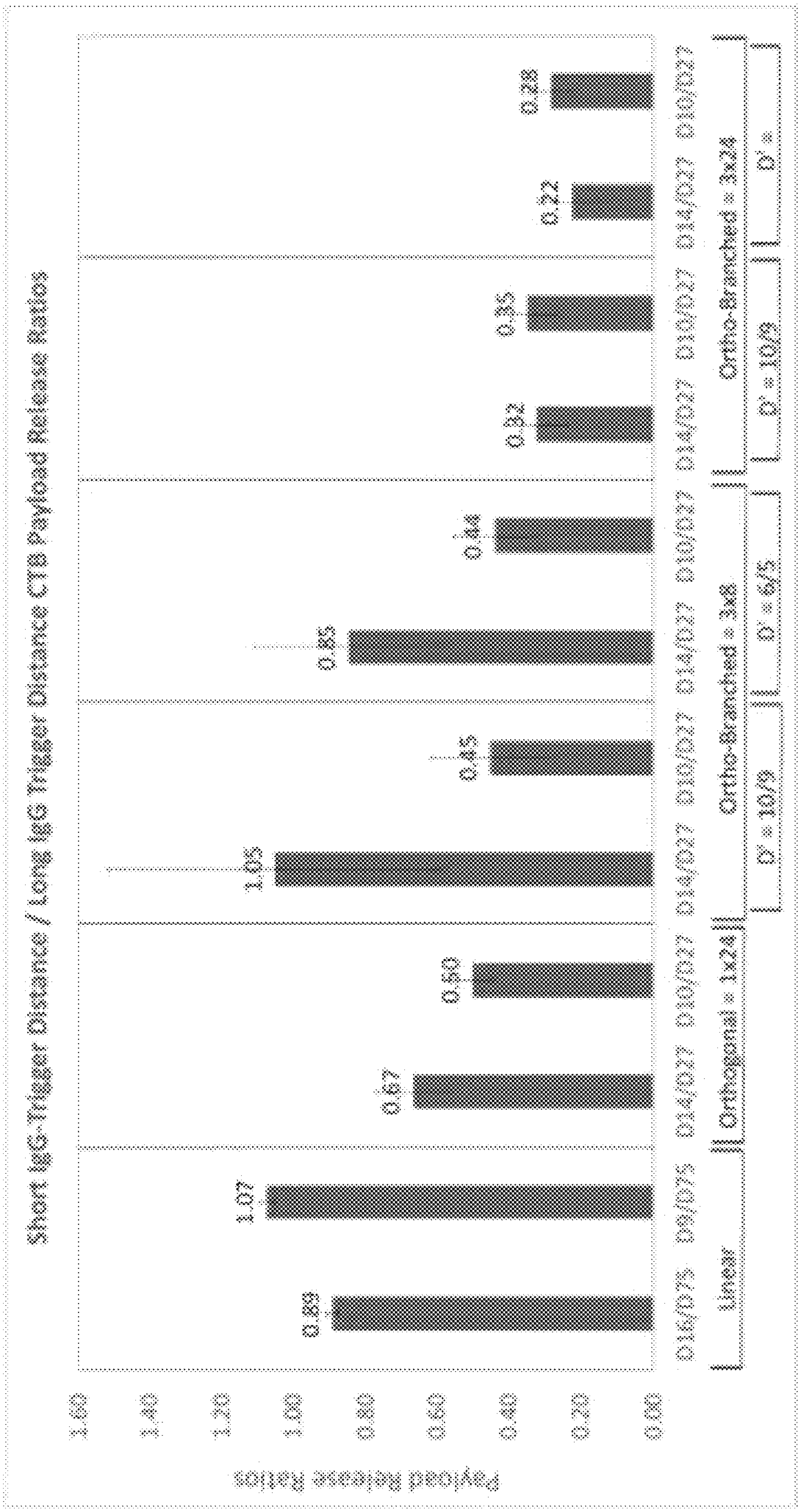
FIG. 25B shows a graph comparing ratios of payload release from the linear, y=1, and y=3 conjugates of FIGS. 16-18 subjected to CTB as antibody-payload distance decreases.

FIGS. 25A-25B show payload release and ratios of payload release by CTB, which is an exopeptidase at pH 5 of the study. According to the data, all orthogonal architectures (y=1 and y=3) show reductions in release. The smaller ratios for y=3 architectures highlight the greater impact of steric shielding from the antibody.

Figure 26A:
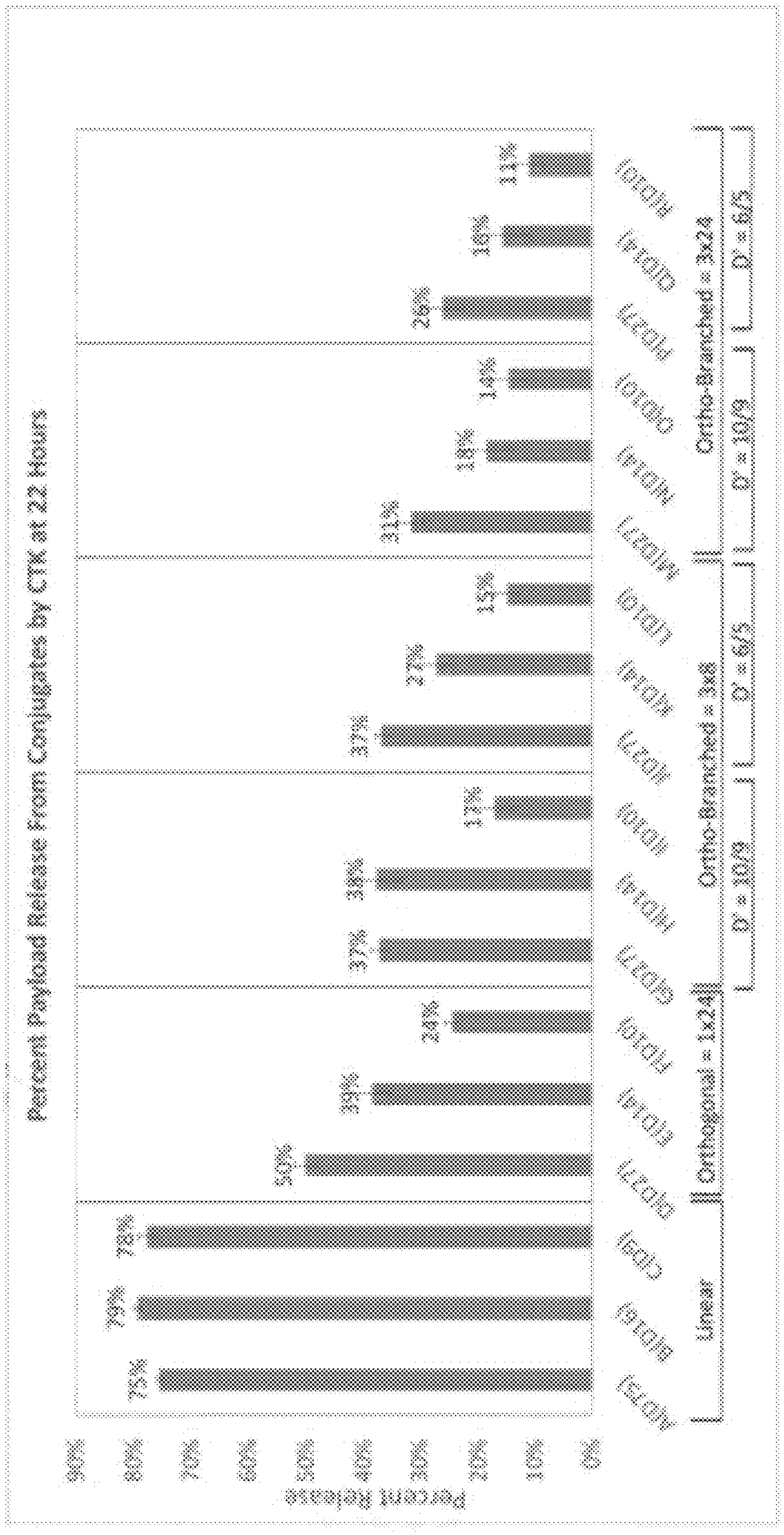
FIG. 26A shows a graph comparing percent payload release from the linear, y=1, and y=3 conjugates of FIGS. 16-18 subjected to CTK as antibody-payload distance decreases.
Figure 26B:
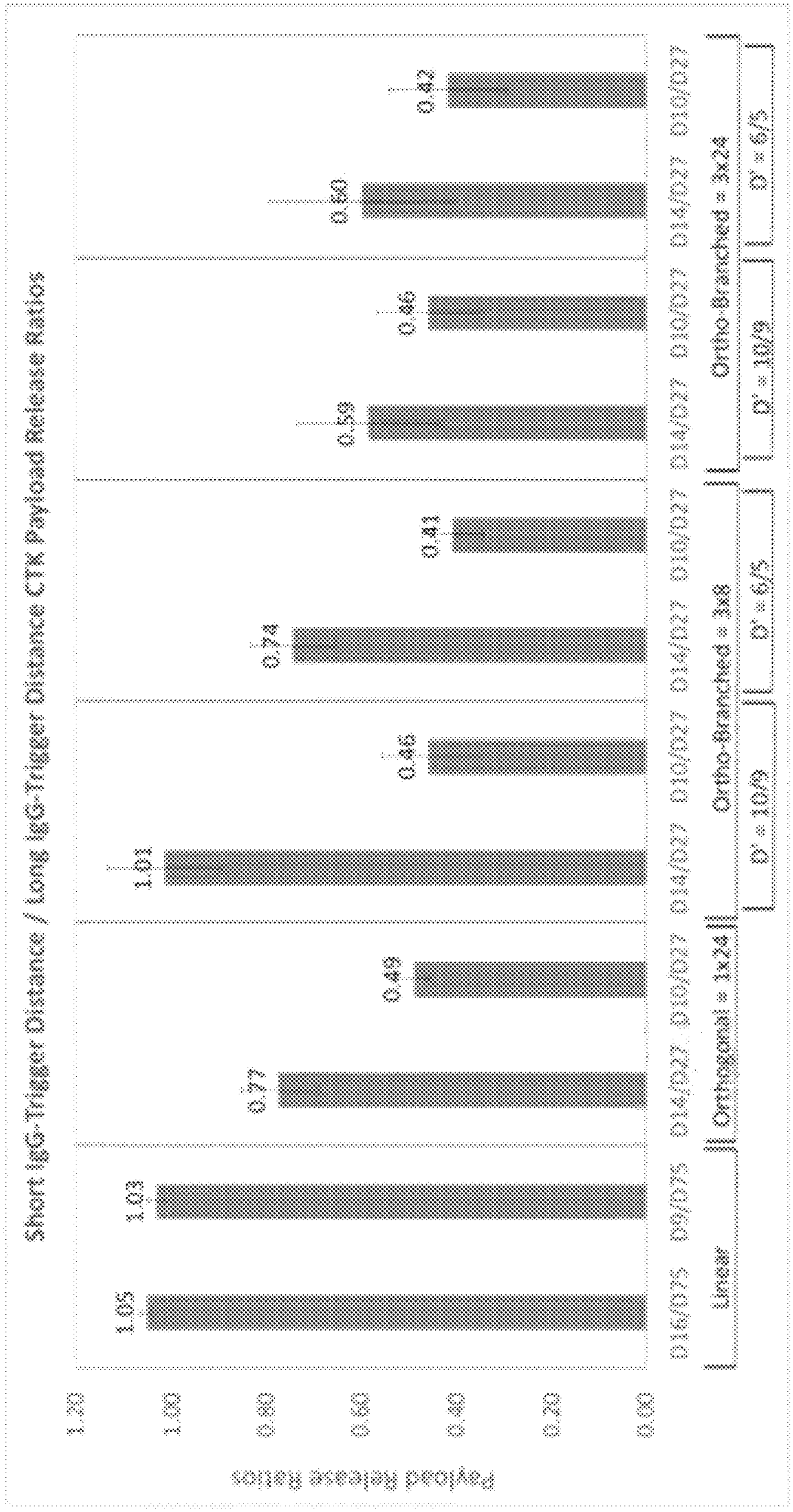
FIG. 26B shows a graph comparing ratios of payload release from the linear, y=1, and y=3 conjugates of FIGS. 16-18 subjected to CTK as antibody-payload distance decreases.

FIGS. 26A-26B show payload release and ratios of payload release by CTK, which is an endopeptidase that is generally tolerant of extended substrates. According to the data, all orthogonal architectures (y=1 and y=3) show reductions in release. The orthogonal architectures show similar ratios of payload release for all y, D', and x.

Figure 27A:
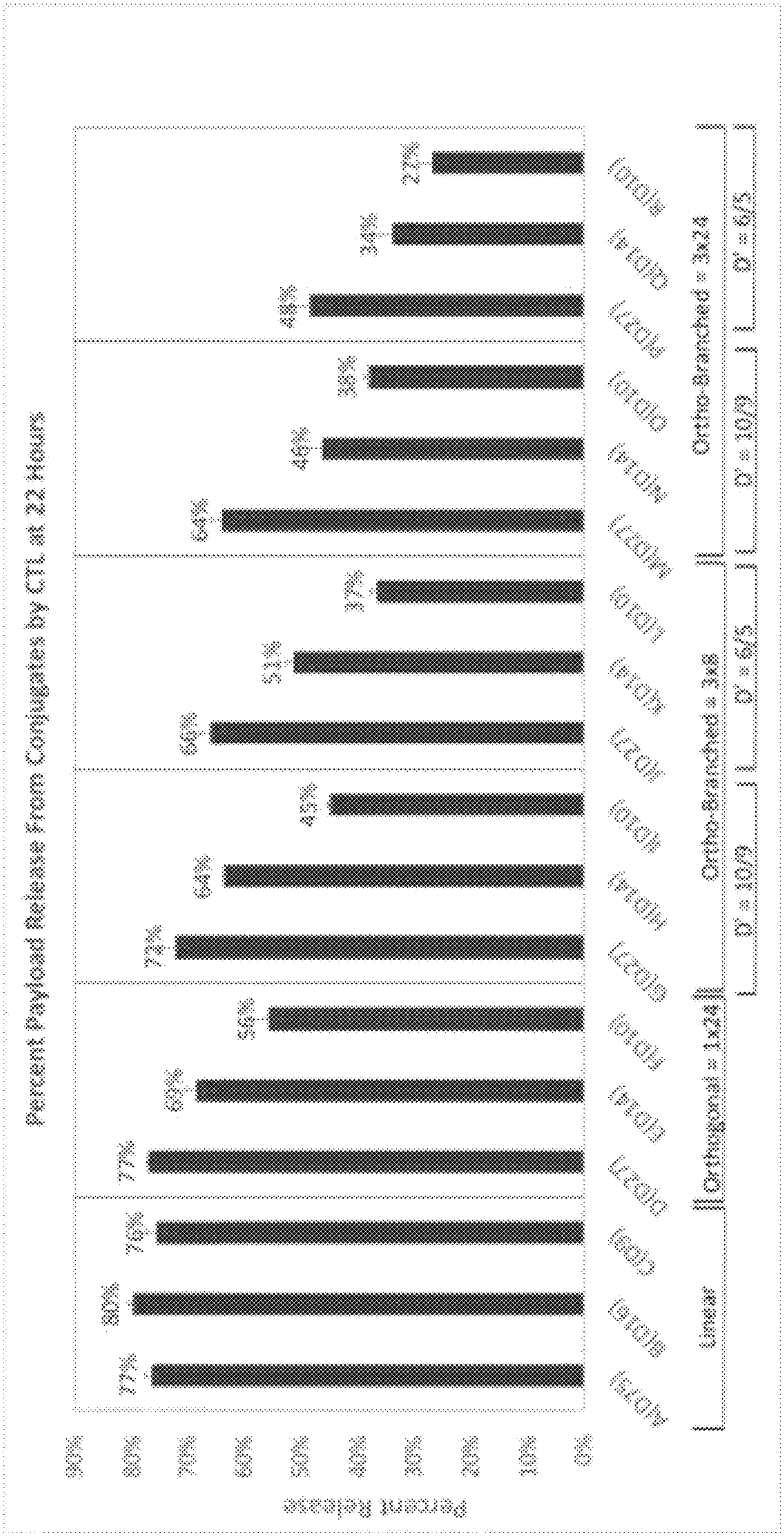
FIG. 27A shows a graph comparing percent payload release from the linear, y=1, and y=3 conjugates of FIGS. 16-18 subjected to CTL as antibody-payload distance decreases.
Figure 27B:
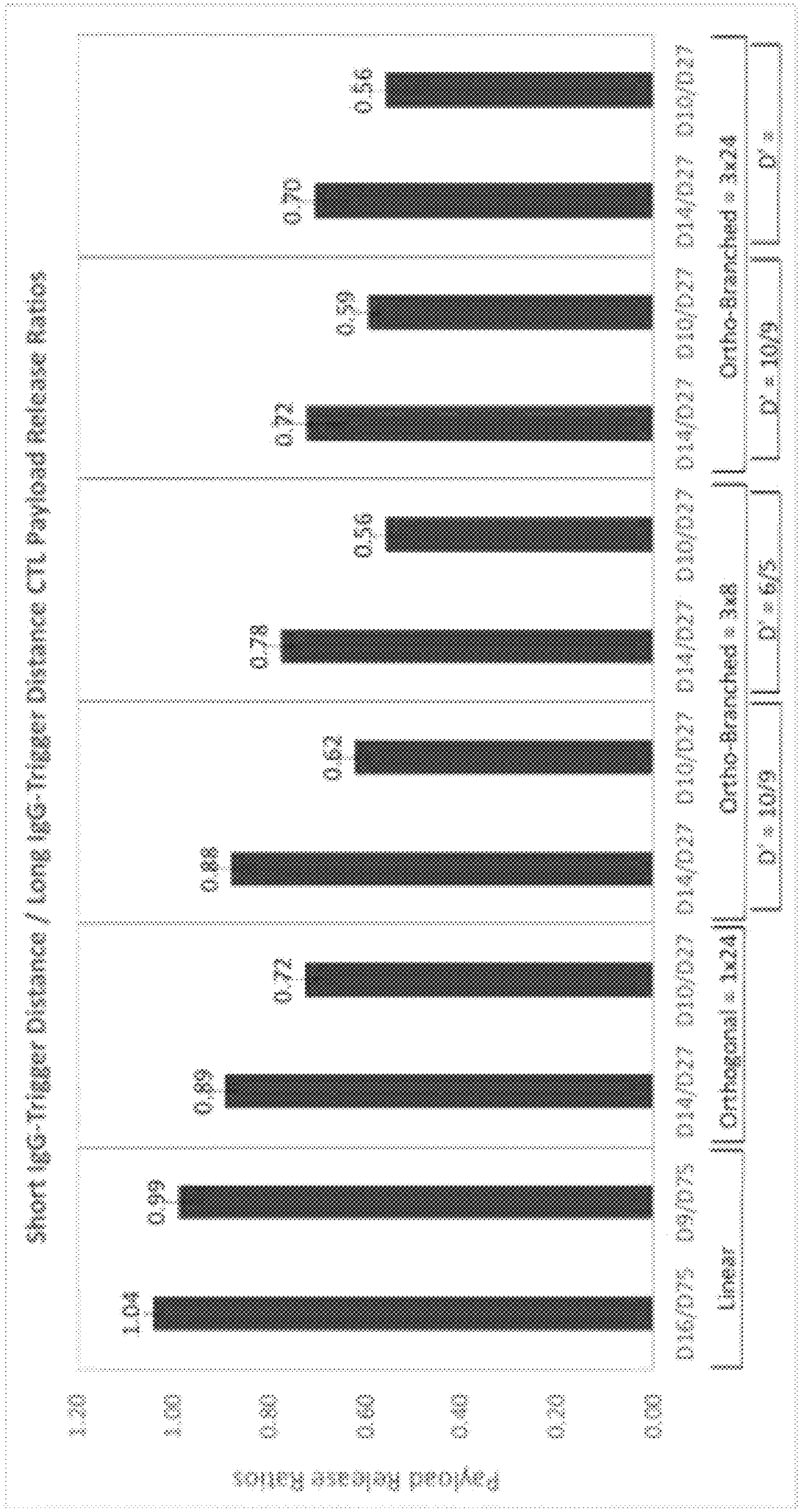
FIG. 27B shows a graph comparing ratios of payload release from the linear, y=1, and y=3 conjugates of FIGS. 16-18 subjected to CTL as antibody-payload distance decreases.

FIGS. 27A-27B show payload release and ratios of payload release by CTL, which is an endopeptidase that is generally less affected by steric hindrance. According to the data, orthogonal architectures (y=1 and y=3) show reductions in release, however the change is not as significant since this is an endopeptidase. The smaller ratios for y=3 architectures highlight the greater impact of steric shielding from antibody when these linkers are used to prepare conjugates.

Figure 28A:
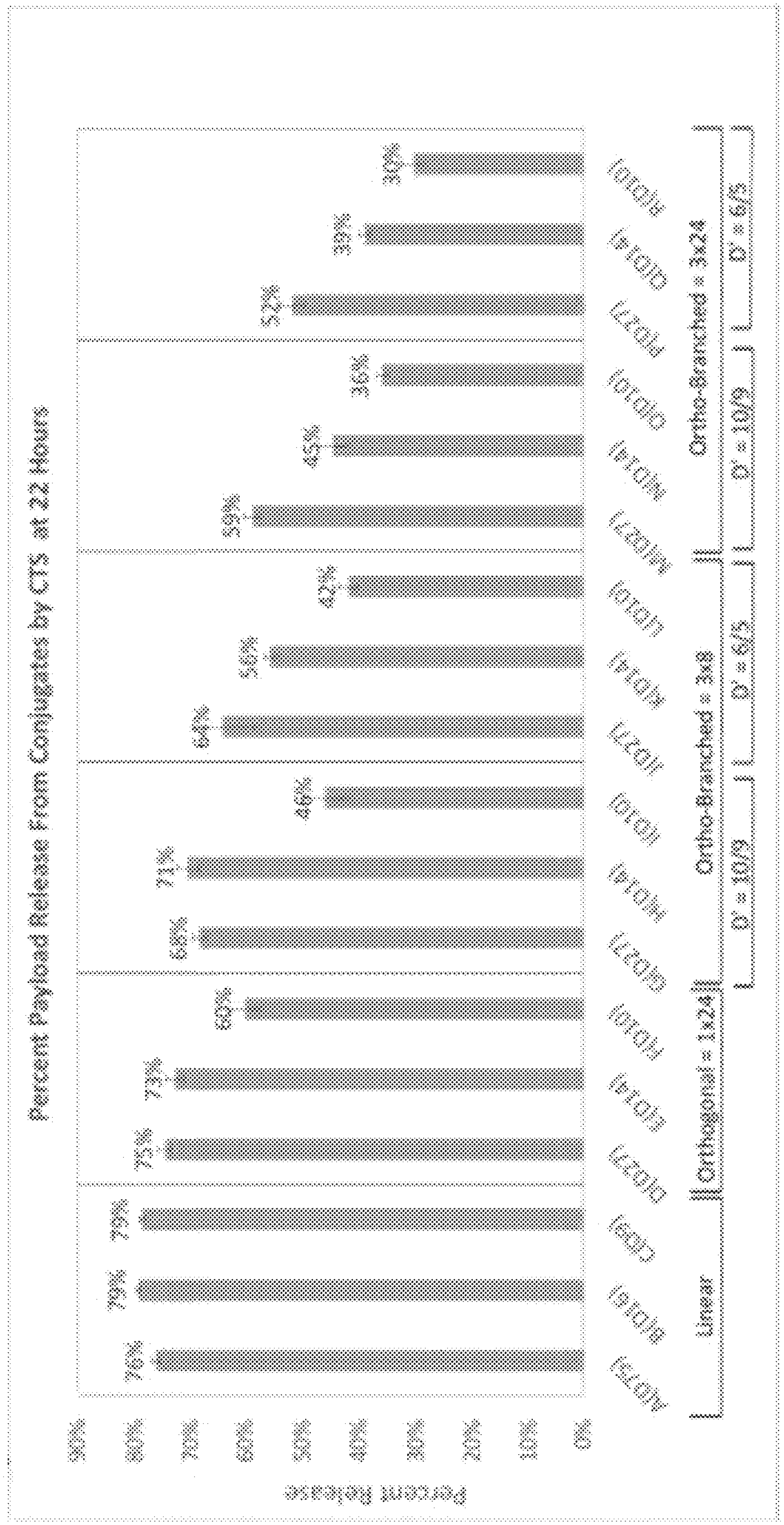
FIG. 28A shows a graph comparing percent payload release from the linear, y=1, and y=3 conjugates of FIGS. 16-18 subjected to CTS as antibody-payload distance decreases.
Figure 28B:
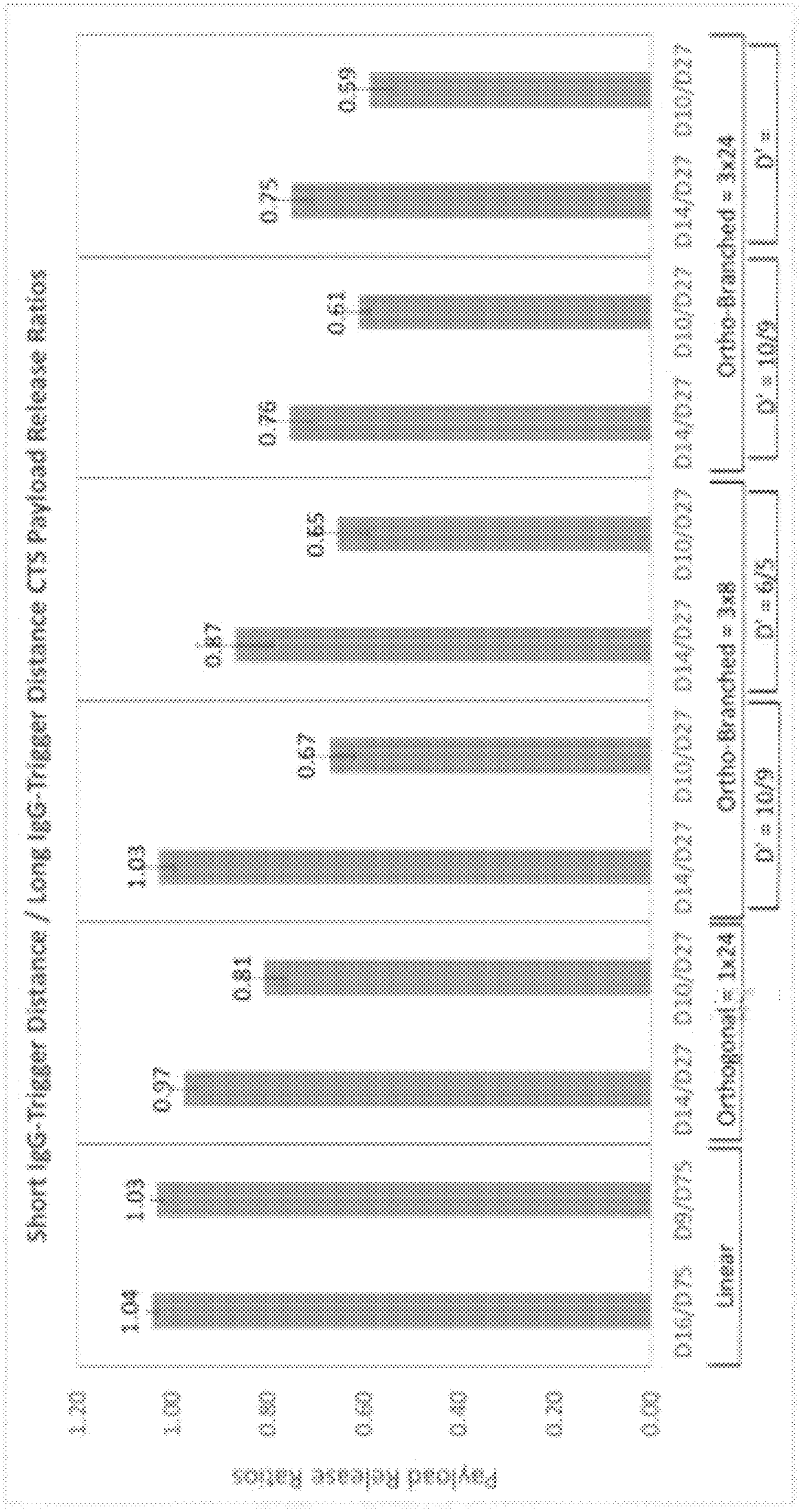
FIG. 28B shows a graph comparing ratios of payload release from the linear, y=1, and y=3 conjugates of FIGS. 16-18 subjected to CTS as antibody-payload distance decreases.

FIGS. 28A-28B show payload release and ratios of payload release by CTS, which is an endopeptidase. According to the data, orthogonal architectures (y=1 and y=3) show reductions in release, however the change is not as significant since this is an endopeptidase. The smaller ratios for y=3 architectures highlight the greater impact of steric shielding from antibody when these linkers are used to prepare conjugates.

Summary

Figure 17:
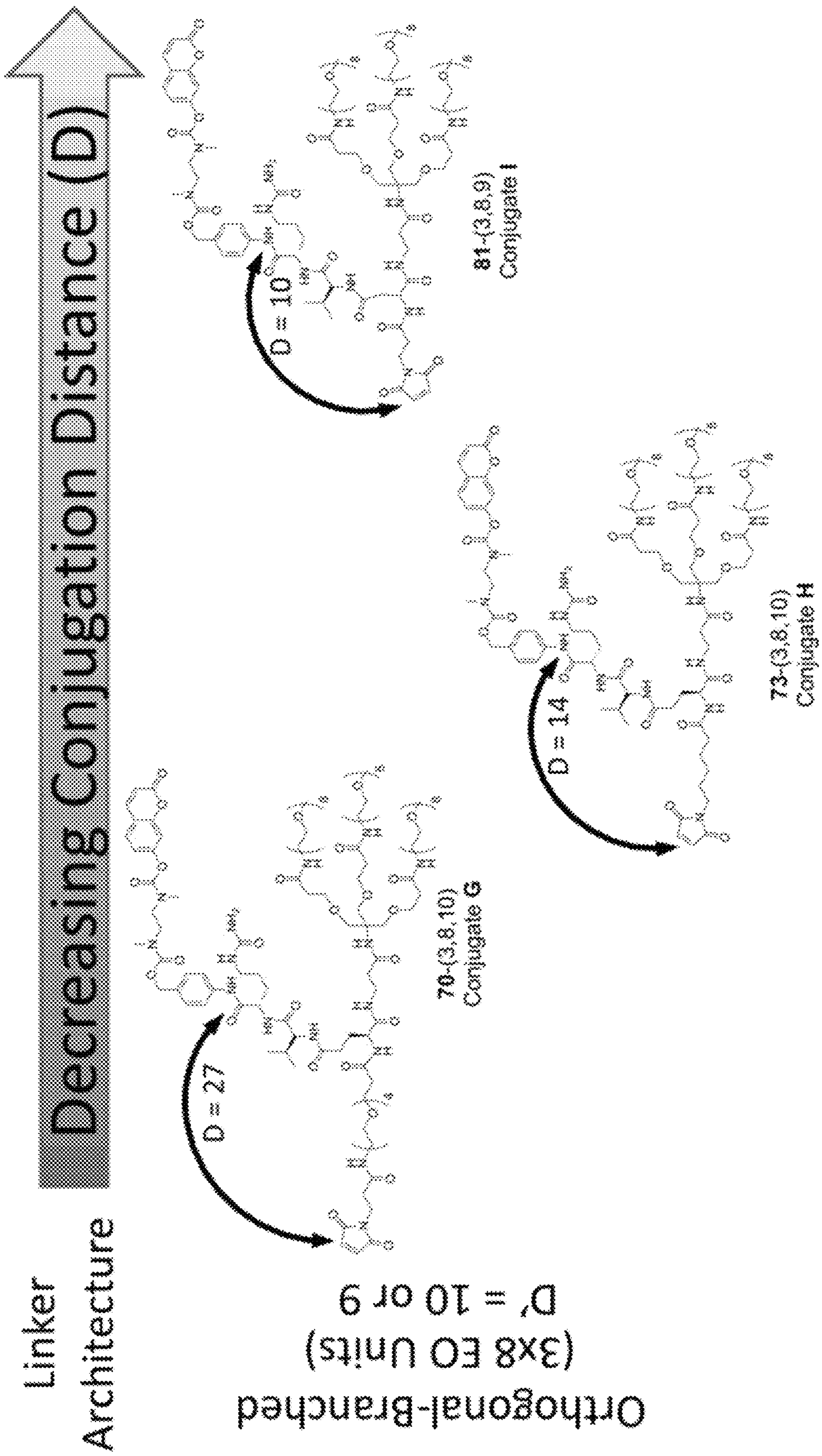
FIG. 17 shows examples of 3×8 conjugates of Formula (II) of the present disclosure having various distances between the payload and targeting vector (e.g., an antibody).
Figure 17:
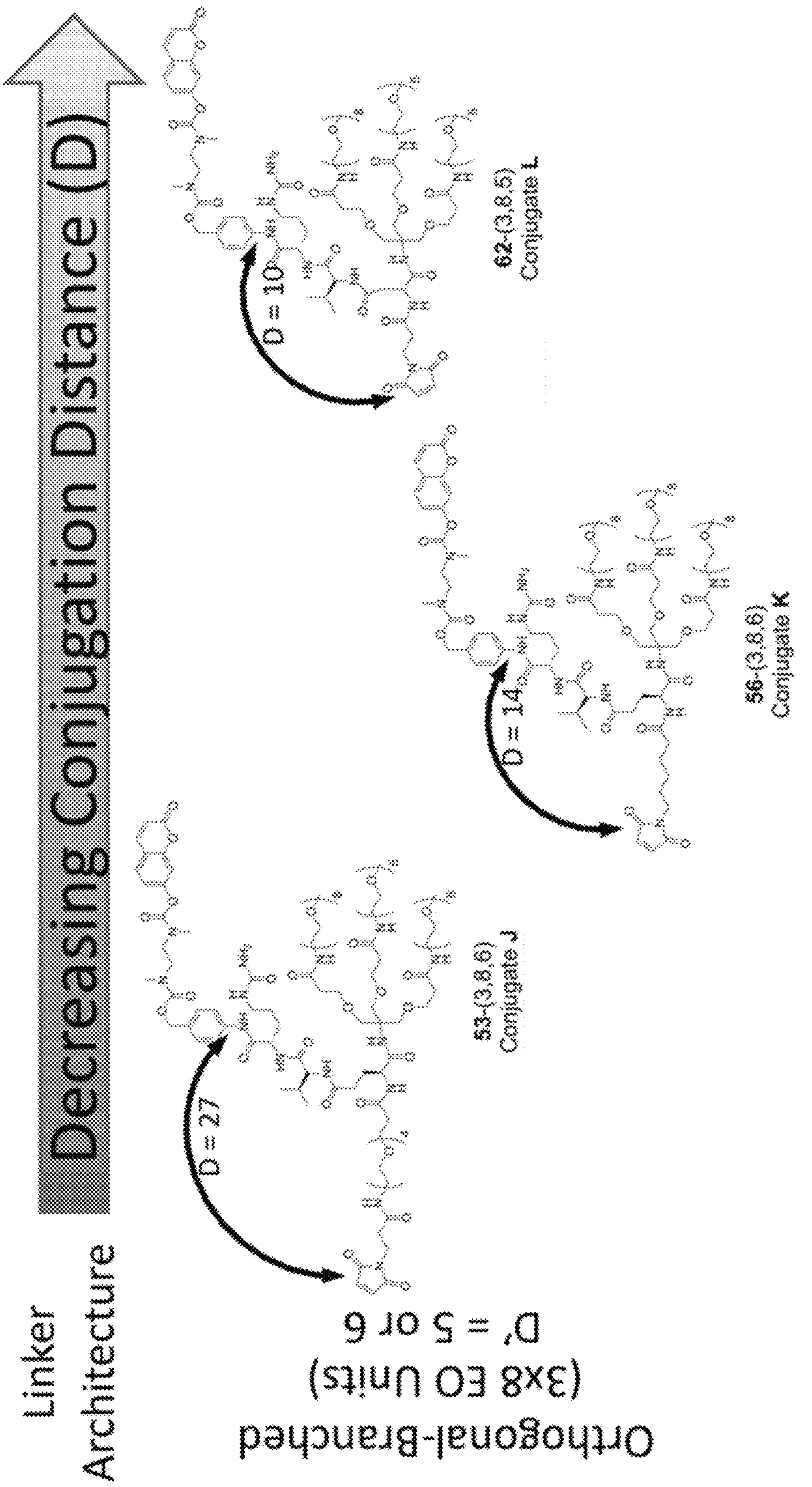
Figure 18:
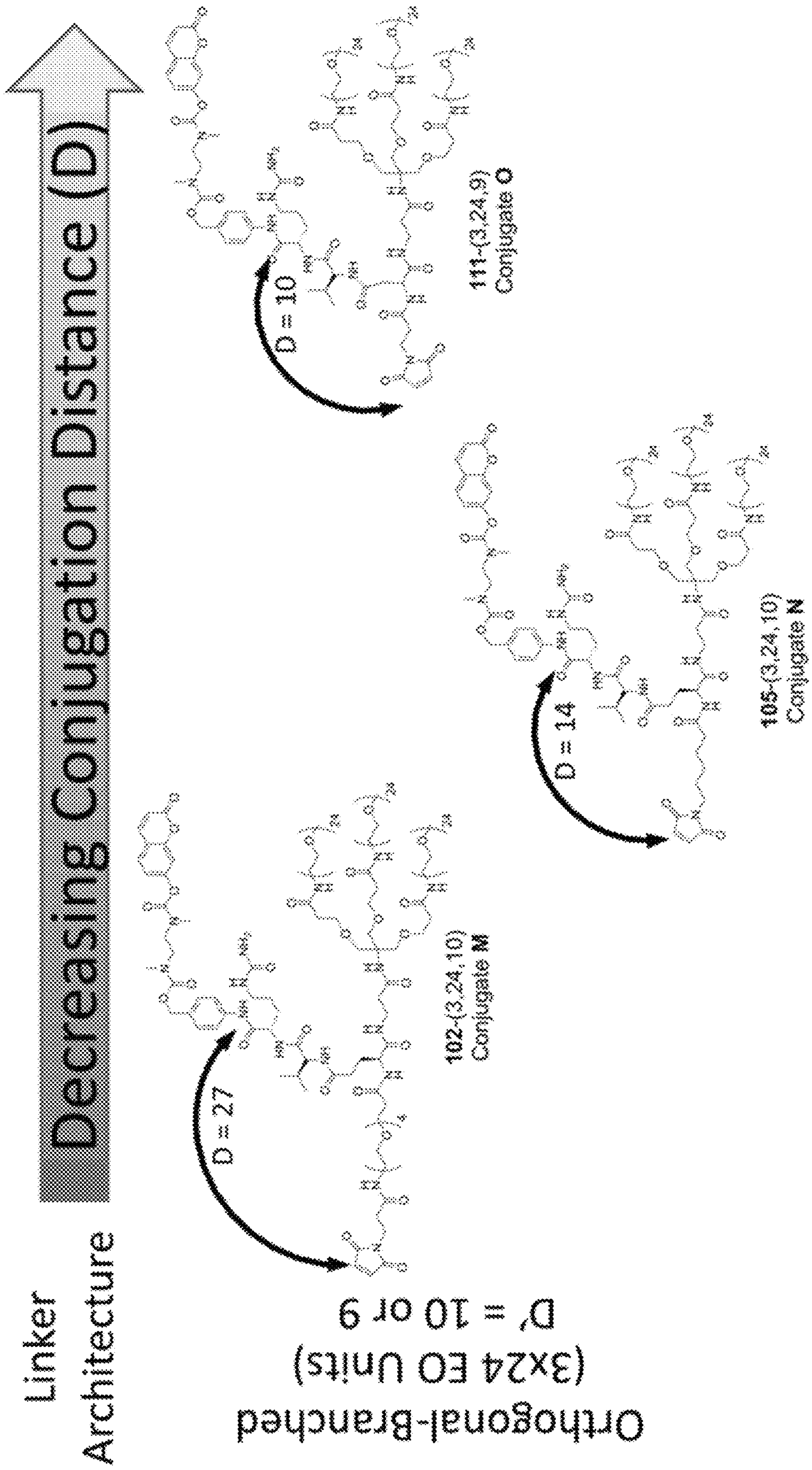
FIG. 18 shows examples of 3×24 conjugates of Formula (II) of the present disclosure having various distances between the payload and targeting vector (e.g., an antibody).
Figure 18:
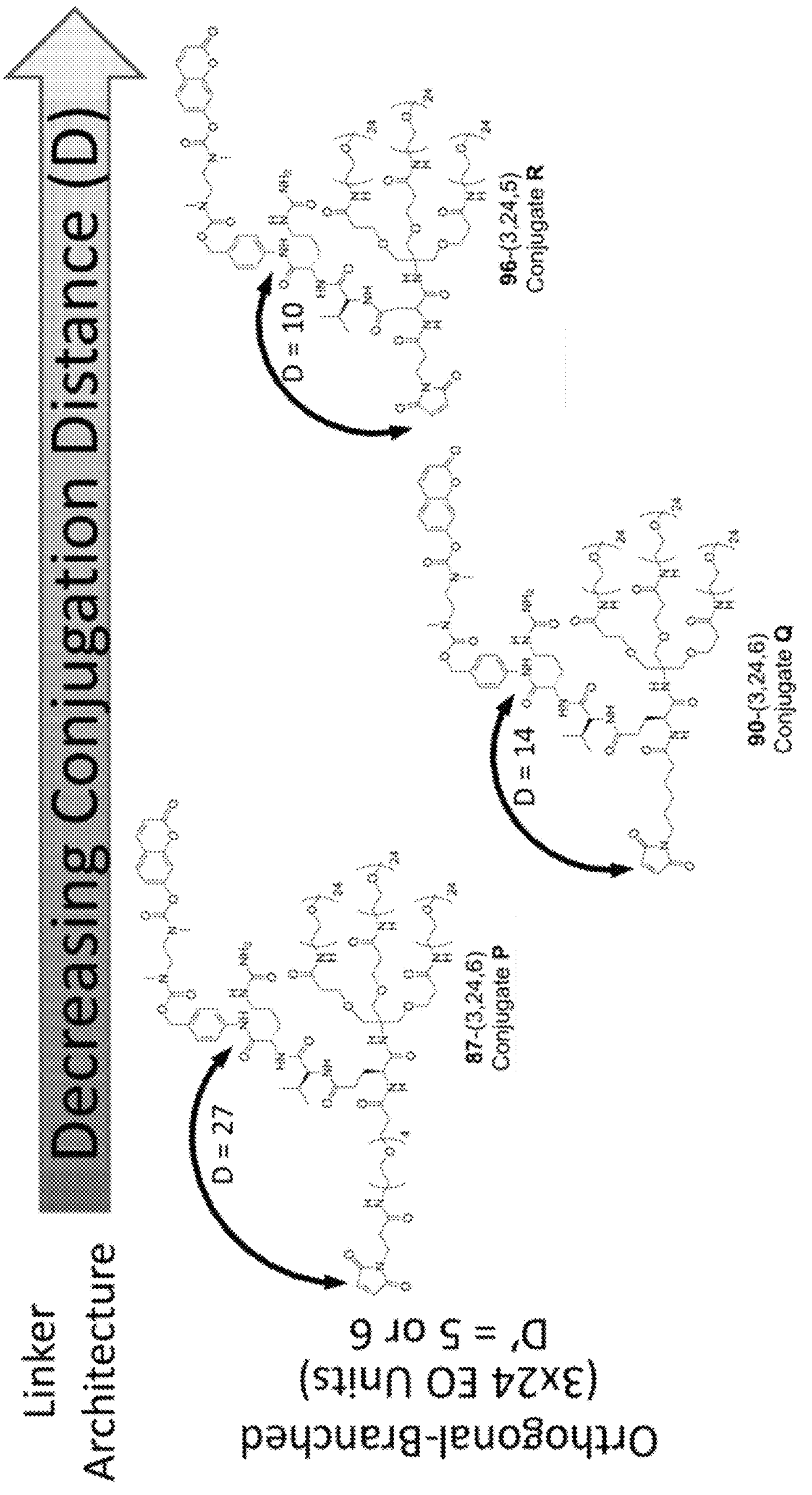
Figure 19:
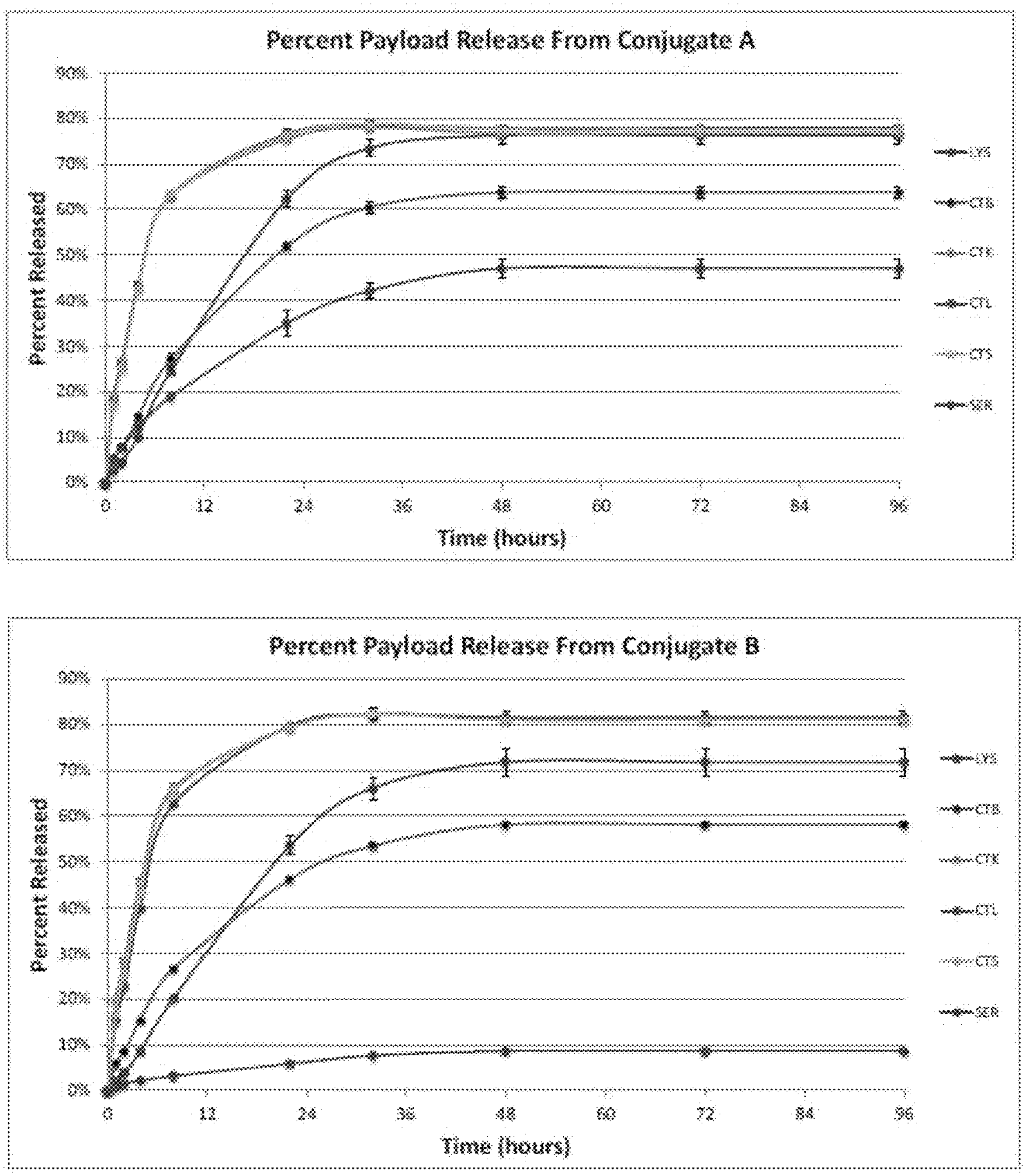
FIG. 19 shows the raw data for payload release from the linear and 1×24 conjugates of FIG. 16 as antibody-payload distance decreases.
Figure 19:
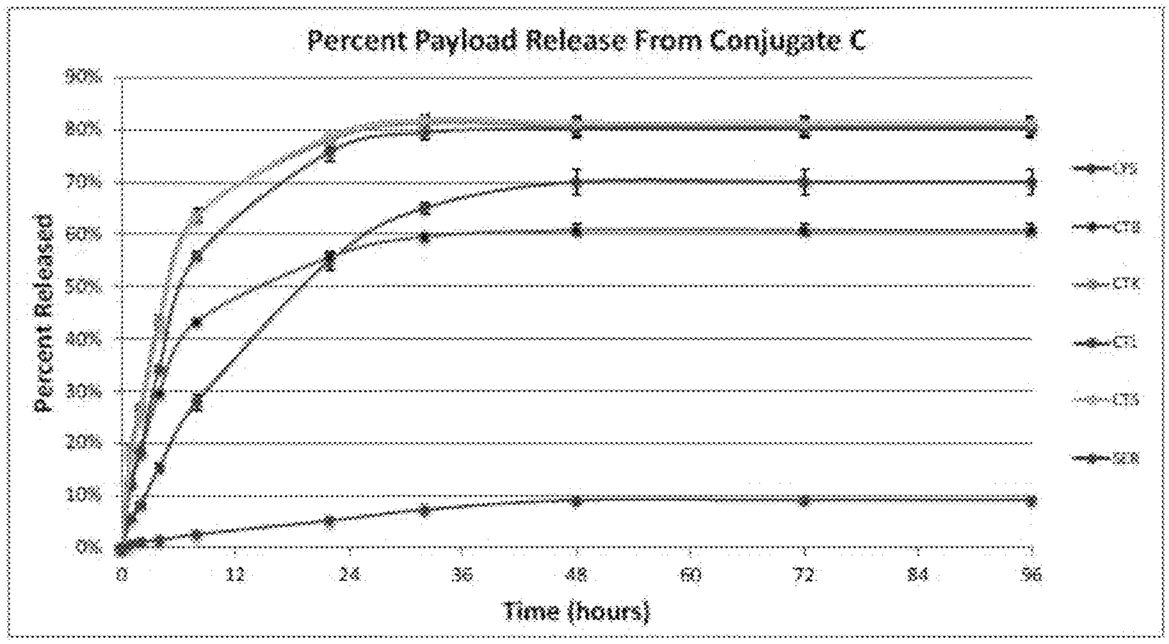
Figure 19:
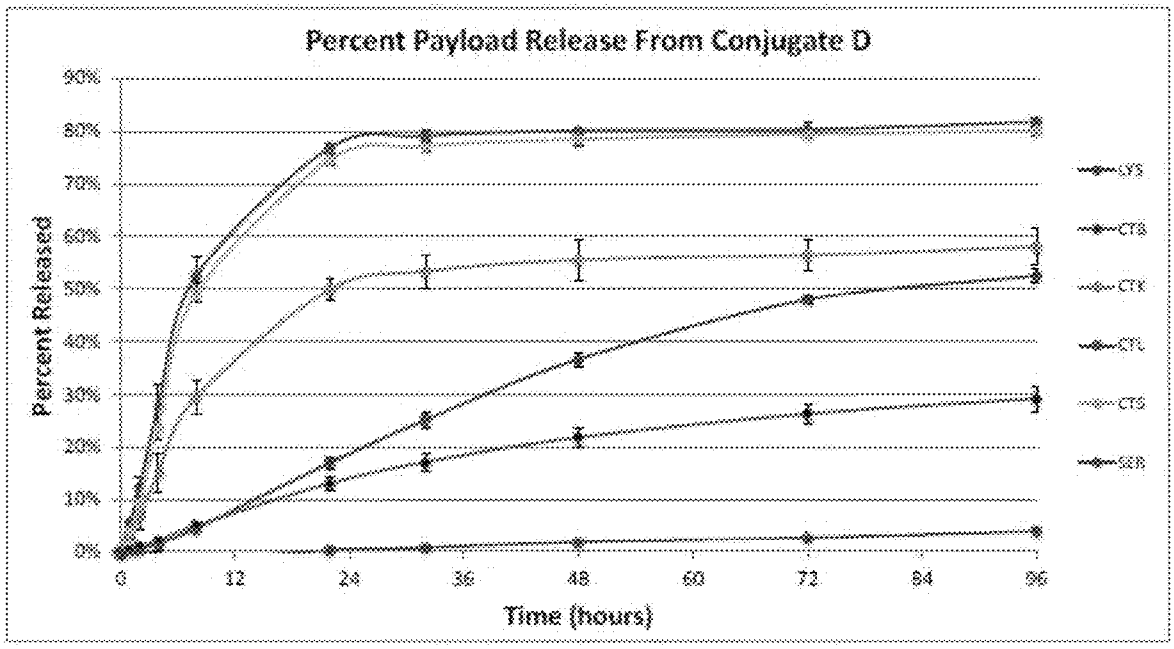
Figure 19:
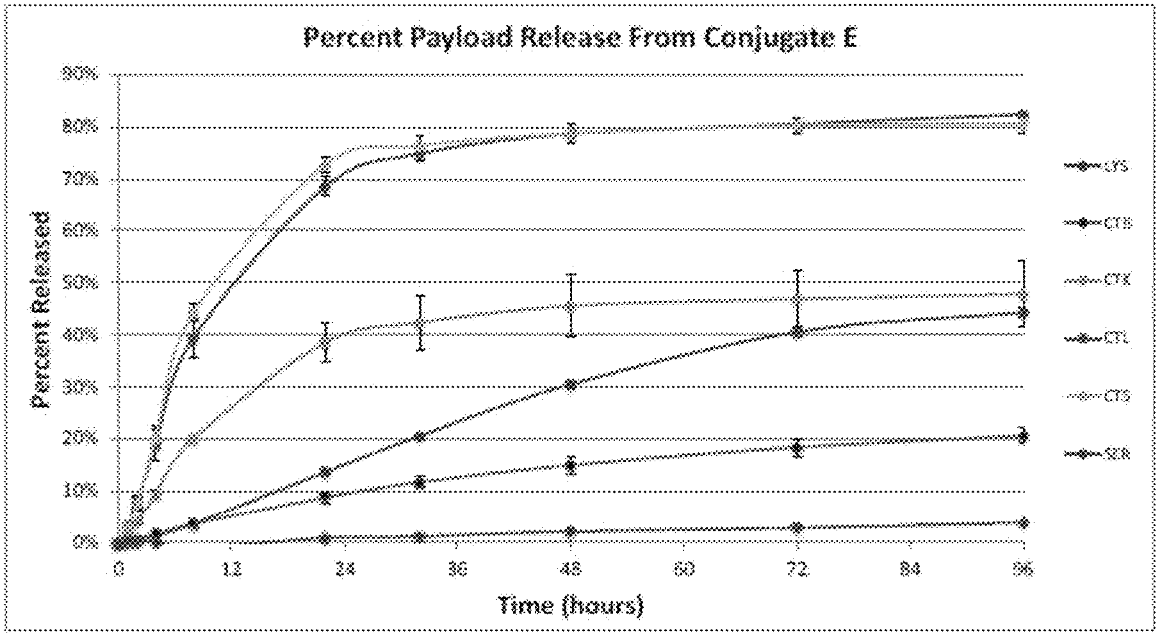
Figure 19:
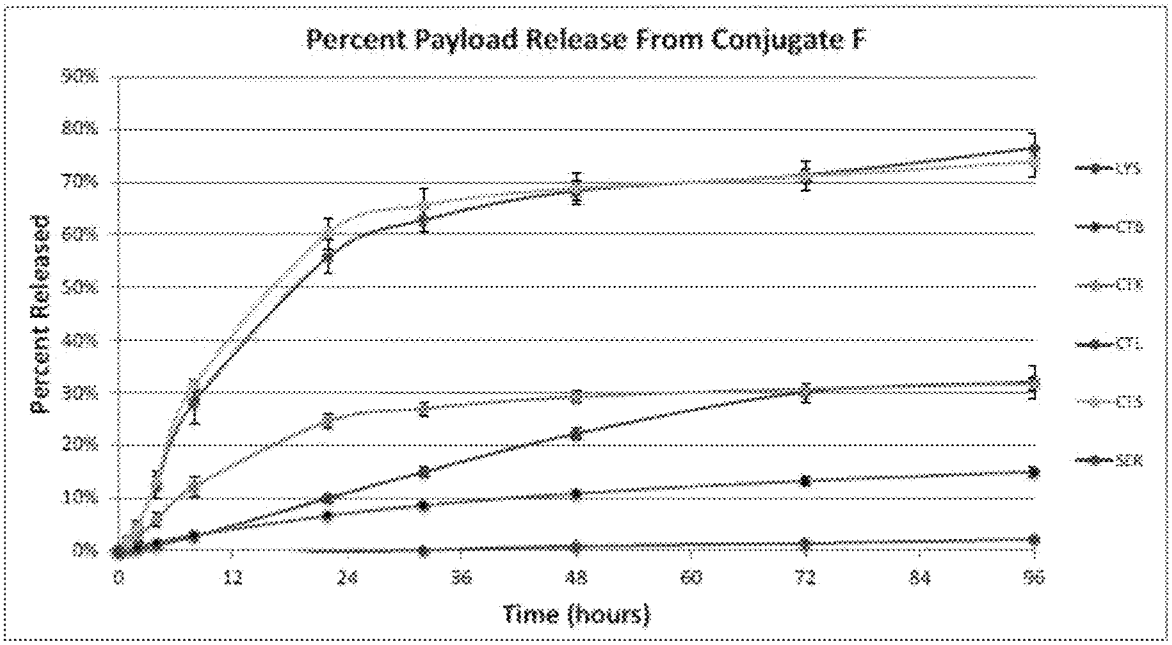
Figure 20:
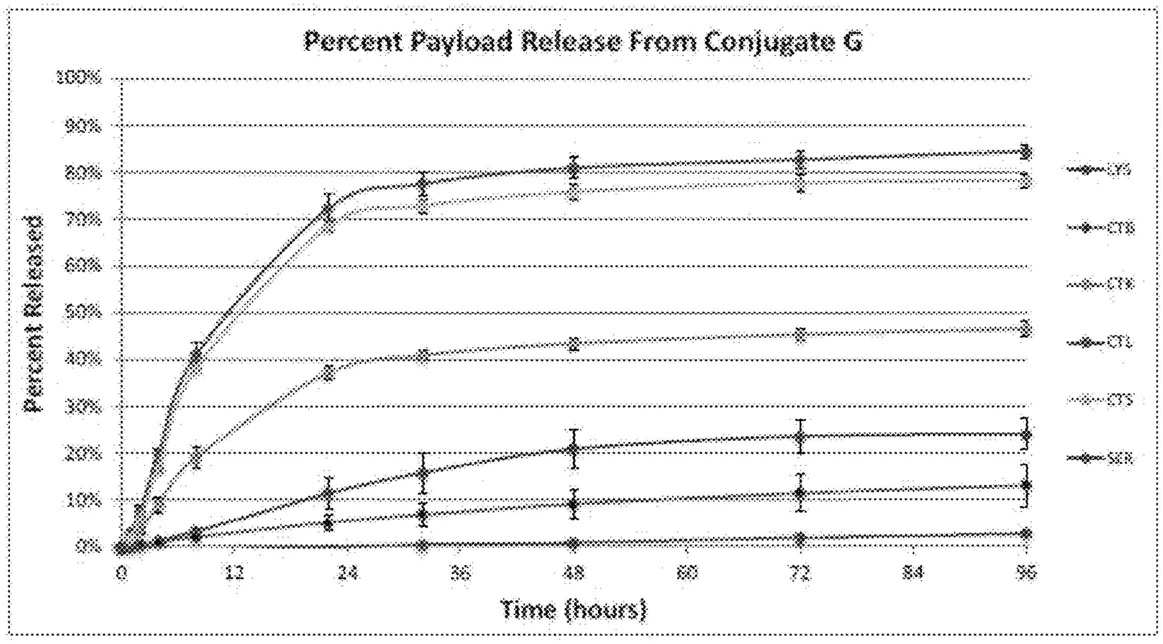
FIG. 20 shows the raw data for payload release from the 3×8 conjugates of FIG. 17 as antibody-payload distance decreases.
Figure 20:
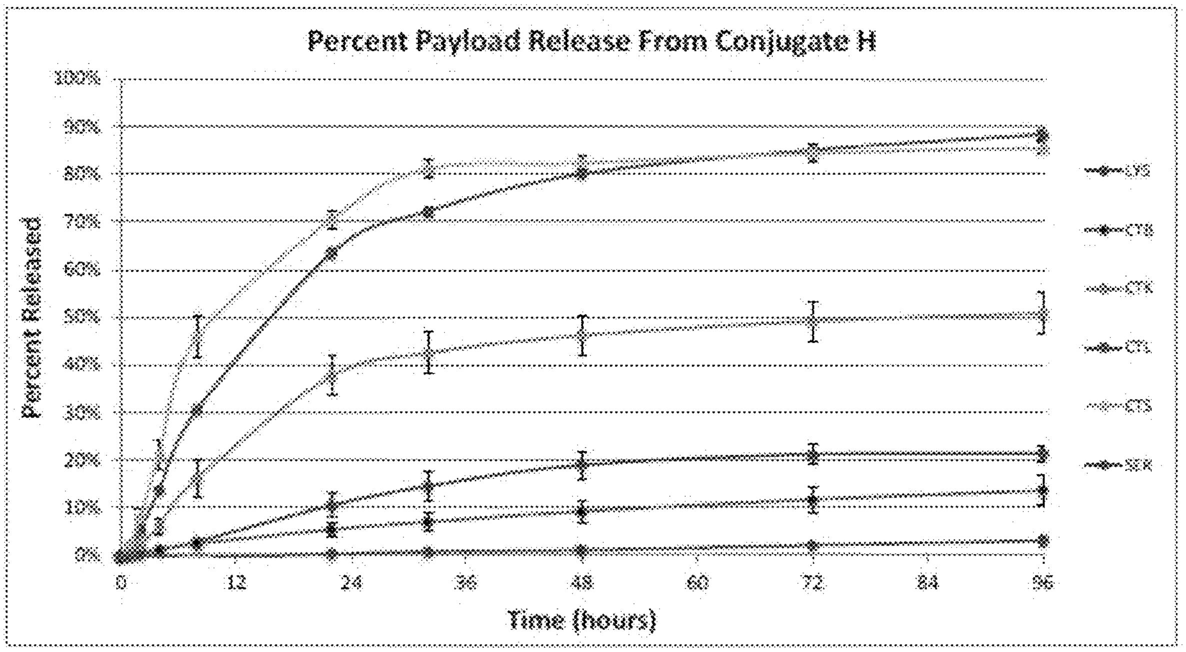
Figure 20:
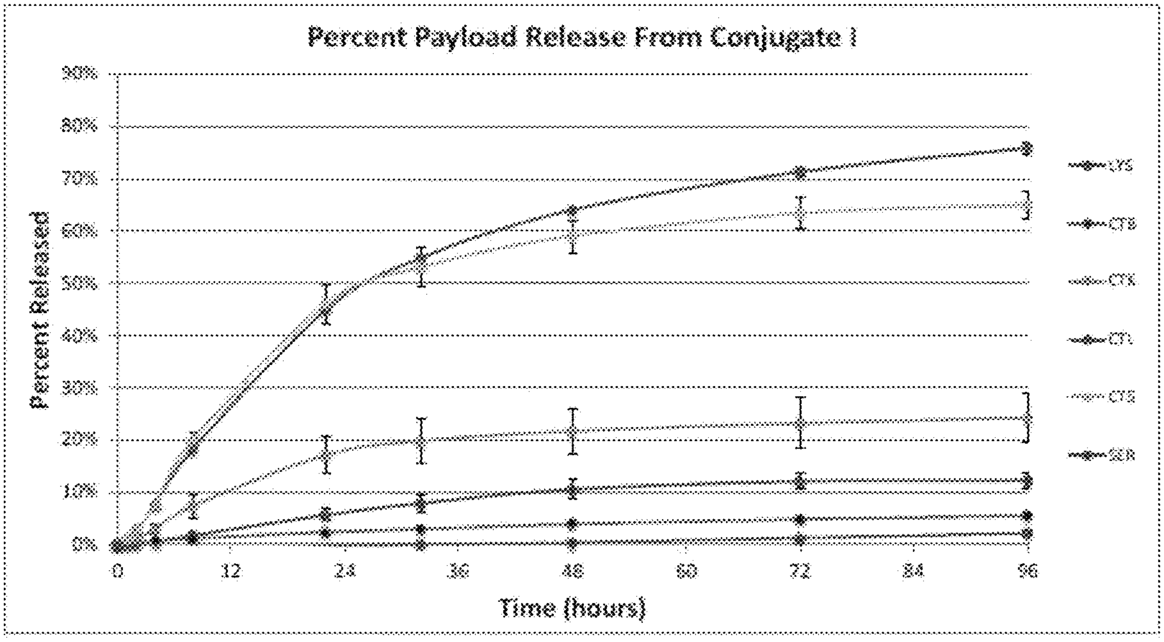
Figure 20:
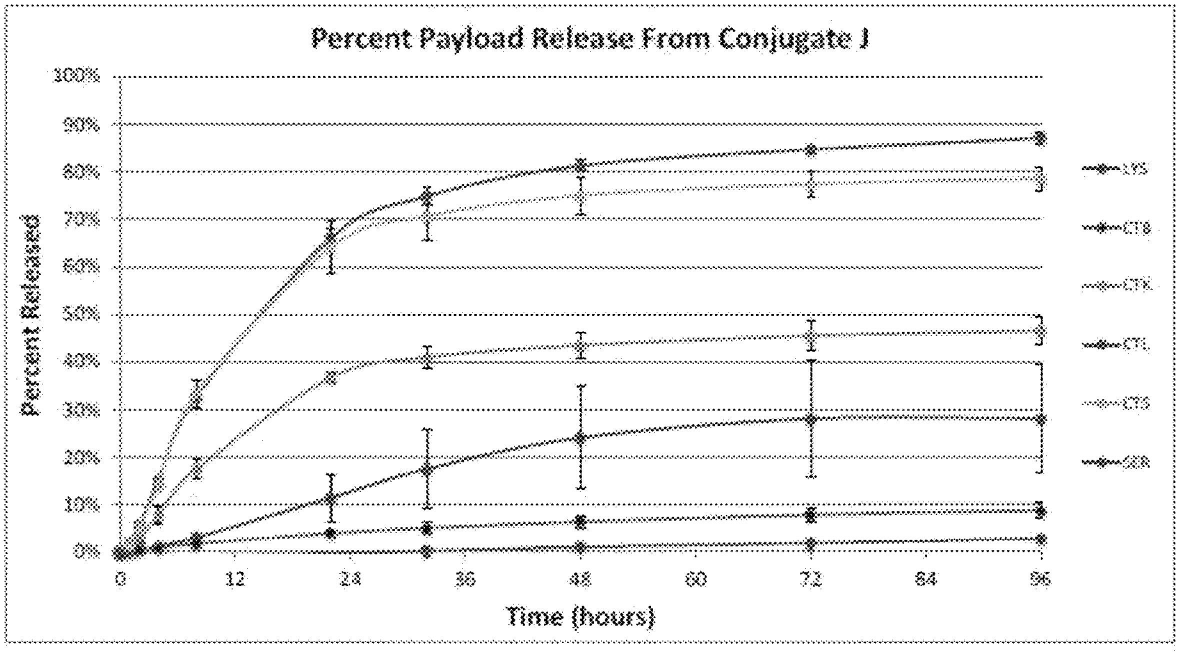
Figure 20:
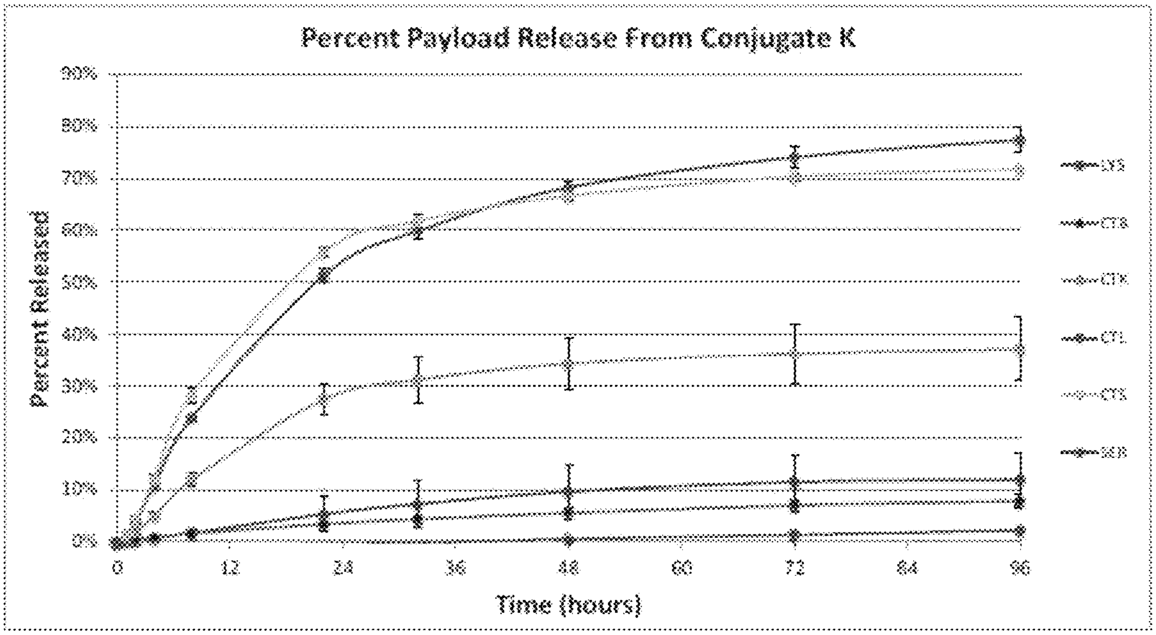
Figure 20:
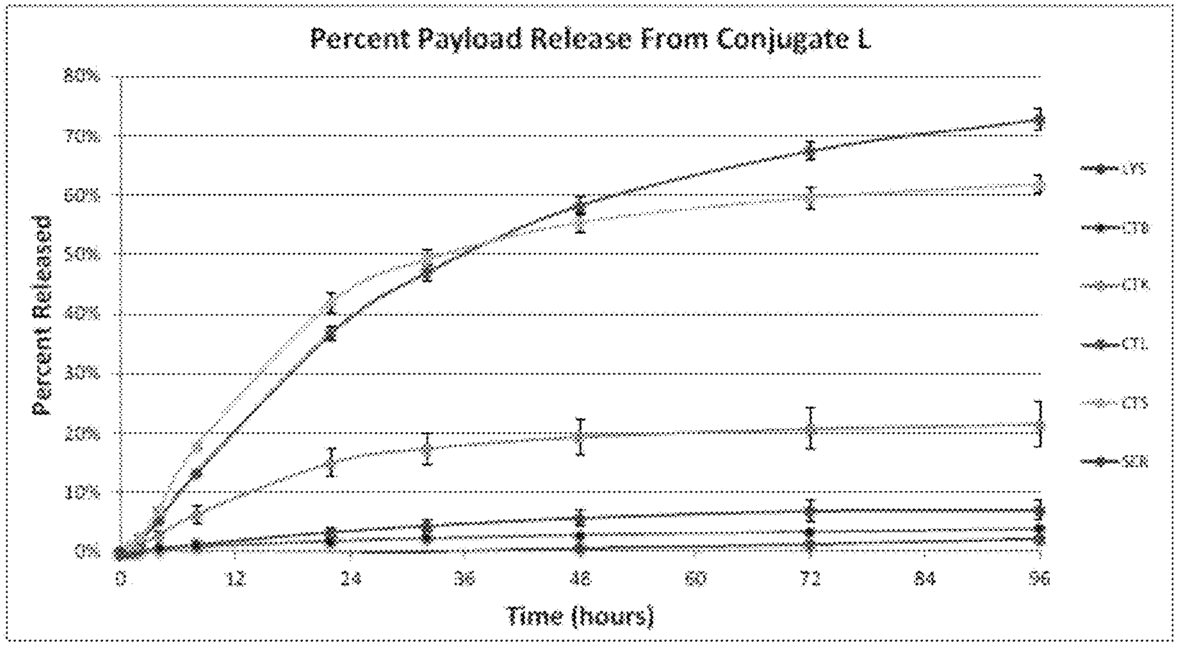
Figure 21:
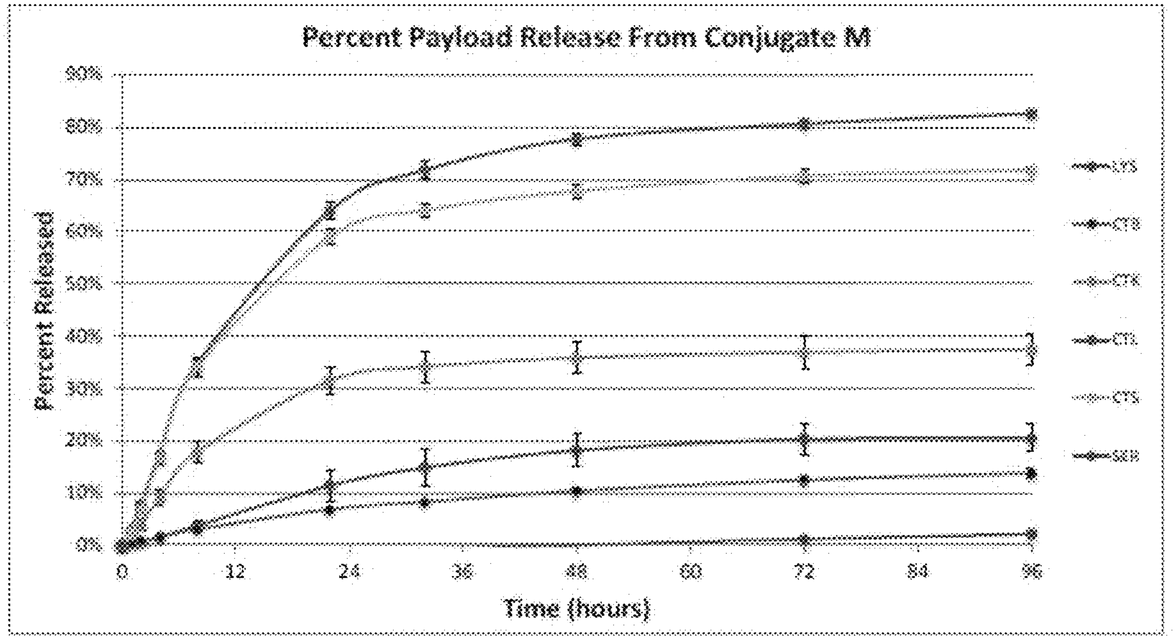
FIG. 21 shows the raw data for payload release from the 3×24 conjugates of FIG. 18 as antibody-payload distance decreases.
Figure 21:
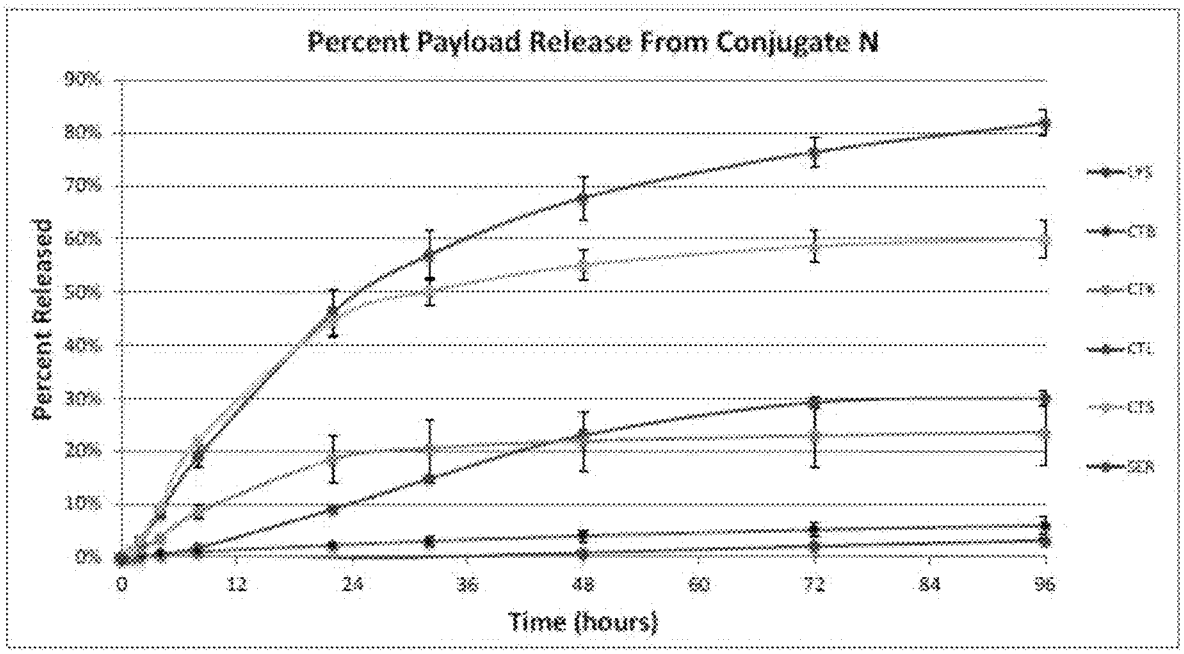
Figure 21:
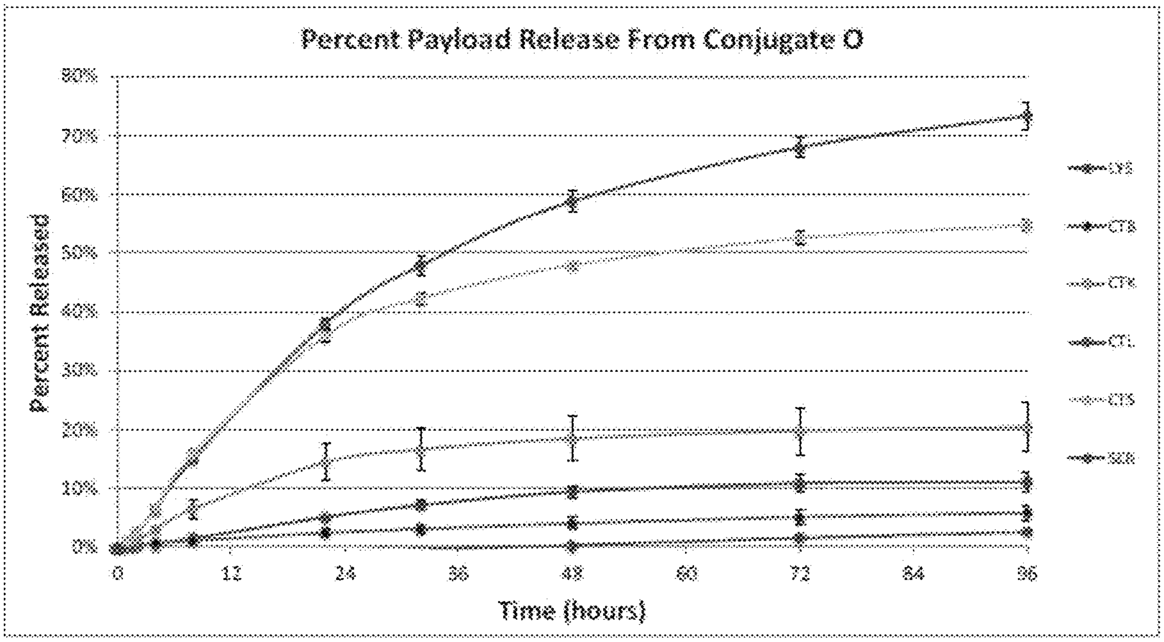
Figure 21:
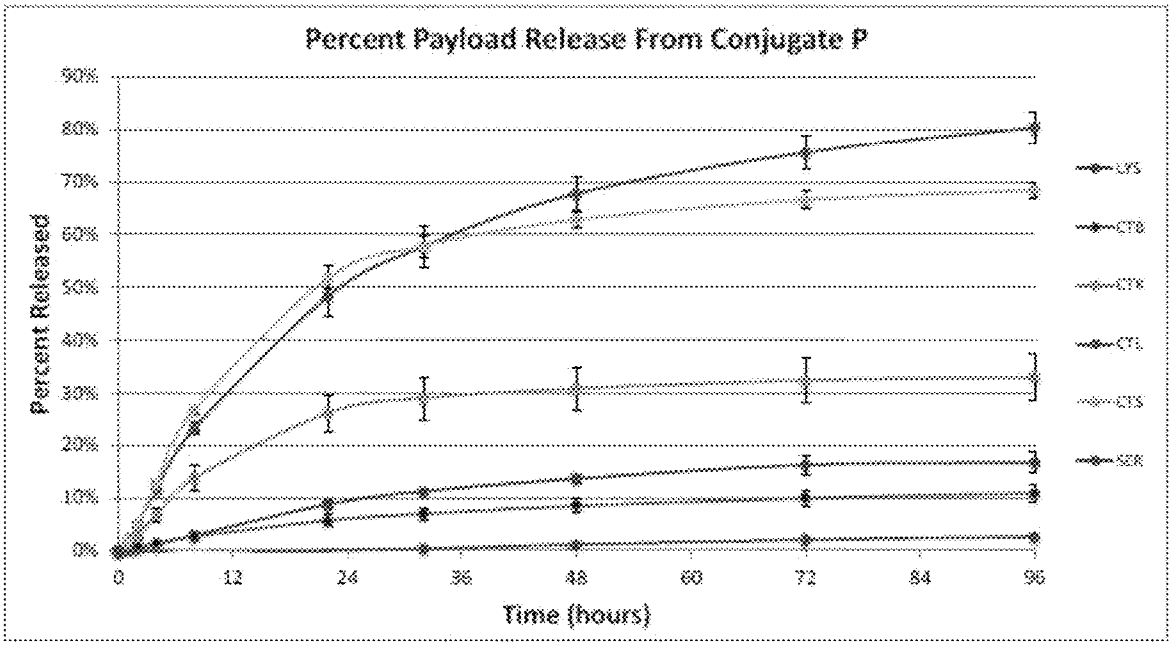
Figure 21:
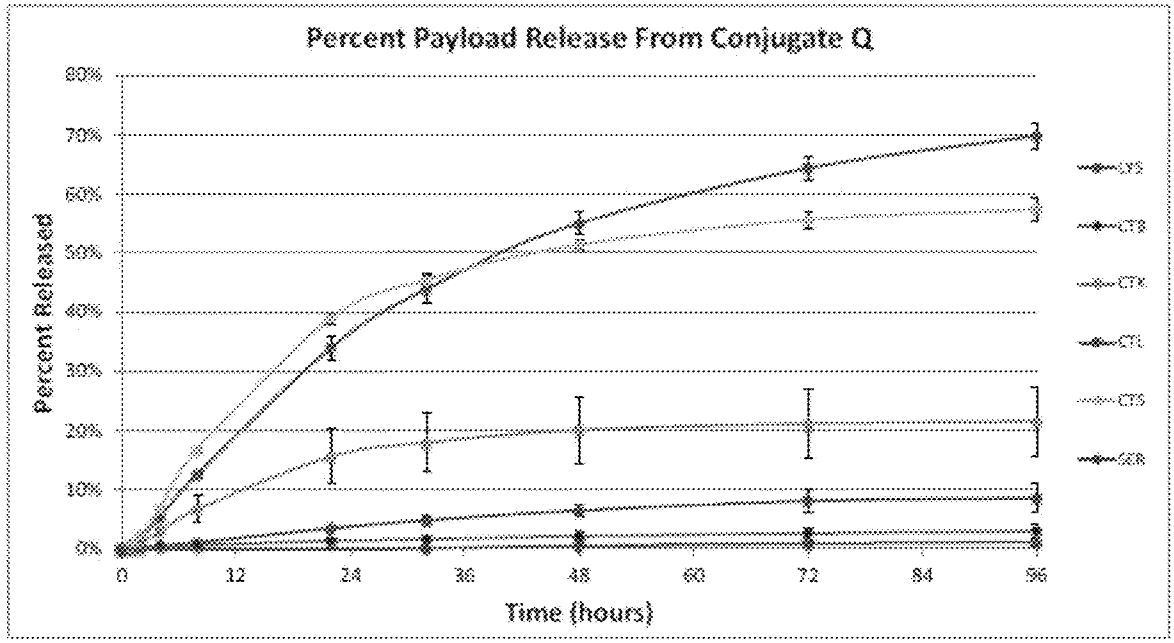
Figure 21:
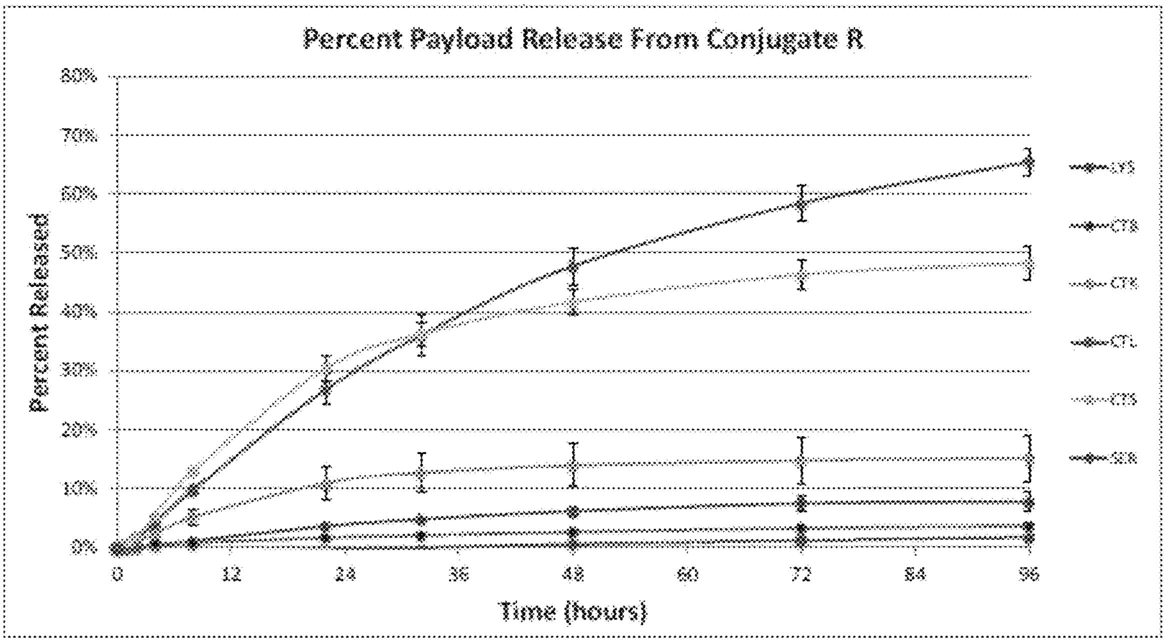

As described above, it was also found that y=3 architectures more effectively leverage steric shielding from the targeting vector (e.g., antibody) to influence cathepsin-mediated payload release. Two additional sets of conjugates were prepared that utilized the same set of linker architectures but decreased the distance between the antibody and the cleavable trigger (D1) from 40 Å (27 atoms) to 25 Å (14 atoms) and then to 20 Å (10 atoms) (FIGS. 17-18). Payload release for each linker architecture at the smaller distances, where steric shielding from the antibody was significant, was compared to release at the larger 27 atoms distance, where steric shielding from the antibody was less important (see FIGS. 19-21 and FIGS. 22A-22B). Payload release ratios of 1.00, calculated as payload release indicated similar release and implied payload release had no dependence on the proximity between the antibody and trigger, while ratios <1.00 indicated slower release at shorter distances and demonstrated that payload release was influenced by the proximity of the targeting vector in the linkers of the present disclosure (FIG. 22B).

Ratios of payload release at decreasing IgG-payload distances (D) were calculated for each architecture by comparing the percent payload release for a given conjugate to the percent payload release for the conjugate in the series having the longest D. As expected, linear linkers exhibited payload release ratios of ~1.00 in lysosomes and all the cathepsins, confirming that cathepsin-mediated release is generally not influenced by the steric hindrance from the antibody. On the other hand, orthogonal linker architectures of the present disclosure exhibited ratios <1.00, and changing from a (y=1, x=24) architecture to a (y=3, x=8) architecture resulted in a substantially greater dependence on antibody proximity, despite the same number of EO units and shorter dPEG arms (85 Å versus 30 Å). This was particularly noticeable for LYS, CTL, and CTS, and could be altered by manipulating the structural variables D' and x (see FIGS. 23A-23B). These results indicate that despite a global reduction in payload release by a given enzyme, y=3 architectures result in greater differentials between conjugates with more or less steric hindrance from the biologic, as measured by D.

FIGS. 23A-28B presents the percentage of payload released from the conjugates with the six different linker architectures, each conjugated at three different distances to the anti-body. The results establish that large hydrophilic shielding structures placed in orthogonal positions can inhibit cathepsin-mediated payload release from conjugates. In general, an overall reduction in payload release is correlated with an increase in steric congestion around the cleavable trigger, which makes intuitive sense. However, steric shielding can be altered by changes in D, D', y, and n, and the resultant effect on payload release is nuanced and depends on both the combination of structural variables and the enzyme. For instance, both 1×24 and 3×8 architectures have a total of 24 EO units, however the 3×8 structures show a greater attenuation of payload release that can be further enhanced when combined with shorter D and/or D'. It also appears that as the enzyme active site becomes more accessible (i.e., esterase<exopeptidase<endopeptidase) the larger y=3 structures and shorter D' spacers are more effective.

Payload release from conjugates in mouse serum was only observed for the linear linkers and was completely eliminated with orthogonal linkers (FIG. 23A). While the Val-Cit trigger is located next to Glu or Asp side-chains in all of the orthogonal structures, studies have shown this only has significant effects on Ces1c-mediated release if these side chains are present as the free carboxylate groups. In this case the elimination of Ces1c-mediated release is likely due to the increase in steric hindrance around the cleavable trigger imparted by the orthogonal dPEG-based shielding structures.

LYS-mediated release closely mirrored CTB-mediated release, which is expected since CTB is the predominant enzyme in the lysosomal preparations. FIGS. 24A and 25A reveal that the length of a linear linker has no effect of on payload release from the conjugates. This could be anticipated based on previous studies that used antibody steric hindrance to improve stability in mouse serum while still allowing for efficient CTB-mediated payload release. Incorporating the cleavable trigger into extended orthogonal linker architectures results in a significant reduction in payload release. The effect was greater for the y=3 structures than the y=1 structures, however within the group of y=3 structures the variables n and D' had less significant impact. This behavior is consistent with the fact that CTB is an exopeptidase at this pH, and the presence of an occluding loop restricts access to the active site and makes it less tolerant of extended substrates.

Payload release by the endopeptidases CTK, CTL, and CTS in FIGS. 26A, 27A, and 28A. The length of a linear linker has no effect on payload release, while all orthogonal linker architectures affect payload release and reductions are observed increasing y, increasing n, de-creasing D', and decreasing D. These results make intui-tive sense and are correlated with steric congestion around the cleavable trigger, and the impact depends on the enzyme with CTK>CTL>CTS. Endopeptidases such as these, with broad substrate specificity and tolerance for large substrates, require greater steric shielding from the substrate to block access to the cleavable trigger.

The change in payload release as antibody steric hindrance changes can be explored by comparing the ratios of payload release for a given linker architecture conjugated at long, intermediate, and short antibody-trigger distances. The analysis in FIGS. 23B-28B presents payload release ratios Dintermediate/Dlong and Dshort/Dlong. These values represent payload release from each of the six linker architectures as the antibody is moved closer, relative to its longest distance. Linker architectures with ratios near one provide conjugates with payload release that is unaffected by changes in steric hindrance. Linker architectures with ratios less than one provide conjugates with payload release that is affected by changes in antibody steric hindrance. Similar ratios for different linker architectures imply similar dependencies on antibody steric hindrance while smaller ratios imply greater dependencies, regardless of differences in absolute payload release rates.

The ratios of Ces1c-mediated payload release from conjugates with linear linkers are D16/D75=0.37 and D10/D75=0.35. These ratios indicate there is significant-ly less payload release at intermediate and short antibody-trigger distances relative to the longest distance. There is little difference between the intermediate and shortest distances. The ratios of cathepsin-mediated payload re-lease from conjugates with linear linkers approach 1.00, especially for the endopeptidases. These ratios indicate little dependence of cathepsin-mediated release on anti-body steric hindrance and a conjugate with a linear linker architecture could be expected to release the same amount of payload regardless of changes in antibody steric shielding.

All the orthogonal architectures result in CTB-mediated payload release ratios less than 1.00, indicating a dependence on antibody steric hindrance, however the dependence is greater for the 3×24 architectures. For these combinations of structural variables, the dependence of CTB-mediated release on antibody steric hindrance appears to be most influenced by the total number of EO units (n), while the number of arms (y) and the distance between the trigger and the hydrophilic shield (D') have little effect. The LYS data appears to follow the same trends, however the combination of a heterogeneous enzyme preparation used for the assays and the data manipulation resulted in large error bars. Conjugates with orthogonal linker architectures may exhibit an inhibition of cathepsin-mediated payload release that is correlated with changes in antibody steric shielding, and the magnitude of the difference is approximately correlated with n.

All orthogonal linker architectures result in conjugates with endopeptidase-mediated release that is inhibited as the proximity to the antibody is decreased, and the smaller ratios for CTK-mediated release suggest it is more affected by changes in antibody steric hindrance than either CTL- or CTS-mediated release. In general, it appears conjugates with the y=3 architectures are more influenced by changes in antibody steric hindrance than conjugates with the y=1 architecture. The y=3 linkers result in similar D10/D27 ratios, while the D14/D27 ratios are smallest for the 3×24 linkers, and within the 3×8 structures there is a small dependence on D'.

The above results suggest there are two general cases. In the first case, represented by the D10/D27 ratios, conjugates are able to leverage the full protection of the anti-body and will show changes in payload release due to changes in antibody steric hindrance that are largely dominated by the presence or absence of the large anti-body. As the proximity of the antibody is changed from D27 to D10 there is a significant reduction in payload re-lease, however the changes are all very similar and ratios vary by only 5% regardless of the orthogonal y=3 linker. Conjugates that leverage the full protection of the biologic may exhibit an inhibition of endopeptidase-mediated payload release that is correlated with changes in anti-body steric shielding, but the difference does not depend on the nuances of linker structure.

In the second case, represented by the D14/D27 ratios, the influence of the biologic is not as great at this intermediate conjugation distance, and does not overwhelm the influence of the linker. As the proximity of the antibody is changed from D27 to D14 there is a reduction in payload release for all linker architectures. However, the type of linker can affect the ratios by 10% (CTL), 15% (CTS), and 27% (CTK) in a manner that correlates with increasing n and/or decreasing D'. Conjugates that do not leverage the full protection of the biologic, either due to linker length, conjugation site, or size may exhibit an inhibition of endopeptidase-mediated payload release that is correlated with changes in antibody steric shielding, and the magnitude of the difference is approximately correlated with increasing n and decreasing D'.

The current results have expanded the set of linker variables and demonstrated that an appropriately designed linker can serve as an effective steric auxiliary to reduce cathepsin-mediated payload release. The hydrophilic nature of the dPEG moieties allows adequate steric shielding to be built up without the liabilities associated with increasing hydrophobicity. This could prove important since extracellular cathepsins have important roles in both physiological functions as well as pathological conditions such as cancer. Thus, these structures may provide another tool for balancing the attenuation of off-target payload release with efficient tumor-targeted release.

In some embodiments, the compound of Formula (III) is further characterized by a value D, which is defined as the number of atoms in a linear chain between the targeting vector X and the trigger T. In some embodiments, the distance D is from 10 to 30 atoms. In some embodiments, the distance D is 10 atoms, 14 atoms, or 27 atoms. In some embodiments, D is 10 atoms. Without being bound by any particular theory, in some embodiments, the percent of payload release for a compound of Formula (III) is reduced as the value D decreases. In some embodiments, there is a synergistic effect between D and D', such that percent payload release for a compound of Formula (III) is reduced when D' is 6 and the value of D is reduced to 10 atoms.

What is claimed is:

1. A conjugate of Formula (II) or a pharmaceutically acceptable salt or solvate thereof:

(II)

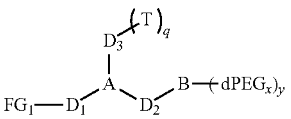

wherein:

$FG_1$ is a reactive functional group capable of conjugation to a targeting vector;

A is a trivalent or tetravalent atom or an amino acid residue;

B, a branch point connecting $(dPEG_x)_y$ to $D_2$, is a carbon atom;

T is a releasable trigger capable of conjugation to a payload;

dPEG is a linear or branched discrete polyethylene glycol-based chain;

q is 1;

x is an integer from 4 to 48;

y is 2 or 3;

$D_1$ is an alkylene, alkenylene, or alkynylene optionally comprising one or more heteroatoms selected from N and O, and optionally substituted with one or more oxo groups;

$D_2$ is —NH— or an alkylene, alkenylene, or alkynylene optionally comprising one or more heteroatoms selected from N and O, and optionally substituted with one or more oxo groups; and $D_3$ is an alkylene optionally comprising one or more heteroatoms selected from N and O, and optionally substituted with one or more oxo groups or the side chain of an amino acid, wherein D', the sum of atoms in a linear chain between B and T, is less than or equal to 22 atoms.

2. The conjugate of claim 1, wherein A is

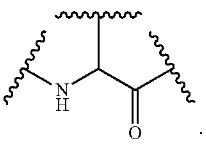 [SMILES: *NC(*)C(*)=O]

3. The conjugate of claim 2, wherein $D_1$ is selected from the group consisting of:

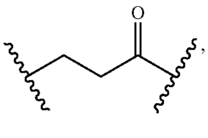,

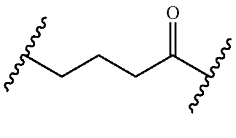,

-continued

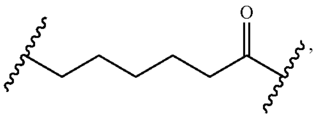,

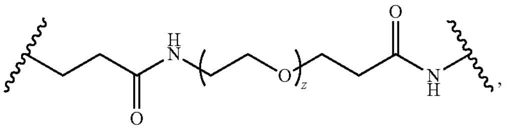, and

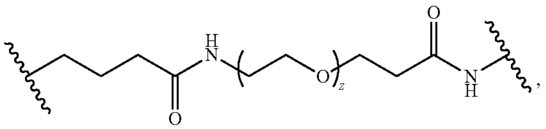, wherein z is 1-4.

4. The conjugate of claim 2, wherein $D_2$ is —NH— or

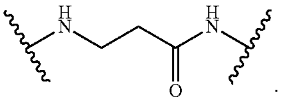 [SMILES: *NCCC(=O)N*]

5. The conjugate of claim 4, wherein $D_3$ is the side chain of a lysine, ornithine, 2,4-diaminobutyric acid (DAB), 2,3-diaminopropanoic acid (DAP), serine, threonine, tyrosine, cysteine, aspartic acid, or glutamic acid residue.

6. The conjugate of claim 1, wherein $D_1$ is an alkylene optionally comprising one or more heteroatoms selected from N and O, and optionally substituted with one or more oxo groups and $D_2$ is —NH— or an alkylene optionally comprising one or more heteroatoms selected from N and O, and optionally substituted with one or more oxo groups.

7. The conjugate of claim 1, wherein $D_3$ is a side chain of an amino acid.

8. The conjugate of claim 1, wherein

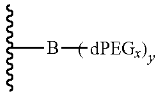 is

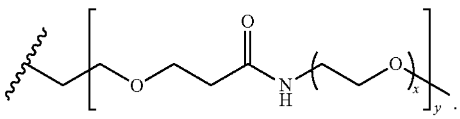

9. The conjugate of claim 8, wherein

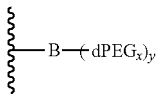

has the structure:

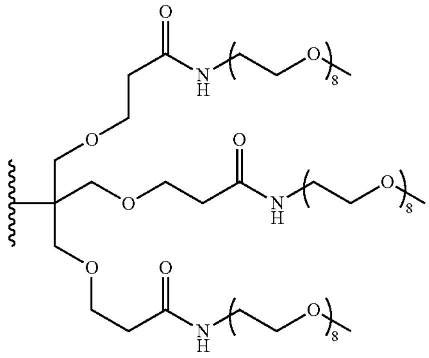

or

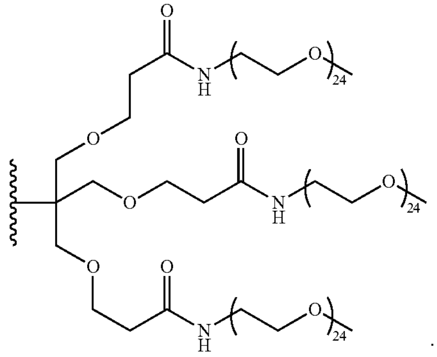

.

10. The conjugate of claim 1, wherein x is 8 or 24.

11. The conjugate of claim 1, wherein x is 8 and y is 3.

12. The conjugate of claim 1, wherein x is 24 and y is 3.

13. The conjugate of claim 1, wherein the releasable trigger T is a releasable trigger capable of enzymatic cleavage.

14. The conjugate of claim 13, wherein the releasable trigger T comprises a polypeptide having 2 to 6 amino acid residues.

15. The conjugate of claim 13, wherein the releasable trigger T comprises a self-immolative moiety selected from the group consisting of para-aminobenzyl alcohol (PABA), thioethyl carbamate, methylene alkoxy carbamate, and bis-carbamate.

16. The conjugate of claim 1, wherein P is a therapeutic or diagnostic moiety.

17. The conjugate of claim 1, wherein $FG_1$ is a carboxylic acid, an active ester, an N-hydroxysuccinimidyl ester, an α,β-unsaturated amide, a maleimide, or an α-halo acetamide.

18. The conjugate of claim 1, wherein $FG_1$ is

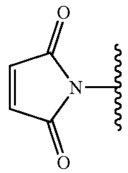

.

19. The conjugate of claim 1, having the structure:

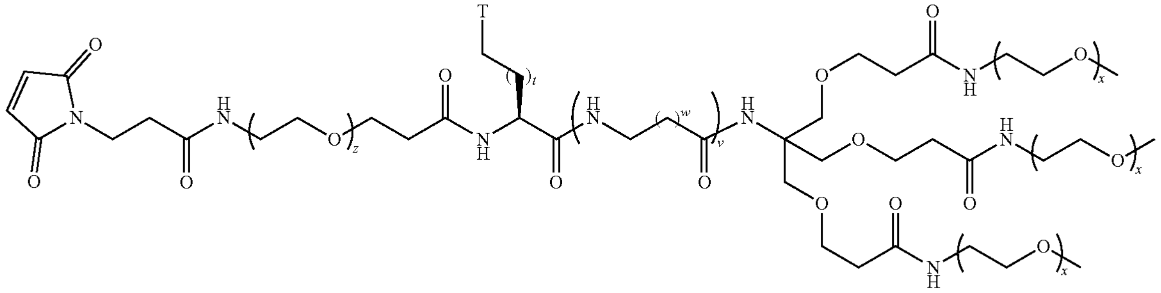

, wherein:

T is capable of conjugation to a payload and comprises a dipeptide residue selected from the group consisting of Valine-Citrulline (Val-Cit), Valine-Alanine (Val-Ala), Valine-Valine (Val-Val), and Phenylalanine-Lysine (Phe-Lys);

t is an integer from 0 to 4;

v is 0 or 1;

w is 1;

x is 8 or 24; and z is an integer from 1 to 4.

* * * * *